US011278482B2

(12) United States Patent
David et al.

(10) Patent No.: US 11,278,482 B2
(45) Date of Patent: Mar. 22, 2022

(54) PROCESS FOR DYEING KERATIN MATERIALS USING AT LEAST ONE BLUE, PURPLE OR GREEN DYE AND AT LEAST ONE DISULFIDE, THIOL OR PROTECTED THIOL FLUORESCENT DYE

(71) Applicant: L'OREAL, Paris (FR)

(72) Inventors: Hervé David, Aulnay-sous-Bois (FR); Christian Blaise, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/622,258

(22) PCT Filed: Jun. 18, 2018

(86) PCT No.: PCT/EP2018/066115
§ 371 (c)(1),
(2) Date: Dec. 12, 2019

(87) PCT Pub. No.: WO2018/009296
PCT Pub. Date: Dec. 20, 2018

(65) Prior Publication Data
US 2020/0179255 A1 Jun. 11, 2020

(30) Foreign Application Priority Data
Jun. 16, 2017 (FR) .................................. 1755482

(51) Int. Cl.
*A61Q 5/10* (2006.01)
*A61K 8/49* (2006.01)
(52) U.S. Cl.
CPC ............. *A61K 8/4933* (2013.01); *A61Q 5/10* (2013.01)
(58) Field of Classification Search
CPC ........ A61Q 5/10; A61K 8/411; A61K 8/4926; A61K 8/494; A61K 8/49; A61K 8/4946; A61K 2800/88; A61K 2800/4324; A61K 2800/882; A61K 2800/884; A61K 8/492; A61K 8/4953; A61K 8/355; A61K 8/4933; C09B 53/00; C09B 55/00; C09B 51/00; C09B 49/00
USPC .................................................... 8/405, 426
See application file for complete search history.

(56) References Cited

U.S. PATENT DOCUMENTS

| 3,100,739 | A | 8/1963 | Kaiser et al. |
| 3,524,842 | A | 8/1970 | Grossmann et al. |
| 3,578,386 | A | 5/1971 | Kalopissis et al. |
| 3,617,163 | A | 11/1971 | Kalopissis et al. |
| 3,817,698 | A | 6/1974 | Kalopissis et al. |
| 3,869,454 | A | 3/1975 | Lang et al. |
| 3,955,918 | A | 5/1976 | Lang |
| 4,003,699 | A | 1/1977 | Rose et al. |
| 4,025,301 | A | 5/1977 | Lang |
| 4,103,145 | A | 7/1978 | Oliveri |
| RE30,199 | E | 1/1980 | Rose et al. |
| 4,308,878 | A | 1/1982 | Silva |
| 4,886,517 | A | 12/1989 | Bugaut et al. |
| 5,046,516 | A | 9/1991 | Barradas |
| 5,087,733 | A | 2/1992 | Deppert et al. |
| 5,494,058 | A | 2/1996 | Chan |
| 5,708,151 | A | 1/1998 | Möckli |
| 5,879,413 | A | 3/1999 | Pengilly et al. |
| 5,888,252 | A | 3/1999 | Möckli |
| 5,919,273 | A | 7/1999 | Rondeau et al. |
| 5,957,140 | A | 9/1999 | McGee |
| 5,983,903 | A | 11/1999 | Nanba et al. |
| 5,993,490 | A | 11/1999 | Rondeau et al. |
| 6,045,591 | A | 4/2000 | Deneulenaere |
| 6,136,042 | A | 10/2000 | Maubru |
| 6,179,881 | B1 | 1/2001 | Henrion et al. |
| 6,284,003 | B1 | 9/2001 | Rose et al. |
| 6,451,069 | B2 | 9/2002 | Matsunaga et al. |
| 6,458,167 | B1 | 10/2002 | Genet et al. |
| 6,730,789 | B1 | 5/2004 | Birault et al. |
| 6,797,013 | B1 | 9/2004 | Lang et al. |
| 6,863,883 | B1 | 3/2005 | Tsujino et al. |
| 7,717,964 | B2 | 5/2010 | Daubresse et al. |

(Continued)

FOREIGN PATENT DOCUMENTS

| CN | 103327953 A | 9/2013 |
| DE | 2359399 A1 | 6/1975 |

(Continued)

OTHER PUBLICATIONS

International Search Report for counterpart Application No. PCT/EP2018/066115, dated Sep. 3, 2018.
International Search Report for counterpart Application No. PCT/EP2018/066114, dated Sep. 3, 2018.
Zviak, Charles, "Science Des Traitements Capillaires," [Hair Treatment Science], published by Masson, 1988, pp. 214-279.
International Search Report and Written Opinion for counterpart Application No. PCT/EP2018/062038, dated Jun. 25, 2018.
Ashford's Dictionary of Industrial Chemicals, Second Edition, 2001, pp. 14-39.

(Continued)

Primary Examiner — Eisa B Elhilo
(74) Attorney, Agent, or Firm — The Marbury Law Group, PLLC

(57) ABSTRACT

The present invention relates to a process for dyeing keratin fibers, in particular human keratin fibers such as the hair, using a) one or more blue, violet or green dyes and b) one or more disulfide, thiol or protected-thiol fluorescent dyes.

The present invention also relates to a cosmetic composition comprising the dyes defined above, and also to a multi-compartment device containing said dyes.

The present invention also relates to the use of said dyes for dyeing light keratin fibers, notably human keratin fibers such as the hair, in chestnut-brown, dark chestnut-brown, brown, brown with a tint, or even black, without using an additional dye other than those defined above.

20 Claims, No Drawings

(56) References Cited

U.S. PATENT DOCUMENTS

| | | | |
|---|---|---|---|
| 7,744,657 | B2 | 6/2010 | Greaves et al. |
| 7,780,743 | B2 | 8/2010 | Greaves et al. |
| 8,038,731 | B2 | 10/2011 | Daubresse et al. |
| 8,840,684 | B2 | 9/2014 | Greaves |
| 9,265,705 | B2 | 2/2016 | Guerin et al. |
| 2006/0080791 | A1 | 4/2006 | Daubresse et al. |
| 2009/0313769 | A1* | 12/2009 | Daubresse ........... A61K 8/4933 8/406 |
| 2010/0000029 | A1 | 1/2010 | Eliu et al. |
| 2013/0227797 | A1 | 9/2013 | Greaves |
| 2013/0283544 | A1 | 10/2013 | Greaves |
| 2014/0075687 | A1 | 3/2014 | Guerin et al. |
| 2014/0259454 | A1* | 9/2014 | Couroux ................ A61K 8/49 8/423 |
| 2015/0101132 | A1* | 4/2015 | David .................... A61Q 5/065 8/426 |
| 2015/0265513 | A1* | 9/2015 | Degeorge ................ A61Q 5/04 8/421 |
| 2020/0100999 | A1 | 4/2020 | Rharbi et al. |
| 2020/0261340 | A1 | 8/2020 | Blaise et al. |
| 2020/0337973 | A1 | 10/2020 | Blaise et al. |

FOREIGN PATENT DOCUMENTS

| | | |
|---|---|---|
| DE | 2527638 A1 | 5/1976 |
| DE | 2538363 A1 | 5/1976 |
| DE | 4137005 A1 | 5/1993 |
| DE | 4220388 A1 | 12/1993 |
| EP | 0714954 A2 | 6/1996 |
| EP | 0770375 A1 | 5/1997 |
| EP | 0850636 A1 | 7/1998 |
| EP | 0850637 A1 | 7/1998 |
| EP | 0860636 A1 | 8/1998 |
| EP | 0918053 A1 | 5/1999 |
| EP | 0920856 A1 | 6/1999 |
| EP | 1062940 A1 | 12/2000 |
| EP | 1133975 A2 | 9/2001 |
| EP | 1133976 A2 | 9/2001 |
| EP | 1386916 A1 | 2/2004 |
| EP | 1647580 A1 | 4/2006 |
| EP | 2004759 A2 | 12/2008 |
| EP | 2070988 A2 | 6/2009 |
| EP | 2075289 A1 | 7/2009 |
| FR | 1221122 A | 5/1960 |
| FR | 1516943 A | 2/1968 |
| FR | 1540423 A | 9/1968 |
| FR | 1560664 A | 3/1969 |
| FR | 1567219 A | 5/1969 |
| FR | 2189006 A1 | 1/1974 |
| FR | 2275462 A1 | 1/1976 |
| FR | 2285851 A1 | 4/1976 |
| FR | 2570946 A1 | 4/1986 |
| FR | 2757385 A1 | 6/1998 |
| FR | 2788433 A1 | 7/2000 |
| FR | 2801308 A1 | 5/2001 |
| FR | 2920779 A1 | 3/2009 |
| FR | 2920780 A1 | 3/2009 |
| FR | 2921256 A1 | 3/2009 |
| FR | 2921379 A1 | 3/2009 |
| FR | 2968954 A1 | 6/2012 |
| GB | 738585 A | 10/1955 |
| GB | 1163385 A | 9/1969 |
| GB | 1195386 A | 6/1970 |
| GB | 1514466 A | 6/1978 |
| JP | 2006-111626 A | 4/2006 |
| JP | 2010-501032 A | 1/2010 |
| JP | 2014-501339 A | 1/2014 |
| WO | 93/16991 A1 | 9/1993 |
| WO | 95/01772 A1 | 1/1995 |
| WO | 95/15144 A1 | 6/1995 |
| WO | 96/15765 A1 | 5/1996 |
| WO | 97/44004 A1 | 11/1997 |
| WO | 99/48465 A1 | 9/1999 |
| WO | 01/66646 A1 | 9/2001 |
| WO | 03/029359 A1 | 4/2003 |
| WO | 2004/039771 A1 | 5/2004 |
| WO | 2005/097051 A2 | 10/2005 |
| WO | 2006/136617 A2 | 12/2006 |
| WO | 2007/110531 A2 | 10/2007 |
| WO | 2007/110532 A2 | 10/2007 |
| WO | 2007/110533 A2 | 10/2007 |
| WO | 2007/110534 A2 | 10/2007 |
| WO | 2007/110535 A2 | 10/2007 |
| WO | 2007/110536 A2 | 10/2007 |
| WO | 2007/110537 A2 | 10/2007 |
| WO | 2007/110538 A2 | 10/2007 |
| WO | 2007/110539 A2 | 10/2007 |
| WO | 2007/110540 A2 | 10/2007 |
| WO | 2007/110541 A2 | 10/2007 |
| WO | 2007/110542 A2 | 10/2007 |
| WO | 2008/019977 A2 | 2/2008 |
| WO | 2009/034059 A2 | 3/2009 |
| WO | 2009/037325 A2 | 3/2009 |
| WO | 2009/040354 A1 | 4/2009 |
| WO | 2017/081314 A1 | 5/2017 |
| WO | 2018/206661 A1 | 11/2018 |
| WO | 2018/229295 A1 | 12/2018 |

OTHER PUBLICATIONS

Greene, T.W., "Protective Groups in Organic Synthesis," John Wiley & Sons, ed., NY, 1981, pp. 193-217.
Kirk-Othmer Encyclopedia of Chemical Technology, "Hair Preparation," 4th Ed., vol. 12, 1994, p. 881-918.
Kocienski, P., "Thiol Protecting Groups," Thieme 3rd Ed., 2005, Chapter 5.
Ullmann's Encyclopedia of Industrial Chemistry, "Hair Preparation," 2002, DOI: 10.1002/14356007.a12_571.
Ullmann's Encyclopedia, "Peptide Synthesis," pp. 4-5, 2005, Wiley-VCH Verlag GmbH & Co. KGaA, Weinheim 10.1002/14356007.a19 157.
International Search Report for counterpart Application No. PCT/EP2016/077555, dated Jan. 2, 2017.
Translated Notice of Reasons for Refusal for counterpart JP Application No. 2018-523810, dated May 27, 2019.
Translation of Chinese Office Action for counterpart Application No. 201680065233.7, dated Jul. 28, 2020.
Non-Final Office Action for copending U.S. Appl. No. 15/774,733, dated Feb. 24, 2021.
Hegazy, M.A. et al., "Novel Cationic Gemini Surfactants as Corrosion Inhibitors for Carbon Steel Pipeline," Corrosion Science, vol. 52, Issue 9, (2010), pp. 2897-2904.
Non-Final Office Action for copending U.S. Appl. No. 16/622,264, dated Oct. 21, 2020.
Non-Final Office Action for copending U.S. Appl. No. 16/611,437, dated Apr. 27, 2021.

* cited by examiner

PROCESS FOR DYEING KERATIN MATERIALS USING AT LEAST ONE BLUE, PURPLE OR GREEN DYE AND AT LEAST ONE DISULFIDE, THIOL OR PROTECTED THIOL FLUORESCENT DYE

The present invention relates to a process for dyeing keratin fibers, in particular human keratin fibers such as the hair, using a) one or more particular blue, violet or green dyes and b) one or more disulfide, thiol or protected-thiol fluorescent dyes.

The present invention also relates to a cosmetic composition comprising the dyes defined above, and also to a multi-compartment device containing said dyes.

The present invention also relates to the use of said dyes for dyeing light keratin fibers, notably human keratin fibers such as the hair, in chestnut-brown, dark chestnut-brown, brown, brown with a tint, or even black, without using an additional dye which colors said fibers, other than those defined hereinabove and hereinbelow.

Many people have sought for a long time to modify the color of their hair and in particular to mask their gray hair.

It is notably known practice to dye keratin fibers, in particular human keratin fibers, with dye compositions containing oxidation dye precursors, which are generally known as oxidation bases. These oxidation bases are colorless or weakly colored compounds which, when combined with oxidizing products, may give rise to colored compounds via a process of oxidative condensation.

The shades obtained with these oxidation bases may be modified by combining them with couplers or color modifiers. The variety of molecules used as oxidation bases and couplers allows a wide range of colors to be obtained.

Another well-known method consists in obtaining "semi-permanent" dyeing by applying to the keratin fibers direct dyes, which are colored and coloring molecules that have affinity for said fibers.

The direct dyes conventionally used are chosen from nitrobenzene, anthraquinone, nitropyridine, azo, xanthene, acridine, azine and triarylmethane direct dyes. The chemical species may be nonionic, anionic (acidic dyes) or cationic (basic dyes). The direct dyes may also be natural dyes.

Conventional direct dyeing processes consist in applying to keratin fibers dye compositions comprising direct dyes. After application, a leave-on time is observed so as to allow the dye molecules to penetrate by diffusion into the fibers. On conclusion of the process, the fibers are rinsed.

In contrast with oxidation dyeing, these direct dyeing processes have a tendency to better protect the integrity of the fibers. The resulting colorings are generally chromatic, but are, however, only semi-temporary. The nature of the interactions that bind the direct dyes to the keratin fibers and their desorption from the surface and/or the core of the fiber are responsible for their weak dyeing power.

Although a wide range of colors is currently accessible, it generally proves necessary to combine three dyes of complementary colors—trichromatic principle—in order to obtain a natural shade (see, for example, WO 95/15144 and WO 95/01772). This three-part combination does not, however, show good persistence with respect to repeated shampooing. It generally, or even systematically, induces an unesthetic changing of the color, which the consumer finds dissuasive. WO 2006/136617 also describes the combination of two or three different disulfide dyes. However, to obtain black colorings, at least three different dyes are mixed according to the trichromatic principle. In addition, each dye has its intrinsic resistance to light, or to shampooing and bad weather, and as such a change in the color as a function of the resistance of each may be observed. Blacks and browns then change to dark purples or other unesthetic colors and unnatural tints.

These colorings are, furthermore, not sufficiently fast in the face of external agents such as light or perspiration.

Thus, there is a real need to implement processes for the direct dyeing of keratin fibers, in particular of human keratin fibers such as the hair, which do not have the drawbacks mentioned above, i.e. which make it possible notably to lead to natural colorings that have good properties, notably in terms of chromaticity, power, intensity, sheen and selectivity, and which are persistent with respect to shampooing.

Another aim of the present invention is thus to be able to dye light keratin fibers efficiently in chestnut-brown, dark chestnut-brown, brown or brown with a tint or even black (preferably black), by mixing direct dyes, and preferably only two types of direct dye.

The Applicant has discovered, surprisingly, that a process for dyeing keratin fibers using:

a) one or more blue, violet or green dyes chosen from:
a1) phenoxazinium, phenothiazinium or phenazinium dyes,
a3) triarylmethane dyes,
a4) naphthoquinone or anthraquinone dyes,
a5) hydrazone dyes,
a6) tetraazapentamethine dyes,
a7) nitro dyes,
a8) azomethine dyes,
a9) self-oxidizing dyes,
a10) oxidation dyes
and
b) one or more disulfide, thiol or protected-thiol fluorescent dyes, makes it possible to achieve the objectives presented above; notably to give natural chestnut-brown, dark chestnut-brown, brown, brown with a tint (notably brown with a matt and coppery tint), or even black colorings, which are not only powerful and vivid, but also resistant to shampooing.

Thus, the main subject of the present invention relates to a process for dyeing keratin materials, in particular keratin fibers, notably human keratin fibers such as the hair, which consists in applying to said materials:

a) one or more blue, violet or green dyes chosen from dyes a1) to a10); and
b) one or more disulfide, thiol or protected-thiol fluorescent dyes;

it being understood that a) the blue, violet or green dye(s) and b) the disulfide, thiol or protected-thiol fluorescent dye(s) are applied to said keratin materials jointly or sequentially.

Another subject of the invention is a cosmetic composition comprising:

a) one or more blue, violet or green dyes chosen from dyes a1) to a10); and
b) one or more disulfide, thiol or protected-thiol fluorescent dyes;
c) optionally, one or more reducing agents, and
d) optionally, the pH of said composition being between 6 and 11 inclusive, preferably between 7 and 10 inclusive, more preferentially between 7.5 and 9.5 inclusive and better still between 9 and 9.5.

The combination of dye(s) a) one or more blue, violet or green dyes chosen from dyes a1) to a10) and b) of disulfide, thiol or protected-thiol fluorescent dye(s) makes it possible notably to obtain natural colorings which have good coloring properties, notably in terms of power, intensity, sheen and selectivity.

Furthermore, the process and the composition according to the invention make it possible to dye light keratin materials efficiently in a chestnut-brown, dark chestnut-brown, brown, brown with a tint (notably brown with a matt or coppery tint), or even black color by mixing a) blue, violet or green dyes chosen from dyes a1) to a10) with b) disulfide, thiol or protected-thiol fluorescent dyes, without the need to use an additional (or complementary) dye which colors said fibers other than a) or b).

Moreover, the colorings obtained by means of the process and the composition according to the invention show good resistance to the various attacking factors to which the hair may be subjected, such as light, bad weather, washing and perspiration. They are in particular persistent with respect to shampooing, notably after at least three shampoo washes.

A subject of the present invention is also a multi-compartment device comprising a first compartment containing one or more dyes (a) chosen from dyes a1) to a10) as defined previously, and also the optical isomers thereof, the geometrical isomers thereof, the tautomers thereof, the organic or mineral acid or base salts thereof, the solvates thereof such as hydrates, and mixtures thereof, and a second compartment containing one or more disulfide, thiol or protected-thiol fluorescent dyes (b) as defined previously.

Another subject of the invention is the use of b) disulfide, thiol or protected-thiol fluorescent dye(s) as defined previously, combined with blue, violet or green dye(s) for dyeing light keratin fiber materials, notably keratin fibers, preferably human keratin fibers such as the hair in a chestnut-brown, dark chestnut-brown, brown, brown with a tint, or even black color, without using an additional dye other than a) or b).

Other subjects, features, aspects and advantages of the invention will emerge even more clearly on reading the description and the examples that follow.

For the purposes of the present invention and unless otherwise indicated:

for the purposes of the present invention, the term "direct dye" means natural and/or synthetic dyes, which are soluble in the cosmetic medium, other than oxidation dyes; these are dyes which diffuse on the surface of the keratin fibers;

a fluorescent direct dye "bearing a disulfide function" is a direct dye including one or more fluorescent chromophores as defined below, and comprising a disulfide bond: —S—S— between two carbon atoms and which is preferably indirectly bonded to the chromophore(s) of the dye, i.e. between the chromophores and the —S—S— function there is at least one methylene group;

a "direct dye bearing a protected-thiol function" is a direct dye including a chromophore, comprising a protected-thiol function —SY in which Y is a protecting group known to those skilled in the art, for instance those described in the publications "*Protective Groups in Organic Synthesis*", T. W. Greene, John Wiley & Sons ed., NY, 1981, pages 193-217; "*Protecting Groups*", P. Kocienski, Thieme, 3rd ed., 2005, chap. 5; and Ullmann's Encyclopedia, "*Peptide Synthesis*", pages 4-5, 2005 Wiley-VCH Verlag GmbH & Co. KGaA, Weinheim 10.1002/14356007.a19 157; it being understood that said protected-thiol function is preferably indirectly bonded to the chromophore of the dye, i.e. between the chromophore and the function —SY there is at least one methylene group;

a "direct dye bearing a thiol function" is a direct dye including a chromophore, and comprising a thiol function —SY' in which Y' is i) a hydrogen atom; ii) an alkali metal; iii) an alkaline-earth metal; iv) an ammonium group: $N^+R^aR^bR^gR^d$ or a phosphonium group: $P^+R^aR^bR^gR^d$ with $R^a$, $R^b$, $R^g$ and $R^d$, which may be identical or different, representing a hydrogen atom or a group $(C_1-C_4)$alkyl, preferentially comprising a thiol function —SY' it being understood that said thiol function is indirectly bonded to the chromophore of the dye, i.e. between the chromophore and the function —SY' there is at least one methylene group;

a "fluorescent chromophore" is a radical derived from a fluorescent dye, that is to say a radical derived from a molecule which absorbs light in the visible range of radiation which is visually perceptible to humans and which appears colored to the naked eye, i.e. which absorbs light at an absorption wavelength $\lambda_{abs}$ preferably between 300 and 700 nm inclusive; said chromophore is also that it is capable of re-emitting in the visible range at an emission wavelength $\lambda_{em}$ greater than the absorption wavelength, i.e. preferably $\lambda_{em}$ re-emitting between 400 and 800 nm inclusive; the difference between the absorption wavelength and emission wavelength, also called the Stoke's shift, is between 1 nm and 100 nm inclusive.

More preferentially, fluorescent chromophores are capable of absorbing at a wavelength $\lambda_{abs}$ inclusively between 420 nm and 550 nm and of re-emitting in the visible range at a wavelength $\lambda_{em}$ inclusively between 470 and 600 nm;

a "chromophore" is said to be "quaternized cationic" or "bearing a quaternized cationic group" if it comprises in its structure at least one permanent cationic charge formed from at least one quaternized nitrogen atom (ammonium) or quaternized phosphorus atom (phosphonium), preferably nitrogen;

a group is said to be "bearing a quaternizable cationic group" when it comprises at least one tertiary amine or tertiary phosphine at the end of a hydrocarbon-based chain, preferably $C_1$-$C_{10}$ alkyl, such as —$(CR'R'')_p$—$N(R_a)$—$R_b$ with R' and R", which may be identical or different, representing a hydrogen atom or a $(C_1-C_6)$ alkyl group; $R_a$ and $R_b$, which may be identical or different, representing a (poly)(hydroxy)$(C_1-C_6)$alkyl group or alternatively $R_a$ and $R_b$ form, together with the nitrogen atom that bears them, a heterocycloalkyl group such as morpholino, piperidino or piperazino; and p representing an integer inclusively between 1 and 10; preferably, R' and R" represent a hydrogen atom, $R_a$ and $R_b$ represent a $(C_1-C_4)$alkyl group and p is between 2 and 5;

the dyes according to the invention contain one or more colored and fluorescent chromophores as defined previously; in particular, they are capable of absorbing light at a wavelength $\lambda_{abs}$ inclusively between 300 and 700 nm and of re-emitting in the visible range at a longer wavelength than the absorption wavelength, in particular $\lambda_{em}$ inclusively between 400 and 800 nm: the difference between the absorption wavelength and the emission wavelength, also known as the Stoke's shift, is inclusively between 1 and 100 nm. More preferentially, fluorescent dyes of the invention are dyes that are capable of absorbing at a wavelength $\lambda_{abs}$ inclusively between 420 nm and 550 nm and of re-emitting in the visible range at a wavelength $\lambda_{em}$ inclusively between 470 and 600 nm;

the chromophores are said to be "different" when they differ in their chemical structure and may be chromophores derived from different families or from the same family on condition that they have different chemical structures: for example, the chromophores may be chosen from the family of azo dyes but differ in the chemical structure of the radicals constituting them or in the respective position of these radicals;

an "alkylene chain" represents an acyclic hydrocarbon-based divalent chain which is of $C_1$-$C_{20}$, particularly $C_1$-$C_6$, more particularly $C_1$-$C_2$ when the chain is linear, optionally substituted with one or more groups, which may be identical or different, chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—C($Z^b$)—$Z^c$—, and v) $R^a$—$Z^a$—S(O)$_t$—$Z^c$— with $Z^a$ and $Z^b$, which may be identical or different, representing an oxygen or sulfur atom, or a group $NR^{a'}$, $Z^c$ representing a bond, an oxygen or sulfur atom, or a group $NR^a$; $R^a$ representing an alkali metal, a hydrogen atom, an alkyl group, or alternatively is absent if another part of the cationic molecule and $R^{a'}$ representing a hydrogen atom or an alkyl group and t is equal to 1 or 2; more particularly, the groups iv) are chosen from carboxylate —C(O)O$^-$ or —C(O)OMetal (Metal=alkali metal), carboxyl —C(O)—OH, guanidino $H_2H$—C($NH_2$)—NH—, amidino $H_2H$—C($NH_2$)—, (thio)ureo $H_2N$—C(O)—NH— and $H_2N$—C(S)—NH—, aminocarbonyl —C(O)—NRa'$_2$ or aminothiocarbonyl —C(S)—NRa'$_2$; carbamoyl Ra'—C(O)—NRa'— or thiocarbamoyl Ra'—C(S)—NRa'— with Ra', which may be identical or different, representing a hydrogen atom or a ($C_1$-$C_4$) alkyl group;

an "optionally substituted, saturated or unsaturated $C_1$-$C_{30}$ divalent hydrocarbon-based chain" represents a, particularly $C_1$-$C_8$, hydrocarbon-based chain optionally comprising one or more conjugated or non-conjugated double bonds p, the hydrocarbon-based chain being in particular saturated; said chain is optionally substituted with one or more groups chosen from i) hydroxyl, ii) ($C_1$-$C_2$)alkoxy, iii) (poly)hydroxy($C_2$-$C_4$)alkoxy (di)($C_1$-$C_2$) (alkyl)amino, iv) $R^a$—$Z^a$—C($Z^b$)—$Z^c$—, and v) $R^a$—$Z^a$—S(O)$_t$—$Z^c$— with $Z^a$, $Z^b$, which may be identical or different, representing an oxygen or sulfur atom, or a group $NR^{a'}$, $Z^c$ representing a bond, an oxygen or sulfur atom, or a group $NR^a$; $R^a$ representing an alkali metal, a hydrogen atom or an alkyl group or else is absent if another part of the cationic molecule and $R^{a'}$ representing a hydrogen atom or an alkyl group and t is 1 or 2; more particularly, the groups iv) are chosen from carbon/late —C(O)O$^-$ or —C(O)OMetal (Metal=alkali metal), carboxyl —C(O)—OH, guanidino $H_2H$—C($NH_2$)—NH—, amidino $H_2H$—C($NH_2$)—, (thio)ureo $H_2N$—C(O)—NH— and $H_2N$—C(S)—NH—, aminocarbonyl —C(O)—NR$_a$'$_2$ or aminothiocarbonyl —C(S)—NR$_a$'$_2$; carbamoyl R$_a$'—C(O)—NR$_a$'— or thiocarbamoyl R$_a$'—C(S)—NR$_a$'— with R$_a$', which may be identical or different, representing a hydrogen atom or a ($C_1$-$C_4$) alkyl group;

the "fluorescent dyes" according to the present invention are to be differentiated from optical brighteners. Optical brighteners, also generally known as "brighteners" or "fluorescent brighteners" or "fluorescent brightening agents" or "fluorescent whitening agents or FWA" or "whiteners" or else "fluorescent whiteners", are compounds that are colorless to the naked eye, which do not impart a color and are consequently not dyes since they do not absorb in the visible light range, but only absorb in the ultraviolet range (wavelength ranging from 200 to 400 nm) and transform the absorbed energy into fluorescent light of a longer wavelength emitted in the visible part of the spectrum in the blue range. The color impression is then generated only by the purely fluorescent light that is predominantly blue;

the "blue-violet-green" dyes according to the invention are dyes which absorb light in the visible spectrum and which appear violet, blue or green visually, i.e. which absorb light at an absorption wavelength $\lambda_{max}$ greater than 520 nm and less than or equal to 700 nm, in particular $\lambda_{max}$ inclusively between 560 nm and 700 nm, preferably in the blue range, i.e. $\lambda_{max}$ between 580 and 620 nm;

as visual color and absorption wavelength associated with said color, mention may be made of the following colors: yellow=$\lambda_{max}$>400 nm up to 440 nm limit inclusive, orange=$\lambda_{max}$>440 nm up to 490 nm limit inclusive, red=$\lambda_{max}$>490 up to 520 nm limit inclusive, purple to violet=$\lambda_{max}$>520 nm and 560 nm limit inclusive, violet=$\lambda_{max}$>560 nm to 580 nm limit inclusive, blue=$\lambda_{max}$>580 nm up to 620 nm limit inclusive, blue-green=$\lambda_{max}$>620 nm up to 650 nm limit inclusive, and green $\lambda_{max}$>650 nm up to 780 nm limit inclusive;

the term "(hetero)aryl" generally means aryl and heteroaryl groups;

the "aryl" or "heteroaryl" radicals or the aryl or heteroaryl part of a radical may be substituted with at least one substituent borne by a carbon atom, chosen from:

a $C_1$-$C_6$ and preferably $C_1$-$C_4$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom such as chlorine;

a hydroxyl or thiol group;

a $C_1$-$C_6$ alkoxy or $C_1$-$C_6$ alkylthio radical;

a (poly)hydroxy($C_2$-$C_6$)alkoxy radical;

an amino radical;

a 5- or 6-membered heterocycloalkyl radical, preferentially morpholino, piperazino, piperidino or pyrolidino, which is optionally substituted with a ($C_1$-$C_4$) alkyl radical, preferentially methyl;

a 5- or 6-membered heteroaryl radical, preferentially imidazolyl, optionally substituted with a ($C_1$-$C_4$) alkyl radical, preferentially methyl;

an amino radical substituted with one or two identical or different $C_1$-$C_6$ alkyl radicals, optionally bearing at least:

i) a hydroxyl group, ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
iii) a quaternary ammonium group —N⁺R'R"R''', Y⁻ for which R', R" and R''', which may be identical or different, represent a $C_1$-$C_4$ alkyl group and Y⁻ represents an anionic counterion,
iv) or an optionally cationic 5- or 6-membered heteroaryl radical, preferentially imidazolium, optionally substituted with a ($C_1$-$C_4$)alkyl radical, preferentially methyl;

an acylamino radical (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;

a carbamoyl radical ((R)$_2$N—C(O)—) in which the radicals R, which may be identical or different, represent a hydrogen atom or a $C_1$-$C_4$ alkyl radical optionally bearing at least one hydroxyl group;

an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;

an aminosulfonyl radical ((R)$_2$N—S(O)$_2$—) in which the R radicals, which may be identical or different, represent a hydrogen atom or a $C_1$-$C_4$ alkyl radical optionally bearing at least one hydroxyl group;

a carboxyl radical in the acid or salified form (preferably salified with an alkali metal or a substituted or unsubstituted ammonium);

a cyano group;

a nitro or nitroso group;

a polyhaloalkyl group, preferably trifluoromethyl;

the cyclic or heterocyclic part of a non-aromatic radical may be substituted with at least one substituent chosen from the following groups:

hydroxyl;

$C_1$-$C_4$ alkoxy, $C_2$-$C_4$ (poly)hydroxyalkoxy;

$C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R—X$_1$—C(O)—) in which the radical R is a $C_1$-$C_4$ alkoxy radical, X$_1$ is an oxygen atom or an amino group optionally substituted with a $C_1$-$C_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

an "aryl" radical generally represents a monocyclic or fused or non-fused polycyclic carbon-based group comprising from 6 to 22 carbon atoms, at least one ring of which is aromatic; preferentially, the aryl radical is a phenyl, biphenyl, naphthyl, indenyl, anthracenyl or tetrahydronaphthyl;

a "cationic heteroaryl radical" is a heteroaryl group as defined previously, which includes an endocyclic or exocyclic cationic group;

when the charge is endocyclic, it is included in the electron delocalization via the mesomeric effect; for example, it is a pyridinium, imidazolium or indolinium group:

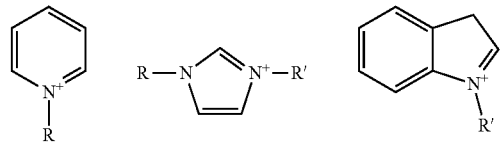

with R and R' being a heteroaryl substituent as defined previously and particularly a (hydroxy)($C_1$-$C_8$)alkyl group, such as methyl;

when the charge is exocyclic, it is not included in the electron delocalization via the mesomeric effect; for example, it is an ammonium or phosphonium substituent R⁺, such as trimethylammonium, which is outside the heteroaryl, such as pyridyl, indolyl, imidazolyl or naphthalimidyl, in question:

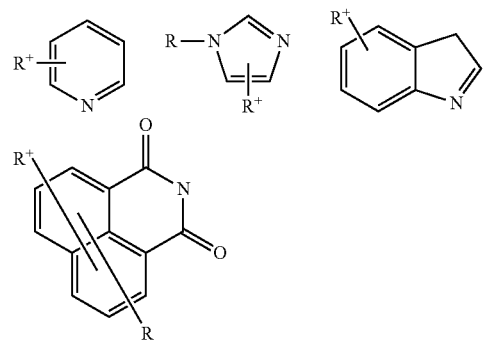

with R being a heteroaryl substituent as defined below and R⁺ an ammonium R$_a$R$_b$R$_c$N⁺—, phosphonium R$_a$R$_b$R$_c$P⁺— or ammonium R$_a$R$_b$R$_c$N⁺—($C_1$-$C_6$)alkylamino, R$_a$R$_b$R$_c$N⁺—($C_1$-$C_6$)alkyl or R$_a$R$_b$R$_c$N⁺—($C_1$-$C_6$)alkoxy group with R$_a$, R$_b$ and R$_c$, which may be identical or different, representing a ($C_1$-$C_8$)alkyl group such as methyl;

a "heteroaryl radical" generally represents a 5- to 22-membered, monocyclic or fused or non-fused polycyclic group, comprising from 1 to 6 heteroatoms chosen from nitrogen, oxygen and sulfur, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salt thereof;

a "heterocyclic radical" is a 5- to 22-membered, monocyclic or fused or non-fused polycyclic radical that may contain one or two unsaturations but is not aromatic, including from 1 to 6 heteroatoms chosen from nitrogen, oxygen and sulfur;

a "heterocycloalkyl radical" is a heterocyclic radical comprising at least one saturated ring;

an "alkyl radical" is a linear or branched $C_1$ to $C_{20}$, preferably $C_1$ to $C_{10}$, more preferentially $C_1$ to $C_8$, better still $C_1$ to $C_6$ and even better still $C_1$ to $C_4$ hydrocarbon-based radical;

the expression "optionally substituted" applied to the alkyl radical implies that said alkyl radical may be substituted with one or more radicals chosen from the following radicals: i) hydroxyl, ii) $C_1$-$C_4$ alkoxy, iii) R—Z—C(X)—Y— with X, Y and Z representing an oxygen or sulfur atom or N(R'), or alternatively X and/or Z represent a bond, R and R', which may be identical or different, represent a hydrogen atom or a ($C_1$-$C_6$)alkyl group, preferably, X represents an oxygen atom, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom; v) a quaternary ammonium group $N^+R'R''R'''$, $M^-$ for which R', R" and R''', which may be identical or different, represent a $C_1$-$C_4$ alkyl group, or alternatively —$N^+R'R''R'''$ forms a 5- or 6-membered heteroaryl such as imidazolium optionally substituted with a $C_1$-$C_4$ alkyl group and $M^-$ represents the anionic counterion, vi) carboxyl C(O)OH, vii) carboxylate C(O)O$^-$, $M^+$ with $M^+$ representing a cationic counterion such as alkali metal or alkaline-earth metal, viii) sulfonic —SO$_3$H, ix) sulfonate —SO$_3^-$, $M^+$ with $M^+$ as defined previously, x) cyano and xi) a carbamoyl radical ((R)$_2$N—C(O)—) in which R, which may be identical or different, represent a hydrogen atom or a $C_1$ to $C_4$ alkyl radical optionally bearing at least one hydroxyl group;

an "alkoxy radical" is generally an alkyl-oxy radical for which the alkyl radical is a linear or branched $C_1$ to $C_8$ and preferentially $C_1$ to $C_6$ hydrocarbon-based radical;

when the alkoxy group is optionally substituted, this implies that the alkyl group is optionally substituted as defined above;

the term "organic or mineral acid salt" more particularly means salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methylsulfonic acid and ethylsulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion or anion" means an organic or mineral cosmetically acceptable anion or anionic group derived from an organic or mineral acid salt associated with the cationic charge of the dye; more particularly, the anion is chosen from: i) halides such as chloride or bromide; ii) nitrates; iii) sulfonates, including $C_1$-$C_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) carboxylates Alk-C(O)—OH with Alk representing a ($C_1$-$C_6$)alkyl group optionally substituted with one or more hydroxyl or carboxylate groups such as citrate; vi) succinate; vii) tartrate; viii) lactate; ix) alkyl sulfates: Alk-O—S(O)O$^-$ such as methyl sulfate and ethyl sulfate; x) aryl sulfates: x) aryl sulfates: Ar—O—S(O)O$^-$ such as benzene sulfate and toluene sulfate; xi) alkyl sulfates: Alk-O—S(O)$_2$O$^-$ such as methyl sulfate and ethyl sulfate; xii) aryl sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; xvi) borates such as tetrafluoroborate; xvii) sulfate S(O)$_2$O$_2^-$ or SO$_4^{2-}$; xviii) hydrogen sulfate HSO$_4^-$; xix) carbonate; xx) hydrogen carbonate; xxi) perchlorate (ClO$_4^-$) and (xxii) dianionic mineral salts such as a zinc tetrachloride;

the anionic counterion, derived from the organic or mineral acid salt, ensures the electrical neutrality of the molecule: thus, it is understood that when the anion comprises several anionic charges, then the same anion may serve for the electrical neutrality of several cationic groups in the same molecule or else may serve for the electrical neutrality of several molecules; for example, a dye which contains two cationic groups may contain either two "singly charged" anionic counterions or a "doubly charged" anionic counterion such as (O=)$_2$S(O$^-$)$_2$ or O=P(O$^-$)$_2$—OH;

in particular, the anionic counterions are chosen from halides such as chloride, bromide, fluoride or iodide; a hydroxide; a sulfate; a hydrogen sulfate; a linear or branched $C_1$-$C_6$ alkyl sulfate, such as the methylsulfate or ethylsulfate ion; carbonates and hydrogen carbonates; carboxylic acid salts such as formate, acetate, citrate, tartrate and oxalate; linear or branched $C_1$-$C_6$ alkylsulfonates, such as the methylsulfonate ion; arylsulfonates for which the aryl part, preferably phenyl, is optionally substituted with one or more $C_1$-$C_4$ alkyl radicals, for instance 4-tolylsulfonate; and alkylsulfonyls such as mesylate;

The term "chemical oxidizing agent" means any oxidizing agent other than atmospheric oxygen conventionally used in the field. Thus, mention may be made of hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. Preferably, the chemical oxidizing agent is hydrogen peroxide.

Moreover, the addition salts that may be used in the context of the invention are notably chosen from addition salts with a cosmetically acceptable base such as the basifying agents as defined below, for instance alkali metal hydroxides such as sodium hydroxide or potassium hydroxide, aqueous ammonia, amines or alkanolamines.

the expression "at least one" is equivalent to "one or more";

the limits of a range of values are included in that range, in particular in the expressions "between" and "ranging from . . . to . . . "; and the expression "inclusively" means that the limits of that range are included in the defined range.

a) The Blue, Violet and Green Dyes

According to a particular embodiment, the blue, violet and green dyes a) chosen from dyes a1) to a10) of the invention are chosen from direct dyes, which are preferably cationic, anionic, zwitterionic or nonionic. According to a preferred embodiment of the invention, the dye(s) a) are cationic. According to another preferred embodiment of the invention, the dyes a) are anionic. According to yet another particular embodiment of the invention, the dyes a) are nonionic. More preferentially, the dyes a) of the invention are blue.

According to a more particular embodiment, the blue, violet and green dyes a) are chosen from the following direct dyes:
  a1) phenoxazinium, phenothiazinium or phenazinium dyes;
  a3) triarylmethane dyes;
  a4) naphthoquinone or anthraquinone dyes;
  a5) hydrazone dyes;
  a6) tetraazapentamethine dyes; and
  a7) nitro dyes;
  more preferentially chosen from a1), in particular phenoxazinium, phenothiazinium, a4) in particular anthraquinones, and a6).

One subject of the present invention is notably a process for dyeing keratin fibers, in particular human keratin fibers such as the hair, comprising the application to said keratin fibers of one or more direct dyes chosen from:
  a1) phenoxazinium, phenothiazinium or phenazinium dyes, preferably chosen from the compounds of formula (Ia) below, the organic or mineral acid or base salts thereof, and also the optical isomers thereof, the geometrical isomers thereof, the tautomers thereof, the organic or mineral acid or base salts thereof, the solvates thereof such as hydrates, and mixtures thereof:

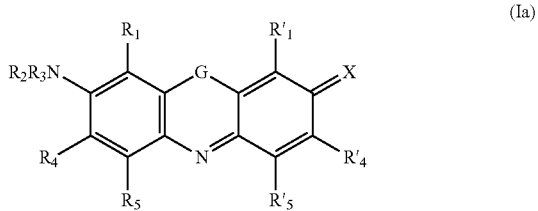

(Ia)

in which formula (Ia):
  X represents an oxygen atom, a sulfur atom, $NR'_2$ or an ammonium radical $N^+R'_2R'_3$;
  G represents an oxygen atom, a sulfur atom or a radical $NR_6$; G preferably represents O or S;
  $R_2$, $R_3$, $R'_2$ and $R'_3$, which may be identical or different, represent, independently of each other:
    a hydrogen atom,
    a phenyl radical which is optionally substituted, notably with one or more halogen atoms, or
    a linear or branched $C_1$ to $C_{20}$, preferably $C_1$ to $C_{10}$ and more preferentially $C_1$ to $C_6$ alkyl radical, said alkyl radical being:
    optionally substituted notably with one or more groups chosen from hydroxyl, $(di)(C_1-C_4)(alkyl)amino$, amino —$NH_2$, $(di)(C_1-C_4)(alkyl)aminocarbonyl$, aminocarbonyl —$C(O)NH_2$, and 5- or 6-membered heterocycloalkyl, which is preferably saturated, such as morpholino, piperazino or piperidino, and/or optionally interrupted with one or more heteroatoms and/or with one or more groups comprising at least one heteroatom, preferably chosen from oxygen, sulfur, —$N(R'_6)$—, —$C(O)$—, —$S(O)$—, —$S(O_2)$— or combinations thereof, preferably —O—, —$N(R'_6)$—, —$N(R'_6)$—$C(O)$—, —$C(O)$—$N(R'_6)$—, with $R'_6$ representing a hydrogen atom or a $(C_1-C_4)$alkyl group;
  $R_5$ and $R'_5$, which may be identical or different, represent:
    a hydrogen atom,
    a linear or branched $C_1$ to $C_6$ alkyl radical,
    an optionally substituted phenyl radical,
    a hydroxycarbonyl or carboxyl radical —$C(O)$—OH,
    a carbon/late radical —$C(O)$—$O^-$,
    a $(di)(C_1-C_6)(alkyl)aminocarbonyl$ radical,
    an aminocarbonyl radical —$C(O)NH_2$,
    a $(di)(C_1-C_6)(alkyl)amino$ radical, or
    an amino radical;
  $R_1$, $R_4$, $R'_1$ and $R'_4$, which may be identical or different, represent, independently of each other:
    a hydrogen atom,
    a $C_1$ to $C_4$ and preferably $C_1$ to $C_2$ alkyl radical,
    a $C_1$ to $C_4$ and preferably $C_1$ to $C_2$ alkoxy radical,
    a hydroxyl radical,
    an amino radical $R_7R_8N$— with $R_7$ and $R_8$, which may be identical or different, representing a hydrogen atom, a $(C_1-C_4)$alkyl group, or a phenyl radical which is optionally substituted, notably with one or more halogen atoms or nitro(so) groups, or
    a nitro(so) radical;
  or alternatively $R_4$ forms, with one of the substituents $R_2$ or $R_3$, a saturated or unsaturated, preferably saturated 5- or 6-membered, optionally substituted heterocycle, preferably morpholinyl, piperazinyl or piperidinyl;
  $R_6$ represents a phenyl radical which is optionally substituted, notably with a $(di)(C_1-C_4)(alkyl)amino$ radical and/or a linear or branched $C_1$ to $C_6$ alkyl radical;
  when the compound of formula (Ia) is cationic, it optionally comprises one or more anions $Y^-$ and optionally one or more cations $M^+$ to ensure the electrical neutrality of the molecule, with
    $Y^-$ represents an anionic counterion or a mixture of organic or mineral anions;
    $M^+$ represents an organic or mineral cationic counterion, preferably an alkali metal or alkaline-earth metal such as sodium, potassium or calcium, or ammonium; and/or
  a2) azo(benz)imidazolium or azo(benzo)pyridinium dyes, preferably chosen from the compounds of formula (IIa) or (II'a) below, the optical isomers thereof, the geometrical isomers thereof, the tautomers thereof, the organic or mineral acid or base salts thereof, the solvates thereof such as hydrates, and mixtures thereof:

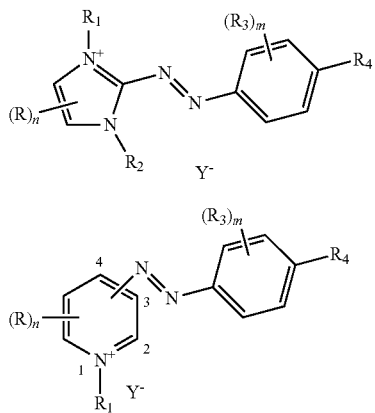

(IIa)

(II'a)

in which formulae (IIa) and (II'a):
R, which may be identical or different, represent an optionally substituted linear or branched $C_1$ to $C_6$ alkyl radical,
n denotes an integer equal to 0, 1 or 2, when n is equal to 2, the two radicals R may form, with the carbon atoms to which they are attached, an optionally substituted, saturated or unsaturated 6-membered ring, preferably benzo,
m denotes an integer ranging from 0 to 4,
when m is equal to 2, 3 or 4, two adjacent radicals $R_3$ may form, with the carbon atoms to which they are attached, a 6-membered aromatic ring, preferably benzo, optionally substituted with one or more hydroxyl or amino groups,
$R_1$ and $R_2$, which may be identical or different, represent an optionally substituted, saturated or unsaturated, linear or branched $C_1$ to $C_6$ alkyl radical;
$R_3$, which may be identical or different, represent:
 a $C_1$ or $C_2$ alkyl radical, preferably a methyl radical,
 a hydroxyl radical,
 a nitro radical (—$NO_2$),
 an amino radical (—$NH_2$),
 a halogen atom, preferably a chlorine atom,
 a linear or branched $C_1$ to $C_6$, preferably $C_1$ to $C_4$ and more preferentially $C_1$ to $C_2$ alkoxy radical, such as a methoxy radical,
 or alternatively, when $R_3$ is borne by the carbon atom located ortho to $R_4$, $R_3$ may form with $R_4$ a saturated or unsaturated, 5- or 6-membered, optionally substituted and preferably unsubstituted heterocycle, which may contain one or two non-adjacent heteroatoms such as oxygen and/or nitrogen,
$R_4$ represents:
 a hydrogen atom,
 a linear or branched $C_1$ to $C_6$, preferably $C_1$ to $C_4$ and more preferentially $C_1$ to $C_2$ alkoxy radical, such as a methoxy radical,
 or a radical of formula (IIIa)

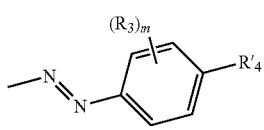

(IIIa)

in which:
 m has the same meaning as previously,
 $R'_3$, which may be identical or different, represent:
  a chlorine atom,
  a $C_1$ to $C_3$ alkyl radical,
  an amino radical, or
  a radical $OR_7$, with $R_7$ representing a hydrogen atom or a $C_1$ or $C_2$ alkyl radical,
  when m is equal to 2, 3 or 4, two adjacent radicals $R'_3$ may form, with the carbon atoms to which they are attached, a 6-membered aromatic ring, preferably benzo, optionally substituted with one or more groups chosen from hydroxyl and amino groups,
 $R'_4$ represents:
  a hydrogen atom,
  a hydroxyl radical,
  a linear or branched $C_1$ to $C_4$ and preferably $C_1$ to $C_2$ alkoxy radical, such as a methoxy or ethoxy radical,
  a radical —$NR'_5R'_6$ in which $R'_5$ and $R'_6$, which may be identical or different, represent, independently of each other, a linear or branched $C_1$ to $C_6$, preferably $C_1$ to $C_4$ and more preferentially $C_1$ to $C_2$ alkyl radical, optionally substituted with one or more hydroxyl groups, or
  when two radicals $R'_3$ are borne on carbons located ortho to $R'_4$, each of the two $R'_3$ may form, respectively, with $R'_5$ or $R'_6$ a 6-membered ring; preferably, the phenyl group substituted with $R'_3$ and $R'_4$ represents a julolidine group, or
 a radical —$NR_5R_6$ in which $R_5$ and $R_6$, which may be identical or different, represent, independently of each other:
  a hydrogen atom,
  a linear or branched $C_1$ to $C_6$ alkyl radical, optionally substituted with one or more hydroxyl groups or a (di)($C_1$-$C_6$)alkylamino group,
  a phenyl optionally substituted with one or more radicals chosen from the following radicals: i) amino, ii) (di)(hydroxy)($C_1$-$C_6$)alkylamino, iii) $C_1$ to $C_6$ alkoxy, iv) ($C_1$-$C_6$)acylamino optionally substituted with a carboxyl radical, v) carboxyl and vi) aromatic or non-aromatic, saturated or unsaturated, 5- or 6-membered heterocycles, optionally substituted with one or more radicals, which may be identical or different, chosen from $C_1$ to $C_6$ alkyl radicals, optionally substituted phenyls, and $C_1$ to $C_6$ alkyl carboxylate radicals,
 $R_5$ and $R_6$ may form, with the nitrogen atom that bears them, a saturated or unsaturated, 4- to 8-membered heterocycle,
 or alternatively, when two radicals $R_3$ are borne on carbons located ortho to $R_4$, each of the two $R_3$ may form, respectively, with $R_5$ or $R_6$ a 6-membered ring; preferably, the phenyl group substituted with $R_3$ and $R_4$ represents a julolidine group, and
 $Y^-$ represents an anionic counterion or a mixture of organic or inorganic anions which ensure the electrical neutrality of the compounds of formula (IIa) or (II'a);
in particular, the compounds of formula (Ira) are such that the azo group is in position 2 or 4, preferably 2, of the pyridinium ring;

a3) the triarylmethane dyes, preferably chosen from the compounds of formula (IVa) below, the optical isomers thereof, the geometrical isomers thereof, the tautomers thereof, the organic or mineral, acid or base salts thereof, the solvates thereof such as hydrates, and mixtures thereof:

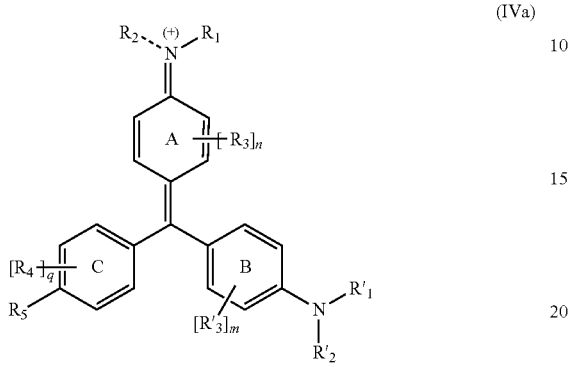

(IVa)

in which formula (IVa),
$R_1$, $R_2$, $R'_1$ and $R'_2$, which may be identical or different, represent:
a hydrogen atom,
a linear or branched $C_1$ to $C_{20}$ alkyl radical;
that is optionally substituted and/or
optionally interrupted with one or more heteroatoms, preferably oxygen or sulfur, and/or with one or more groups comprising at least one heteroatom, preferably chosen from oxygen, sulfur, C(O), S(O), S(O)$_2$ and SO$_3^-$, or combinations thereof, or
a benzyl radical optionally substituted with one or more SO$_3^-$ or SO$_3$H groups;
$R_3$ and $R'_3$, which may be identical or different, represent, independently of each other:
a linear or branched $C_1$ to $C_6$ alkyl radical,
a sulfonate group SO$_3^-$, or
a sulfonic group SO$_3$H;
n and m, which may be identical or different, represent two integers ranging from 0 to 4;
the radicals $R_4$, which may be identical or different, represent, independently of each other:
a linear or branched $C_1$ to $C_6$ alkyl radical,
a hydroxyl radical,
an SO$_3^-$ group,
an SO$_3$H group,
a halogen atom, preferably a chlorine atom,
or alternatively two adjacent radicals $R_4$ together form an unsaturated 6-membered ring, preferably an aromatic ring such as benzo, optionally substituted with one or more SO$_3^-$ or SO$_3$H groups;
q is an integer ranging from 0 to 4;
$R_5$ represents:
a hydrogen atom,
a halogen atom, preferably a chlorine atom,
an amino radical,
a hydroxyl radical,
a group which is electron-withdrawing via the mesomeric effect, such as SO$_3^-$ or SO$_3$H, or
a radical —NR$_6$R$_7$, in which $R_6$ and $R_7$, which may be identical or different, represent, independently of each other:
a hydrogen atom,
a linear or branched $C_1$ to $C_6$ alkyl radical;
it being understood that:
the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and
the compound of formula (IVa) optionally comprises one or more anions An$^-$ and optionally one or more cations M$^+$ to ensure the electrical neutrality of the molecule;
with:
An$^-$ representing an anionic counterion, preferably chosen from halides such as bromide or chloride, alkyl sulfates such as methyl sulfate, aryl sulfates such as p-toluenesulfonate or a mixture of these anions; and
M$^+$ representing a cationic counterion, preferably chosen from cations of alkali metals or alkaline-earth metals such as sodium, potassium, magnesium, calcium, zinc, ammonium or a mixture of these ions;
a4) naphthoquinone or anthraquinone dyes, preferably chosen from the compounds of formulae (Va) to (VI'a) below, the geometrical isomers thereof, the tautomers thereof, the organic or mineral, acid or base salts thereof, the solvates thereof such as hydrates, and mixtures thereof:

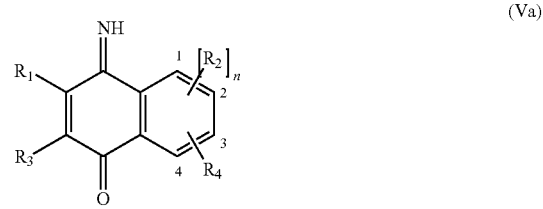

(Va)

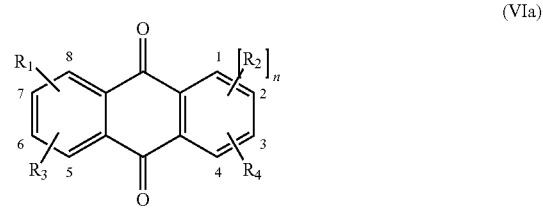

(VIa)

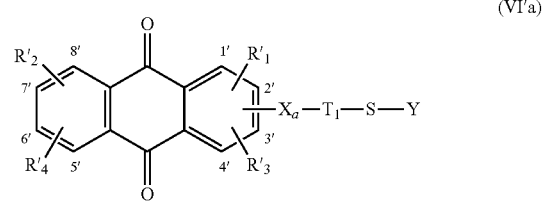

(VI'a)

in which formulae (Va) to (VI'a):
$X_a$ represents an oxygen atom or a group N—R with R representing a hydrogen atom or a group from among ($C_1$-$C_6$)alkyl, optionally substituted (hetero)aryl such as phenyl or (hetero)aryl($C_1$-$C_6$)alkyl such as benzyl; preferably, R represents a hydrogen atom;
Y is as defined represents: i) a hydrogen atom; ii) an alkali metal; iii) an alkaline-earth metal; iv) an ammonium group: N$^+$R$^a$R$^b$R$^g$R$^d$ or a phosphonium group: P$^+$R$^a$R$^b$R$^g$R$^d$ with R$^a$, R$^b$, R$^g$ and R$^d$, which may be identical or different, representing a hydrogen atom or a ($C_1$-$C_4$) alkyl group; or v) a thiol-function protecting group; or vi) the group (b) below:

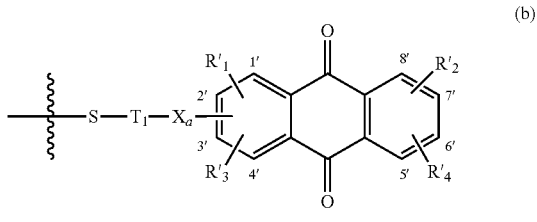
(b)

$R_1$, $R_2$, $R_3$, $R_4$, $R_1'$, $R_2'$, $R_3'$ and $R_4'$, which may be identical or different, represent an atom or group chosen from:
hydrogen;
halogen such as bromine and chlorine,
hydroxyl,
$C_1$-$C_4$ alkoxy,
hydroxysulfonyl (—$SO_3H$) or sulfonate (—$SO_3^-$, $M^+$), with $M^+$ representing a cationic counterion, in particular an alkali metal, alkaline-earth metal or ammonium, such as $Na^+$ or $K^+$;
optionally substituted $C_1$-$C_6$ alkyl,
—$NR_5R_6$ in which $R_5$ and $R_6$, which may be identical or different, represent an atom or radical chosen from: i) hydrogen, ii) ($C_1$-$C_4$)alkylcarbonyl such as methylcarbonyl (—$COCH_3$), iii) arylsulfonyl such as phenylsulfonyl (—$SO_2Ph$), iv) Het-ALK-C(O)— with Het representing a heterocycloalkyl group which is optionally substituted, notably with one or more ($C_1$-$C_4$)alkyl groups and ALK represents a ($C_1$-$C_6$)alkylene group optionally substituted with one or more hydroxyl or (di)(hydroxy)($C_1$-$C_4$)(alkyl) amino groups; Het-ALK-C(O)— is such as (piperidin-1-yl)acetyl, 2-methyl-2-(piperidin-1-yl)propanoyl, 2-(morpholin-4-yl)ethyl-b-alaninoyl, v) optionally substituted aryl, in particular phenyl optionally substituted with at least one radical chosen from a) $C_1$-$C_6$ alkyl, b) hydroxyl, c) hydroxysulfonyl, d) $C_1$-$C_4$ alkoxy, e) carboxyl (—COOH), f) ($C_1$-$C_4$)alkoxycarbonyl, g) amino, h) (di)($C_1$-$C_4$) alkylamino, one of the alkyl radicals possibly being substituted with a hydroxyl or hydroxysulfonyl radical —$SO_3H$, or —$OSO_3H$, vi) optionally substituted aryl($C_1$-$C_4$)alkyl, in particular benzyl optionally substituted with a (di)($C_1$-$C_4$)(alkyl)amino group, viii) optionally substituted $C_1$-$C_{20}$ alkyl, optionally interrupted with one or more heteroatoms and/or with one or more groups comprising at least one heteroatom, preferably chosen from oxygen, nitrogen, sulfur, CO, SO, $SO_2$ or combinations thereof; when said alkyl radical is substituted, it is substituted with one or more atoms or groups chosen from a) halogens, preferably one or more chlorine atoms, b) hydroxyl, c) ($C_1$-$C_6$)alkylcarbonylamino, in particular acylamino, d) 5- or 6-membered heterocycloalkyl such as tetrahydro-2H-pyran-4-amine, morpholino, piperidino or piperazino, e) (di)($C_1$-$C_4$)(alkyl)amino, f) hydroxysulfonyl($C_1$-$C_4$)alkylamino, or hydroxysulfonyloxy($C_1$-$C_4$)alkylamino, g) (di)(hydroxy) ($C_1$-$C_4$)(alkyl)amino, h) 5- or 6-membered heteroaryl such as imidazole, and i) formylamino (—NHCOH);
group (a):

—N($R_7$)—$X_1$—$W_1$ (a)

in which group (a):
$R_7$ represents a hydrogen or a $C_1$-$C_4$ alkyl radical,
$X_1$ represents a divalent radical chosen from $C_1$-$C_{20}$ alkylene optionally interrupted with one or more heteroatoms or groups chosen from oxygen, nitrogen, sulfur, CO, SO, $SO_2$, arylene such as phenylene, or combinations thereof; particularly, $X_1$ represents:
($C_1$-$C_{10}$)alkylene,
—($C_1$-$C_{10}$)alkylcarbonyl-,
-carbonyl($C_1$-$C_{10}$)alkyl-,
—($C_1$-$C_{10}$)alkylaminocarbonyl($C_1$-$C_{10}$)alkyl-,
—($C_1$-$C_{10}$)alkylcarbonylamino($C_1$-$C_{10}$)alkyl-,
-phenyl($C_1$-$C_{10}$)alkyl-,
—($C_1$-$C_{10}$)alkylphenyl-, or
phenylene,
preferably, $X_1$ represents ($C_1$-$C_6$)alkylene, and phenylene,
$W_1$ represents a cationic radical chosen from:

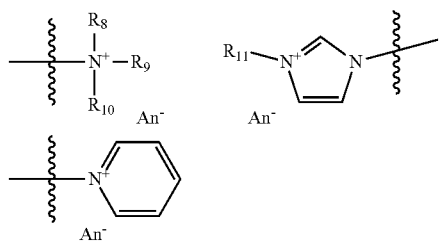

with $R_8$, $R_9$, $R_{10}$ and $R_{11}$, which may be identical or different, representing a $C_1$-$C_6$ alkyl group, a benzyl radical, a $C_1$-$C_6$ alkyl sulfonate radical; the radicals $R_8$ and $R_9$ may optionally form, with the nitrogen atom to which they are attached, a saturated or unsaturated, optionally substituted 5- to 7-membered heterocycle, optionally comprising another non-nitrogen heteroatom, preferably an oxygen atom, An$^-$ represents an anionic counterion. preferably, $W_1$ represents a tri($C_1$-$C_4$)alkylammonium group;
$T_1$ represents a linear or branched divalent hydrocarbon-based chain comprising from 1 to 20 carbon atoms, optionally interrupted with one or more heteroatoms or groups, or combinations thereof, chosen from oxygen, sulfur, N($R_b$), C(O), —$N^+R_8)(R_9)$— An, optionally cationic and optionally substituted heteroaryl, such as imidazolium, An with $R_8$ and $R_9$, which may be identical or different, representing a $C_1$-$C_6$ alkyl radical; $R_b$ representing a hydrogen atom or a (hydroxy)($C_1$-$C_4$) alkyl group; preferably, said hydrocarbon-based chain is interrupted with one or more groups chosen from N($R_b$), C(O), and a combination thereof such as —C(O)—N($R_b$)— or —N($R_b$)—C(O)—, and —$N^+$($R_8$)($R_9$)-An, An is an organic or inorganic anionic counterion, which ensures the electrical neutrality of the dyes of formulae (I) and (VIa) or (VI'a);
n is an integer ranging from 1 to 3; preferably, n is equal to 1 or 2,

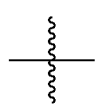

being the part of the bond that is connected to the rest of the molecule;

it being understood that:
the naphthoquinone and anthraquinone dye(s) of formula (Va), (VIa) or (VI'a) include at least one radical $R_1$, $R_3$, $R_4$, $R_1'$, $R_3'$ or $R_4'$, other than a hydrogen atom; and
when the compounds of formula (Va), (VIa) or (VI'a) are cationic, then they comprise an anionic counterion An or $An^-$ to ensure the electrical neutrality, or else, if they comprise a sulfonate group, then $M^+$ and An or $An^-$ may be absent to ensure the electrical neutrality of said molecule.

a5) hydrazone dyes, preferably chosen from the compounds of formula (VIIa) below, the geometrical isomers thereof, the tautomers thereof, the organic or mineral, acid or base salts thereof, the solvates thereof such as hydrates, and mixtures thereof:

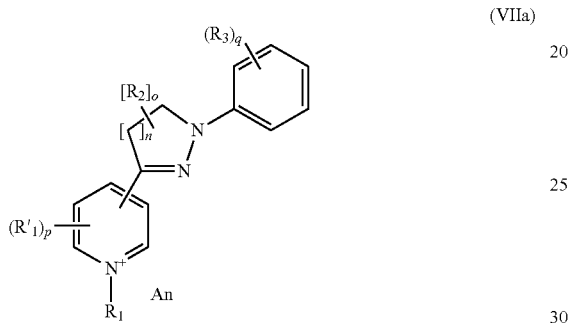

(VIIa)

in which formula (VIIa):
$R_1$, which may be identical or different, represents:
an optionally substituted $C_1$-$C_{20}$ alkyl radical, optionally interrupted with one or more heteroatoms and/or with one or more groups comprising at least one heteroatom, preferably chosen from oxygen, sulfur, CO, SO and $SO_2$ or combinations thereof or with a cationic group of the type such as ammonium, imidazolium, pyridinium or phosphonium;
a $C_1$-$C_4$ trialkylsilyl radical;
an optionally substituted phenyl radical;
an optionally substituted benzyl radical;
$R_1'$, which may be identical or different, represents:
a halogen atom;
an optionally substituted $C_1$-$C_{16}$ alkyl radical;
a hydroxyl radical;
a $C_1$-$C_4$ alkoxy radical;
an amino radical optionally substituted with one or two identical or different $C_1$-$C_4$ alkyl radicals, optionally bearing at least one hydroxyl group;
an alkylcarbonylamino radical (RCO—NR'—) in which the radical R represents a $C_1$-$C_4$ alkyl radical and R' represents a hydrogen or a $C_1$-$C_4$ alkyl radical;
an alkylsulfonylamino group ($RSO_2$—NR'—) in which the radical R represents a $C_1$-$C_4$ alkyl radical and the radical R' represents a hydrogen atom or a $C_1$-$C_4$ alkyl radical;
two adjacent radicals $R_1'$ may form, together and with the carbon atoms to which they are attached, a substituted or unsubstituted 5- or 6-membered aromatic or non-aromatic (hetero)cyclic radical;
p is an integer between 0 and 4;
$R_2$, which may be identical or different, represents:
a hydrogen atom,
an optionally substituted (hetero)aryl radical;
an optionally substituted $C_1$-$C_{16}$ alkyl radical;
two adjacent radicals $R_2$ may form an optionally substituted, saturated or unsaturated, 5- to 7-membered (hetero)cycle, optionally fused to another aromatic nucleus, optionally comprising another nitrogen or non-nitrogen heteroatom;
o is an integer equal to 0, 1, 2, 3 or 4;
n is an integer equal to 1 or 2;
$R_3$ represents:
a hydrogen;
an optionally substituted $C_1$-$C_{20}$ alkyl radical;
a halogen atom preferably chosen from bromine, chlorine and fluorine;
a hydroxyl group;
a $C_1$-$C_4$ alkoxy group;
an alkoxycarbonyl group (RO—CO—) in which R represents a $C_1$-$C_4$ alkyl radical;
an alkylcarbonyloxy radical (RCO—O—) in which R represents a $C_1$-$C_4$ alkyl radical;
an optionally substituted aryloxy group;
a group $NR'_3R''_3$ in which $R'_3$ and $R''_3$ represent, independently of each other: i) a hydrogen atom, ii) a $C_1$-$C_4$ alkyl radical, optionally bearing at least one hydroxyl or $C_1$-$C_2$ alkoxy group, said alkyl radicals possibly forming, with the nitrogen atom to which they are attached, an optionally aromatic, optionally substituted, saturated or unsaturated, 5- or 7-membered heterocycle, optionally comprising another nitrogen or non-nitrogen heteroatom;
a phenylamino radical;
an aminophenylamino radical;
a 4-N,N-diethylaminophenylamino radical;
a methoxyphenylamino radical;
an alkylcarbonylamino group (RCO—NR'—) in which the radical R represents a $C_1$-$C_4$ alkyl radical and the radical R' represents a hydrogen atom or a $C_1$-$C_4$ alkyl radical;
a ureido group ($N(R)_2$—CO—NR'—) in which the radicals R and R', independently of each other, represent a hydrogen atom or a $C_1$-$C_4$ alkyl radical;
an alkylthio radical (R—S—) in which the group R represents a $C_1$-$C_4$ alkyl radical;
two adjacent radicals $R_3$ may form, together and with the carbon atoms to which they are attached, a substituted or unsubstituted 5- or 6-membered aromatic or non-aromatic (hetero)cyclic radical;
q is an integer between 0 and 5; and
one of the radicals $R'_3$ or $R''_3$ may also form, with the nitrogen atom to which it is attached and with a carbon atom of the aromatic nucleus located ortho to the $NR'_3R''_3$ group, a substituted or unsubstituted, 5- or 6-membered saturated or unsaturated heterocycle;
An represents an anionic counterion or a mixture of organic or inorganic anions which ensure the electrical neutrality of the compounds of formula (VIIa);
a6) tetraazapentamethine dyes, preferably chosen from the compounds of formula (VIIIa) and/or (IXa) below, the geometrical isomers thereof, the tautomers thereof, the organic or mineral, acid or base salts thereof, the solvates thereof such as hydrates, and mixtures thereof:

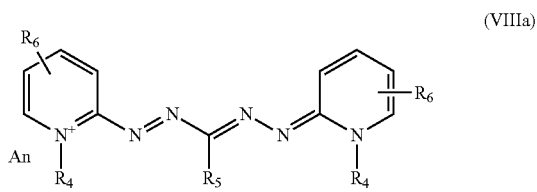

(VIIIa)

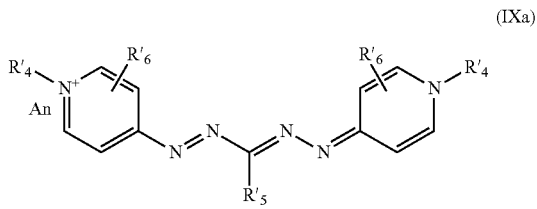

(IXa)

in which formulae (VIIIa) and (IXa):

$R_4$ and $R'_4$, which may be identical or different, represent:
- a linear or branched $C_1$-$C_4$ alkyl radical optionally substituted with one to three radicals chosen from hydroxyl, $C_1$-$C_2$ alkoxy, $C_2$-$C_4$ (poly)hydroxyalkoxy, amino, $C_1$-$C_2$ (di)alkylamino and carboxyl radicals;

$R_5$, $R'_5$, $R_6$ and $R'_6$, which may be identical or different, represent:
- a hydrogen atom,
- a linear or branched $C_1$-$C_{16}$ hydrocarbon-based chain, this chain possibly being saturated or unsaturated with one to three unsaturations, this chain being unsubstituted or substituted with one to three radicals chosen from hydroxyl, $C_1$—$C_2$ alkoxy, (poly)hydroxy($C_2$-$C_4$)alkoxy, amino, $C_1$-$C_2$ (di)alkylamino, carboxyl, sulfonylamino and (poly)hydroxy($C_2$-$C_4$)alkylamino radicals or a halogen atom such as chlorine, fluorine or bromine;
- a phenyl radical optionally substituted with one to three radicals chosen from hydroxyl, $C_1$-$C_2$ alkoxy, (poly)hydroxy($C_2$-$C_4$)alkoxy, amino, $C_1$-$C_2$ (di)alkylamino, carboxyl, sulfonylamino and (poly)hydroxy($C_2$-$C_4$)alkylamino radicals or a halogen atom such as chlorine, fluorine or bromine;
- a heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals; in addition, this hydrocarbon-based chain may be interrupted with one or two oxygen, nitrogen or sulfur atoms or with an SO2 radical, it being understood that $R_5$, $R'_5$, $R_6$ and $R'_6$ do not include any peroxide bonds, or any diazo or nitroso radicals, An represents an anionic counterion or a mixture of organic or inorganic anions which ensure the electrical neutrality of the compounds of formula (VIIIa) or (IXa);

a7) nitro dyes, preferably chosen from the compounds of formula (Xa) below, the geometrical isomers thereof, the tautomers thereof, the organic or mineral, acid or base salts thereof, the solvates thereof such as hydrates, and mixtures thereof:

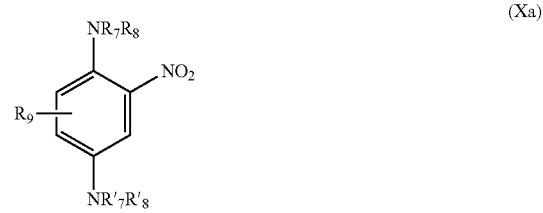

(Xa)

in which formula (Xa):

$R_7$, $R'_7$, $R_8$ and $R'_8$, which may be identical or different, represent:
- a hydrogen atom,
- a linear or branched $C_1$-$C_{18}$ hydrocarbon-based chain, this chain possibly being saturated or unsaturated with one to four unsaturations, this chain being unsubstituted or substituted with one to three radicals chosen from hydroxyl, $C_1$-$C_2$ alkoxy, (poly)hydroxy($C_2$-$C_4$)alkoxy, amino, $C_1$-$C_2$ (di)alkylamino optionally substituted with a hydroxyl, carboxyl, sulfonylamino and (poly)hydroxy($C_2$-$C_4$) alkylamino radicals or a halogen atom such as chlorine, fluorine or bromine, hydroxycarbonyl, hydroxysulfonyl, aminocarbonylmethyl, piperidine, carbonylamino, aminocarbonylamino, chloromethylcarbonylamino, ($C_1$-$C_2$)alkoxycarbonyl, imidazole;
- a phenyl radical optionally substituted with one to three radicals chosen from hydroxyl, $C_1$-$C_2$ alkoxy, (poly)hydroxy($C_2$-$C_4$)alkoxy, amino, $C_1$-$C_2$ (di)alkylamino, carboxyl, sulfonylamino and (poly)hydroxy ($C_2$-$C_4$)alkylamino radicals or a halogen atom such as chlorine, fluorine or bromine;

$R_9$ represents:
- a hydrogen;
- an optionally substituted $C_1$-$C_{20}$ alkyl radical;
- a halogen atom preferably chosen from bromine, chlorine and fluorine;
- a $C_1$-$C_4$ alkoxy group;
- an alkylcarbonyloxy radical (RCO—O—) in which R represents a $C_1$-$C_4$ alkyl radical;
- a phenyl radical;

a8) azomethine dyes and the leuco forms thereof, preferably chosen from the compounds of formula (XIa) and/or (XIIa) below, the geometrical isomers thereof, the tautomers thereof, the organic or mineral, acid or base salts thereof, the solvates thereof such as hydrates, and mixtures thereof:

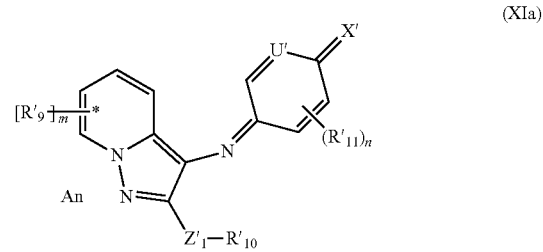

(XIa)

-continued

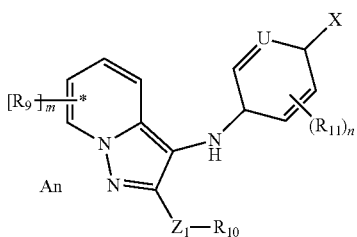

(XIIa)

in which formulae (XIa) and (XIIa):
$Z_1$ and $Z'_1$, which may be identical or different, represent:
  a covalent single bond,
  an oxygen atom,
  a radical —$NR_{12}(R_{13})$p-, with p being equal to 0 or 1, and
  when p is equal to 0 then $R_{12}$ represents a hydrogen atom or a $C_1$-$C_6$ alkyl radical, or $R_{12}$, with $R_{10}$, form, together with the nitrogen atom to which they are attached, a substituted or unsubstituted, saturated or unsaturated, aromatic or nonaromatic, 5- to 8-membered heterocycle, optionally containing one or more heteroatoms or groups chosen from N, O, S, $SO_2$ and —CO—, it being possible for the heterocycle to be cationic and/or substituted with a cationic or noncationic radical, and
  when p is equal to 1 then —$NR_{12}R_{13}$— is a cationic radical in which $R_{12}$ and $R_{13}$ independently represent an alkyl radical,
$Z_1$ and/or $Z'_1$ may also represent a divalent radical —S—, —SO— or —$SO_2$— when $R_1$ is a methyl radical;
$R_{10}$ and $R'_{10}$ represent, independently of each other:
  a hydrogen,
  an optionally substituted $C_1$-$C_{10}$ alkyl radical optionally interrupted with a heteroatom or a group chosen from O, N, Si, S, SO and $S(O)_2$,
  a $C_1$-$C_{10}$ alkyl radical substituted and/or interrupted with a cationic radical,
  a halogen,
  an $SO_3H$ radical,
  a substituted or unsubstituted, saturated, unsaturated or aromatic, 5- to 8-membered ring, optionally containing one or more heteroatoms or groups chosen from N, O, S, $S(O)_2$ and —C(O)—, the ring possibly being cationic and/or substituted with a cationic radical,
  when $Z_1$ and/or $Z'_1$ represent a covalent bond, then $R_1$ may also represent a radical: i) optionally substituted $C_1$-$C_6$ alkylcarbonyl—O—C(O)—R, —C(O)—O—R, —N(R)—C(O)—R' or —C(O)—NRR' in which R and R' independently represent a hydrogen atom or ii) an optionally substituted $C_1$-$C_6$ alkyl radical;
$R_9$ and $R'_9$, which may be identical or different, represent:
  a hydrogen atom,
  a hydroxyl radical,
  a $C_1$-$C_6$ alkoxy radical,
  a $C_1$-$C_6$ alkylthio radical,
  an amino radical,
  a monoalkylamino radical,
  a $C_1$-$C_6$ dialkylamino radical in which the alkyl radicals may form, with the nitrogen atom to which they are attached, a saturated or unsaturated, aromatic or nonaromatic, 5- to 8-membered heterocycle, which may contain one or more heteroatoms or groups chosen from N, O, S, $SO_2$ and C(O), the heterocycle possibly being cationic and/or substituted with a cationic radical,
  an optionally substituted $C_1$-$C_6$ alkylcarbonyl radical,
  a radical —O—C(O)—R, —C(O)—O—R, N(R)—C(O)—R' or —C(O)—NRR' with R and R' as defined previously,
  a halogen,
  an —$NHSO_3H$ radical,
  an optionally substituted $C_1$-$C_4$ alkyl radical,
  a saturated, unsaturated or aromatic, optionally substituted carbon-based ring;
or two radicals $R_9$, and/or two radicals $R'_9$ may form in pairs a saturated or unsaturated ring,
m and m' are integers ranging from 0 to 4,
n and n' are integers ranging from 0 to 4 when U and/or U' represent(s) a carbon atom and from 0 to 3 when U and/or U' represent(s) a nitrogen atom,
U and/or U' represent(s) a carbon atom substituted with a radical $R_{11}$ and/or $R'_{11}$,
X and/or X' represent(s):
  an oxygen atom,
  an NH radical,
the radicals $R_{11}$ and/or $R'_{11}$, which may be identical or different, represent, independently of each other:
  a hydrogen,
  an amino radical,
  a linear or branched $C_1$-$C_4$ alkyl radical,
  an alkoxy radical —OR in which R represents a $C_1$-$C_4$ alkyl radical optionally substituted with a hydroxyl,
  a halogen chosen from chlorine, fluorine and bromine,
  a radical —$NR_{13}$ in which $R_{13}$ represents a linear $C_1$-$C_4$ alkyl optionally substituted with a hydroxyl, with a di($C_1$-$C_3$)alkylamino or with a tri($C_1$-$C_3$)alkylammonium.

According to another particular embodiment, the blue, violet and green dyes a) of the invention are chosen from the self-oxidizing dyes a9).

The process for preparing the coloring agent(s) of the invention uses one or more self-oxidizing compounds, which may be identical or different, and are preferably identical.

The term "self-oxidizing compound" means a colorless or weakly colored compound, known to those skilled in the art, which can become colored in the presence of atmospheric oxygen (see, for example, Kirk-Othmer's Encyclopedia of Chemical Technology, Hair Preparation, 4th Ed., Vol. 12, 1994, page 904; Ullmann's Encyclopedia of Industrial Chemistry, Hair preparation 2002 DOI: 10.1002/14356007.a12_571).

In general, the intermediates are compounds which include at least one (hetero)aryl group substituted with at least two groups that are electron-donating via the mesomeric effect (+M) such as hydroxyl or amino or (di)(alkyl) amino, ($C_1$-$C_6$)alkoxy with the optionally substituted alkyl group(s) borne by N or O. In particular, these compounds often comprise three electron-donating groups. Preferentially, the self-oxidizing compounds are chosen from trihydroxybenzenes, dihydroxyanilines, diaminophenols, triaminobenzenes, dihydroxynaphthalenes, aminonaphthols, diaminonaphthalenes, dihydroxyindoles, diaminoindoles and aminohydroxyindoles.

More preferentially, the self-oxidizing compounds of the invention are of formulae (I'a) to (IV'a) below:

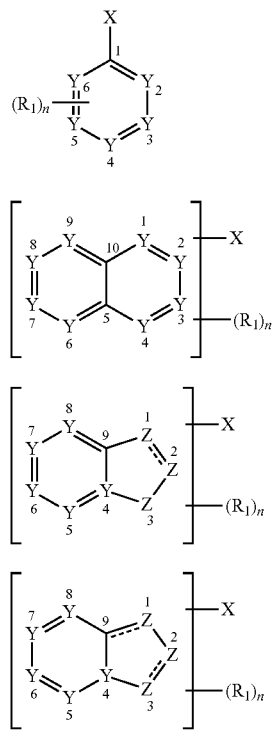

and also the organic or mineral acid or base salts thereof, the optical isomers, geometrical isomers and tautomers thereof, and/or the solvates thereof such as hydrates;

in which formulae (I'a) to (IV'a):

═ represents a single bond or a double bond;

X represents i) an amino radical, ii) a $C_1$-$C_6$ (di)alkylamino radical which may optionally be substituted with one or more hydroxyl, $C_1$-$C_6$ alkoxy, amino, $C_1$-$C_6$ alkylamino, carboxylic (—$CO_2$H) or sulfonic (—$SO_3$H) radicals; iii) a hydroxyl radical;

$R_1$ represents a radical covalently bonded to a carbon atom, chosen from:
i) hydroxyl,
ii) thiol —SH,
iii) (di)($C_1$-$C_{12}$ alkyl)amino the alkyl group(s) of which may optionally be substituted with one or more radicals from among: a) hydroxyl, b) $C_1$-$C_6$ alkoxy, c) amino, d) amide (—$CONH_2$), e) $C_1$-$C_6$ (di)alkylamino, f) carboxylic (—$CO_2$H), g) sulfonic (—$SO_3$H), h) piperidine, i) pyridine, j) pyrrolidine, k) morpholine, l) $C_1$-$C_6$ N-alkyl piperazino, m) benzene, n) halogen, o) nitrile, p) tetrahydrofuran, q) $C_1$-$C_6$ N-alkyl pyrrolidine, r) imidazole, s) $C_1$-$C_6$ trialkylammonium, t) $C_1$-$C_6$ N-alkylimidazolium, u) $C_1$-$C_6$ N,N dialkylpiperazinium, v) $C_1$-$C_6$ N,N dialkylpiperazinium, w) $C_1$-$C_6$ N-alkyl,N'-alkyl piperazinium, x) $C_1$-$C_6$ N-alkylpiperidinium, y) $C_1$-$C_6$ N-alkylmorpholinium, z) $C_1$-$C_6$ N-alkylpyrrolidinium, aa) $C_1$-$C_6$ N-alkylpyridinium, ab) $C_1$-$C_6$ (di)alkylacetamido, ac) $NHSO_2R_2$, ad) $C_1$-$C_6$ alkylcarbonyl, ae) urea (—$NHCONH_2$), af) acetamido $CH_3CONH$—, ag) -aminocarbonyl —$CONH_2$;
iv) $C_1$-$C_6$ alkyl which may be optionally substituted with one or more radicals a) to ag) as defined for iii) above;
v) $C_1$-$C_6$ alkyloxy which may be optionally substituted with one or more radicals a) to ag) as defined for iii) above, the alkyl chain of the alkoxy possibly being interrupted with one or more oxygen atoms;
vi) $C_1$-$C_6$ alkylthio which may be optionally substituted with one or more radicals a) to ag) as defined for iii) above;
vii) halogen;
viii) —NHPh;
ix) arylthio —S-Ph;
x) aryloxy such as phenoxy —OPh;
xi) —$NHCOR_2$;
xii) —$OCOR_2$;
xiii) —$SCOR_2$;
xiv) —$NHCONHR_2$;
xv) —$NHCSNHR_2$;
xvi) —$NHSO_2R_2$;
xvii) —$OSO_2R_2$;
xviii) —$SOR_2$;
xix) —$SO_2R_2$;
xx) —$SO_2NHR_2$;
xxi) piperidino which may be functionalized with one or more —$CONH_2$, $C_1$-$C_6$ alkyl which may be functionalized with a hydroxyl radical, $C_1$-$C_6$ N-alkylimidazolium;
a pyrrolidino radical which may be functionalized with one or more hydroxyl, $C_1$-$C_6$ alkyl, —$NHR_2$, amino, $C_1$-$C_6$ trialkylammonium, $C_1$-$C_6$ N-alkylimidazolium or (di)($C_1$-$C_6$)alkylamino radicals;
xxii) piperazino which may be functionalized with one or more $C_1$-$C_6$ alkyl radicals;
xxiii) $C_1$-$C_6$ N,N-dialkylpiperazinium;
xxiv) diazepane;
xxv) morpholino;
xxvi) azepane;
xxvii) —$CO_2R_2$;
xxviii) —$SO_3R_2$;
xxix) —$CONHR_2$;
xxx) nitrile (—CN);
xxxi) —$NHCO_2R_2$;
xxxii) —$COR_2$;
xxxiii) —$NHCNHNH_2$;
a phenyl radical;

$R_2$ represents i) a hydrogen atom, ii) a $C_1$-$C_{12}$ alkyl radical, iii) a phenyl radical, or iv) a 4-methylphenyl radical;

n represents an integer between 1 and 6;

Y represents a carbon atom or a nitrogen atom;

Z represents i) a carbon atom, ii) an oxygen atom, iii) a nitrogen atom, iv) a radical —$NR_3$ in which $R_3$ represents:
a hydrogen atom,
a $C_1$-$C_6$ alkyl radical which may optionally be substituted with one or more hydroxyl, $C_1$-$C_6$ alkoxy, amino, $C_1$-$C_6$ alkylamino, carboxylic (—$CO_2$H) or sulfonic (—$SO_3$H) radicals;

it being understood that:
when n is greater than or equal to two, the radicals $R_1$ are identical or different;
when the compounds of formulae (I'a) to (IV'a) comprise a cationic group, it is combined with an anionic counterion to achieve the electrical neutrality of the molecule,
the compounds of formula (I'a) contain at least three substituents chosen from X and $R_1$ which are electron-donating via the mesomeric effect (+M);

the compounds of formula (II'a) or (III'a) contain at least two substituents chosen from X and $R_1$ which are electron-donating via the mesomeric effect (+M);

for formula (II'a), X or $R_1$ are bonded to the carbon atoms 1 to 4 or 6 to 9;

for formula (III'a) or (IV'a), X or $R_1$ are bonded to the carbon atoms 1, 2 and 5 to 8 or to a carbon or nitrogen atom 3.

Preferably, compounds a9) of formulae (I'a) to (III'a) are such that Y represents a carbon atom. According to an advantageous variant, the self-oxidizing compounds a9) are of formula (III'a) and are particularly such that Z in position 1 or 2 represents a carbon atom and Z in position 3 represents a nitrogen atom or $NR_3$.

Preferentially, compounds a9) of formula (IV'a) are such that Y in position 4 and Z in position 3 represent a nitrogen atom, the Y in positions 5 to 8 represent a carbon atom and the Z in position 1 and 2 represent a carbon atom.

According to a particular embodiment of the invention, the self-oxidizing dyes a9) are chosen from compounds (IV'a) and preferably of formula (IV'a1) below:

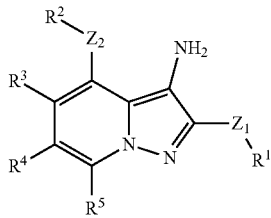

(IV'a1)

and also the organic or mineral acid or base salts thereof, the optical isomers, geometrical isomers and tautomers thereof, and/or the solvates thereof such as hydrates; in which formula (IV'a1):

$Z_1$ and $Z_2$, which may be identical or different, represent:
a covalent single bond,
a divalent radical chosen from
an oxygen atom,
a radical —$NR^6(R^7)_p$—, with p=0 or 1,
when p is equal to 0 then $R^6$ represents a hydrogen atom or a $C_1$-$C_6$ alkyl radical, or $R^6$, with $R^1$ or, respectively, with $R^2$, form, together with the nitrogen atom to which they are attached, a substituted or unsubstituted, saturated, unsaturated, aromatic or non-aromatic, 5- to 8-membered heterocycle, optionally containing one or more heteroatoms or groups chosen from N, O, S, —S(O)—, —S(O)$_2$— and —C(O)—, the heterocycle possibly being cationic and/or substituted with a cationic or noncationic radical, such as piperazinium, piperidinium, morpholinium or imidazolium substituted with one or more ($C_1$-$C_4$)alkyl groups,
when p is equal to 1 then —$NR^6R^7$— is a cationic radical in which $R^6$ and $R^7$, which may be identical or different, represent a ($C_1$-$C_6$)alkyl radical,
it being understood that at least one from among $Z_1$ and $Z_2$ is other than a covalent single bond, $R^1$ and $R^2$, which may be identical or different, represent:
a hydrogen,
an optionally substituted $C_1$-$C_{10}$ alkyl radical optionally interrupted with a heteroatom or a group chosen from O, N, Si, S, —S(O)— and —S(O)$_2$—, a $C_1$-$C_{10}$ alkyl radical substituted and/or interrupted with a cationic radical, preferably optionally substituted with $R_aR_bR_cN^+$—, or a monovalent or divalent, saturated or unsaturated, aromatic or non-aromatic 5- to 7-membered cationic heterocycle, preferably chosen from imidazolium, piperazinium, piperidinium or morpholinium, more preferentially imidazolium, and $R_a$ $R_bR_c$, which may be identical or different, represent a ($C_1$-$C_6$)alkyl group optionally substituted with one or more hydroxyl groups,
a halogen,
an $SO_3H$ radical,
a substituted or unsubstituted, saturated, unsaturated or aromatic, 5- to 8-membered ring, optionally containing one or more heteroatoms or groups chosen from N, O, S, S(O)$_2$ and —C(O)—, the ring possibly being cationic and/or substituted with a cationic radical, when $Z_1$ or, respectively, $Z_2$ represents a covalent bond, then $R^1$ or, respectively, $R^2$ may also represent a radical:
an optionally substituted $C_1$-$C_6$ alkylcarbonyl radical,
—O—C(O)—R, —C(O)—O—R, N(R)—C(O)—R' or —C(O)—N(R)—R' in which R and R' independently represent a hydrogen atom or an optionally substituted $C_1$-$C_6$ alkyl radical,
$R^3$, $R^4$ and $R^5$, which may be identical or different, represent:
a hydrogen atom,
a hydroxyl radical,
a $C_1$-$C_6$ alkoxy radical,
a $C_1$-$C_6$ alkylthio radical,
an amino radical,
a monoalkylamino radical,
a $C_1$-$C_6$ dialkylamino radical in which the alkyl radicals may form, with the nitrogen atom to which they are attached, a saturated or unsaturated, aromatic or nonaromatic, 5-membered heterocycle, which may contain one or more heteroatoms or groups chosen from N, O, S, S(O)$_2$ and C(O), the heterocycle possibly being cationic and/or substituted with a cationic radical; the heterocycle preferably represents an imidazolium, piperazinium, piperidinium or morpholinium group,
an optionally substituted $C_1$-$C_6$ alkylcarbonyl radical,
a radical —O—C(O)—R, —C(O)—O—R, N(R)—C (O)—R' or —C(O)—N(R)—R' with R and R' as defined previously,
a halogen,
an —$NHSO_3H$ radical,
an optionally substituted $C_1$-$C_4$ alkyl radical,
a saturated, unsaturated or aromatic, optionally substituted carbon-based ring,
$R^3$ and $R^4$ and/or $R^4$ and $R^5$, may also form, together with the carbon atoms that bear them, a saturated or unsaturated ring, preferably benzo;
more preferentially, $R^3$, $R^4$ and $R^5$ represent a hydrogen atom; and
X represents an anionic counterion for ensuring the electronegativity of the derivative of formula (IV'a1).

The term "cationic radical" means a radical chosen from a monovalent or divalent radical $R_aR_bR_cN^+$—, —($R_a$)($R_b$) $N^+$— and a monovalent or divalent, saturated or unsaturated, aromatic or non-aromatic 5- to 7-membered cationic heterocycle, preferably chosen from imidazolium, piperazinium, piperidinium or morpholinium, more preferentially imidazolium, and $R_aR_bR_c$, which may be identical or different, represent a ($C_1$-$C_6$)alkyl group optionally substituted with one or more hydroxyl groups.

Preferably, (IV'a1) at least one of the groups $Z_1$, $R^1$, $Z_2$ and $R^2$ represents a cationic radical.

Preferably, compounds a9 are of formula (IV'a1) and are such that $R^2$—$Z_2$ represents a radical $R^2$—$NR^6(R^7)_p$— with $R^2$, $R^6$, $R^7$ and p as defined previously. According to one embodiment, the compounds of formula (IV'a1) are such that $R^1$—$Z_1$ represents $R^1$—$NR^6(R^7)_p$— with $R^1$, $R^6$, $R^7$ and p as defined previously. According to another embodiment, the compounds of formula (IV'a1) are such that $R^1$—$Z_1$ are such that $R_1$ represents a hydrogen atom and $Z_1$ represents a bond; more preferentially in this case $R^2$—$Z_2$ represents a radical $R^2$—$NR^6(R^7)_p$—.

More preferentially, the self-oxidizing dyes a9) are chosen from pyrazolopyridines chosen from those of formulae (IV'a2) to (IV'a4) and also the organic or mineral, acid or base salts thereof, the optical or geometrical isomers thereof, the tautomers thereof and the solvates thereof such as hydrates:

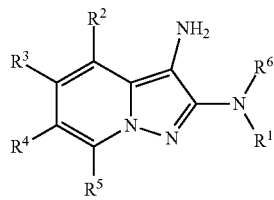
(IV'a2)

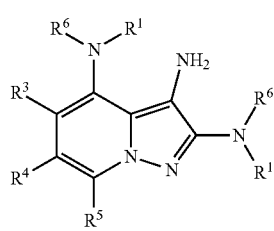
(IV'a3)

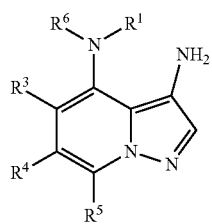
(IV'a4)

in which formulae (IV'a2) to (IV'a4):
$R^2$ to $R^5$, which may be identical or different, are as defined previously; in particular, $R^2$ to $R^4$ represent a hydrogen atom,
$R^1$ and $R^6$ are as defined previously, in particular $R^1$ represents an alkyl group substituted with a 5- or 6-membered cationic heterocyclic group which is preferably aromatic such as imidazolium, said heterocycle being optionally substituted with one or more $(C_1-C_4)$ alkyl groups, and $R^6$ represents a hydrogen atom or a $(C_1-C_6)$alkyl group.

More preferentially, the self-oxidizing compounds a9) of the invention are chosen from the derivatives (I'a), (III'a) and (IV'a), particularly the following derivatives:
a) monocyclic benzene compounds comprising at least three electron-donating substituents (or electron donors via +M effect) of which at least two of said electron-donating substituents are contiguous (i.e. they are ortho to each other), said substituents preferably being chosen from hydroxyl, (di)$(C_1-C_6)$(alkyl)amino and $(C_1-C_6)$alkoxy, the alkyl groups being optionally substituted with a hydroxyl or imidazolium group; in particular chosen from amino and hydroxyl, and
b) indole or indoline compounds substituted in positions 5 and 6 or 7 with two groups chosen from hydroxyl and optionally substituted with one or two $(C_1-C_6)$alkyl groups in position 2 and/or 3.
c) 3-aminopyrazolopyridine compounds substituted in position 2 with a 5- or 6-membered cationic heterocyclic group such as piperazinium or piperidinium, or with a group: Het-$(C_1-C_6)$alkylamino with Het representing a 5- or 6-membered cationic heterocyclic group, optionally substituted with one or more $(C_1-C_4)$ alkyl groups, such as piperazinium, piperidinium, pyridinium or imidazolium optionally substituted with one or more $(C_1-C_4)$alkyl groups, notably methyl.

Preferably, the self-oxidizing dye(s) a9) of the invention are chosen from 3-aminopyrazolopyridine dyes substituted in position 2 with a cationic heterocyclic group such as piperazinium or piperidinium, or with a group: Het-$(C_1-C_6)$ alkylamino with Het representing a 5- or 6-membered cationic heterocyclic group such as piperazinium, piperidinium or imidazolium, preferably imidazolium, optionally substituted with one or more $(C_1-C_4)$alkyl groups, notably methyl.

According to another particular embodiment, the blue, violet and green dyes a) of the invention are chosen from the oxidation dyes a10).

The oxidation dyes a10) are generally chosen from one or more oxidation bases, optionally combined with one or more coupling agents.

By way of example, the oxidation bases a10) are chosen from para-phenylenediamines, bis(phenyl)alkylenediamines, ortho-aminophenols and heterocyclic bases, and the corresponding addition salts.

Among the para-phenylenediamines that may be mentioned as dye a10) are, for example, para-phenylenediamine (PPD), para-toluenediamine (PTD), 2-chloro-1,4-phenylenediamine, 2,3-dimethyl-1,4-phenylenediamine, 2,6-dimethyl-1,4-phenylenediamine, 2,6-diethyl-1,4-phenylenediamine, 2,5-dimethyl-1,4-phenylenediamine, N,N-dimethyl-1,4-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, hydroxyethyl)amino-2-methylaniline, 4-N,N-bis(β-hydroxyethyl)amino-2-chloroaniline, 2-β-hydroxyethyl-1,4-phenylenediamine, 2-methoxymethyl-1,4-phenylenediamine, 2-fluoro-1,4-phenylenediamine, 2-isopropyl-1,4-phenylenediamine, N-(β-hydroxpropyl)-para-phenylenediamine, 2-hydroxymethyl-1,4-phenylenediamine, N,N-dimethyl-3-methyl-1,4-N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-1,4-phenylenediamine, 2-β-acetylaminoethyloxy-1,4-phenylenediamine, N-(β-methoxyethyl)-para-phenylenediamine, 4-aminophenylpyrrolidine, 2-thienyl-1,4-phenylenediamine, 2-β-hydroxyethylamino-5-aminotoluene and 3-hydroxy-1-(4'-aminophenyl) pyrrolidine, and the corresponding addition salts with an acid. Preferentially, the oxidation base(s) of the invention are chosen from PPD, PTD, N,N-bis(β-hydroxyethyl)-para-phenylenediamine, 2-β-hydroxyethyl-1,4-phenylenediamine, 2-methoxyoxyethyl-1,4-phenylenediamine and 2-isopropyloxyethyl-1,4-phenylenediamine; more preferentially PPD.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts.

Among the ortho-aminophenols that may be mentioned, for example, are 2-aminophenol, 2-amino-5-methylphenol, 2-amino-6-methylphenol and 5-acetamido-2-aminophenol, and the corresponding addition salts.

Among the heterocyclic bases that may be mentioned, for example, are pyridine, pyrimidine and pyrazole derivatives.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include 2-acetylaminopyrazolo[1,5-a]pyrid-3-ylamine, 2-morpholin-4-ylpyrazolo[1,5-a]pyrid-3-ylamine, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 2-[(3-aminopyrazolo[1,5-a]pyrid-5-yl)(2-hydroxyethyl)-amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine; 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the heterocyclic bases that may be mentioned as dye a10) are in particular pyrazole derivatives. In particular, the pyrazoles are chosen from the compounds of formula (Va) below:

and also the acid salts thereof, the tautomers thereof, and the solvates thereof such as hydrates:

in which formula (Va):

R represents a ($C_1$-$C_{10}$)alkyl group optionally substituted with one or more hydroxyl groups, R' represents a hydrogen atom or a ($C_1$-$C_4$)alkyl group optionally substituted with a hydroxyl or amino group; preferably, R' represents a ($C_1$-$C_4$)alkyl group such as methyl.

Preferably, the oxidation bases a10) are heterocyclic and are chosen from the bases of formula (Va) in which R' represents a hydrogen atom or methyl, and R represents an ethyl, β-hydroxyethyl or n-hexyl group. The heterocyclic bases are chosen from compounds (VIIa1) to (VIIa4) below, and also the organic or mineral acid salts thereof, and the solvates thereof such as hydrates:

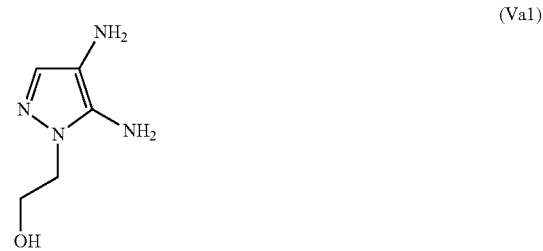

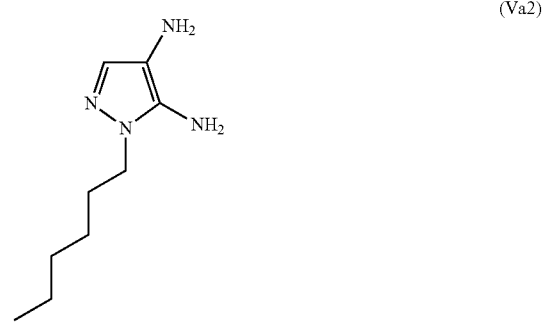

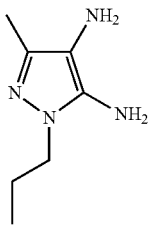

(Va3)

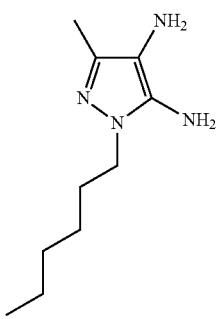

(Va4)

According to a particular embodiment of the invention, the dye(s) a10) are chosen from oxidation bases combined with one or more couplers chosen from those conventionally used in the dyeing of keratin fibers.

Among these couplers, mention may be made in particular of meta-phenylenediamines, meta-aminophenols, meta-diphenols, naphthalene-based coupling agents and heterocyclic coupling agents, and also the corresponding addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the corresponding addition salts with an acid and the corresponding mixtures.

In general, the addition salts of oxidation bases and couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the composition and of the ready-to-use composition.

The coupler(s), if it (they) are present, each advantageously represent from 0.001% to 10% by weight relative to the total weight of the composition, and preferably from 0.005% to 5% by weight relative to the total weight of the composition and of the ready-to-use composition.

According to a particular embodiment of the invention, the keratin fiber dyeing process and the cosmetic composition according to the present invention use a) one or more blue, violet or green dyes chosen from a1) azinium dyes, and more particularly those of formula (Ia), as defined previously, the optical isomers thereof, the geometrical isomers thereof, the tautomers thereof, the organic or mineral acid or base salts thereof, the solvates thereof such as hydrates, and mixtures thereof.

Preferably, the dyes of formula (Ia) are such that $R_2$, $R_3$, $R'_2$ and $R'_3$, which may be identical or different, represent, independently of each other:
 a hydrogen atom,
 a phenyl radical, or
 an optionally substituted, linear or branched $C_1$ to $C_{10}$ and more preferentially $C_1$ to $C_6$ alkyl radical, one or more radicals chosen from hydroxyl, amino —$NH_2$, aminocarbonyl —$C(O)NH_2$, and saturated 5- or 6-membered heterocycloalkyl radicals.

Preferably, the dyes of formula (Ia) are such that $R_5$ and $R'_5$, which may be identical or different, represent a hydrogen atom, a linear or branched $C_1$ to $C_6$ and more preferentially $C_1$ to $C_4$ alkyl radical, such as a methyl, a (di)($C_1$-$C_6$)(alkyl)amino radical, an amino radical —$NH_2$, a hydroxycarbonyl radical —$C(O)$—$OH$ or an aminocarbonyl radical —$C(O)NH_2$.

According to a first particular embodiment, the dyes of formula (I) are such that X represents an oxygen atom.

According to another particular embodiment, the dyes of formula (I) are such that X represents a cationic radical $N^+R'_2R'_3$, in which $R'_2$ and $R'_3$ are as defined previously, preferably $R'_2$ and $R'_3$, which may be identical or different, represent, independently of each other, a hydrogen atom or a linear or branched $C_1$ to $C_{10}$ and more preferentially $C_1$ to $C_6$ alkyl radical, optionally substituted with one or more radicals chosen from the following radicals:
 hydroxyl,
 amino, optionally substituted with one or two identical or different $C_1$-$C_4$ alkyl radicals, said alkyl radicals possibly forming, with the nitrogen atom that bears them, a 5- to 7-membered heterocycle, or
 carbamoyl ((R)$_2$N—C(O)—), in which R, which may be identical or different, represent a hydrogen atom or a $C_1$ to $C_4$ alkyl radical.

As seen previously, $Y^-$ denotes a cosmetically acceptable anionic counterion or mixture of anions intended to ensure the electrical neutrality of the compounds of formula (I). Preferably, $Y^-$ is chosen from halides, such as chloride, methosulfates; alkylsulfonates: Alk-S(O)$_2$O$^-$ such as methylsulfonate or mesylate and ethylsulfonate; arylsulfonates: Ar—S(O)$_2$O$^-$ such as benzenesulfonate and toluenesulfonate or tosylate; citrate; succinate; tartrate; lactate; alkyl sulfates: Alk-O—S(O)O$^-$ such as methyl sulfate; aryl sulfates such as benzene sulfate and toluene sulfate; phosphate; acetate; triflate; perchlorate; borates such as tetrafluoroborate; carbonate; and hydrogen carbonate; and more preferentially from a halide such as chloride, bromide, fluoride or iodide; a dianionic inorganic salt such as zinc tetrachloride; a hydroxide; a sulfate; a hydrogen sulfate; a linear or branched $C_1$ to $C_6$ alkyl sulfate, such as the methylsulfate or ethylsulfate ion; carbonates and hydrogen carbonates; carboxylic acid salts such as formate, acetate, citrate, tartrate or oxalate; linear or branched $C_1$ to $C_6$ alkylsulfonates, such as the methylsulfonate ion; arylsulfonates for which the aryl part, preferably phenyl, is optionally substituted with one or more $C_1$ to $C_4$ alkyl radicals such as 4-tolylsulfonate; alkylsulfonyls such as mesylate; tetrafluoroborate; perchlorate; and mixtures thereof.

As the anionic counterion derived from an organic or mineral acid salt ensures the electrical neutrality of the molecule, it is understood that when the anion comprises several anionic charges, then the same anion may serve for the electrical neutrality of several cationic groups in the same molecule or else may serve for the electrical neutrality of several molecules. For example, a dye of formula (I) which contains two cationic groups may either contain two "singly charged" anionic counterions or contain a "doubly charged" anionic counterion, such as $S(O)_2O_2^-$ or $O=P(O^-)_2-OH$.

When the compounds of formula (I) bear a carboxylate group $C(O)O^-M^+$, it is understood that the compounds of formula (I) may respect the electrical neutrality by comprising neither $M^+$ nor $Y^-$, the carboxylate being "electro-compensated" by the presence of a cationic charge $N^+R'_2R'_3$ or $-N^+R'R''R'''$.

The term "cation or cationic counterion" means a cosmetically acceptable organic or inorganic cation or cationic group derived from an organic or mineral base salt associated with the anionic charge of the dye; more particularly, the cationic counterion is chosen from i) alkali metals such as $Na^+$ and $K^+$, ii) alkaline-earth metals such as $Ca^{++}$ and $Mg^{++}$, and iii) ammoniums such as $R_aR_bR_cR_dN^+$ with $R_a$, $R_b$, $R_c$ and $R_d$, which may be identical or different, representing a hydrogen atom or a hydroxyl or $(C_1-C_8)$alkyl group.

The dye of the invention may also be in the form of solvates, for example a hydrate or a solvate of a linear or branched alcohol such as ethanol or isopropanol.

Preferably, the blue, violet or green dyes of the invention are included among the following dyes:

Dye 7                                    Dye 8
                                         Family (Ia)                                                    Family (Ia)

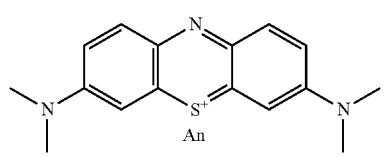    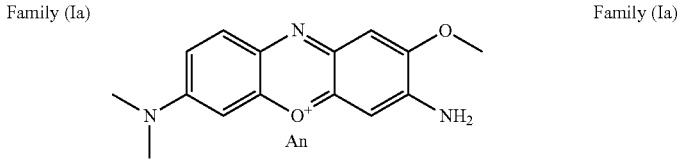

Dye 13                                   Dye 14
                                         Family (IVa)                                                   Family (IVa)

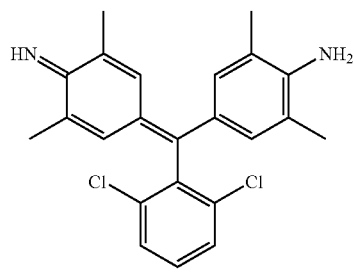    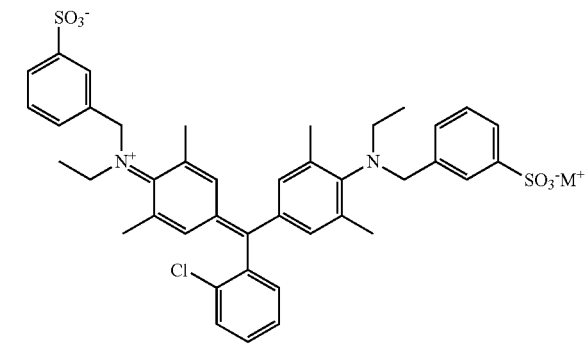

Dye 4                                    Dye 4'
                                         Family (Va)                                                    Family (Va)

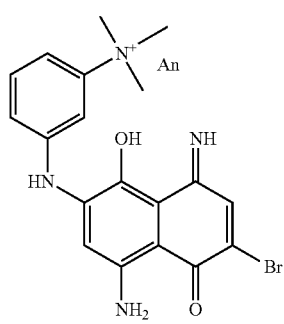    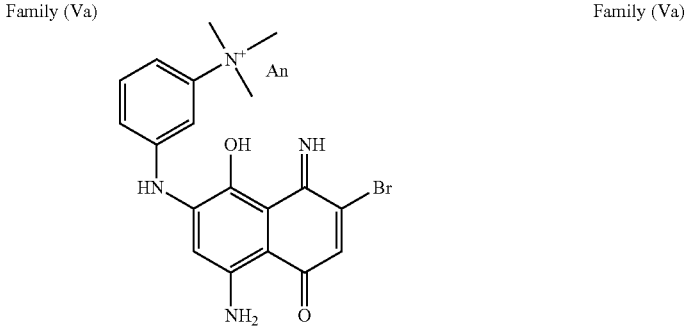

-continued
Dye 3
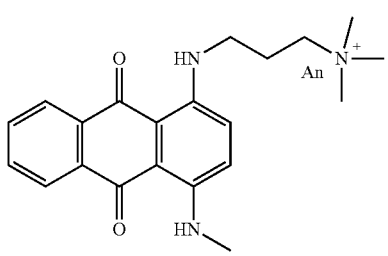
Family (VIa)
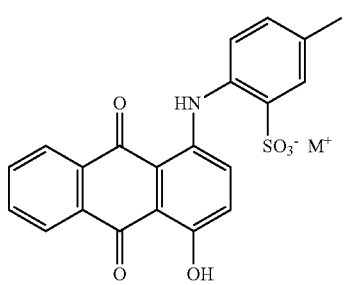
Family (VIa)
Family (VIa)
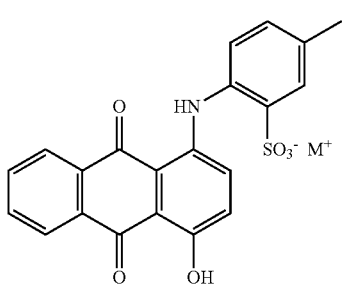
Family (VIa)
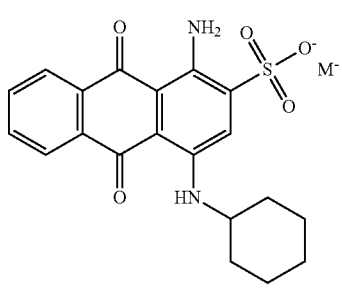
Dye 2
Dye 1
Family (VIIa)
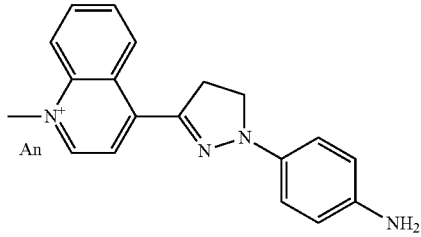
Family (VIIIa)
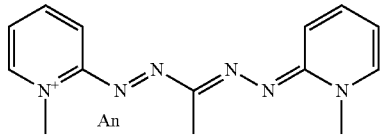
Dye 9
Dye 10
Family (Xa)
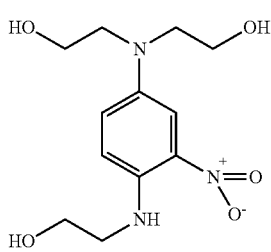
Family (Xa)
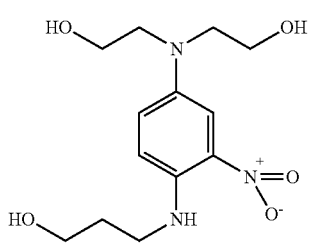
Dye 15
Dye 16
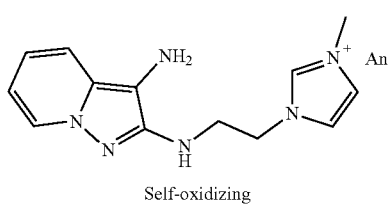
Self-oxidizing
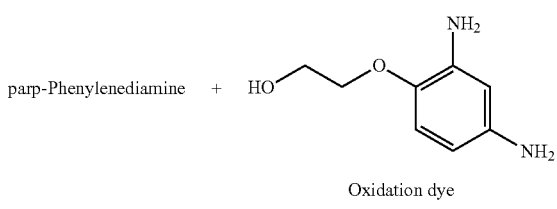
Oxidation dye Dye 17

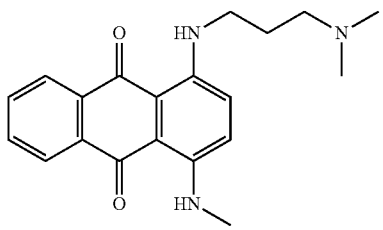

Dye 18

Family (VIa)

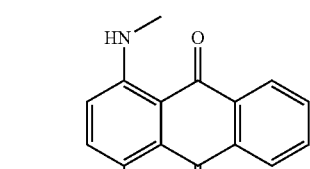

Family (VI'a)

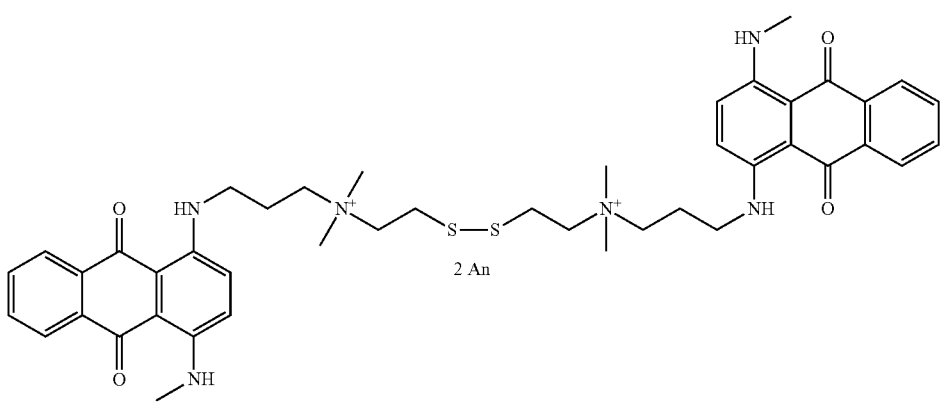

with An representing an anionic counterion as defined previously, in particular halide, and M⁺ representing a cationic counterion such as an alkali metal, for instance $Na^+$ or $K^+$; more preferentially, the blue, violet or green dye(s) a) are chosen from dyes 1, 7, 8, 15, 17 and 18.

b) The Disulfide, Thiol or Protected-Thiol Fluorescent Dyes

The keratin fiber dyeing process and the composition according to the present invention also use, or comprise, b) one or more disulfide, thiol or protected-thiol fluorescent dyes.

In particular, the disulfide, thiol or protected-thiol fluorescent dye(s) (b) of the invention are dyes which absorb light in the yellow, orange and red, particularly red, range, preferably in the absorption wavelength $\lambda_{abs}$ between 400 nm and 500 nm inclusive.

Preferably, the disulfide, thiol or protected-thiol fluorescent dye(s) are chosen from those of formula (Ib): A—$(X)_p$—$C_{sat}$—S—U and also the organic or mineral acid or base salts thereof, the optical and geometric isomers thereof, the tautomers thereof and the solvates thereof such as hydrates, in which formula (Ib):

U represents a radical chosen from:
a) —S—$C'_{sat}$—$(X')_{p'}$-A'; and
b) —Y;

A and A' which may be identical or different, represent a radical containing at least one quaternized cationic fluorescent chromophore or at least one fluorescent chromophore bearing a quaternized or quaternizable cationic group;

Y represents i) a hydrogen atom; or ii) a thiol-function-protecting group;

X and X', which may be identical or different, represent a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
—N(R)—, —N⁺(R)(R)—, —O—, —S—, —C(O)—, —S(O)— and —$SO_2$—, with R, which may be identical or different, chosen from a hydrogen and a $C_1$-$C_4$ alkyl, hydroxyalkyl or aminoalkyl radical;
an aromatic or non-aromatic, saturated or unsaturated, fused or non-fused (hetero)cyclic radical optionally comprising one or more identical or different, optionally substituted heteroatoms;

p and p', which may be identical or different, are equal to 0 or 1;

$C_{sat}$ and $C'_{sat}$, which may be identical or different, represent an optionally substituted linear or branched, or cyclic, $C_1$-$C_{18}$ alkylene chain.

According to one particular mode of the invention, the dyes (Ib) are disufide dyes, i.e. for which U represents the following radical a) —S—$C'_{sat}$—$(X')_{p'}$-A', and more particularly the dyes of formula (Ib) are symmetrical i.e. are such that A=A', $C_{sat}$=$C'_{sat}$, X=X' and p=p'.

According to another particular mode of the invention, the dyes of formula (Ib) bearing a thiol function are as defined previously, i.e. U representing the radical b) Y.

Another particular embodiment of the invention relates to fluorescent dyes bearing a disulfide, thiol or protected-thiol function.

According to a particular embodiment of the invention, the fluorescent dye of formula (Ib) is a thiol dye, i.e. Y represents i) a hydrogen atom.

In accordance with another particular embodiment of the invention, in the abovementioned formula (Ib), Y is a protecting group known to those skilled in the art, for instance those described in the publications "*Protective Groups in Organic Synthesis*", T. W. Greene, published by John Wiley & Sons, N Y, 1981, pages 193-217; "Protecting Groups", P. Kocienski, Thieme, 3rd edition, 2005, chapter 5, and Ullmann's Encyclopedia, "Peptide Synthesis", pages 4-5, 2005 Wiley-VCH Verlag GmbH & Co. KGaA, Weinheim 10.1002/14356007.a19 157.

In particular, Y represents a thiol-function protecting group chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
carboxyl;
$SO_3^-$; $M^+$ with $M^+$ representing an alkali metal such as sodium or potassium, or else a counterion of the cationic chromophore A and $M^+$ are absent;
optionally substituted aryl such as phenyl, dibenzosuberyl or 1,3,5-cycloheptatrienyl;
optionally substituted heteroaryl; notably including the cationic or non-cationic heteroaryl comprising from 1 to 4 heteroatoms below:
i) 5-, 6- or 7-membered monocyclic groups such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;
ii) 8- to 11-membered bicyclic groups such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$)alkyl, for instance methyl, or polyhalo($C_1$-$C_4$)alkyl, for instance trifluoromethyl;
iii) or the following tricyclic ABC group:

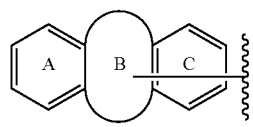

in which the two rings A and C optionally include a heteroatom, and ring B is a 5-, 6- or 7-membered ring, particularly a 6-membered ring, and contains at least one heteroatom, for instance piperidyl or pyranyl;
optionally cationic, optionally substituted heterocycloalkyl, the heterocycloalkyl group in particular represents a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as ($C_1$-$C_4$) alkyl, oxo or thioxo; or the heterocycle represents the following group:

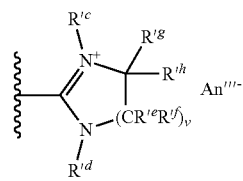

in which $R'^c$, $R'^d$, $R'^e$, $R'^f$, $R'^g$, and $R'^h$, which may be identical or different, represent a hydrogen atom or a ($C_1$-$C_4$)alkyl group, or alternatively two groups $R'^g$ with $R'^h$, and/or $R'^e$ with $R'^f$ form an oxo or thioxo group, or alternatively $R'^g$ with $R'^e$ together form a cycloalkyl; and v represents an integer between 1 and 3 inclusive; preferentially, $R'^c$ to $R'^h$ represent a hydrogen atom; and $An'''^-$ represents a counterion;

—C($NR'^cR'^d$)=$N^+R'^eR'^f$; $An'''^-$ with $R'^c$, $R'^d$, $R'^e$ and $R'^f$, which may be identical or different, representing a hydrogen atom or a ($C_1$-$C_4$)alkyl group; preferentially, $R'^c$ to $R'^f$ represent a hydrogen atom; and $An'''^-$ represents a counterion;

—C($NR'^cR'^d$)=$NR^+R'^eR'^f$; with $R'^c$, $R'^d$ and $R'^e$ as defined previously;

optionally substituted (di)aryl($C_1$-$C_4$)alkyl such as 9-anthracenylmethyl, phenylmethyl or diphenylmethyl optionally substituted with one or more groups in particular chosen from ($C_1$-$C_4$) alkyl, ($C_1$-$C_4$) alkoxy such as methoxy, hydroxyl, alkylcarbonyl or (di)($C_1$-$C_4$)(alkyl)amino such as dimethylamino;

optionally substituted (di)heteroaryl($C_1$-$C_4$)alkyl, the heteroaryl group notably being a cationic or non-cationic, 5- or 6-membered monocyclic radical comprising from 1 to 4 heteroatoms chosen from nitrogen, oxygen and sulfur, such as pyrrolyl, furyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl($C_1$-$C_4$)alkyl is (di)heteroarylmethyl or (di)heteroarylethyl;

$CR^1R^2R^3$ with R1, $R^2$ and $R^3$, which may be identical or different, representing a halogen atom or a group chosen from:
($C_1$-$C_4$)alkyl;
($C_1$-$C_4$)alkoxy;
optionally substituted aryl such as phenyl optionally substituted with one or more groups, for instance ($C_1$-$C_4$)alkyl, ($C_1$-$C_4$)alkoxy or hydroxyl;
optionally substituted heteroaryl such as thiophenyl, furanyl, pyrrolyl, pyranyl or pyridyl, optionally substituted with a ($C_1$-$C_4$)alkyl group;
$P(Z^1)R^{11}R'^{12}R'^3$ with $R^{11}$ and $R'^2$, which may be identical or different, representing a hydroxyl, ($C_1$-$C_4$)alkoxy or alkyl group, $R'^3$ representing a hydroxyl or ($C_1$-$C_4$)alkoxy group, and $Z^1$ representing an oxygen or sulfur atom;

a sterically hindered ring; and optionally substituted alkoxyalkyl, such as methoxymethyl (MOM), ethoxyethyl (EOM) and isobutoxyethyl.

According to a particular embodiment, the thiol-protected dyes of formula (Ib) include a group Y chosen from i) aromatic cationic 5- or 6-membered monocyclic heteroaryl comprising from 1 to 4 heteroatoms chosen from oxygen, sulfur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium, imidazolium; ii) cationic 8- to 11-membered bicyclic heteroaryl such as indolinium, benzimidazolium, benzoxazolium, benzothiazolium, these monocyclic or bicyclic heteroaryl groups optionally being substituted with one or more groups such as alkyl, for instance methyl, or polyhalo($C_1$-$C_4$)alkyl such as trifluoromethyl; iii) or the following heterocyclic:

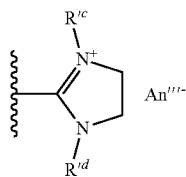

in which $R'^c$ and $R'^d$, which may be identical or different, represent a ($C_1$-$C_4$)alkyl group; preferentially $R'^c$ to $R'^d$ represent a ($C_1$-$C_4$)alkyl group such as methyl; and $An'''^-$ represents a counterion.

In particular, the fluorescent dye(s) of formula (Ib) are such that Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzimidazolium, benzoxazolium, benzothiazolium, these groups being optionally substituted with one or more ($C_1$-$C_4$)alkyl groups, notably methyl.

In particular, the fluorescent dye(s) of formula (Ib) are such that Y represents a protective group such as:
($C_1$-$C_4$)alkylcarbonyl, for instance methylcarbonyl or ethylcarbonyl;
arylcarbonyl such as phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

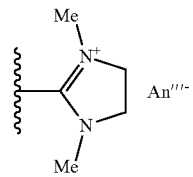 [SMILES: *C1=[N+](C)CCN1C]

—C($NH_2$)=$N^+H_2$; $An''''^-$; with $An''''^-$ being an anionic counterion as defined previously;
—C($NH_2$)=NH; and
$SO_3^-$, $M^+$ with $M^+$ representing an alkali metal such as sodium or potassium.

As indicated previously, in the fluorescent dye(s) of formula (Ib), $C_{sat}$ and $C'_{sat}$, independently of each other, represent a linear or branched or cyclic, optionally substituted $C_1$-$C_{18}$ alkylene chain.

Substituents of said $C_1$-$C_{18}$ alkylene chain that may be mentioned include the following groups: i) amino, ii) ($C_1$-$C_4$)alkylamino, iii) ($C_1$-$C_4$)dialkylamino, or the group iv) $R^a$—$Z^a$—C($Z^b$)—$Z^c$—, in which $Z^a$, $Z^b$, which may be identical or different, represent an oxygen or sulfur atom, or a group $NR^{a'}$, $Z^c$ represents a bond, an oxygen or sulfur atom or a group $NR^a$, and $R^a$ represents an alkali metal, a hydrogen atom or a $C_1$-$C_4$ alkyl group and $R^{a'}$ represents a hydrogen atom or a $C_1$-$C_4$ alkyl group; more particularly, the groups iv) are chosen from carboxylate —C(O)$O^-$ or —C(O)OMetal (Metal=alkali metal), carboxyl —C(O)—OH, guanidino $H_2$H—C($NH_2$)—NH—, amidino $H_2$H—C($NH_2$)—, (thio)ureo $H_2$N—C(O)—NH— and $H_2$N—C(S)—NH—, aminocarbonyl-C(O)—$NR^{a'}_2$ or aminothiocarbonyl —C(S)—$NR^{a'}_2$; carbamoyl $R^{a'}$—C(O)—$NR^{a'}$— or thiocarbamoyl $R^{a'}$—C(S)—$NR^{a'}$— with $R^{a'}$, which may be identical or different, representing a hydrogen atom or a ($C_1$-$C_4$) alkyl group; said substituent(s) are preferably present on the carbon in the beta or gamma position relative to the sulfur atoms of the disulfide, thiol or protected-thiol group. Preferably, the fluorescent dye(s) of formulae (Ib) are such that $C_{sat}$ and $C'_{sat}$ represent a —($CH_2$)$_k$— chain with k being an integer between 1 and 8 inclusive.

In accordance with one particular embodiment of the invention, the fluorescent dye(s) of formulae (Ib) are such that, when p and p' are equal to 1, X and X', which may be identical or different, represent the following sequence: -(T)$_t$-(Z)$_z$-(T')$_{t'}$- said sequence being bonded in formula (Ib) symmetrically as follows:—$C_{sat}$ (or $C'_{sat}$)-(T)$_t$-(Z)$_z$-(A or A'); in which:

T and T', which may be identical or different, represent one or more radicals or combinations thereof chosen from: —O—; —S—; —N(R)—; —$N^+$(R)($R^o$)—; —S(O)—; —S(O)$_2$—; —C(O)—; with R, $R^o$, which may be identical or different, representing a hydrogen atom, a $C_1$-$C_4$ alkyl radical, $C_1$-$C_4$ hydroxyalkyl radical or an aryl($C_1$-$C_4$)alkyl radical; and a cationic or noncationic, preferentially monocyclic heterocycloalkyl or heteroaryl radical, preferentially containing two heteroatoms (more preferentially two nitrogen atoms) and preferentially being 5- to 7-membered, more preferentially imidazolium;

the indices t and t', which may be identical or different, are equal to 0 or 1;

Z represents:
—($CH_2$)$_m$— with m an integer between 1 and 8;
—($CH_2CH_2O$)$_q$— or —(O$CH_2CH_2$)$_q$— in which q is an integer between 1 and 5 inclusive;

an aryl, alkylaryl or arylalkyl radical in which the alkyl radical is $C_1$-$C_4$ and the aryl radical is preferably $C_6$, being optionally substituted with at least one group $SO_3M$ with M representing a hydrogen atom, an alkali metal or an ammonium group substituted with one or more identical or different, linear or branched $C_1$-$C_{18}$ alkyl radicals optionally bearing at least one hydroxyl;

z is equal to 0 or 1.

Moreover, according to one particular embodiment of the invention, Z represents:

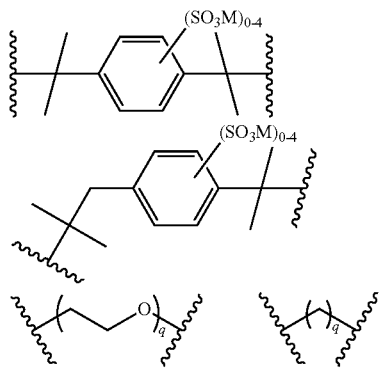

in which M represents a hydrogen atom, an alkali metal or an ammonium group or an ammonium group substituted with one or more identical or different, linear or branched $C_1$-$C_{10}$ alkyl radicals optionally bearing at least one hydroxyl; 0-4 represents an integer inclusively between 0 and 4, and q represents an integer inclusively between 1 and 6.

The fluorescent dye(s) of formulae (Ib) are such that A and/or A' represent a quaternized cationic fluorescent chromophore or at least one chromophore bearing a quaternized or quaternizable cationic group. According to one preferred embodiment of the invention, the dyes (Ib) according to the invention are disulfides and comprise identical quaternized cationic chromophores A and A'. More particularly, the dyes of formula (Ib) according to the invention are disulfides and symmetrical, i.e. they contain a $C_2$ axis of symmetry, i.e. formula (Ib) is such that:

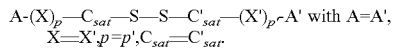

According to one variant, A and/or A' of formulae (Ib) contain at least one cationic radical borne by or included in at least one of the fluorescent chromophores.

Preferably, the cationic radical is a quaternary ammonium; more preferentially, the cationic charge is endocyclic. These cationic radicals are, for example, a cationic radical:
  bearing an exocyclic (di/tri)($C_1$-$C_8$)alkylammonium charge, or
  bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

According to one embodiment of the invention, the fluorescent dye(s) are of formula (Ib) in which A and/or A' represent(s) a chromophore chosen from those derived from acridine, acridone, benzanthrone, benzimidazole, benzimidazolone, benzindole, benzoxazole, benzopyran, benzothiazole, coumarin, difluoro{2-[(2H-pyrrol-2-ylidene-kN)methyl]-1H-pyrrolato-kN}boron (BODIPY®), diketopyrrolopyrrole, fluorindine, (poly)methine (in particular cyanin and styryl/hemicyanin), naphthalimide, naphthanilide, naphthylamine (such as dansyl), oxadiazole, oxazine, perilones, perinone, perylene, polyene/carotenoid, squarane, stilbene and xanthene fluorescent dyes; preferably, (poly)methines, such as styryl or naphthalimide fluorescent dyes, more particularly of formulae (IIb) and (IIIb) or of formulae (IVb) and (Vb) as defined below.

Mention may also be made of the chromophores A and/or A' derived from fluorescent dyes described in EP 1 133 975, WO 03/029 359, EP 860 636, WO 95/01772, WO 95/15144, EP 714 954 and those listed in the encyclopaedia *The chemistry of synthetic dye* by K. Venkataraman, 1952, Academic Press, vol. 1 to 7, in the *Kirk Othmer Encyclopedia of Chemical Technology*, in the chapter "Dyes and dye Intermediates", 1993, Wiley and Sons, and in various chapters of *Ullmann's Encyclopedia of Industrial Chemistry* 7th edition, Wiley and Sons, and in *The Handbook—A Guide to Fluorescent Probes and Labeling Technologies,* 10th Ed Molecular Probes/Invitrogen—Oregon 2005 circulated on the Internet or in the preceding printed editions.

According to a preferred variant of the invention, the disulfide, thiol or protected-thiol fluorescent dye(s) of formula (Ib) are such that A and/or A' are of formulae (IIb) and (IIIb) below:

 (IIb)

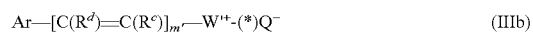 (IIIb)

with, in formula (IIb) or (IIIb):
  $W^+$ representing a cationic heterocyclic or heteroaryl group, particularly comprising a quaternary ammonium optionally substituted with one or more ($C_1$-$C_8$)alkyl groups optionally substituted notably with one or more hydroxyl groups;
  $W'^-$ representing a divalent heterocyclic or heteroaryl radical as defined for $W^+$;
  Ar representing an aryl group such as phenyl or naphthyl, optionally substituted preferentially with i) one or more halogen atoms such as chlorine or fluorine; ii) one or more groups ($C_1$-$C_8$)alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino or (di)($C_1$-$C_8$)alkylamino groups, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidinyl or 5- or 6-membered heteroaryl such as pyrrolidinyl, pyridinyl and imidazolinyl;
  Ar' is a divalent aryl radical as defined for Ar;
  m' represents an integer between 1 and 4 inclusive, and in particular m has the value 1 or 2; more preferentially 1;

R^c, R^d, which may be identical or different, represent a hydrogen atom or an optionally substituted ($C_1$-$C_8$) alkyl group, preferentially of $C_1$-$C_4$, or alternatively R^c contiguous with W^+ or W'^+ and/or R^d contiguous with Ar or Ar' form, with the atoms that bear them, a (hetero)cycloalkyl, particularly R^c is contiguous with W^+ or W'^+ and forms a (hetero)cycloalkyl such as cyclohexyl;

Q^- is an organic or mineral anionic counterion as defined previously;

(*) represents the part of the chromophore bonded to the rest of formula (Ib).

According to another variant, the disulfide, thiol or protected-thiol dye(s) of the invention are quaternized or quaternizable fluorescent dyes of formula (Ib) with A and/or A' representing a naphthalimidyl chromophore optionally bearing an exocyclic cationic charge of formula (IVb) or (Vb):

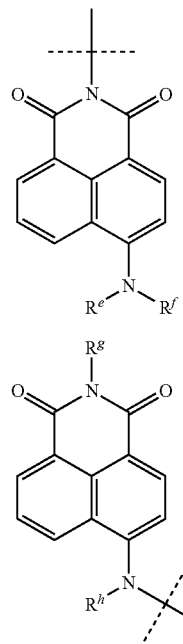

(IVb)

(Vb)

in which formulae (IVb) and (Vb):

R^e, R^f, R^g and R^h, which may be identical or different, represent a hydrogen atom or a $C_1$-$C_6$ alkyl group which is optionally substituted, preferentially with a di($C_1$-$C_6$)alkylamino or tri($C_1$-$C_6$)alkylammonium group such as trimethylammonium;

representing the bond which bonds the naphthalimidyl radical to the rest of the molecule via X or X', if p=1 or p'=1 or else via $C_{sat}$ or $C_{sat'}$ if p=0 or p'=0.

According to a particular embodiment of the invention, the disulfide, thiol or protected-thiol dye(s) are fluorescent dyes of formula (Ib) of the invention and are such that A and/or A' are of formulae (IIb) and (IIIb) as defined previously, X and X' which may be identical or different, represent the following sequence -(T)$_t$-(Z)$_z$-(T')$_{t'}$- with p=1, z=t'=0, t=1 and T represents —N(R)—, preferably in the para position on Ar relative to the olefin function —C(R^c)=C(R^d)—. Particularly, in one variant, p=1, z=t=0, t=1 and T represents —N(R)—, preferably in the para position on Ar relative to the styryl function —C(R^c)=C(R^d)— and represents a group —N(R)— or —N^+(R)(R^o)— or an imidazolium. Preferably, A and/or A' are of formulae (IIb) and (IIIb) as defined previously with W^+ or W'^+ representing a group chosen from imidazolium, pyridinium, benzimidazolium, pyrazolium, benzothiazolium and quinolinium, optionally substituted with one or more $C_1$-$C_4$ alkyl radicals, which may be identical or different.

According to a particularly preferred embodiment of the invention, the disulfide, thiol or protected-thiol dye(s) of the invention are quaternized fluorescent dyes of formula (Ib) such that A and/or A' represent the chromophore (IIIb) as defined previously, m'=1, Ar representing a phenyl group substituted in the para position of the styryl group —C(R^d)=C(R^c)— with a (di)(hydroxy)($C_1$-$C_6$)(alkyl)amino group such as dihydroxy($C_1$-$C_4$)alkylamino, and W'^+ representing an imidazolium or pyridinium group, preferentially ortho- or para-pyridinium.

According to another preferred embodiment, the disulfide, thiol or protected-thiol dye(s) are fluorescent dyes of formula (Ib) in which A and/or A' represent a styrylpyridinium group having the following formula:

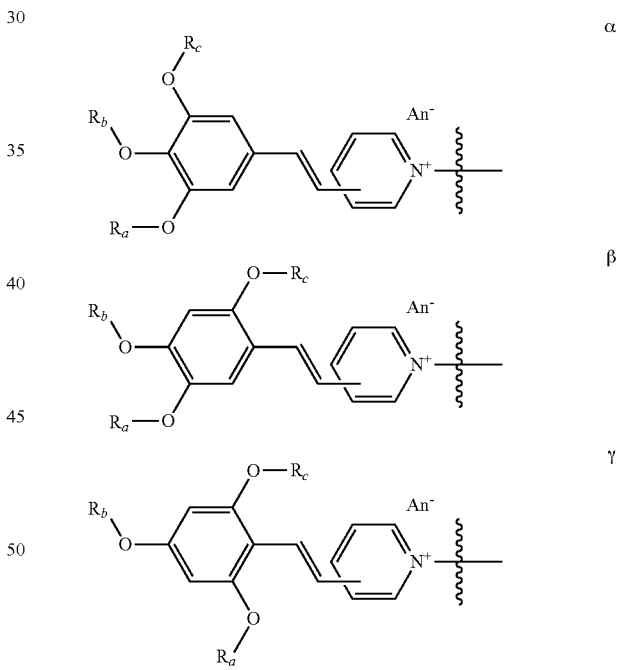

with

R_a, R_b and R_c representing a hydrogen atom or a ($C_1$-$C_6$) alkyl group, preferably a ($C_1$-$C_6$)alkyl group such as methyl;

representing the bond which bonds the styryl radical to the rest of the molecule and An⁻ represents an anionic counterion as defined previously. Preferably, A and A' represent a β group.

According to a particular embodiment of the invention, the disulfide, thiol or protected-thiol fluorescent dye(s) of formula (Ib) are chosen from the dyes of formulae (VIb) to (X'b) below:

(VIb)

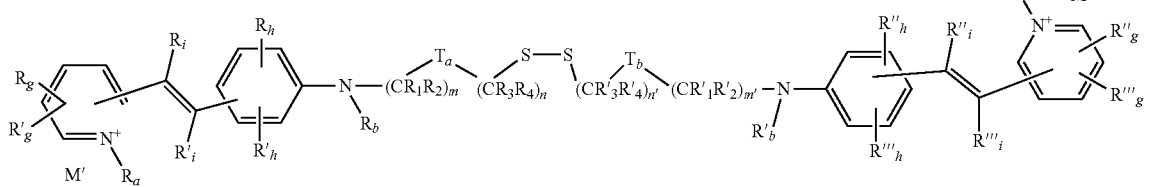

(VI'b)

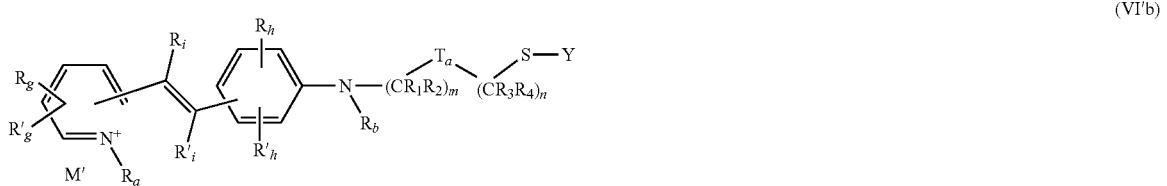

(VIIb)

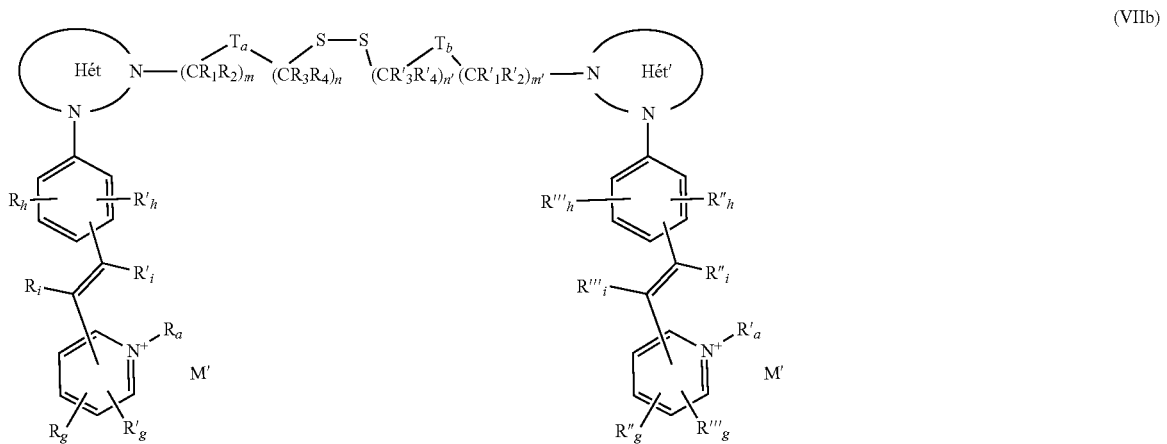

(VII'b)

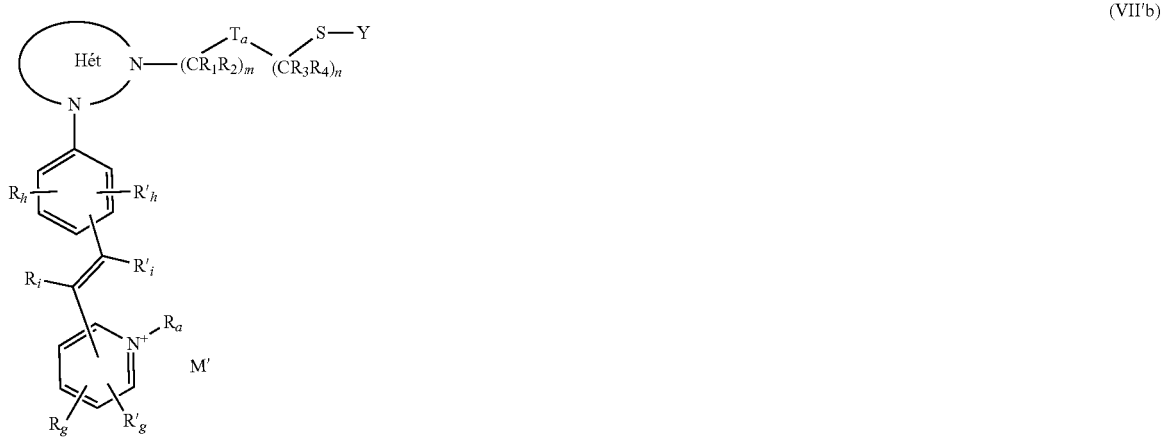

(VIIIb)
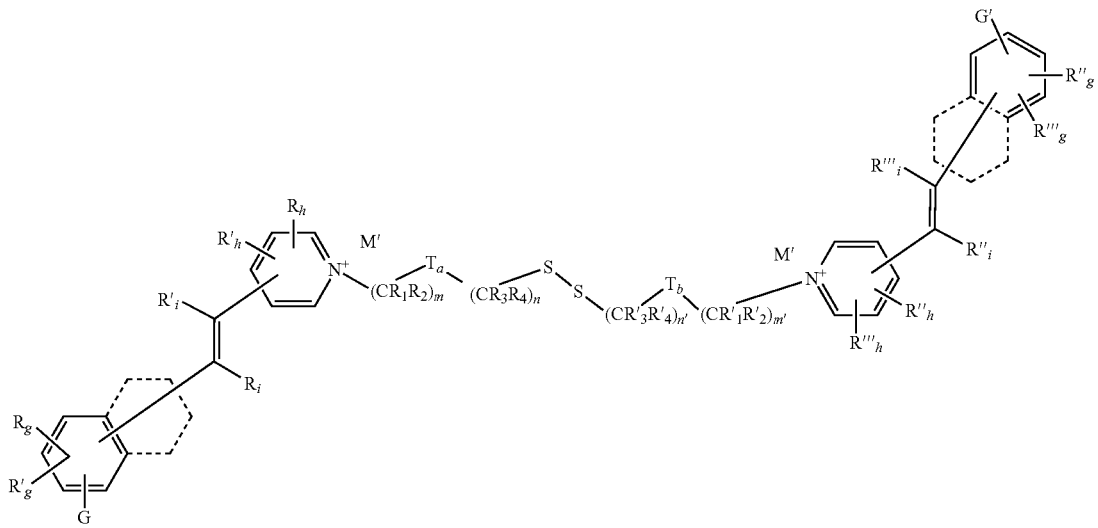
(VIIIb′)
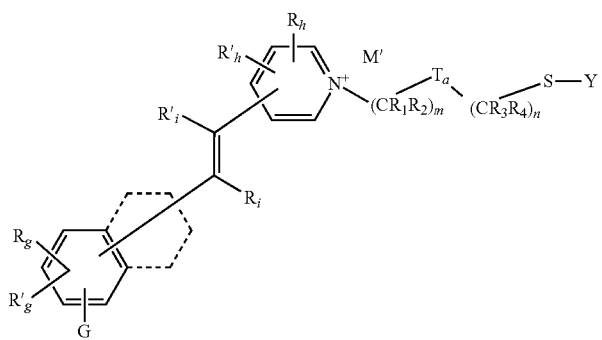
(IXb)
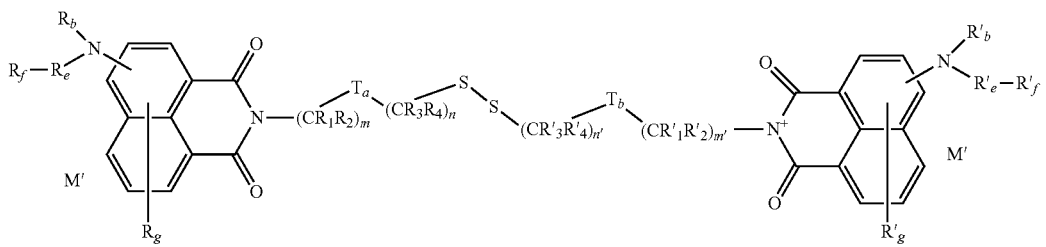
(IXb′)
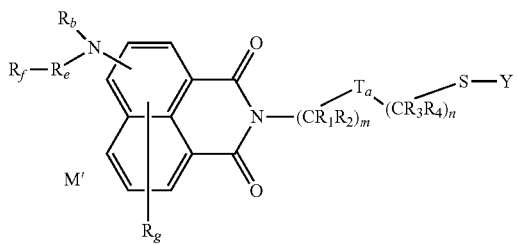

-continued

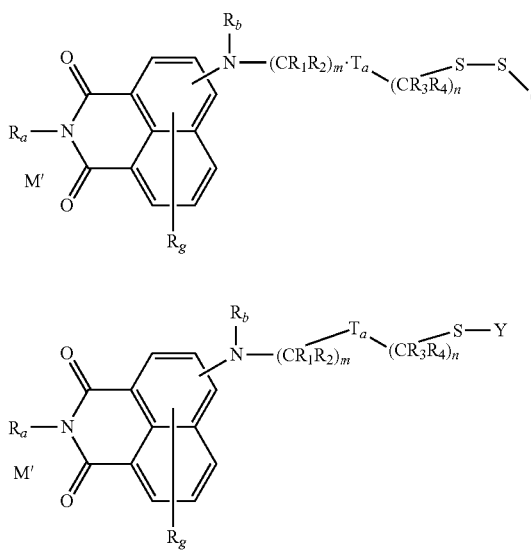

(Xb)

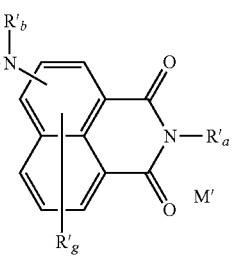

(Xb')

and also the organic or mineral acid or base salts thereof, the optical and geometric isomers thereof, the tautomers thereof, and the solvates thereof such as hydrates;

in which formulae (VIb) to (Xb'):

- G and G', which may be identical or different, represent a group —$NR_cR_d$, —$NR'_cR'_d$ or $C_1$-$C_6$ alkoxy which is optionally substituted, preferentially unsubstituted; preferentially, G and G' represent a group —$NR_cR_d$ or —$NR'_cR'_d$, respectively;
- $R_a$ and $R'_a$, which may be identical or different, represent an aryl($C_1$-$C_4$)alkyl group or a $C_1$-$C_6$ alkyl group optionally substituted with a hydroxyl or amino, $C_1$-$C_4$ alkylamino or $C_1$-$C_4$ dialkylamino group, said alkyl radicals possibly forming, with the nitrogen atom that bears them, a 5- to 7-membered heterocycle, optionally comprising another nitrogen or non-nitrogen heteroatom; preferentially, $R_a$ and $R'_a$ represent a $C_1$-$C_3$ alkyl group optionally substituted with a hydroxyl group, or a benzyl group;
- $R_b$ and $R'_b$, which may be identical or different, represent a hydrogen atom, an aryl($C_1$-$C_4$)alkyl group or a $C_1$-$C_6$ alkyl group that is optionally substituted; preferentially, $R_b$ and $R'_b$ represent a hydrogen atom or a $C_1$-$C_3$ alkyl or benzyl group;
- $R^c$, $R'_c$, $R_d$ and $R'_d$, which may be identical or different, represent a hydrogen atom, an aryl($C_1$-$C_4$)alkyl or $C_1$-$C_6$ alkoxy group or a $C_1$-$C_6$ alkyl group that is optionally substituted; $R_c$, $R'_c$, $R_d$ and $R'_d$ preferentially represent a hydrogen atom, a hydroxyl, $C_1$-$C_3$ alkoxy, amino or $C_1$-$C_3$ (di)alkylamino group, or a $C_1$-$C_3$ alkyl group that is optionally substituted with i) a hydroxyl group, ii) amino, iii) $C_1$-$C_3$ (di)alkylamino, or iv) quaternary ammonium (R'')(R''')(R'''')$N^+$—;
- or alternatively two adjacent radicals $R_c$ and $R_d$, $R'_c$ and $R'_d$ borne by the same nitrogen atom together form a heterocyclic or heteroaryl group; preferentially, the heterocycle or heteroaryl is monocyclic and 5- to 7-membered; more preferentially, the groups are chosen from imidazolyl and pyrrolidinyl;
- $R_e$ and $R'_e$, which may be identical or different, represent a linear or branched $C_1$-$C_6$ alkylene or $C_2$-$C_6$ alkenylene hydrocarbon-based chain;
- $R_f$ and $R'_f$, which may be identical or different, represent a group di($C_1$-$C_4$)alkylamino, (R'')(R''')N— or a quaternary ammonium group (R'')(R''')(R'''')$N^+$— in which R'', R''' and R'''', which may be identical or different, represent a hydrogen atom or a $C_1$-$C_4$ alkyl group or alternatively (R'')(R''')(R'''')$N^+$— represents an optionally substituted cationic heteroaryl group, preferentially an imidazolinium group optionally substituted with a $C_1$-$C_3$ alkyl group;
- $R_g$, $R'_g$, $R''_g$, $R'''_g$, $R_h$, $R'_h$, $R''_h$ and $R'''_h$, which may be identical or different, represent a hydrogen atom, a halogen atom, an amino, $C_1$-$C_4$ alkylamino, $C_1$-$C_4$ dialkylamino, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxyl, cyano, carboxyl, amino, $C_1$-$C_4$ alkylamino and $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom; preferentially, $R_g$, $R'_g$, $R''_g$, $R'''_g$, $R_h$, $R'_h$, $R''_h$ and $R'''_h$ represent a hydrogen or halogen atom or a $C_1$-$C_3$ alkyl group;
- or alternatively two groups $R_g$ and $R'_g$; $R''_g$ and $R'''_g$; $R_h$ and $R'_h$; $R''_h$ and $R'''_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $C_1$-$C_4$ alkylamino, $C_1$-$C_4$ dialkylamino, nitro, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with: a group chosen from $C_1$-$C_{12}$ alkoxy, hydroxyl, cyano, carboxyl, amino, $C_1$-$C_4$ alkylamino, $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom; preferentially, $R_g$ and $R'_g$; $R''_g$ and $R'''_g$ together form a benzo group;

or alternatively two groups $R_i$ and $R_g$; $R'''_i$ and $R'''_g$; $R'_i$ and $R'_h$; and/or $R''_i$ and $R''_h$ together form a fused (hetero)cycloalkyl, preferentially cycloalkyl such as cyclohexyl;

or alternatively when G represents —$NR_cR_d$ and G' represents —$NR'_cR'_d$, two groups $R_c$ and $R'_g$; $R'_c$ and $R''_g$; $R_d$ and $R_g$; $R'_d$ and $R'''_g$ together form a saturated heteroaryl or heterocycle, optionally substituted with one or more $C_1$-$C_6$ alkyl groups, preferentially a 5- to 7-membered heterocycle containing one or two heteroatoms chosen from nitrogen and oxygen; more preferentially, the heterocycle is chosen from morpholinyl, piperazinyl, piperidinyl and pyrrolidinyl groups;

$R_i$, $R'_1$, $R''_i$ and $R'''_i$, which may be identical or different, represent a hydrogen atom or a $C_1$-$C_4$ alkyl group;

$R_1$, $R_2$, $R_3$, $R_4$, $R'_1$, $R'_2$, $R'_3$ and $R'_4$, which may be identical or different, represent a hydrogen atom or a $C_1$-$C_4$ alkyl, $C_1$-$C_{12}$ alkoxy, hydroxyl, cyano, carboxyl, amino, $C_1$-$C_4$ alkylamino or $C_1$-$C_4$ dialkylamino group, said alkyl radicals possibly forming, with the nitrogen atom which bears them, a 5- to 7-membered heterocycle optionally comprising another nitrogen or non-nitrogen heteroatom; preferentially, $R_1$, $R_2$, $R_3$, $R_4$, $R'_1$, $R'_2$, $R'_3$ and $R'_4$ are hydrogen atoms, or a ($C_1$-$C_4$)alkyl or amino group; more preferentially, $R_1$, $R_2$, $R_3$, $R_4$, $R'_1$, $R'_2$, $R'_3$ and $R'_4$ represent a hydrogen atom;

$T_a$ and $T_b$, which may be identical or different, represent i) either a covalent bond s, ii) or one or more radicals or combinations thereof chosen from —$SO_2$—, —O—, —S—, —N(R)—, —$N^+(R)(R^o)$— and —CO—, with R and $R^o$, which may be identical or different, representing a hydrogen atom, a $C_1$-$C_4$ alkyl or a $C_1$-$C_4$ hydroxyalkyl radical; or an aryl($C_1$-$C_4$)alkyl radical; preferentially, $T_a$ is identical to $T_b$ and they represent a covalent bond s or a group chosen from —N(R)—, —C(O)—N(R)—, —N(R)—C(O)—, —O—C(O)—, —C(O)—O— and —$N^+(R)(R^o)$—, with R and $R^o$, which may be identical or different, representing a hydrogen atom or a $C_1$-$C_4$ alkyl group; more preferentially, $T_a$ and $T_b$ represent a bond s; iii) or a cationic or non-cationic, preferentially monocyclic heterocycloalkyl or heteroaryl radical, which are preferentially identical, preferentially containing two heteroatoms (more preferentially two nitrogen atoms) and preferentially being 5- to 7-membered, such as imidazolium;

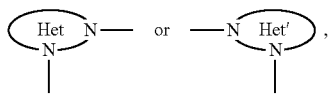

which may be identical or different, represent an optionally substituted heterocyclic group; preferentially, the heterocycles are identical, monocyclic, saturated and 5- to 8-membered and comprise in total two nitrogen atoms;

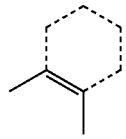

represent an aryl or heteroaryl group fused to the imidazolium or phenyl ring; or alternatively is absent from the imidazolium or phenyl ring; preferentially, when the ring is present, the ring is a benzo;

m, m', n and n', which may be identical or different, represent an integer between 0 and 6 inclusive, with m+n and m'+n', which may be identical or different, representing an integer between 1 and 10 inclusive; preferentially, m+n=m'+n'=an integer between 2 and 4 inclusive; more preferentially, m+n=m'+n'=an integer equal to 2;

Y is as defined previously; in particular, Y represents a hydrogen atom or a protective group such as:
($C_1$-$C_4$)alkylcarbonyl, for instance methylcarbonyl or ethylcarbonyl;
arylcarbonyl such as phenylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl such as dimethylaminocarbonyl;
($C_1$-$C_4$)(alkyl)arylaminocarbonyl;
optionally substituted aryl such as phenyl;
5- or 6-membered monocyclic heteroaryl such as imidazolyl or pyridyl;
cationic 5- or 6-membered monocyclic heteroaryl such as pyrylium, pyridinium, pyrimidinium, pyrazinium, pyridazinium, triazinium, imidazolium; these groups being optionally substituted with one or more identical or different ($C_1$-$C_4$)alkyl groups such as methyl;
cationic 8- to 11-membered bicyclic heteroaryl such as benzimidazolium or benzoxazolium; these groups being optionally substituted with one or more identical or different ($C_1$-$C_4$)alkyl groups such as methyl;
cationic heterocycle having the following formula:

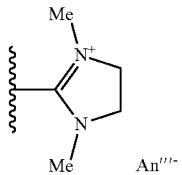 [SMILES: *C1=[N+](C)CCN1C]

—$C(NH_2)=N^+H_2$; $An''''^-$; with $An''''^-$ being an anionic counterion as defined previously;
—$C(NH_2)=NH$;
$SO_3^-$, $M^+$ with $M^+$ representing an alkali metal such as sodium or potassium; and M' representing an anionic counterion, derived from a salt of an organic or mineral acid, or of an organic or mineral base that ensures the electrical neutrality of the molecule.

In particular, the dyes of formula (Ib) are chosen from disulfide, thiol or protected-thiol dyes bearing a naphthalidimyl chromophore, chosen from formulae (VIIIb), (VIII'b), (IXb) and (IX'b) as defined previously.

According to a preferred mode of the invention, the dyes of formula (Ib) are chosen from disulfide, thiol or protected-thiol dyes chosen from formulae (XIb) to (XI'b) below:

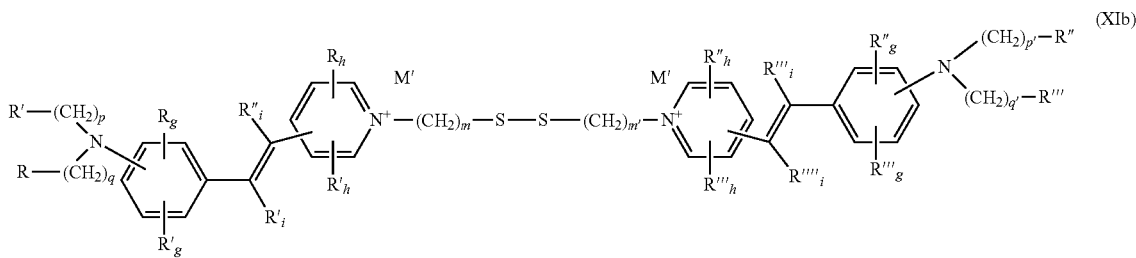

(XIb)

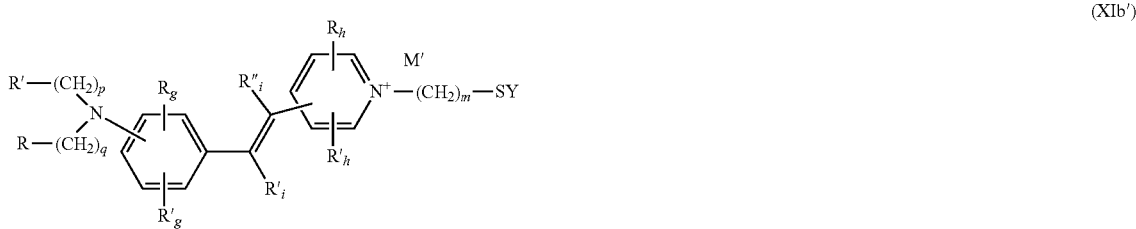

(XIb')

and also the organic or mineral acid or base salts thereof, the optical isomers thereof, the geometric isomers thereof, and the solvates thereof such as hydrates;

in which formulae (XIb) and (XI'b):

R and R''', which may be identical or different, represent a hydroxyl group, an amino group ($NR_aR_b$) or an ammonium group ($N^+R_aR_bR_c$), $An^-$; preferentially hydroxyl; with $R_a$, $R_b$ and $R_c$, which may be identical or different, representing a hydrogen atom or a ($C_1$-$C_4$) alkyl group;

or alternatively two alkyl groups $R_a$ and $R_b$ of the amino or ammonium group form a 5- to 7-membered heterocycle optionally comprising another nitrogen or non-nitrogen heteroatom, such as morpholinyl, piperazinyl, piperidinyl, pyrrolyl, morpholinium, piperazinium, piperidinium or pyrrolinium, and $An^-$ representing an anionic counterion;

R' and R'' which may be identical or different, represent a hydrogen atom or a group as defined for R and R''' respectively;

$R_g$, $R'_g$, $R''_g$, $R'''_g$, $R_h$, $R'_h$, $R''_h$ and $R'''_h$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy, ($C_1$-$C_4$)alkoxycarbonyl, ($C_1$-$C_4$)alkylcarbonylamino, acylamino, carbamoyl or ($C_1$-$C_4$)alkylsulfonylamino group, an aminosulfonyl radical or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_g$, $R'_g$, $R''_g$, $R'''_g$, $R_h$, $R'_h$, $R''_h$ and $R'''_h$ represent a hydrogen atom or a ($C_1$-$C_4$)alkyl group;

$R'_i$, $R''_i$, $R'''_i$ and $R''''_i$, which may be identical or different, represent a hydrogen atom or a ($C_1$-$C_4$)alkyl group; in particular $R'_i$, $R''_i$, $R'''_i$, and $R''''_i$ represent a hydrogen atom;

m, and m', which may be identical or different, represent an integer between 1 and 10 inclusive; in particular, an integer between 2 and 4 inclusive; preferentially m and m' are equal to 2;

p, p', q and q', which may be identical or different, represent an integer between 1 and 6 inclusive;

M' representing an anionic counterion; and

Y is as defined previously;

it being understood that, when the compound of formula (XIb) or (XIb') contains other cationic parts, it is associated with one or more anionic counterions making it possible to achieve electron neutrality of formula (XI) or (XIb').

According to a particular mode of the invention, the disulfide, thiol or protected-thiol fluorescent dyes b) belong to formula (XIIb) or (XIIb') which bear an ethylene group connecting the pyridinium part to the phenyl ortho or para to the pyridinium, i.e. 2-4', 4-2', 4-4':

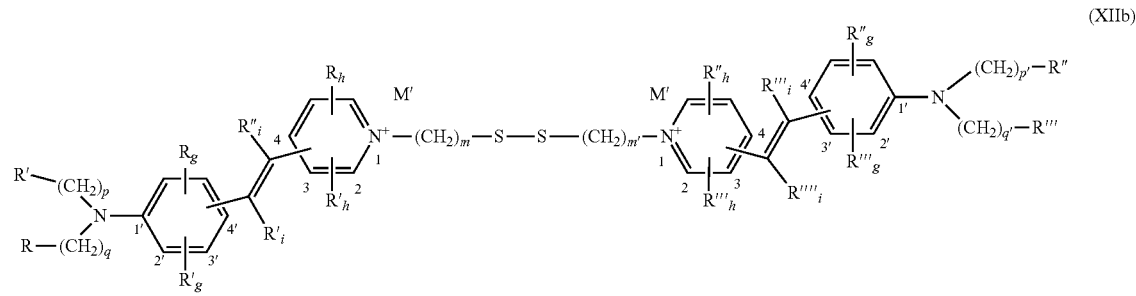

(XIIb)

-continued

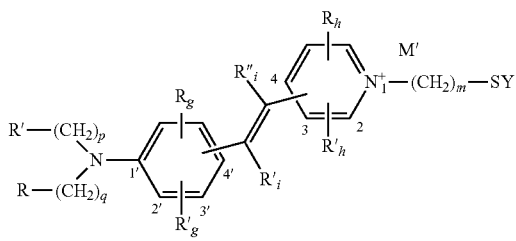
(XIIb')

and also the organic or mineral acid or base salts thereof, the optical and geometric isomers and tautomers thereof, and the solvates thereof such as hydrates;

in which formulae (XIIb) and (XIIb'), R, R', R'', R''', $R_g$, $R'_g$, $R''_g$, $R'''_g$, $R_h$, $R'_h$, $R''_h$, $R'''_h$, $R'_i$, $R''_i$, $R'''_i$, $R''''_i$, m, m', p, p', q, q', Y and M' are as defined previously in formulae (XIb) and (XIb'). In particular, $R_h$ and $R''_h$ are ortho to the pyridinium group and $R'_h$ and $R'''_h$ represent a hydrogen atom. Another aspect of the invention concerns the dyes of formula (XIIb) or (XIIb') bearing groups $R_g$, $R''_g$ in position 3' and $R'_g/R'''_g$ which represent a hydrogen atom.

Advantageously, the dyes of formulae (XIIb) and (XIIb') bear their ethylene group para to the phenyl bearing the amino group: $R'(CH_2)_p$—N—$(CH_2)_q$—R and/or $R'''$$(CH_2)_{p'}$—N—$(CH_2)_{q'}$—$R'''$, i.e. in position 4', preferentially bear an ethylene or styryl group linking the pyridinium part to the phenyl ortho to the pyridinium, i.e. 2-4'.

According to another particular mode of the invention, the disulfide, thiol or protected-thiol fluorescent dyes b) belong to formula (XIIIb) or (XIII'b) below:

or alternatively the groups $R_1$ and $R_2$ form, together with the nitrogen atom that bears them, a saturated heterocyclic radical substituted with at least one hydroxyl, (poly)hydroxy($C_1$-$C_4$)alkyl and/or —C(O)OR' group with R' representing a hydrogen atom, a $C_1$-$C_4$ alkyl group or a group —C(O)—O⁻ and, in the latter case, an anionic counterion An⁻ is absent; such as pyrrolidinyl and piperidyl;

$R_3$ represents a hydrogen atom or a group —C(O)OR'' with R'' representing a hydrogen atom, an alkali metal or a $C_1$-$C_6$ alkyl group or alternatively $R_3$ represents a group —C(O)—O⁻ and, in the latter case, an anionic counterion An⁻ is absent;

Z represents a divalent amido group —C(O)—N(R)—, —N(R)—C(O)—, or a divalent $C_1$-$C_{10}$ alkylene group interrupted with an amido group —C(O)—N(R)—, —N(R)—C(O)— such as —$(CH_2)_{n'}$—C(O)—N(R)—$(CH_2)_p$—, —$(CH_2)_{n''}$—, —N(R)—C(O)—$(CH_2)_p$—, with n' representing an integer inclusively between 0 and 3; preferentially, n' is equal to 0, 2, 3; p representing

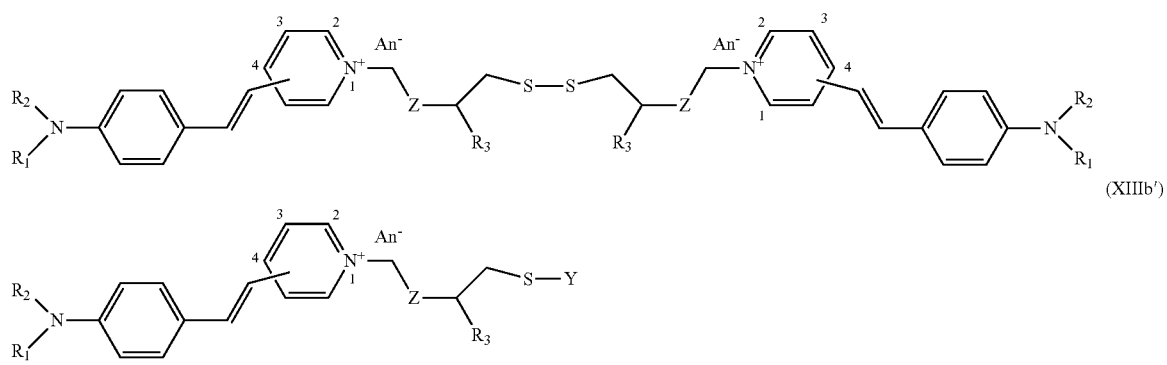

and also the organic or mineral acid or base salts thereof, the optical and geometric isomers and tautomers thereof, and the solvates thereof such as hydrates;

in which formulae (XIIIb) and/or (XIIIb'):
  $R_1$ represents a $C_1$-$C_6$ alkyl group substituted with one or more hydroxyl groups or —C(O)OR' with R' representing a hydrogen atom, a $C_1$-$C_4$ alkyl group or a group —C(O)—O⁻ and, in the latter case, an anionic counterion An⁻ is absent; in particular $R_1$ represents a $C_1$-$C_6$ alkyl group substituted with one or more hydroxyl groups and more specifically with only one hydroxyl group;
  $R_2$ represents a $C_1$-$C_6$ alkyl group optionally substituted with one or more hydroxyl groups;

an integer inclusively between 0 and 4, n'' representing an integer inclusively between 0 and 3 and notably n'=n''=p=0 and R representing a hydrogen atom or a $C_1$-$C_6$ alkyl group;

An⁻ represents an anionic counterion;

Y is as defined previously;

it being understood that when the compound of formula (XIIIb) or (XIIIb') contains other cationic parts, it is combined with one or more anionic counterions that afford formula (XIIIb) or (XIIIb') electrical neutrality.

According to a particular mode of the invention, the dyes of the invention belong to formula (XVIb) or (XVI'''b) below:

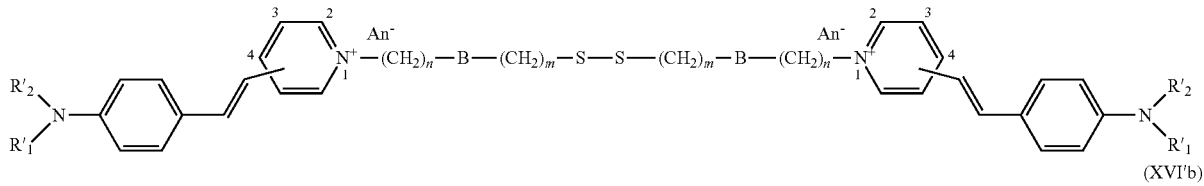
(XVIb)

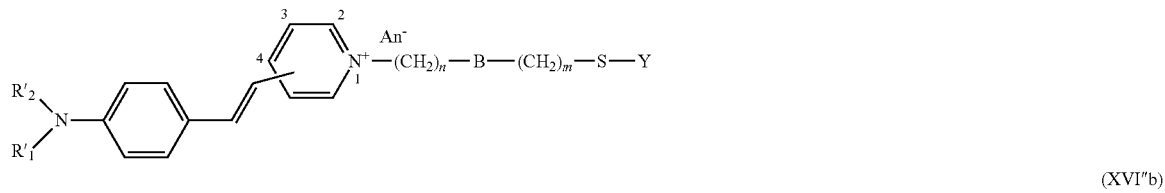
(XVI'b)

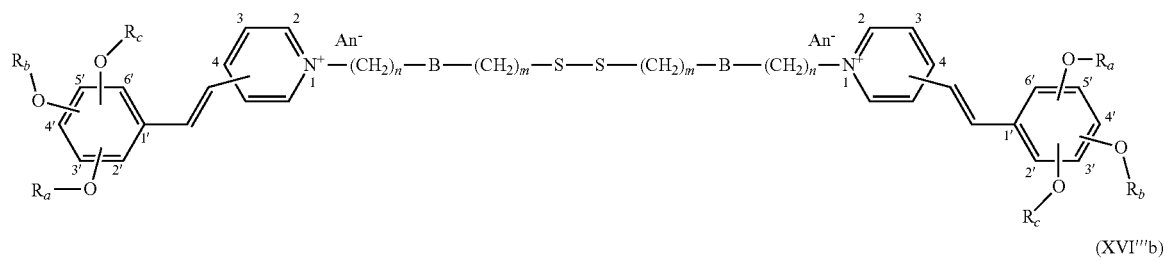
(XVI''b)

(XVI'''b)

and also the organic or mineral acid or base salts thereof, the optical and geometric isomers thereof, the tautomers thereof, and the solvates thereof such as hydrates;

in which formula (XVIb) or (XVI'''b):

$R'_1$ represents a $C_1$-$C_4$ alkyl group substituted with one or more hydroxyl groups, particularly with only one hydroxyl group, or —C(O)OR' with R' representing a hydrogen atom, a $C_1$-$C_4$ alkyl group or a —C(O)—O⁻ group and, in the latter case, an anionic counterion An⁻ is absent; preferentially, $R'_1$ represents a $C_1$-$C_4$ alkyl group substituted with a hydroxyl group;

$R'_2$ represents a $C_1$-$C_4$ alkyl group optionally substituted with one or more hydroxyl groups, particularly with only one hydroxyl group;

more particularly, $R'_1$ and $R'_2$ are identical;

$R_a$, $R_b$ and $R_c$ represent a $(C_1$-$C_6)$alkyl group such as methyl, they are in particular in positions 3', 4' and 5', or 2', 4' and 5' or 2', 4' and 6', they are preferably in positions 2', 4' and 5';

An⁻ represents an anionic counterion as defined previously;

B represent a bond or a divalent amido group —C(O)—N(R)— or —N(R)—C(O)—, with R representing a hydrogen atom or a $(C_1$-$C_6)$alkyl group; preferentially, R=H;

n and m, which may be identical or different, represent an integer between 1 and 4 inclusive; preferentially n is equal to 3 and m is equal to 2;

Y is as defined previously;

it being understood that the bond between the pyridinium ring and the double bond of the ethylene or styryl group is located in position 2 or 4 of the pyridinium, preferentially at 4.

By way of example, the disulfide, thiol and protected-thiol direct dyes of the invention b) have the following chemical structures:

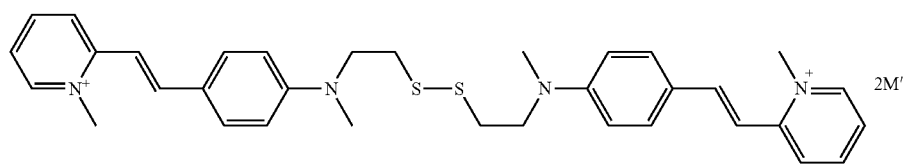

-continued
9
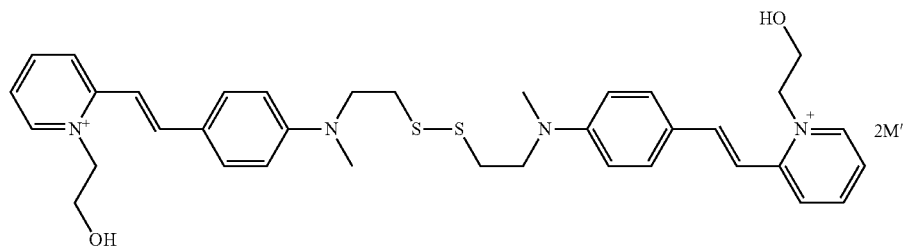
10
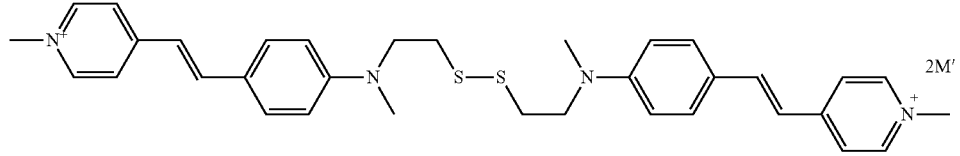
11
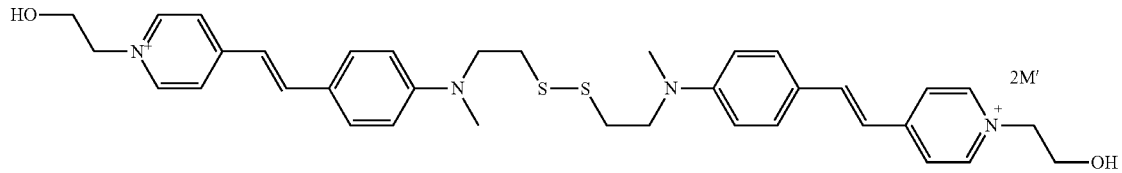
16
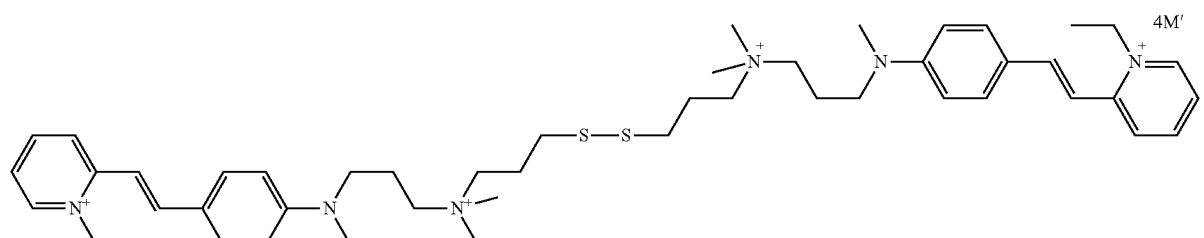
17
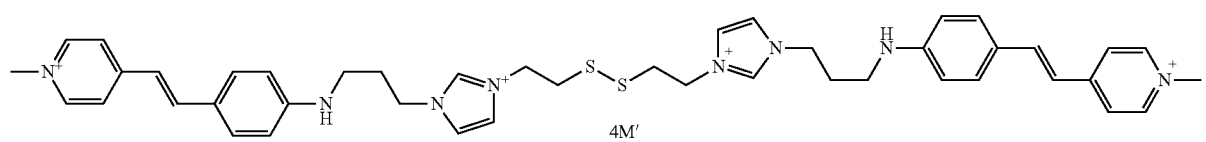
18
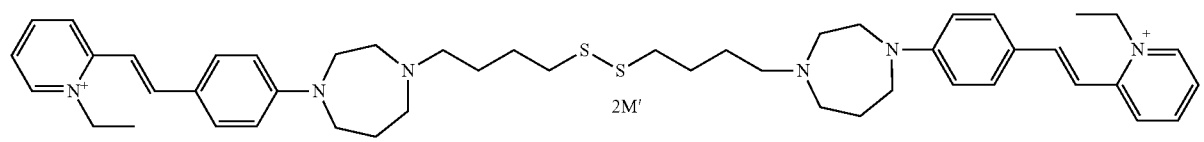
20
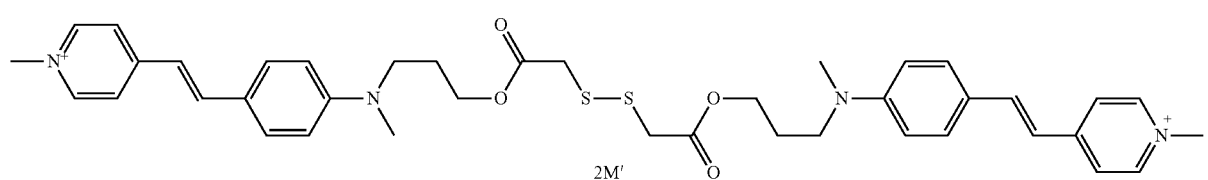
21
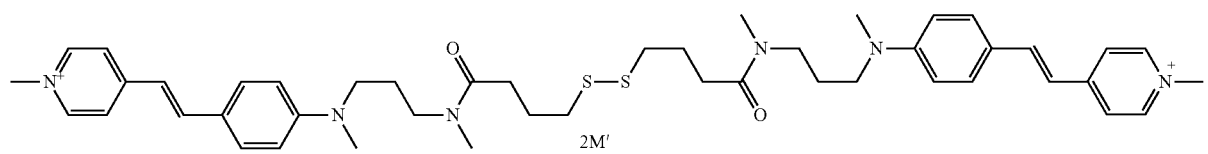

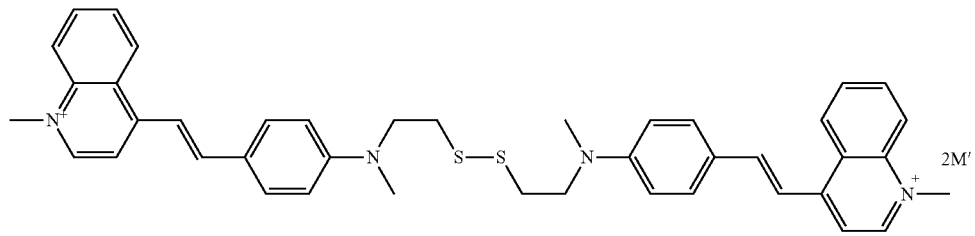
22
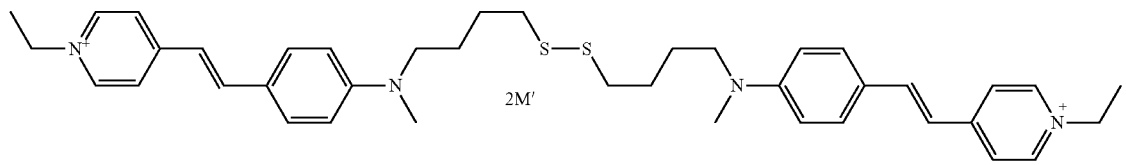
23
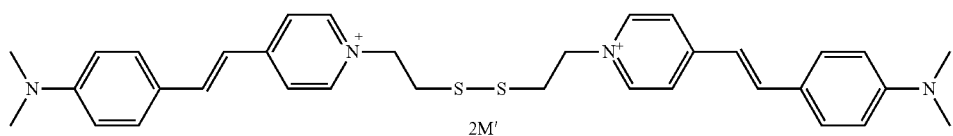
24
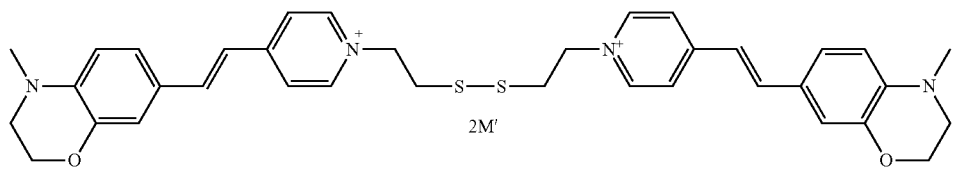
25
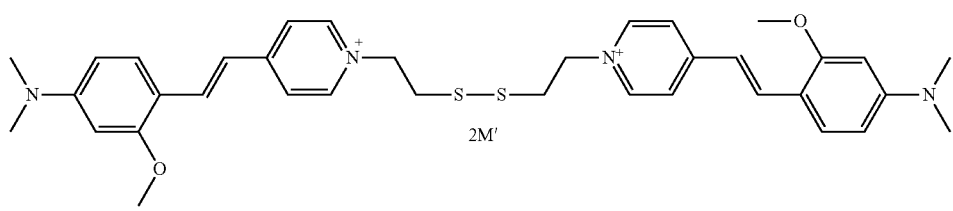
26
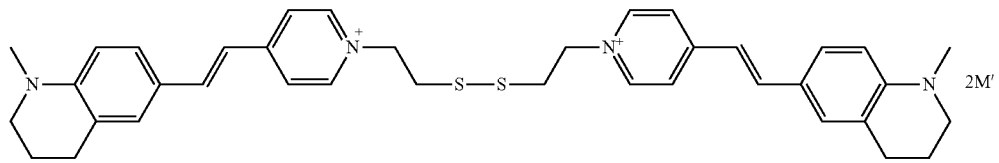
27
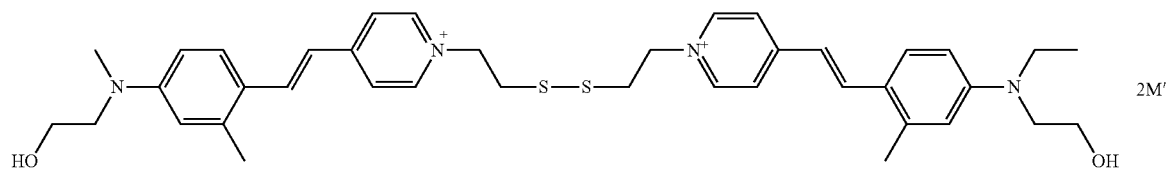
28
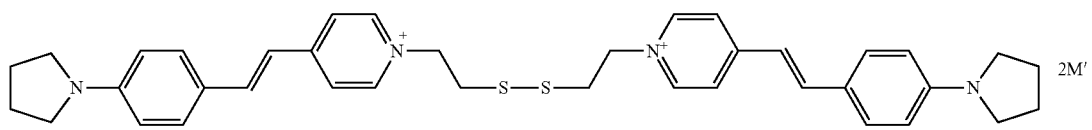
29
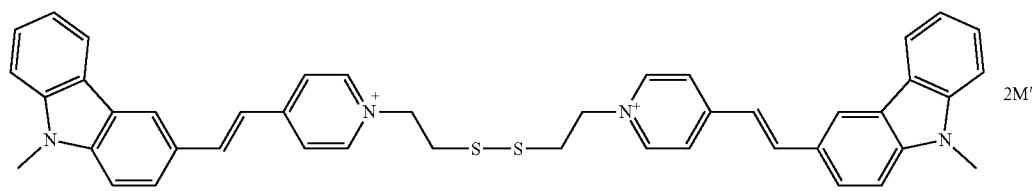
30

31
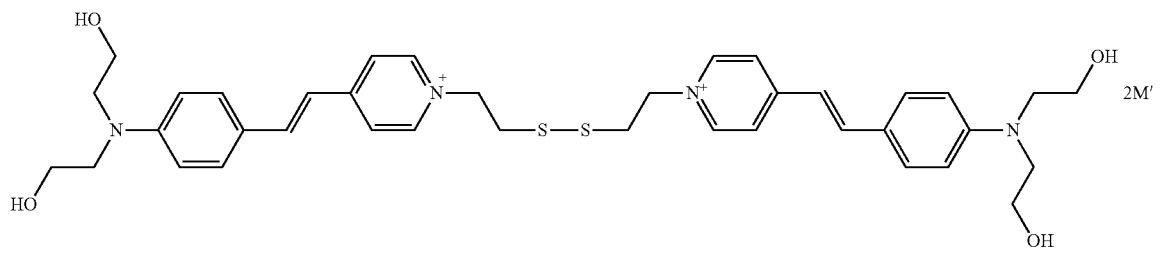
2M'
32
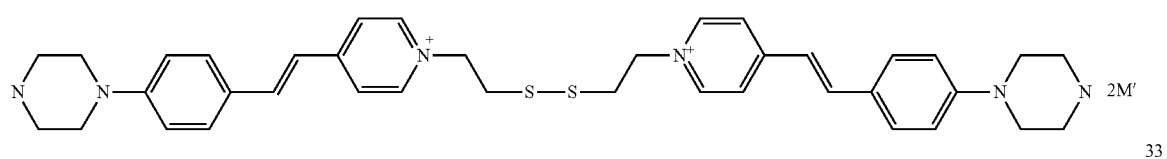
2M'
33
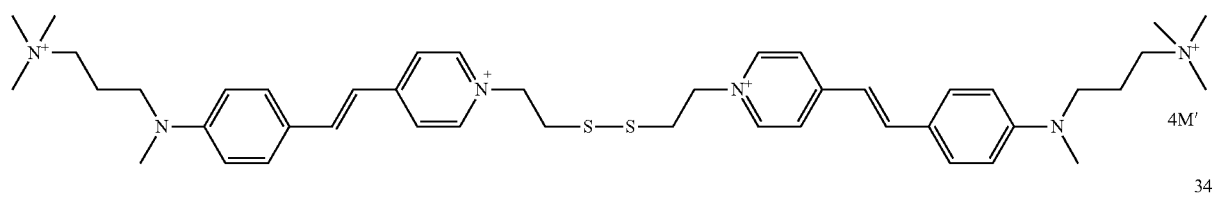
4M'
34
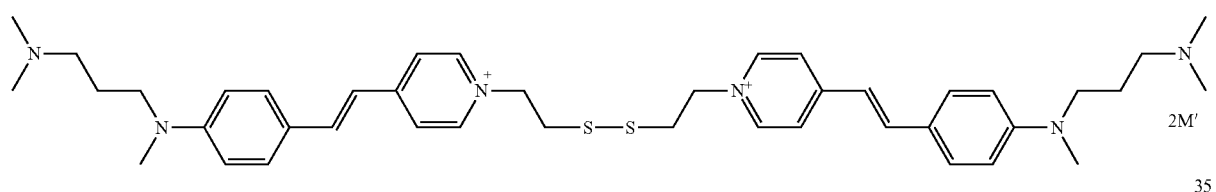
2M'
35
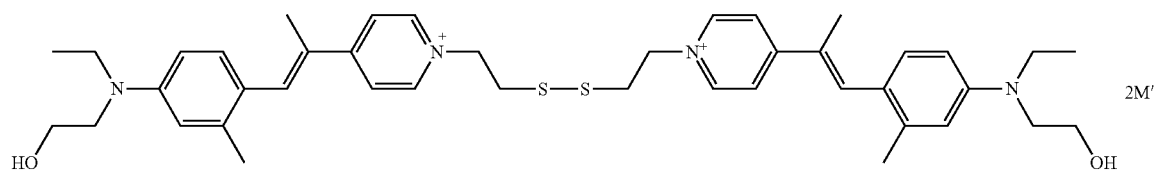
2M'
36
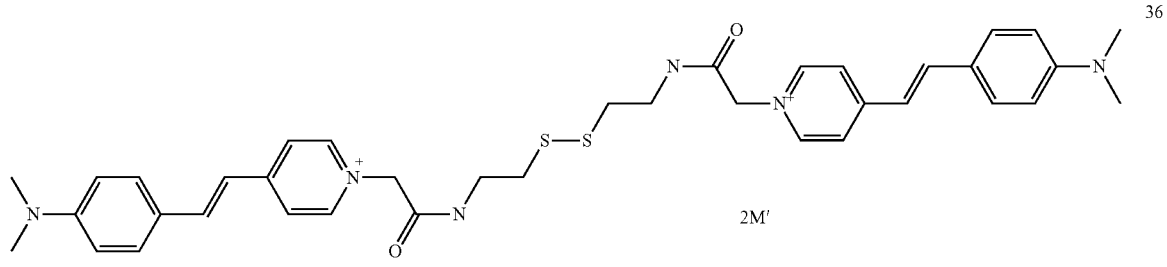
2M'
37
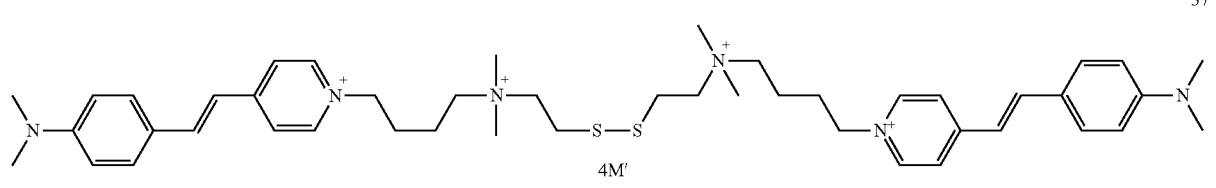
4M'
38
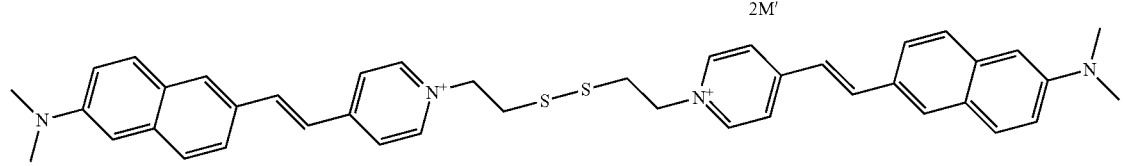
2M'

39
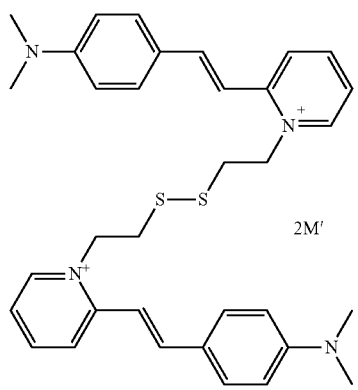
2M'
40
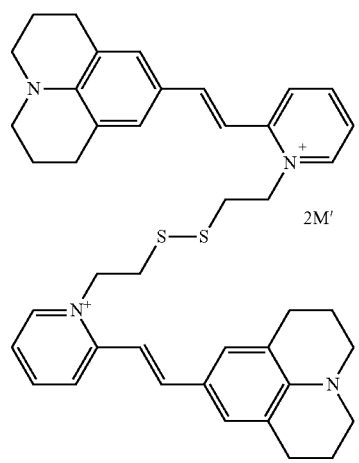
2M'
41
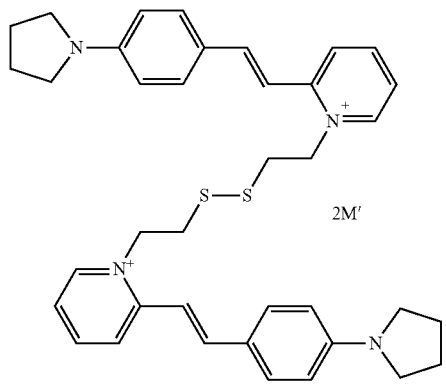
2M'
42
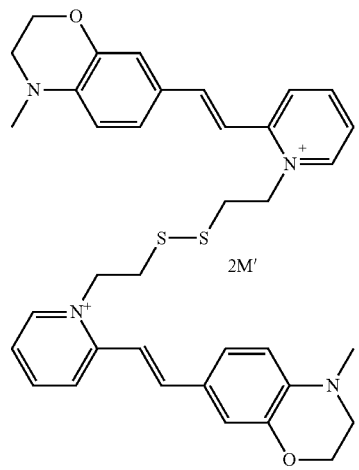
2M'
43
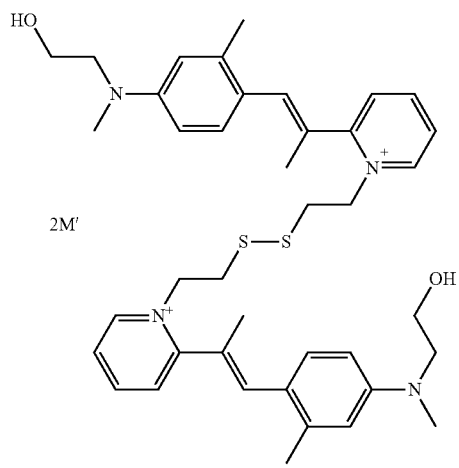
2M'
44
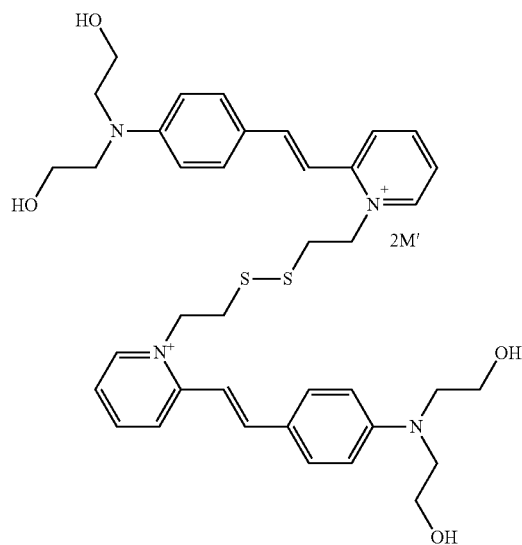
2M'

-continued
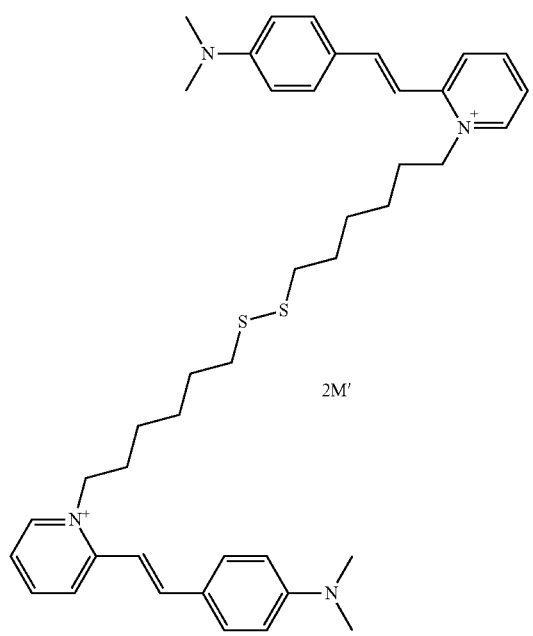
45
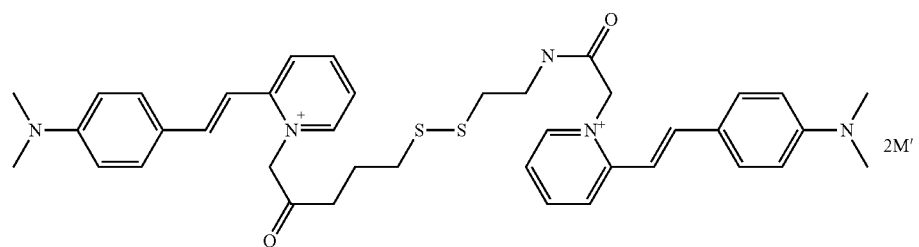
46
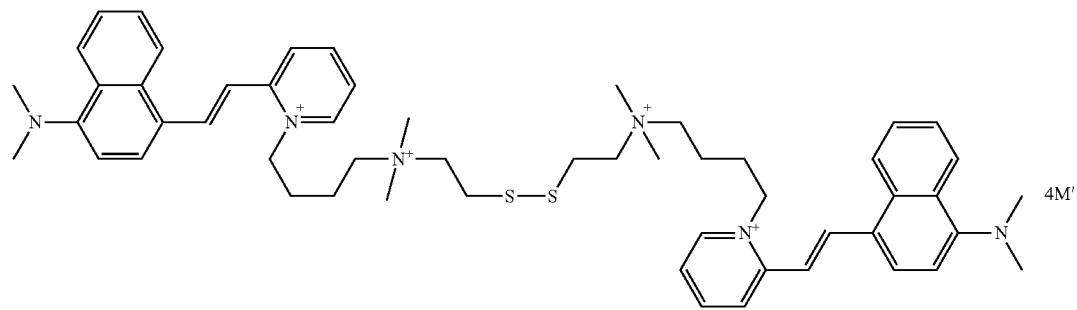
47
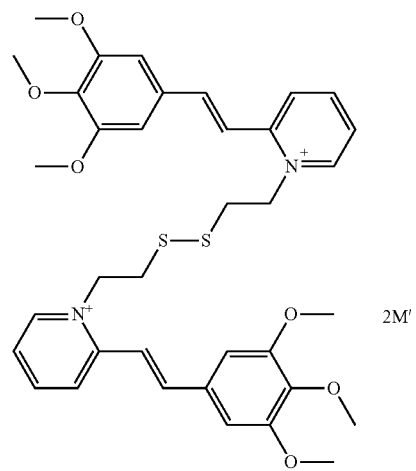
48

-continued
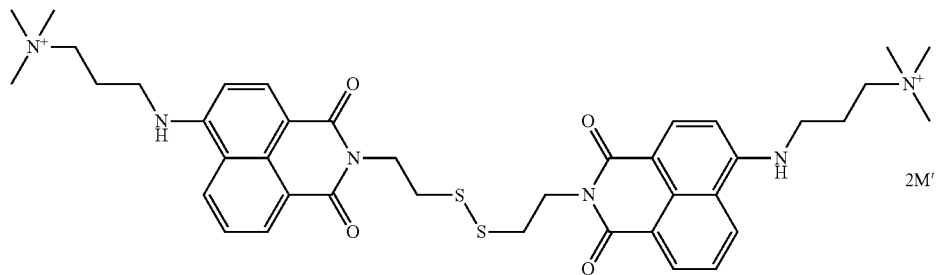
49
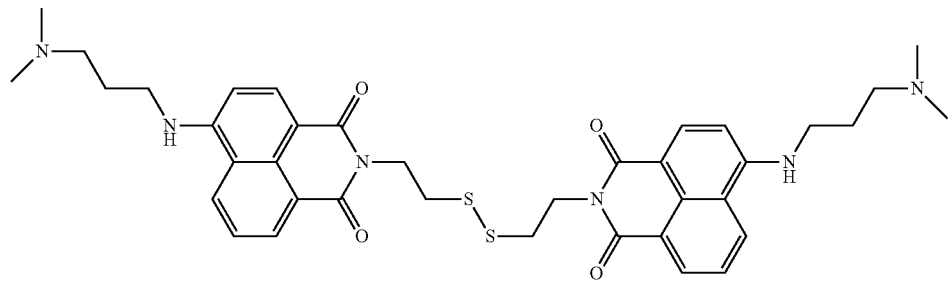
49bis
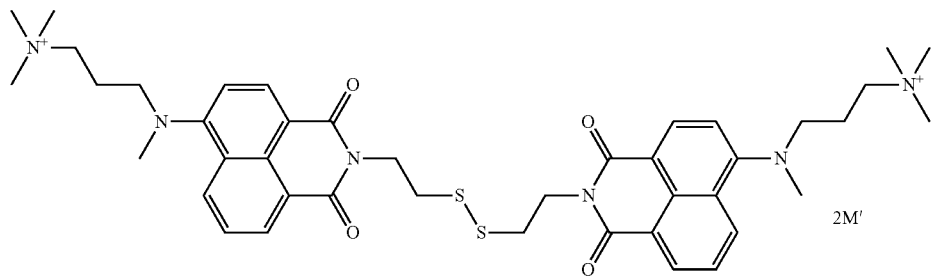
50
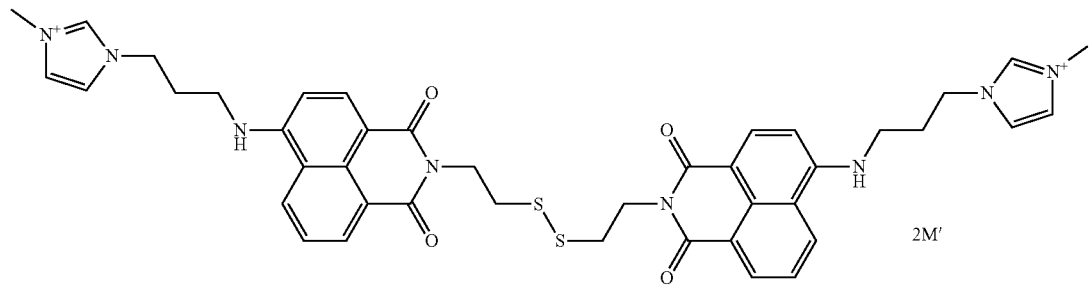
51
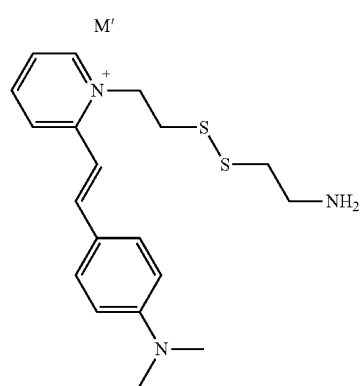
52
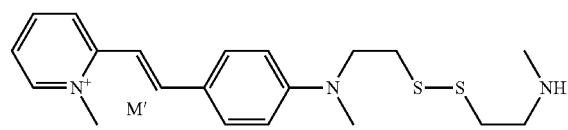
53

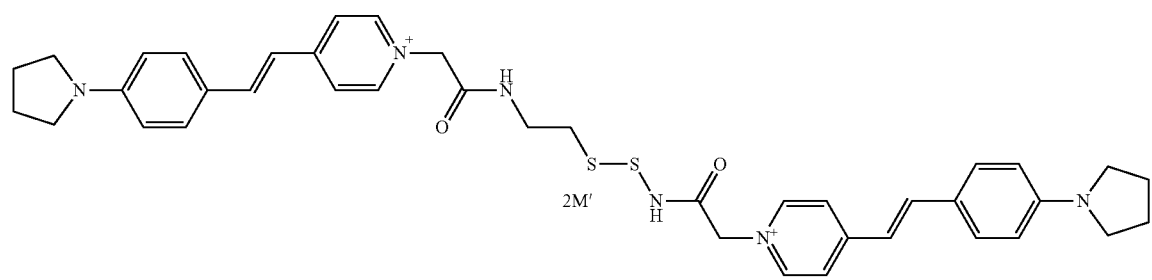
54
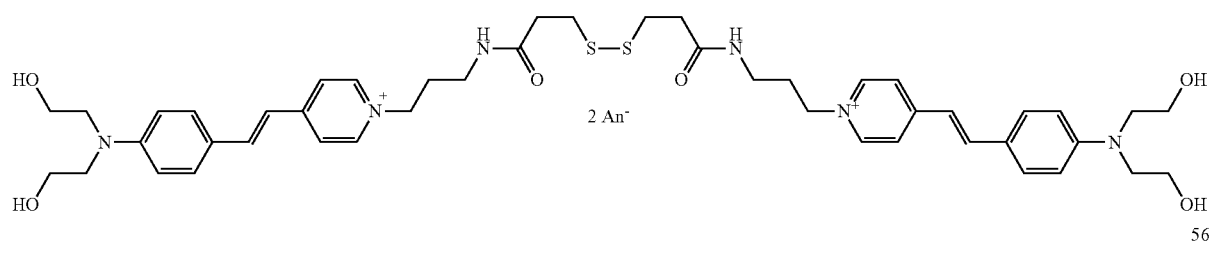
55
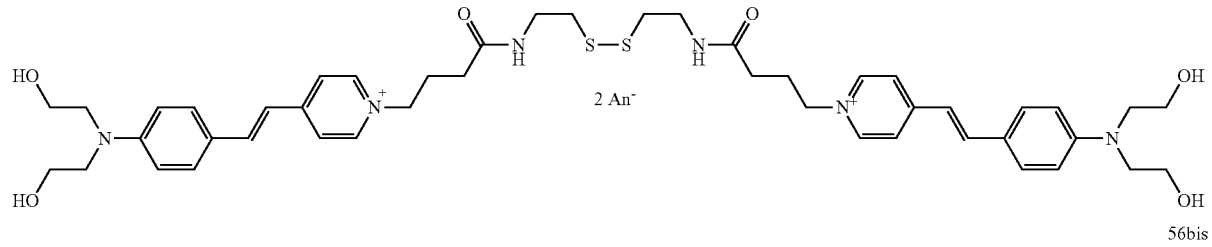
56
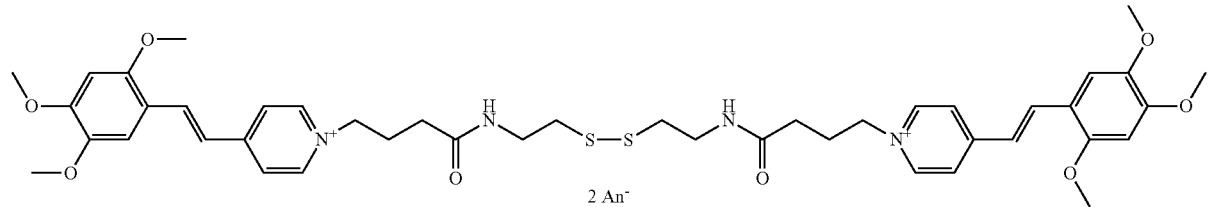
56bis
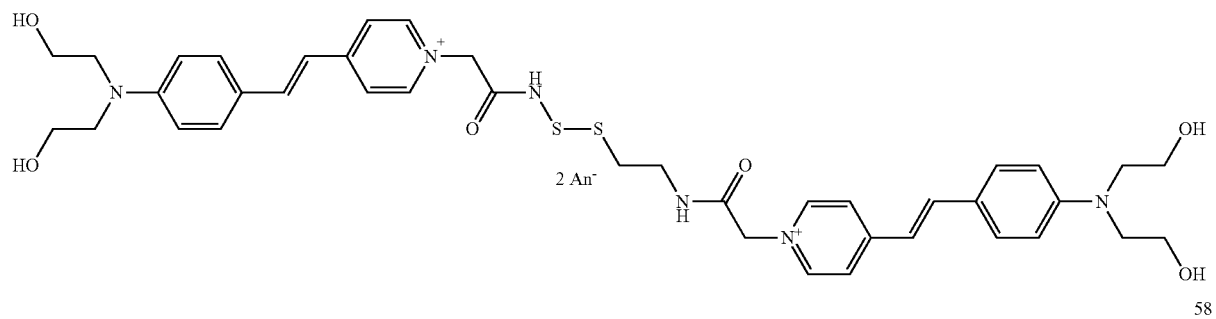
57
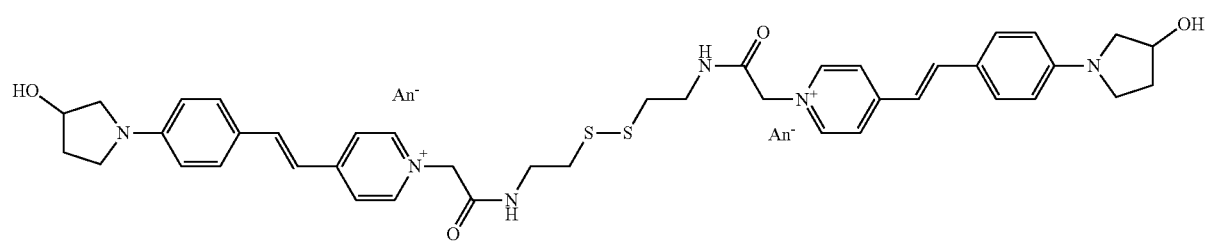
58

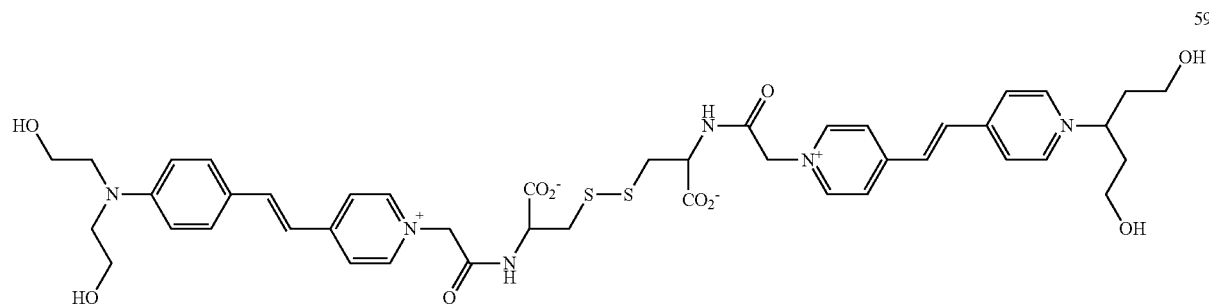
59
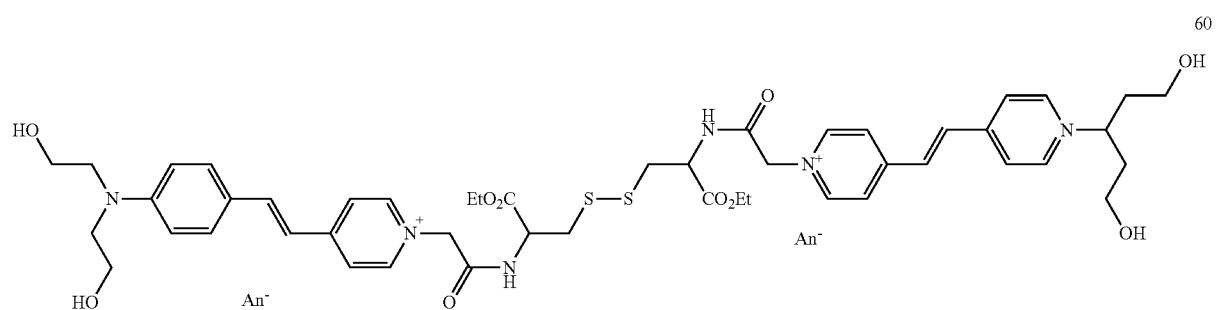
60
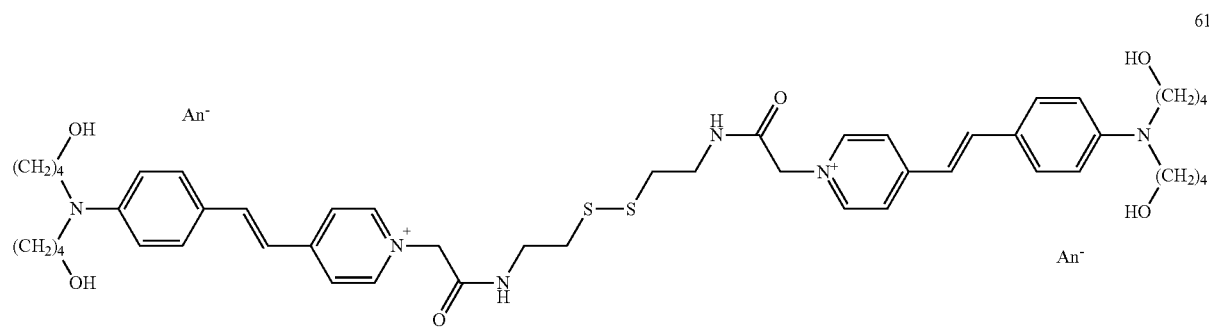
61
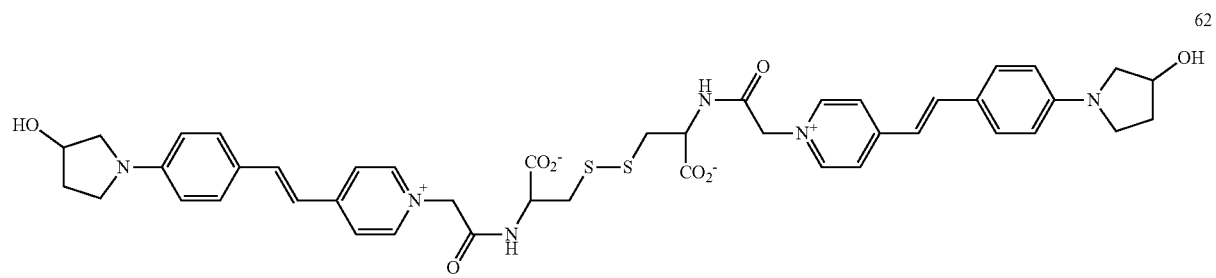
62
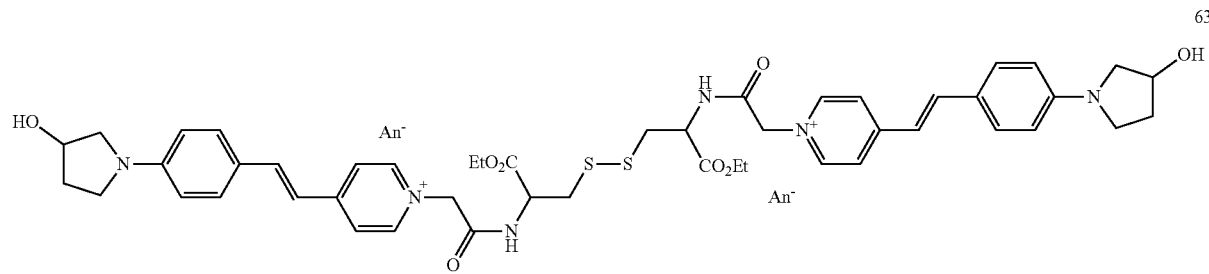
63

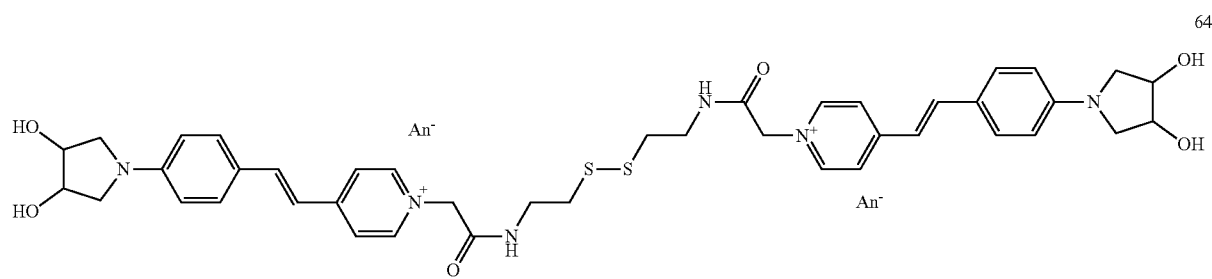
64
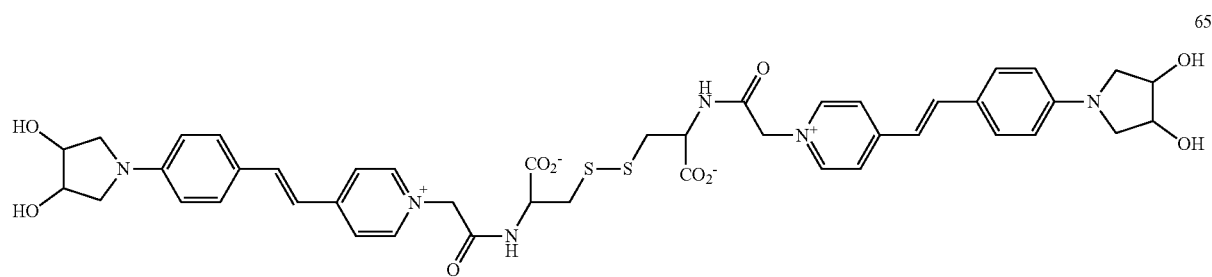
65
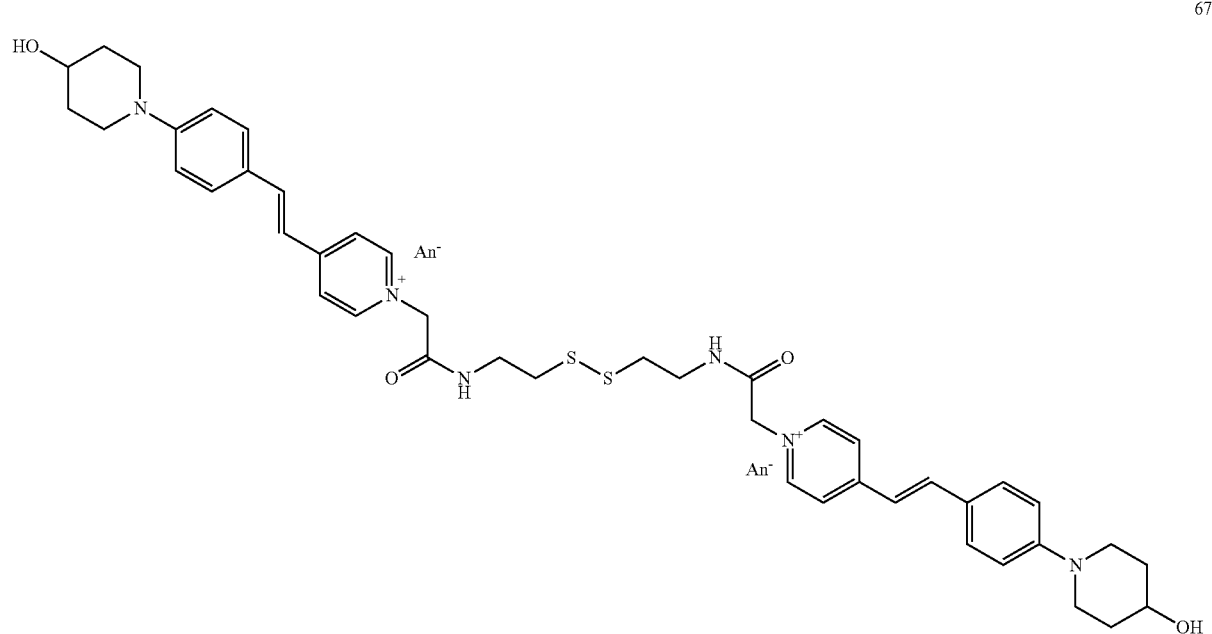
67
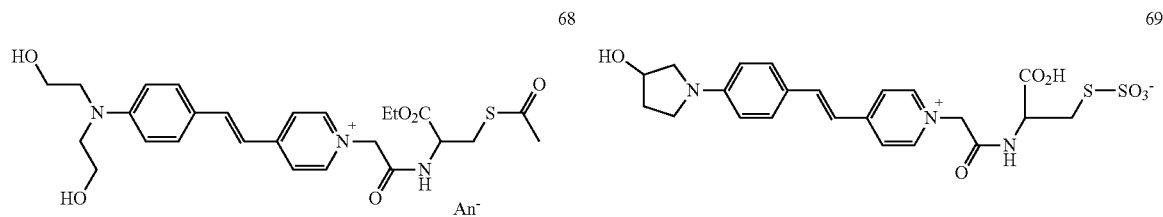
68 69

-continued
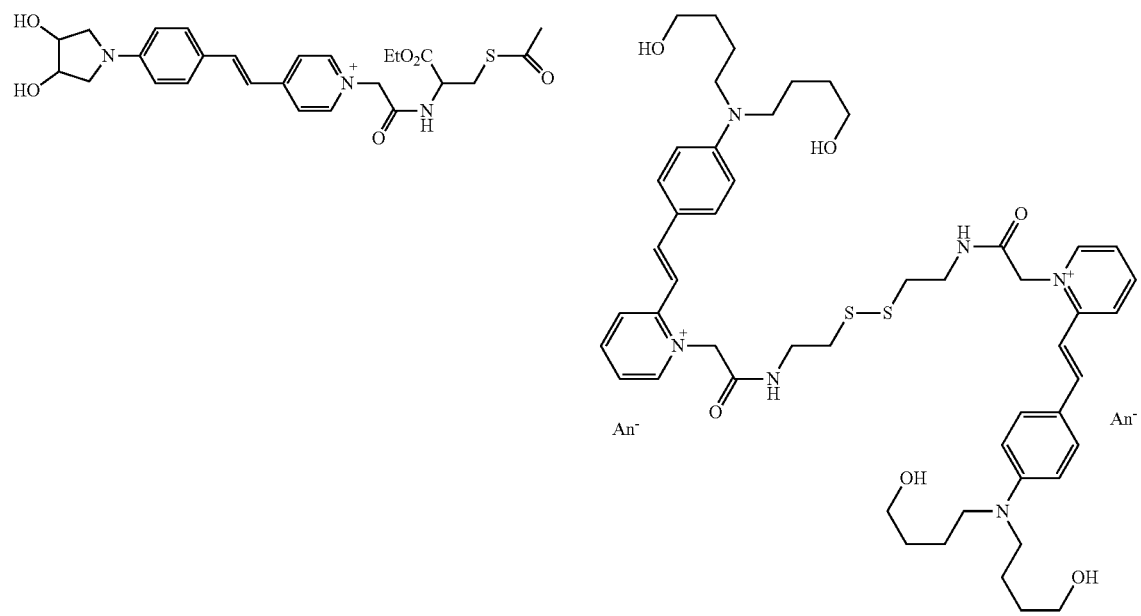
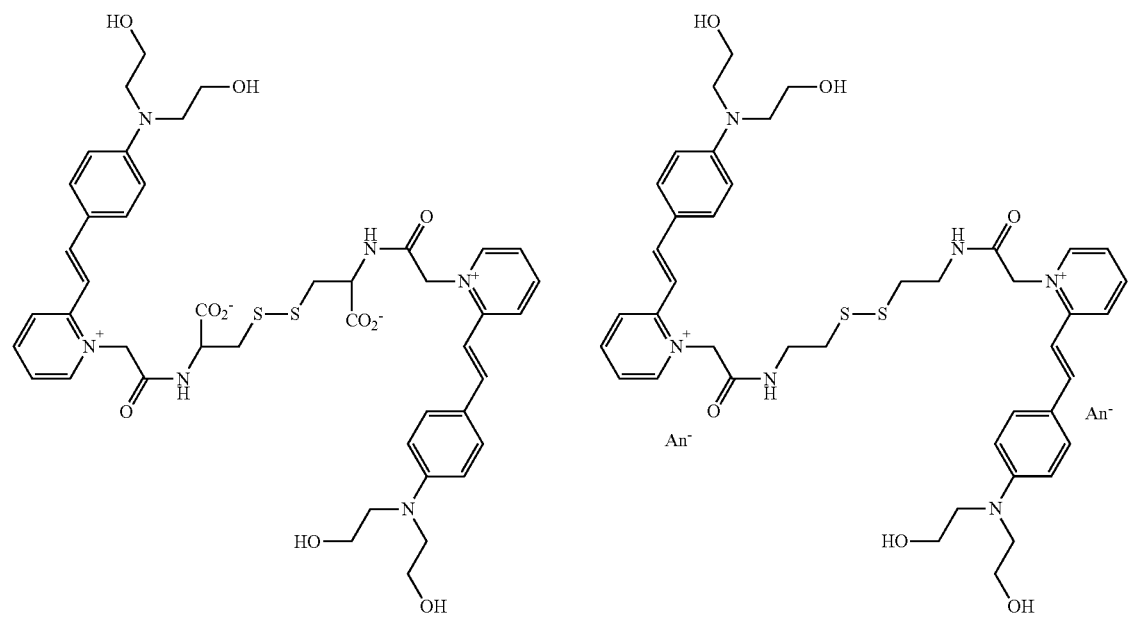

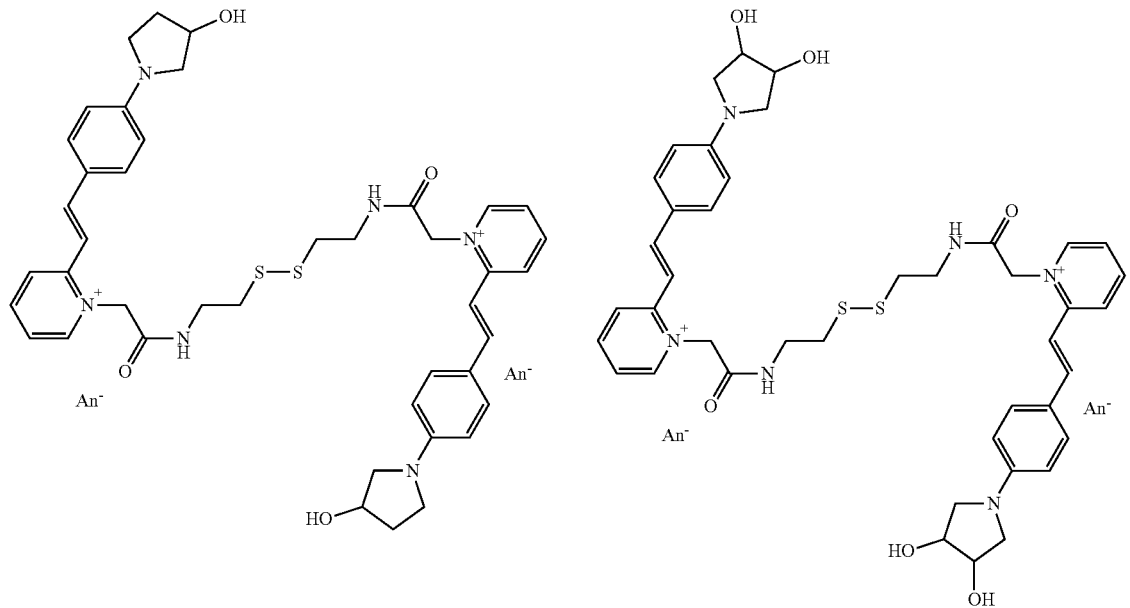
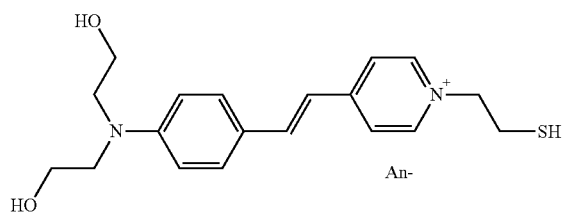
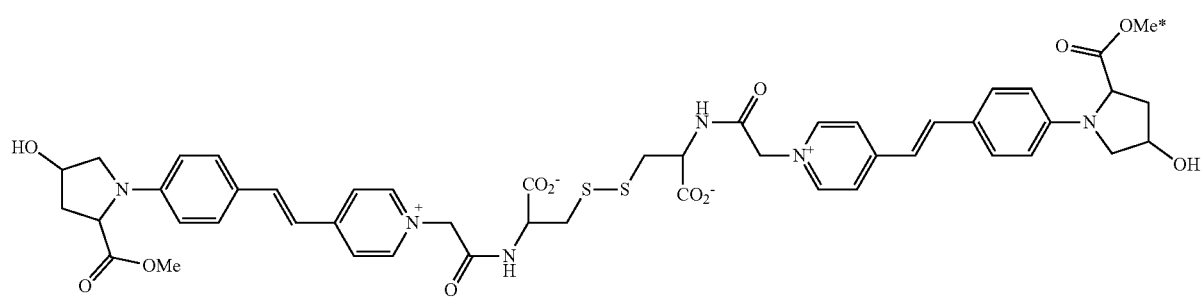
Me* represents an alkali metal or 1/2 an alkaline-earth metal; or a methyl
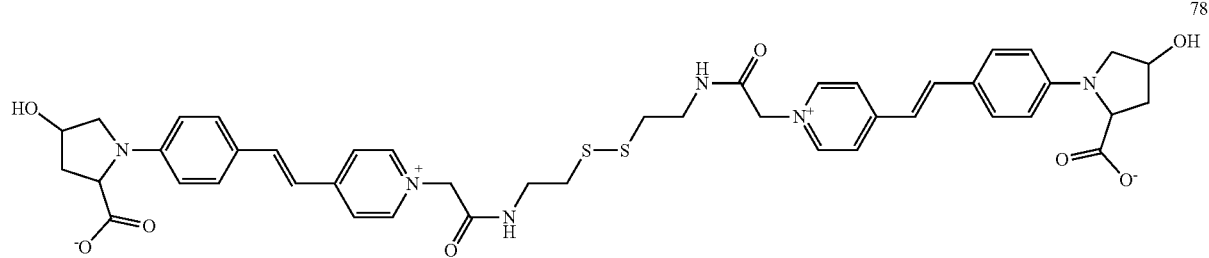

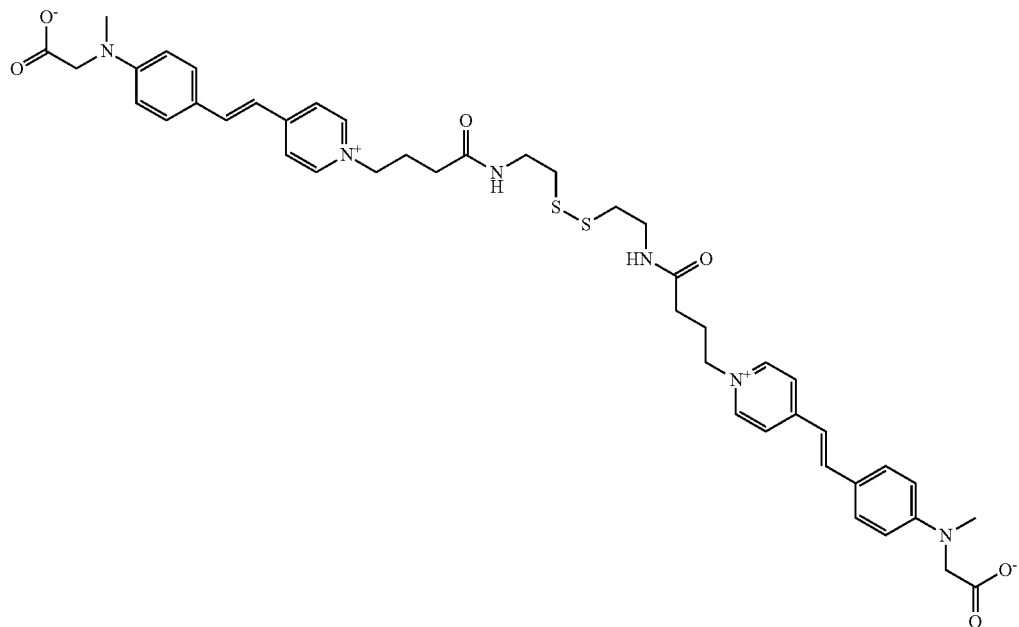
81
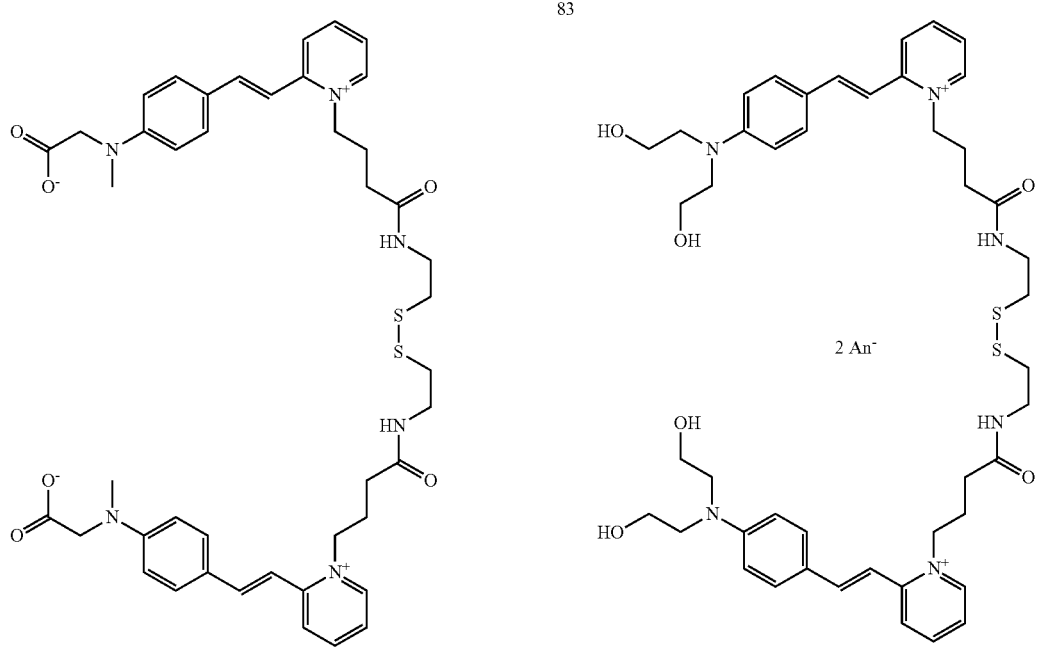
83
84
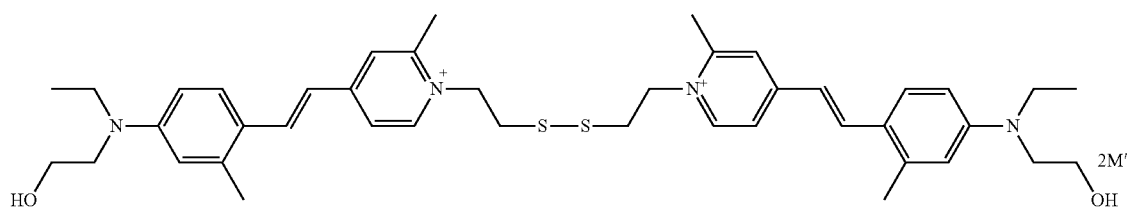
86

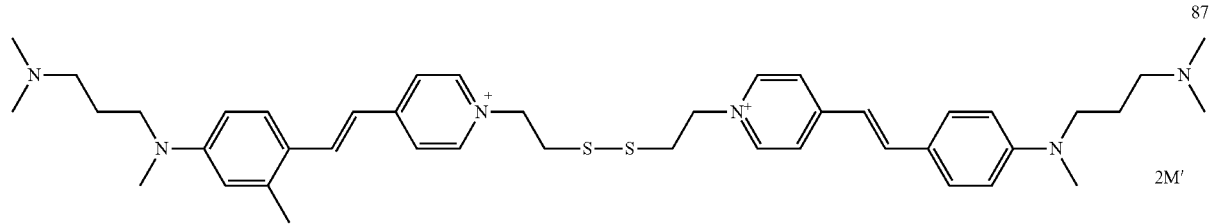
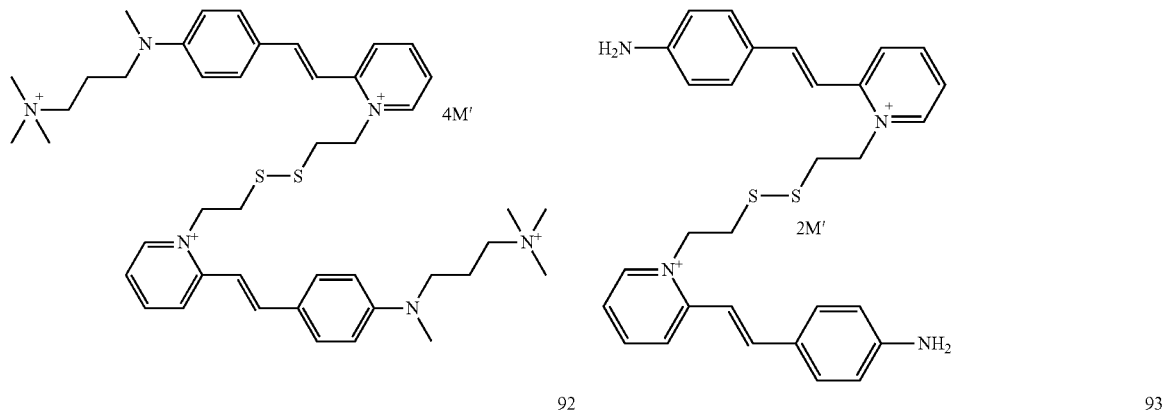
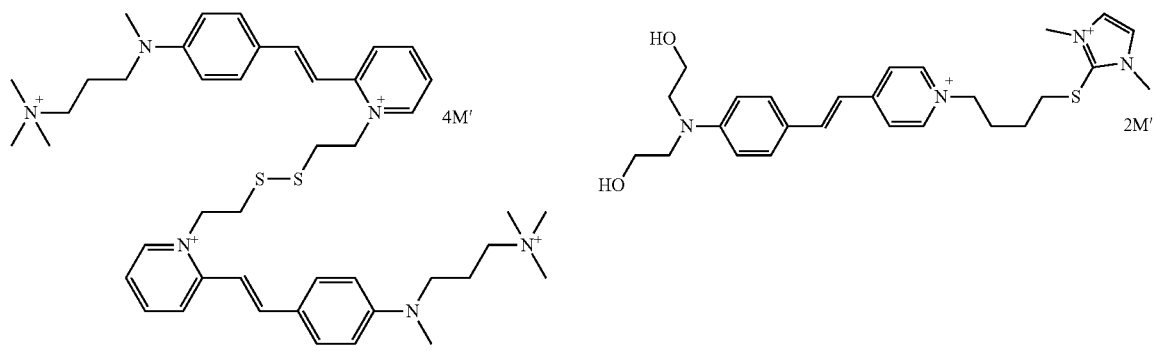
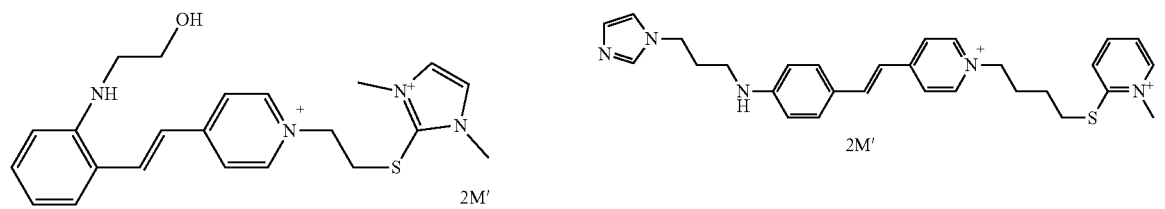
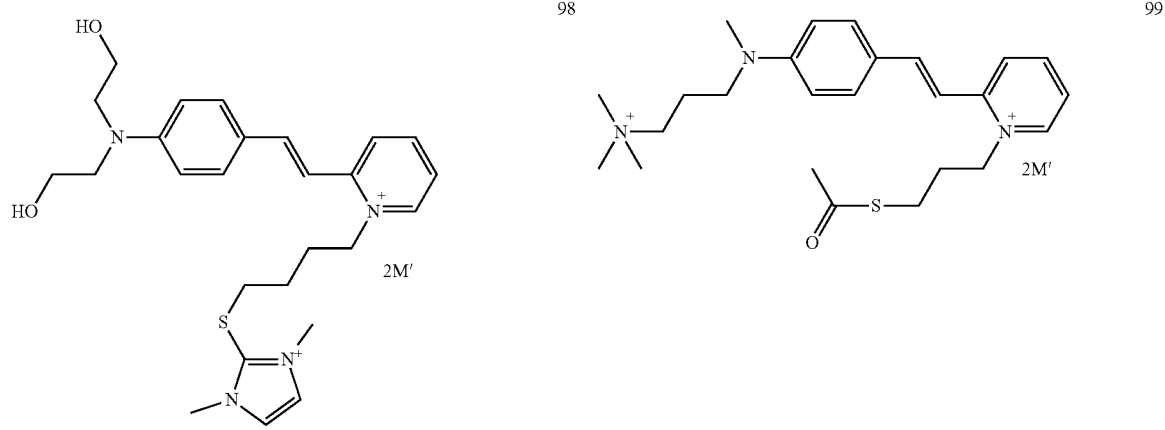

100 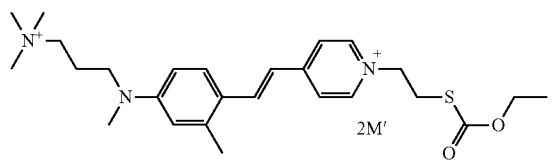
101 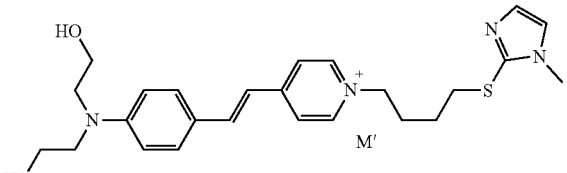
102 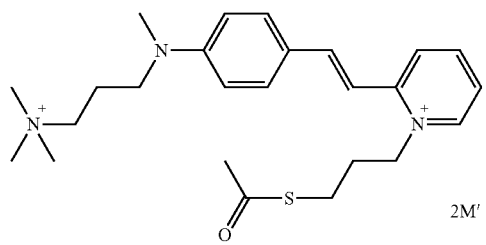
103 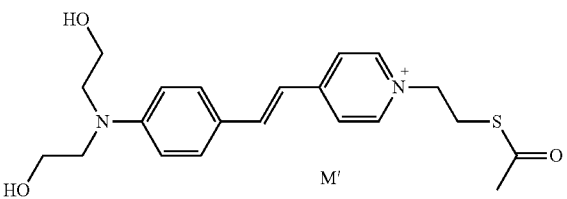
104 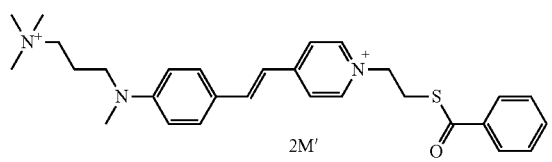
105 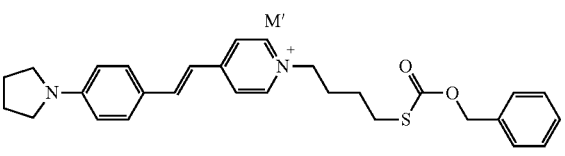
106 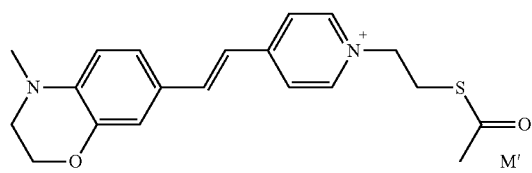
107 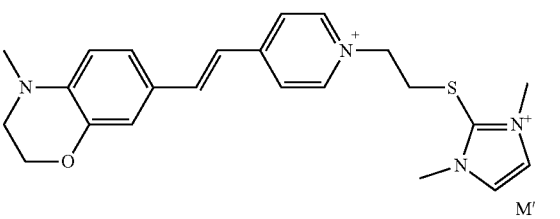
108 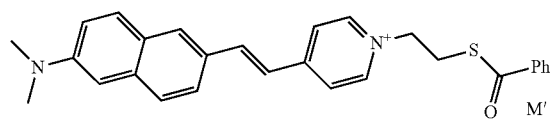
109 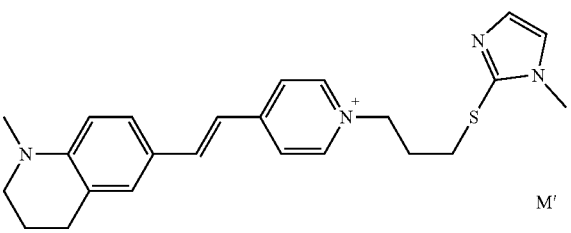
110 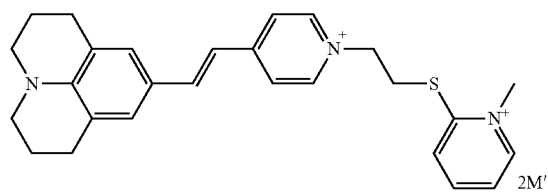
111 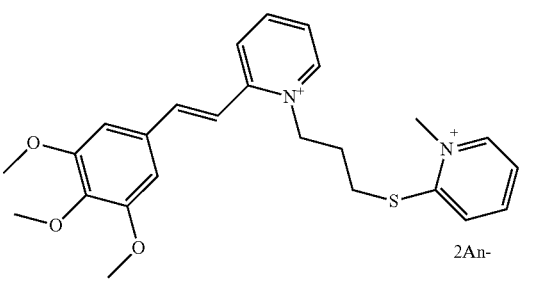

-continued

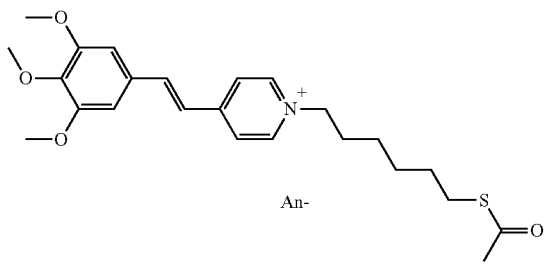

112

113

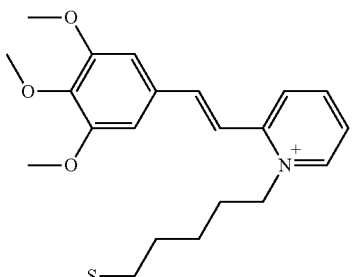

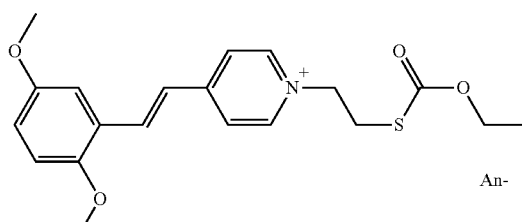

114

115

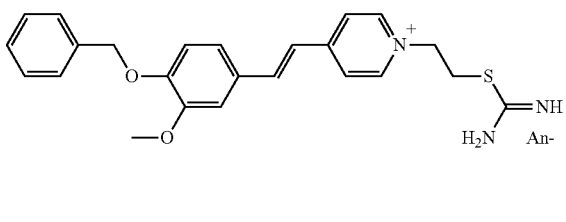

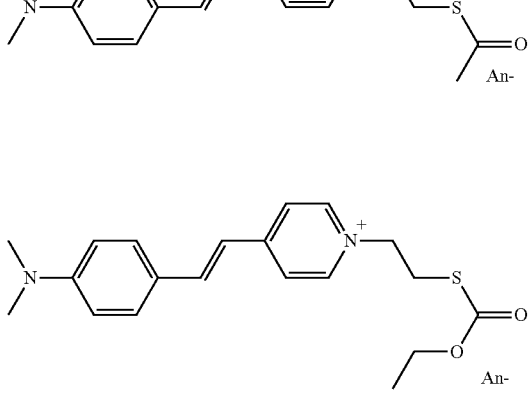

116

118

120

117

119

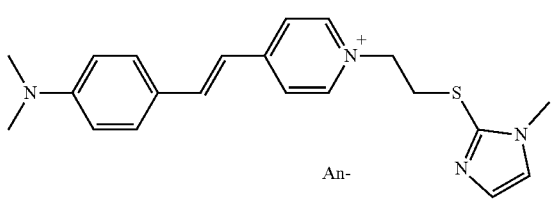

with An⁻ and M', which may be identical or different, preferentially identical, representing anionic counterions. More particularly, the anionic counterion is chosen from halides such as chloride, alkyl sulfates such as methyl sulfate, mesylate and $\frac{1}{2}(O=)_2SO^{2-}$ or $\frac{1}{2}SO_4^{2-}$.

More preferentially, the disulfide, thiol or protected-thiol fluorescent dyes b) as defined previously are chosen from compounds 31, 44, 49, 49bis and 55 56 56bis notably 44, 56 and 56bis.

According to a particularly advantageous embodiment of the invention, the disulfide, thiol or protected-thiol fluorescent dye b) is a dye comprising a "permanent" cationic charge, i.e. containing in its structure at least one quaternized nitrogen atom (ammonium) or quaternized phosphorus atom (phosphonium); preferentially quaternized nitrogen.

The composition according to the invention contains, in a cosmetic medium, an amount of disulfide, thiol or protected-thiol fluorescent dyes as defined previously, notably of formula (Ib) as defined previously, generally inclusively between 0.001% and 30% relative to the total weight of the composition.

Preferably, the amount of disulfide, thiol or protected-thiol fluorescent dyes as defined previously, notably of formula (Ib), is inclusively between 0.01% and 5% by weight relative to the total weight of the composition. By way of example, the dye(s) are in an amount of between 0.01% and 2% inclusive.

The Reducing Agents c)

The process for dyeing keratin fibers and the cosmetic composition according to the present invention may also optionally use, or comprise, c) one or more reducing agents.

The reducing agent(s) c) that are useful in the present invention are advantageously chosen from the compounds of formula (Ic) below, and also the addition salts thereof and mixtures thereof:

  (Ic)

in which formula (Ic),

X represents P, S or $SO_2$, q represents an integer equal to 0 or 1, t represents an integer equal to 1 or 2, and $R_{10}$ represents a linear or branched, saturated or unsaturated $C_1$ to $C_{20}$ alkyl radical, optionally interrupted with a heteroatom, and/or optionally substituted with one or more radicals chosen from hydroxyl, halo, amine, carboxyl, (($C_1$-$C_{30}$)alkoxy)carbonyl, amido, (($C_1$-$C_{30}$)alkyl)aminocarbonyl, (($C_1$-$C_{30}$)acyl)amino, mono- or dialkylamino, and mono- or dihydroxylamino radicals.

Preferably, the reducing agent(s) c) are chosen from thioglycolic acid, thiolactic acid, glyceryl monothioglycolate, cysteamine, N-acetylcysteamine, N-propionylcysteamine, cysteine, N-acetylcysteine, thiomalic acid, pantetheine, 2,3-dimercaptosuccinic acid, N-(mercaptoalkyl)-ω-hydroxyalkylamides, N-mono- or N,N-dialkylmercapto-4-butyramides, aminomercaptoalkylamides, N-(mercaptoalkyl)succinamic acid and N-(mercaptoalkyl)succinimide derivatives, alkylamino mercaptoalkylamides, the azeotropic mixture of 2-hydroxypropyl thiogluconate and of (2-hydroxy-1-methyl)ethyl thioglycolate, mercaptoalkylaminoamides, N-mercaptoalkylalkanediamides and formamidinesulfinic acid derivatives, salts thereof, and mixtures thereof.

Preferably, the reducing agent(s) c) are also chosen from salts such as sodium sulfite, sodium dithionite or sodium thiosulfate, and mixtures thereof.

The reducing agent(s) c) of the invention are chemical and are advantageously applied in the form of an aqueous solution of which the content of chemical reducing agents is preferably between 0.01% and 10% by weight and more preferentially between 0.1% and 5% by weight, relative to the total weight of the aqueous solution.

According to a particular embodiment of the invention, the dyeing process does not use any reducing agent.

According to this preferred embodiment of the invention, the cosmetic composition comprising ingredients a) and b) does not comprise any reducing agent.

The Oxidizing Agents d)

The process for dyeing keratin fibers and the cosmetic composition according to the present invention may also optionally use, or comprise, one or more oxidizing agents d).

Preferably, the oxidizing agent(s) d) are chosen from chemical oxidizing agents.

The term "chemical oxidizing agent" means an oxidizing agent other than atmospheric oxygen.

More particularly, the chemical oxidizing agent(s) d) are chosen from hydrogen peroxide, hydrogen peroxide-generating systems, urea peroxide, alkali metal bromates or ferricyanides, peroxygenated salts, for instance persulfates, perborates, peracids and precursors thereof and percarbonates of alkali metals or alkaline-earth metals, and mixtures thereof.

Preferably, the chemical oxidizing agent(s) d) are chosen from hydrogen peroxide and hydrogen peroxide-generating systems.

According to a preferred embodiment, the hydrogen peroxide-generating system(s) are chosen from urea peroxide; polymeric complexes that can release hydrogen peroxide, chosen from polyvinylpyrrolidone/$H_2O_2$; oxidases; perborates; and percarbonates.

Preferably, the chemical oxidizing agent(s) d) are hydrogen peroxide, and more preferentially hydrogen peroxide in aqueous solution (aqueous hydrogen peroxide).

The chemical oxidizing agent(s) d) are advantageously applied in the form of an aqueous solution in which the content of chemical oxidizing agents is preferably between 0.05% and 5% by weight and more preferentially between 0.1% and 2% by weight, relative to the total weight of the aqueous solution.

According to a preferred embodiment of the invention, the dyeing process does not use any chemical oxidizing agent.

According to this preferred embodiment of the invention, the cosmetic composition comprising ingredients (a) and (b) does not comprise any oxidizing agent.

The Cosmetic Medium and the Solvents

The blue, violet and green dye(s) a), as defined previously, and b) the disulfide, thiol or protected-thiol fluorescent dye(s), as defined previously, and also, when they are present, the oxidizing agent(s) d) and/or the reducing agent(s) c), may be dissolved beforehand before being applied to the keratin fibers.

In other words, the ingredients used in the dyeing process of the present invention may be present in one or more compositions.

The composition(s) comprising the ingredients according to the present invention are cosmetic compositions, i.e. they are preferably aqueous. Besides water, they may comprise one or more organic solvents, or mixtures thereof.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The pH

The pH of the composition(s) used in the dyeing process of the invention and of the composition of the invention comprising ingredients a) and b) as defined previously is preferably between 2 and 12 and more preferentially between 3 and 11. It may be adjusted to the desired value by means of acidifying or alkaline agents usually used in the dyeing of keratin fibers, or alternatively using standard buffer systems.

The pH of the composition which comprises the ingredients a) and/or b) and/or c) and that of the composition(s) used in the dyeing process of the invention (notably the composition which comprises the reducing agent(s) c) when they are present) is preferably between 6 and 11 inclusive, more preferentially between 7 and 10, and better still between 7.5 and 9.5, such as between 9 and 9.5.

Among the acidifying agents, mineral and organic acids as defined previously, examples that may be mentioned include mineral or organic acids, for instance hydrochloric acid, orthophosphoric acid or sulfuric acid, carboxylic acids, for instance acetic acid, tartaric acid, citric acid or lactic acid, and sulfonic acids.

The alkaline agent(s) may be chosen notably from mineral, organic or hybrid alkaline agents, and mixtures thereof.

The mineral alkaline agent(s) are preferably chosen from ammonia, alkaline carbonates or bicarbonates such as ammonium, sodium or potassium carbonate or bicarbonate, ammonium, sodium or potassium hydroxide, or mixtures thereof.

The organic alkaline agent(s) are preferably chosen from organic amines with a $pK_b$ at 25° C. of less than 12, preferably less than 10 and even more advantageously less than 6. It should be noted that this is the $pK_b$ corresponding to the function of highest basicity. In addition, the organic amines do not comprise any alkyl or alkenyl fatty chain comprising more than ten carbon atoms.

The organic alkaline agent(s) are preferably chosen from alkanolamines, in particular mono-, di- or tri-hydroxy($C_1$-$C_6$)alkylamines, such as triethanolamine, oxyethylenated and/or oxypropylenated ethylenediamines, amino acids, polyamines of formula (Ie) below, and mixtures thereof:

(Ie)

in which formula (Ie), W is a divalent $C_1$ to $C_6$ alkylene radical optionally substituted with one or more hydroxyl groups or a $C_1$ to $C_6$ alkyl radical, and/or optionally interrupted with one or more heteroatoms such as O, or $NR_u$; $R_x$, $R_y$, $R_z$, $R_t$, and $R_u$, which may be identical or different, represent a hydrogen atom, a $C_1$ to $C_6$ alkyl or $C_1$ to $C_6$ hydroxyalkyl or $C_1$ to $C_6$ aminoalkyl radical.

Examples of amines of formula (Ie) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and include at least one acid function chosen more particularly from carboxylic acid, sulfonic acid, phosphonic acid and phosphoric acid functions. The amino acids may be in neutral or ionic form.

As amino acids that may be used in the present invention, mention may notably be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the following formula (IIe) R—$CH_2$—CH($NH_2$)—C(O)—OH and also the salts thereof; in which formula (IIe), R represents a group chosen from imidazolyl, preferably imidazolyl-4-yl; aminopropyl; aminoethyl; —$(CH_2)_2$N(H)—C(O)—$NH_2$; and —$(CH_2)_2$—N(H)—C(NH)—$NH_2$. The compounds corresponding to formula (IIe) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made notably of carnosine, anserine and balenine.

The organic amine may also be chosen from compounds including a guanidine function. As amines of this type that may be used in the present invention, besides arginine, which has already been mentioned as an amino acid, mention may be made notably of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) that are useful in the invention are chosen from aqueous ammonia, alkanolamines, amino acids in neutral or ionic form, in particular basic amino acids, and preferably corresponding to those of formula (IIe).

More preferentially, the alkaline agent(s) are chosen from and mixtures thereof, and better still from aqueous ammonia, ammonium bicarbonate, ammonium hydroxide, mono-, di- or tri-hydroxy($C_1$-$C_6$)alkylamines, such as MEA, and mixtures thereof.

Forms of the Composition

The composition(s) comprising the blue, violet or green dye(s) a) as defined previously, and the disulfide, thiol or protected-thiol fluorescent dye(s) b), as defined previously, may be in various presentation forms, such as in the form of liquids, lotions, creams or gels or in any other form that is suitable for dyeing keratin fibers.

It (they) may also be packaged under pressure in an aerosol container in the presence of a propellant or in a non-aerosol container and may form a foam.

Additives

When the ingredients used in the dyeing process according to the present invention are present in one or more composition(s), said composition(s) may also optionally comprise one or more additives, different from the ingredients of the invention and among which mention may be made of fatty substances, cationic, anionic, nonionic, amphoteric or zwitterionic surfactants, cationic, anionic, nonionic or amphoteric polymers or mixtures thereof, antidandruff agents, anti-seborrhea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, notably polymeric thickeners, opacifiers or nacreous agents, antioxidants, hydroxy acids, fragrances, preserving agents, pigments and ceramides.

Needless to say, a person skilled in the art will take care to select this or these optional additional compound(s) such that the advantageous properties intrinsically associated with the composition(s) according to the invention are not, or are not substantially, adversely affected by the envisaged addition(s).

The above additives may generally be present in an amount, for each of them, of between 0 and 20% by weight relative to the total weight of the composition comprising them.

The Dyeing Process

The process for dyeing keratin fibers according to the present invention comprises the application to said keratin fibers of the following ingredients:
  a) one or more blue, violet or green dyes as defined previously, and
  b) one or more disulfide, thiol or protected-thiol fluorescent dyes, as defined previously,
it being understood that the blue, violet or green dye(s) (ingredients a)) and the disulfide, thiol or protected-thiol fluorescent dye(s) (ingredients b)) are applied to said keratin fibers jointly or sequentially.

In other words, the dyeing process according to the present invention may be performed in one or more steps.

According to a particularly preferred embodiment, the blue, violet or green dye(s) a) and the disulfide, thiol or protected-thiol fluorescent dye(s) b), as defined previously, are applied jointly (or together), i.e. simultaneously, to the keratin fibers. According to this embodiment, the dyeing process is performed in one step.

According to this one-step embodiment, the process comprises a step of applying to said keratin fibers a cosmetic composition according to the invention which comprises one or more blue, violet or green dyes a) as defined previously, and one or more disulfide, thiol or protected-thiol fluorescent dyes b) as defined previously, to the keratin fibers.

According to another particularly preferred embodiment, the blue, violet or green dye(s) a), as defined previously, and the disulfide, thiol or protected-thiol fluorescent dye(s) b), as defined previously, are applied sequentially, i.e. successively. According to this other embodiment, the dyeing process is performed in at least two steps.

According to a first embodiment in at least two steps, the disulfide, thiol or protected-thiol fluorescent dye(s) b), as defined previously, are applied to the keratin fibers subsequently to the blue, violet or green dye(s) a), as defined previously. In other words, the disulfide, thiol or protected-thiol fluorescent dye(s) b), as defined previously, are applied after the blue, violet or green dye(s) a), as defined previously.

According to this first embodiment, the process for dyeing keratin fibers comprises at least the following two successive steps:
  a first step of applying to said keratin fibers a cosmetic composition comprising one or more blue, violet or green dyes a) as defined previously, followed by
  a second step of applying to said keratin fibers a cosmetic composition which comprises one or more disulfide, thiol or protected-thiol fluorescent dyes b) as defined previously.

According to a preferred embodiment in at least two steps, the blue, violet or green dye(s) a), as defined previously, are applied to the keratin fibers subsequently to the fluorescent dye(s) b), as defined previously. In other words, the blue, violet or green dye(s) a), as defined previously, are applied after the disulfide, thiol or protected-thiol fluorescent dyes b), as defined previously.

According to this preferred embodiment, the process for dyeing keratin fibers comprises at least the following two successive steps:
  a first step of applying to said keratin fibers a cosmetic composition comprising one or more disulfide, thiol or protected-thiol fluorescent dyes b) as defined previously, followed by
  a second step of applying to said keratin fibers a cosmetic composition comprising one or more blue, violet or green dyes a) as defined previously.

The keratin fibers, in particular human keratin fibers such as the hair, which are treated with the process of the invention, may be pretreated with one or more reducing agents c) as defined previously, in particular if the process of the invention uses ingredient b) before ingredient a).

According to a particular embodiment of the process of the invention, the blue, violet or green dye(s) a), as defined previously, and the disulfide, thiol or protected-thiol fluorescent dye(s) b), as defined previously, are applied jointly to the keratin fibers; preferably, the process comprises a step of applying to the keratin fibers a cosmetic composition which comprises one or more blue, violet or green dyes a) as defined in any previously and one or more disulfide, thiol or protected-thiol fluorescent dyes (b), as defined previously.

Preferably, ingredients a) and b) are applied to the keratin fibers in a bath ratio that may range from 0.1 to 10 and more particularly from 0.2 to 8. For the purposes of the present invention, the term "bath ratio" means the ratio between the total weight of ingredient a) or b) and the total weight of keratin fibers to be treated.

When the dyeing process is performed in one step, ingredients a) and b) are advantageously left to stand on the keratin fibers for a time ranging from 1 to 90 minutes and more preferentially for a time ranging from 5 to 60 minutes.

When the dyeing process is performed in at least two steps, each of the ingredients a) and b) may be advantageously left to stand on the keratin fibers for a time ranging from 1 to 60 minutes and more preferentially for a time ranging from 5 to 50 minutes.

On conclusion of the dyeing process according to the invention, in one or at least two steps, the keratin fibers are advantageously rinsed with water. They may optionally be washed with a shampoo, followed by rinsing with water, before being dried or left to dry.

When the dyeing process is performed in at least two steps, the keratin fibers are advantageously rinsed with water between each step. In other words, the dyeing process may comprise an intermediate rinsing step between the application of the first ingredient and the application of the second ingredient. During this intermediate rinsing step, the keratin fibers may optionally be washed with a shampoo, followed by rinsing with water, before being dried or left to dry.

The dyeing process according to the present invention may be performed at room temperature (25° C.) or with heating.

According to a particular embodiment, the process of the invention also comprises the application to said keratin fibers of one or more reducing agents c), as defined previously, said reducing agent(s) c) possibly being applied before, at the same time as or after the application of the blue, violet or green dye(s) as defined previously and/or the application of the disulfide, thiol or protected-thiol fluorescent dye(s) as defined previously; or alternatively, said reducing agent(s) c) are present with the blue, violet or green dye(s) a) as defined previously, and/or the disulfide, thiol or protected-thiol fluorescent dye(s) as defined previously; preferably, said reducing agent(s) are chosen from i) the reducing agents of formula (Ic) as defined previously, ii) thioglycolic acid, iii) thiolactic acid, iv) glyceryl monothioglycolate, v) cysteamine, vi) N-acetylcysteamine, vii) N-propionylcysteamine, viii) cysteine, ix) N-acetylcysteine, x) thiomalic acid, xi) pantetheine, xii) 2,3-dimercaptosuccinic acid, xiii) N-(mercaptoalkyl)-ω-hydroxyalkylamides, xiv) N-mono or N,N-dialkylmercapto-4-butyramides, xv) aminomercaptoalkylamides, xvi) N-(mercaptoalkyl)succinamic acid derivatives, xvii) N-(mercaptoalkyl)succinimide acid derivatives, xviii) alkylaminomercaptoalkylamides, ix) the azeotropic mixture of 2-hydroxypropyl thioglyconate and of (2-hydroxy-1-methyl)ethyl thioglycolate, x) mercaptoalkylaminoamides, xi) N-mercaptoalkylalkanediamides, xii) formamidinesulfinic acid derivatives, addition salts thereof and mixtures thereof; preferably, the reducing agent(s) c) are in the presence of the blue, violet or green dye(s) a) as defined previously, and of the disulfide, thiol or protected-thiol fluorescent dye(s) as defined previously, or alternatively the reducing agent(s) c) are applied at the same time as the dye(s) a) as defined previously, and of the disulfide, thiol or protected-thiol fluorescent dye(s) as defined previously.

When they are present, the reducing agent(s) c) may therefore be applied separately or jointly with one of the ingredients a) or b). Preferably, when they are present, the reducing agent(s) c) are applied jointly with ingredient (b).

When they are present, the oxidizing agent(s) may be applied separately or jointly with one of the ingredients a) or b). Preferably, when they are present, the oxidizing agent(s) are applied after application of ingredients a) and b).

According to a particular embodiment, the process for dyeing keratin fibers according to the present invention comprises the following successive steps:

a first step of applying to said keratin fibers a cosmetic composition comprising one or more blue, violet or green dyes a) as defined previously, followed by a second step of applying to said keratin fibers a cosmetic composition comprising one or more disulfide, thiol or protected-thiol fluorescent dye(s) b), as defined previously, and one or more reducing agents c), as defined previously.

According to a particular embodiment of the dyeing process of the invention, no step of said process involves an oxidizing agent.

According to another advantageous embodiment of the dyeing process of the invention, no step of said process involves a reducing agent.

The dyeing process according to the present invention may be applied to wet or dry, preferably dry, keratin fibers.

The Multi-Compartment Device

The present invention also relates to a multi-compartment device comprising a first compartment containing one or more blue, violet or green dyes a), as defined previously, and a second compartment containing one or more disulfide, thiol or protected-thiol fluorescent dyes b), as defined previously, optionally a third compartment comprising one or more reducing agents c), as defined previously, and optionally another compartment comprising one or more oxidizing agents d) as defined previously.

Use

A subject of the present invention is also the use of one or more fluorescent dye(s) b), as defined previously, combined with one or more blue, violet or green dyes a), as defined previously, for the dyeing of light keratin fibers, notably human keratin fibers such as the hair, in chestnut-brown, dark chestnut-brown, brown, brown with a tint or even black, without using an additional dye other than a) or b).

According to a particular embodiment, the "keratin fibers" are human keratin fibers and more particularly the hair.

The examples that follow serve to illustrate the invention without, however, being limiting in nature.

EXAMPLES

In the examples that follow, all the amounts are given as weight percentages relative to the total weight of the composition, unless otherwise indicated.

| Blue dyes | structures |
|---|---|
| Dye 1 | 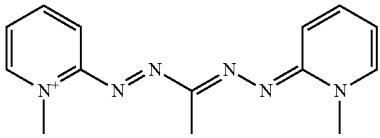 |
| Dye 2 | 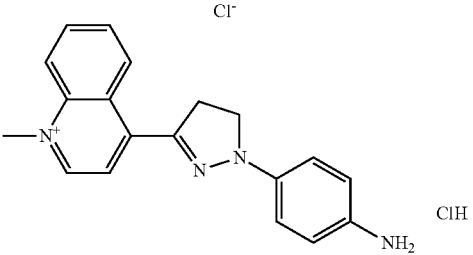 [SMILES: [Cl-] ; C[n+]1ccc(C2=NN(c3ccc(N)cc3)CC2)c2ccccc21 ; Cl] |

| Blue dyes | structures |
|---|---|
| Dye 3 | 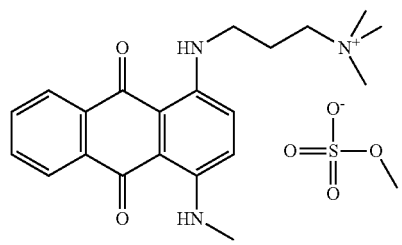 |
| Dye 4 | 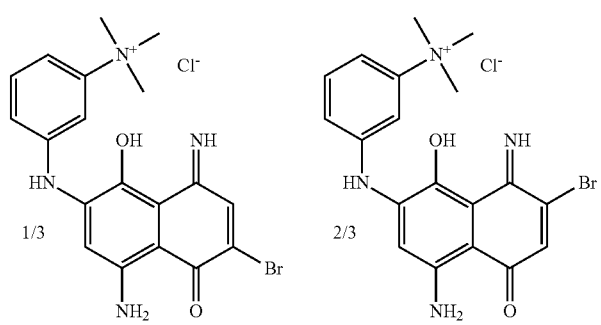 [SMILES: C[N+](C)(C)c1cccc(Nc2cc(N)c3c(c2O)C(=N)C=C(Br)C3=O)c1 ; [Cl-] ; C[N+](C)(C)c1cccc(Nc2cc(N)c3c(c2O)C(=N)C(Br)=CC3=O)c1 ; [Cl-]] |
| Dye 7 | 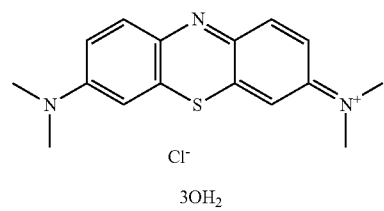 |
| Dye 8 | 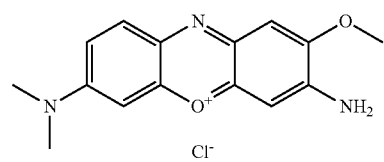 |
| Dye 9 | 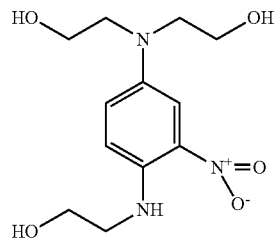 [SMILES: O=[N+]([O-])c1cc(N(CCO)CCO)ccc1NCCO] |
| Dye 10 | 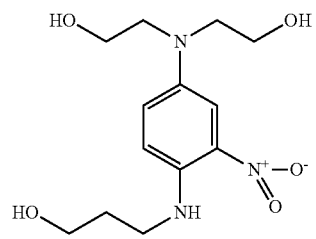 [SMILES: O=[N+]([O-])c1cc(N(CCO)CCO)ccc1NCCCO] |

-continued
| Blue dyes | structures |
|---|---|
| Dye 11 | 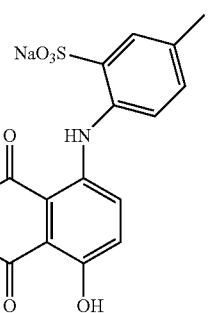 |
| Dye 12 | 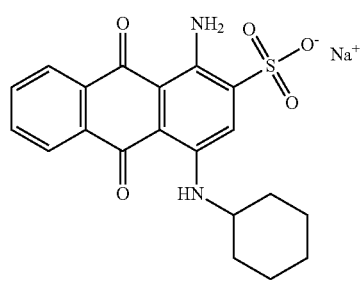 [SMILES: Nc1c(S(=O)(=O)[O-])cc(NC2CCCCC2)c2c1C(=O)c1ccccc1C2=O ; [Na+]] |
| Dye 13 | 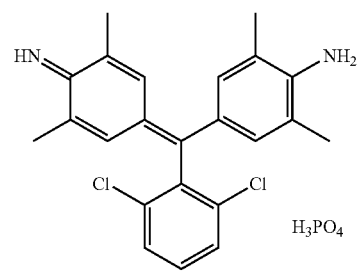 |
| Dye 14 | 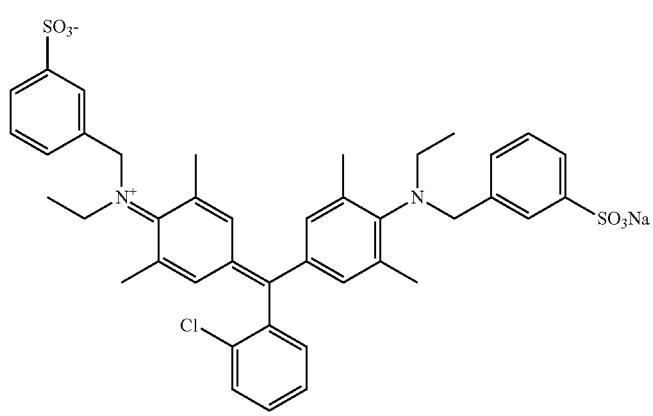 |
| Dye 15 | 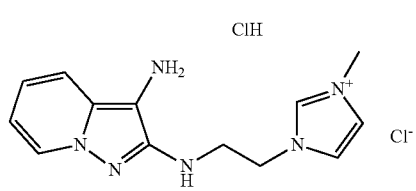 [SMILES: Cl ; C[n+]1ccn(CCNc2nn3ccccc3c2N)c1 ; [Cl-]] |

-continued
| Blue dyes | structures |
|---|---|
| Dye 16 | 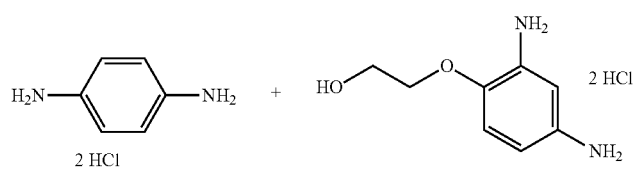 [SMILES: Nc1ccc(N)cc1 ; Nc1ccc(OCCO)c(N)c1] |
| Dye 17 | 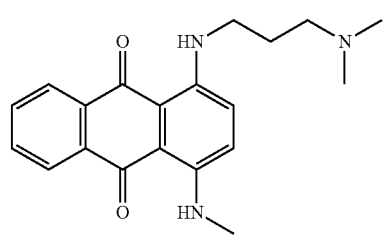 [SMILES: CNc1ccc(NCCCN(C)C)c2c1C(=O)c1ccccc1C2=O] |
| Dye 18 | 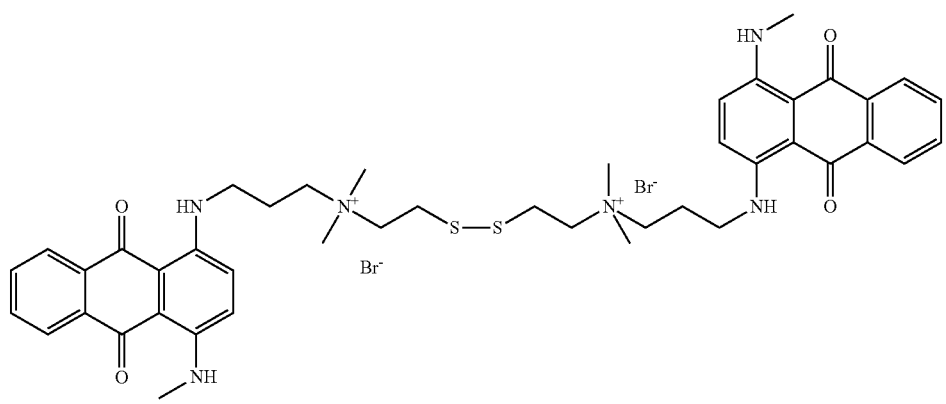 [SMILES: CNc1ccc(NCCC[N+](C)(C)CCSSCC[N+](C)(C)CCCNc2ccc(NC)c3c2C(=O)c2ccccc2C3=O)c2c1C(=O)c1ccccc1C2=O ; [Br-] ; [Br-]] |

| Dye | Structure of thiol/protected-thiol/disulfide fluorescent dyes |
|---|---|
| a | 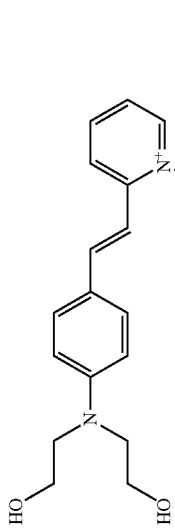 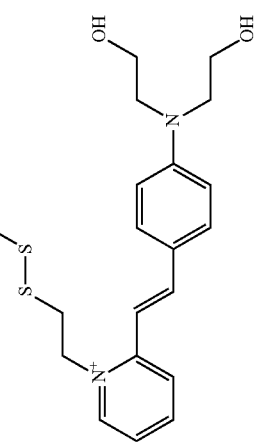 |
| b | 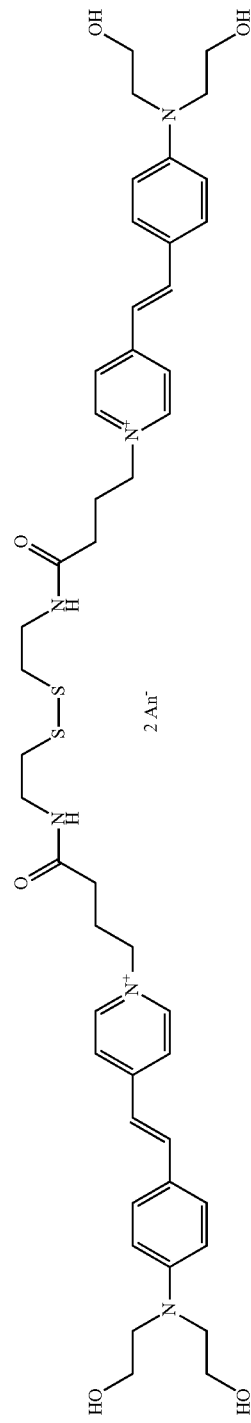 |

Example 1

The dyes studied were tested at a mass concentration of 0.3 g % of each dye. The solutions are adjusted to pH 9 with aqueous ammonia solution.

Dyes 4 and b; 8 and b are tested on locks of natural hair containing 90% white hairs, as a mixture (1 g), according to two application methods:

The dyes are mixed in identical 1/1 ratios at a concentration of 0.3 g per 100 g of the composition comprising 0.15% of dye 4 and 0.15% of dye b, for example (0.15%/0.15%: g/g).

The dye composition (aqueous dyeing medium) is applied according to two treatment methods:
- a treatment in reducing medium, i.e. the reducing agent is added to the dye composition.
- a treatment without reducing medium.

For these two treatments, a fixing phase, containing aqueous hydrogen peroxide solution, is prepared subsequently As an example of application, the process is performed in the following manner:

Treatment in reducing medium with fixing phase described as follows:
1) application of 10 ml of medium consisting of: 90% dyeing medium+10% reducing medium; leave-on time of 20 minutes; rinsing
2) fixing in oxidizing medium by applying 1 ml of the fixing medium: leave-on time of 5 minutes; rinsing, and then
3) shampooing/rinsing Aqueous Dyeing Medium

| Ingredients | Amount per 100 g of composition |
| --- | --- |
| Dyes | 0.3 g |
| Water | qs 100 g |

Reducing Medium

| Ingredients | Amount per 100 g of composition |
| --- | --- |
| Thioglycolic acid (TGA) | 10 |
| Monoethanolamine (MEA) | 0.605 |
| Water | qs 100 g |

Fixing Medium

| Ingredients | Amount per 100 g of composition |
| --- | --- |
| $H_2O_2$ (50 volumes) | 0.48 |
| Antioxidant | 0.02 |
| 85% Orthophosphoric acid | 0.012 |
| Water | qs 100 g |

In Non-Reducing Medium
Dyeing medium/water (0.15%/0.15% g/g)

| Ingredients | Amount per 100 g of composition |
| --- | --- |
| Dyes | 0.3 g |
| Water | qs 100 g |

1) treatment (build-up) in simplex aqueous medium: leave-on time of 25 minutes; rinsing
2) shampooing/rinsing The light and shampoo resistances are evaluated for the various combinations Light Resistance
1) irradiation in an Oriel 1600 W solar simulator—irradiation time: 2 hours 40 minutes
2) colorimetric reading at the end of the cycle 24 hours later Shampoo Resistance
1) 20 shampoo washes broken down into four cycles of five shampoo washes
2) drying and colorimetric reading after each cycle of five shampoo washes The hair dyeing results are as follows:

| Blue dye | Fluorescent dye | Medium | Color obtained | Light resistance | Shampoo resistance |
| --- | --- | --- | --- | --- | --- |
| Dye 4 | Dye b | Reducing agent | Matt dark brown | + | +++ |
| Dye 8 | Dye b | Reducing agent | Black | ++ | +++ |
| Dye 4 | Dye b | Without reducing agent | Dark brown | +++ | ++ |
| Dye 8 | Dye b | Without reducing agent | Black | +++ | +++ |

With +: weak, ++: moderate, +++ strong

Example 2

The dyes 13 (tested at a set mass concentration of 0.2 g %) and b (tested at two mass concentrations in combination with compound 13-0.2 g %/0.5 g %) are combined on locks of natural hair containing 90% white hairs in a one-stage or two-stage process in the presence of reducing agent (for the disulfide fluorescent dye) followed by a fixing phase at the end of application; it should be noted that the blue dye 13 is applied at the spontaneous pH (pH 4.5) or at alkaline pH (pH 8.45) in the two-stage process and at the pH of the combination (pH 8.5) in the one-stage process. The pH adjustment is performed in the presence of MEA.

The following combinations were prepared:

| Test | Dye studied |
| --- | --- |
| 1 | Two stages: b (fluorescent) in reducing medium at 0.2% and then 13 (blue) at 0.2% |
| 2 | Two stages: b (fluorescent) in reducing medium at 0.5% and then 13 (blue) at 0.2% |
| 3 | One stage: 13 (blue) at 0.2% + b (fluorescent) in reducing medium at 0.2% |
| 4 | One stage: 13 (blue) at 0.2% + b (fluorescent) in reducing medium at 0.5% |

Application Protocol:

Application in Two Stages—Disulfide Fluorescent Dye and then Blue Dye:

1—Application of the Fluorescent Dye b in Reducing Medium:

The 1-g lock is laid flat in a trough at room temperature. 9 ml of the disulfide fluorescent dye b at 0.5% (or 0.2%)+1 ml of reducing solution at 0.6% at pH 8.5 are then added and maintained in contact with the lock for 20 minutes. The lock is then rinsed with water and then wrung dry between the fingers.

2—Application of the Blue Dye 13:

The lock is once again laid flat in a trough at room temperature. 10 ml of solution of dye 13 at 0.2% are then added and maintained in contact with the lock for 20 minutes. The lock is then rinsed with water and then wrung dry between the fingers.

3—Fixing Phase:

The lock is once again laid flat in a trough at room temperature. 9 ml of water+1 ml of oxidizing solution at 0.6% are then added and maintained in contact with the lock for 10 minutes. The lock is then rinsed with water and one shampoo wash is then performed. It is then dried under a hood at 40° C. and the colorimetric measurements are then taken.

One-Stage Application

The 1-g lock is laid flat in a trough at room temperature. 5 ml of solution of the blue dye 13 at 0.2% at the spontaneous pH and 5 ml of solution of fluorescent dye 13 at 0.4% (or 1%) at pH 8.45+1 ml of reducing solution at 0.6% at pH 8.5 are then added and maintained in contact with the lock for 20 minutes. The lock is then rinsed with water and then wrung dry between the fingers. It is once again laid flat in a trough at room temperature. 9 ml of water+1 ml of oxidizing solution at 0.6% are then added and maintained in contact with the lock for 10 minutes. The lock is then rinsed with water and one shampoo wash is then performed. It is dried under a hood at 40° C. and the colorimetric measurements are then taken.

The treatment in reducing medium with (or without) a fixing phase described as follows:

Aqueous Dyeing Medium (Two Concentrations Tested)

| Ingredients | Amount per 100 g of composition |
|---|---|
| Fluorescent dye | 0.5 g/0.2 g |
| Water | qs 100 g |

Reducing Medium

| Ingredients | Amount per 100 g of composition (pH 8.5) |
|---|---|
| TGA | 10 |
| MEA | 0.605 |
| Water | qs 100 g |

Fixing Medium

| Ingredient | Amount per 100 g of composition |
|---|---|
| $H_2O_2$ 50 volumes | 0.48 |
| Water | qs 100 g |

1—treatment in reducing medium: [90% dyeing medium+10% reducing medium]; leave-on time of 20 minutes; rinsing
2—fixing in oxidizing medium at the end of application of the dyes: leave-on time of 10 minutes; rinsing
3—shampooing/rinsing The following dyeing results were obtained:

| Blue dye | Fluorescent dye | Process | Color obtained |
|---|---|---|---|
| Dye 13 | Dye b | One stage | Dark brown |
| Dye 13 | Dye b | Two stages | Coppery brown |

Example 3

The blue dyes (tested depending on the dye at two molar concentrations of $5\times10^{-3}$ mol % or $2.5\times10^{-3}$ mol %) and the fluorescent dye a (tested at the mass concentration of 0.5 g % in combination with the blue compounds of the example) are combined on locks of natural hair containing 90% white hairs in a two-stage process in the presence of reducing agent (for the fluorescent dye) followed by a fixing step;

The following combinations were prepared:

| Blue dye | Disulfide fluorescent dye |
|---|---|
| Dye 1 | Dye a |
| Dye 2 | Dye a |
| Dye 3 | Dye a |
| Dye 4 | Dye a |
| Dye 8 | Dye a |

The dyeing tests are performed on 0.5 g locks of 90% NW Caucasian hair. Irrespective of the application order, the dyes are applied successively in the following manner Condition for application of the blue/violet direct dyes: dissolution of the dye in water (concentration: $5\times10^{-3}$ mol per 100 ml of application water for 30 minutes at room temperature; rinsing with water (temperature 30° C.) and then one shampoo wash is performed; drying is performed under a hood for 10 minutes/gram of hair (temperature: 40° C.)

Aqueous Dyeing Medium

| Ingredient | Amount per 100 g of composition |
|---|---|
| Fluorescent dye | 0.5 g |
| Water | qs 100 g |

Reducing Medium

| Ingredient | Amount per 100 g of composition (pH 8.5) |
|---|---|
| TGA | 10 |
| MEA | 0.605 |
| Water | qs 100 g |

Fixing Medium

| Ingredient | Amount per 100 g of composition |
|---|---|
| $H_2O_2$/50 volumes | 0.48 |
| Water | qs 100 g |

1—treatment in reducing medium: [90% dyeing medium+10% reducing medium]; leave-on time of 20 minutes; rinsing
2—fixing in oxidizing medium at the end of application of the dyes: leave-on time of 5 minutes; rinsing
3—shampooing/rinsing/drying under a hood for 10 minutes/gram of hair Three application orders were evaluated:
blue/violet dye and then disulfide fluorescent dye (bf application order)
disulfide fluorescent dye and then blue/violet dye (fb application order)
The following dyeing results were obtained:

| Blue dye (concentration) | Fluorescent dye | Application sense | Color obtained |
|---|---|---|---|
| Dye 1 ($5 \times 10^{-3}$ mol %) | Dye a | bf | Black |
| Dye 2 ($5 \times 10^{-3}$ mol %) | Dye a | bf | Coppery brown |
| Dye 2 ($5 \times 10^{-3}$ mol %) | Dye a | fb | Brown |
| Dye 3 ($5 \times 10^{-3}$ mol %) | Dye a | bf | Brown |
| Dye 3 ($5 \times 10^{-3}$ mol %) | Dye a | fb | Brown |
| Dye 4 ($5 \times 10^{-3}$ mol %) | Dye a | bf | Brown with a matt tint |
| Dye 4 | Dye a | fb | Brown |

-continued

| Blue dye (concentration) | Fluorescent dye | Application sense | Color obtained |
|---|---|---|---|
| ($5 \times 10^{-3}$ mol %) | | | |
| Dye 8 ($5 \times 10^{-3}$ mol %) | Dye a | bf | Black |
| Dye 8 ($5 \times 10^{-3}$ mol %) | Dye a | bf | Black with a matt tint |
| Dye 8 ($5 \times 10^{-3}$ mol %) | Dye a | fb | Black |

Blue direct dyes: 7
Blue self-oxidizing dye: 15,
Oxidation dyes: combination in oxidizing medium leads to a blue color: 16+16',
Blue anthraquinone dyes: 17 and
Blue disulfide anthraquinone dyes: 18

The fluorescent dye combined, in a second stage, is the disulfide fluorescent dye b.

In a first stage, the blue dyes are applied to the keratin fibers and a composition comprising the disulfide fluorescent dyes b as defined previously is then applied

| Compounds | Type of dye Color | Structure |
|---|---|---|
| 15 | Self-oxidizing blue | 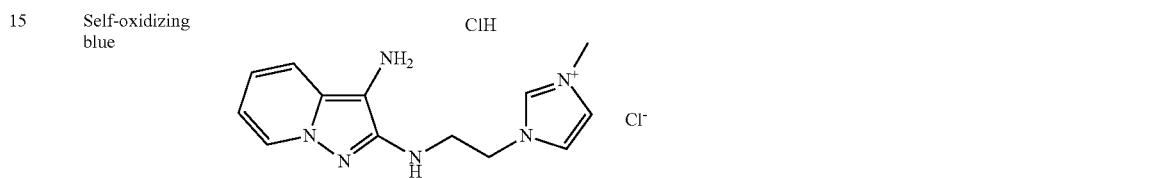 |
| 16 | Oxidation base + Oxidation coupler | 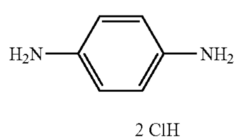 |
| 16' | Blue | 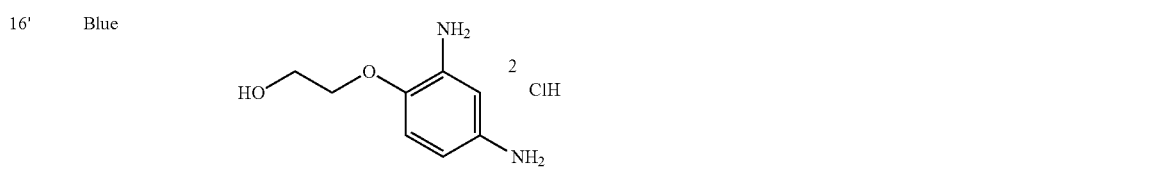 |
| 7 | Blue direct | 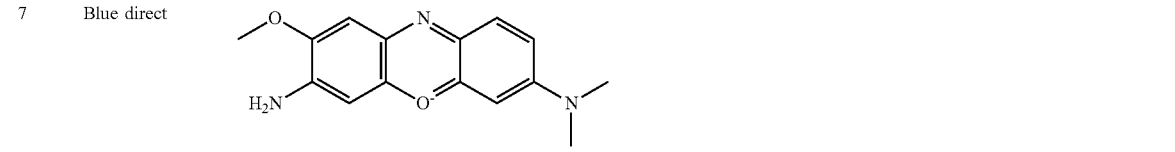 |
| 17 | Blue direct | 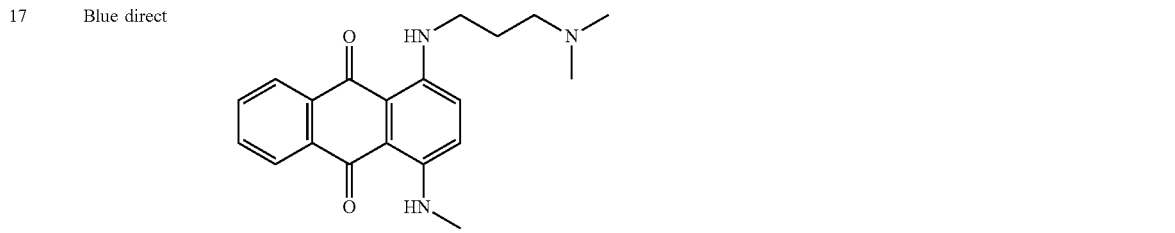 |

| Compounds | Type of dye Color | Structure |
|---|---|---|
| 18 | Blue disulfide | (structure: anthraquinone dimer with 2 Br⁻ counterions, linked via disulfide-bridged bis-ammonium chain) |

Application Protocol:

The process of the invention and the compositions of the invention were evaluated on NW 90% white Caucasian hair The reducing solution of the process is a composition of thioglycolic acid TGA in water at 0.6% (by mass) brought to pH=8.5 with MEA. The oxidizing solution is an aqueous hydrogen peroxide composition at 0.6% in water. The composition comprising the blue dyes is a composition at 0.5% (by mass) in water. The composition comprising the disulfide fluorescent dyes at 0.5% (by mass) in water.

1—Application of the Dye in Reducing Medium:

The 1-g lock is laid flat in a trough at room temperature. 9 ml of solution of the dye to be studied at 0.5%+1 ml of reducing composition at 0.6% are then added and maintained in contact with the lock for 20 minutes. The lock is then rinsed with water and then wrung dry between the fingers.

2—Application of the Fluorescent Dye b in Reducing Medium:

The lock is once again laid flat in a trough at room temperature. 9 ml of composition of the fluorescent dye at 0.5%+1 ml of reducing solution at 0.6% are then added and maintained in contact with the lock for 20 minutes. The lock is then rinsed with water and then wrung dry between the fingers.

3—Application of the Oxidizing Medium:

The lock is once again laid flat in a trough at room temperature. 9 ml of water+1 ml of oxidizing solution at 0.6% are then added and maintained in contact with the lock for 10 minutes. The lock is then rinsed with water and one shampoo wash is then performed. The lock is then dried with a hairdryer and the colorimetric measurements are then taken.

Results in the L*a*b* System

The color of the locks was evaluated in the L*a*b* system, using a Minolta® CM 3600D spectrocolorimeter, (Illuminant D65).

In this L*a*b* system, L* represents the lightness, a* indicates the green/red color axis and b* indicates the blue/yellow color axis. The higher the value of L, the lighter or less intense the color. Conversely, the lower the value of L, the darker or more intense the color. The higher the value of a*, the redder the shade, and the higher the value of b*, the yellower the shade.

Study on the hair containing 90% white hairs (90 NW):

Table of results: L, a, b measurements

| Dyes | L* (D65) | Associated color |
|---|---|---|
| Dye alone (comparative) | | |
| 7 | 20.31 | blue |
| 15 | 31.91 | |
| 16 + 16' | 57.67 | |
| 16 + 16' pH 9.5 | 56.75 | |
| 17 | 39.86 | |
| 18 | 31.37 | |
| b + TGA | 45.74 | red |
| Dye and then fluorescent (invention) | | |
| 7 + b | 19.09 | Intense black |
| 15 + b | 20.09 | Brown-black |
| 18 + b | 23.60 | Blueish black |
| 17 + b | 23.55 | Blueish black |

The colorimetric data measurements above show that, in a first stage, the treatment in reducing medium of the blue dye affords a significantly greater intensity of coloring than the control without reducing medium. The dyeing combination of blue followed by a dyeing treatment with the disulfide fluorescent dyes of the invention b leads to a change in the color toward browns with coppery or black shades. It should be noted that dye 7 followed by application of the disulfide fluorescent dye b leads to a very intense and luminous black coloring.

| Dyes | L* (D65) |
|---|---|
| 16 + 16' (comparative) | 57.67 |
| 16 + 16' pH 9.5 (comparative) | 56.75 |
| b + TGA (comparative) | 45.74 |
| 16 + 16' + b (invention) | 39.93 |

Moreover, it was shown that for the combination of oxidation dyes 16 and 16' combined with the disulfide dye b, the intensity was significantly improved by the presence of a fluorescent dye b according to the invention versus the dyes taken alone independently.

The invention claimed is:

1. A process for dyeing light keratin materials, wherein the process comprises applying to the light keratin materials:
   a) at least one blue, violet, or green dye chosen from:
      a1) phenoxazinium, phenothiazinium, or phenazinium dyes;
      a3) triarylmethane dyes;
      a4) naphthoquinone or anthraquinone dyes;
      a5) hydrazone dyes;
      a6) tetraazapentamethine dyes;
      a7) nitro dyes;
      a8) azomethine dyes;
      a9) self-oxidizing dyes; and/or
      a10) oxidation dyes; and
   b) at least one disulfide, thiol, or protected-thiol fluorescent dye;
   wherein a) the at least one blue, violet, or green dye and b) the at least one disulfide, thiol, or protected-thiol fluorescent dye are applied to said keratin materials jointly or sequentially;
   wherein a weight ratio of a) the at least one blue, violet, or green dye to b) the at least one disulfide, thiol, or protected-thiol fluorescent dye applied to the light keratin materials ranges from 0.1 to 10; and
   wherein the process does not comprise using an additional dye other than the dyes a) and b).

2. The process of claim 1, wherein a) the at least one blue, violet or green dye is chosen from direct dyes chosen from:
   a1) phenoxazinium, phenothiazinium, or phenazinium dyes;
   a3) triarylmethane dyes;
   a4) naphthoquinone or anthraquinone dyes;
   a5) hydrazone dyes;
   a6) tetraazapentamethine dyes;
   a7) nitro dyes; and/or
   a8) azomethine dyes.

3. The process of claim 1, wherein a) the at least one blue, violet, or green dye is chosen from:
   a1) phenoxazinium, phenothiazinium or phenazinium dyes;
   a3) triarylmethane dyes;
   a4) naphthoquinone or anthraquinone dyes;
   a5) hydrazone dyes;
   a6) tetraazapentamethine dyes; and/or
   a7) nitro dyes.

4. The process of claim 1, wherein a) the at least one blue, violet, or green dye is chosen from:
   a1) phenoxazinium, phenothiazinium, or phenazinium dyes of formula (Ia) below, organic or mineral acid or base salts thereof, optical isomers thereof, geometrical isomers thereof, tautomers thereof, solvates thereof, or mixtures thereof:

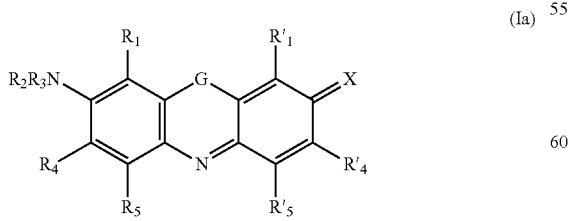

wherein formula (Ia):
   X represents an oxygen atom, a sulfur atom, $NR'_2$, or an ammonium radical $N^+R'_2R'_3$;
   G represents an oxygen atom, a sulfur atom or a radical $NR_6$;
   $R_2$, $R_3$, $R'_2$ and $R'_3$, which may be identical or different, represent, independently of each other:
      a hydrogen atom,
      a phenyl radical which is optionally substituted with one or more halogen atoms, or
      a linear or branched $C_1$ to $C_{20}$ alkyl radical, wherein the alkyl radical is:
   optionally substituted with one or more groups chosen from hydroxyl, $(di)(C_1\text{-}C_4)(alkyl)amino$, amino $—NH_2$, $(di)(C_1\text{-}C_4)(alkyl)aminocarbonyl$, aminocarbonyl $—C(O)NH_2$, and 5- or 6-membered heterocycloalkyl, optionally interrupted with one or more heteroatoms or with one or more groups comprising at least one heteroatom;
   $R_5$ and $R'_5$, which may be identical or different, represent:
      a hydrogen atom,
      a linear or branched $C_1$ to $C_6$ alkyl radical,
      an optionally substituted phenyl radical,
      a hydroxycarbonyl or carboxyl radical $—C(O)—OH$,
      a carboxylate radical $—C(O)—O^-$,
      a $(di)(C_1\text{-}C_6)(alkyl)aminocarbonyl$ radical,
      an aminocarbonyl radical $—C(O)NH_2$,
      a $(di)(C_1\text{-}C_6)(alkyl)amino$ radical, or
      an amino radical,
   $R_1$, $R_4$, $R'_1$ and $R'_4$, which may be identical or different, represent, independently of each other:
      a hydrogen atom,
      a $C_1$ to $C_4$ alkyl radical,
      a $C_1$ to $C_4$ alkoxy radical,
      a hydroxyl radical,
      an amino radical $R_7R_8N—$ with $R_7$ and $R_8$, which may be identical or different, representing a hydrogen atom, a $(C_1\text{-}C_4)alkyl$ group, or a phenyl radical which is optionally substituted with one or more halogen atoms or nitro(so) groups, or
      a nitro(so) radical;
   or alternatively $R_4$ forms, with one of the substituents $R_2$ or $R_3$, a saturated or unsaturated, optionally substituted heterocycle;
   $R_6$ represents a phenyl radical which is optionally substituted with a $(di)(C_1\text{-}C_4)(alkyl)amino$ radical and/or a linear or branched $C_1$ to $C_6$ alkyl radical;
   wherein when the compound of formula (Ia) is cationic, it optionally comprises one or more anions $Y^-$ and optionally one or more cations $M^+$ to ensure the electrical neutrality of the molecule, with
      $Y^-$ represents an anionic counterion or a mixture of organic or mineral anions;
      $M^+$ represents an organic or mineral cationic counterion;
   a3) the triarylmethane dyes chosen from the compounds of formula (IVa) below, optical isomers thereof, geometrical isomers thereof, tautomers thereof, organic or mineral, acid or base salts thereof, solvates thereof, or mixtures thereof:

(IVa)

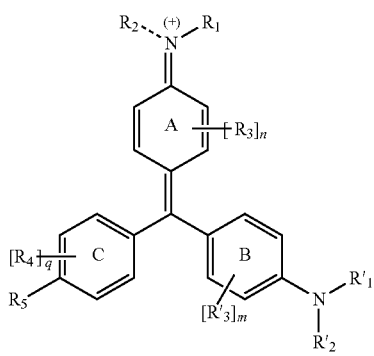

in which formula (IVa),
R$_1$, R$_2$, R'$_1$ and R'$_2$, which may be identical or different, represent:
a hydrogen atom,
a linear or branched C$_1$ to C$_{20}$ alkyl radical,
that is optionally substituted and/or
optionally interrupted with one or more heteroatoms, or
a benzyl radical optionally substituted with one or more SO$_3^-$ or SO$_3$H groups;
R$_3$ and R'$_3$, which may be identical or different, represent, independently of each other:
a linear or branched C$_1$ to C$_6$ alkyl radical,
a sulfonate group SO$_3^-$, or
a sulfonic group SO$_3$H;
n and m, which may be identical or different, represent two integers ranging from 0 to 4;
the radicals R$_4$, which may be identical or different, represent, independently of each other:
a linear or branched C$_1$ to C$_6$ alkyl radical,
a hydroxyl radical,
an SO$_3^-$ group,
an SO$_3$H group,
a halogen atom,
or alternatively two adjacent radicals R$_4$ together form an unsaturated 6-membered ring, optionally substituted with one or more SO$_3^-$ or SO$_3$H;
q is an integer ranging from 0 to 4;
R$_5$ represents:
a hydrogen atom,
a halogen atom,
an amino radical,
a hydroxyl radical,
a group which is electron-withdrawing via the mesomeric effect, or
a radical —NR$_6$R$_7$, in which R$_6$ and R$_7$, which may be identical or different, represent, independently of each other:
a hydrogen atom,
a linear or branched C$_1$ to C$_6$ alkyl radical;
wherein:
the radical R$_2$ is present or absent, symbolized by the dashed bond, when R$_2$ is present, the nitrogen atom that bears it is in cationic ammonium form, when R$_2$ is absent, the nitrogen atom that bears it is not charged, (+) is not present, and
the compound of formula (IVa) optionally comprises one or more anions An$^-$ and optionally one or more cations M$^+$ to ensure the electrical neutrality of the molecule;

with:
An$^-$ representing an anionic counterion; and
M$^+$ representing a cationic counterion;
a4) naphthoquinone or anthraquinone dyes chosen from the compounds of formula (Va) to (VI'a) below, optical isomers thereof, the geometrical isomers thereof, tautomers thereof, the organic or mineral, acid or base salts thereof the solvates thereof, or mixtures thereof:

(Va)

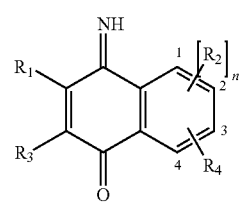

(VIa)

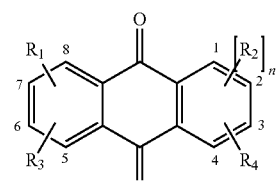

(VI'a)

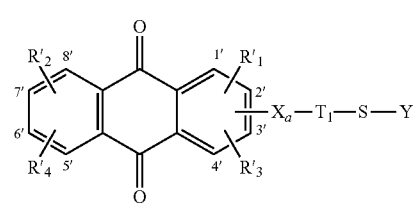

wherein in formulae (Va), (VIa), and (VI'a):
X$_a$ represents an oxygen atom or a group N—R with R representing a hydrogen atom or a group from among (C$_1$-C$_6$)alkyl, optionally substituted (hetero)aryl or (hetero)aryl(C$_1$-C$_6$)alkyl;
Y represents: i) a hydrogen atom; ii) an alkali metal; iii) an alkaline-earth metal; iv) an ammonium group: N$^+$R$^a$R$^b$R$^g$R$^d$ or a phosphonium group: P$^+$R$^a$R$^b$R$^g$R$^d$ with R$^a$, R$^b$, R$^g$ and R$^d$, which may be identical or different, representing a hydrogen atom or a (C$_1$-C$_4$) alkyl group; or v) a thiol-function protecting group; or vi) the group (b) below:

(b)

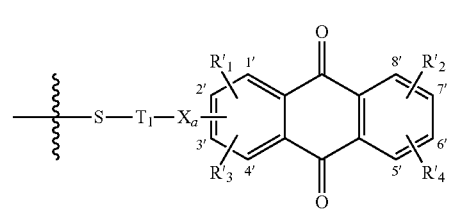

R$_1$, R$_2$, R$_3$, R$_4$, R$_1$', R$_2$', R$_3$' and R$_4$', which may be identical or different, represent an atom or group chosen from:
hydrogen;
halogen,
hydroxyl,
C$_1$-C$_4$ alkoxy,
hydroxysulfonyl (~SO$_3$H) or sulfonate (~SO$_3^-$, M$^+$), with M$^+$ representing a cationic counterion, optionally substituted $C_1$-$C_6$ alkyl,
—$NR_5R_6$ in which $R_5$ and $R_6$, which may be identical or different, represent an atom or radical chosen from: i) hydrogen, ii) ($C_1$-$C_4$), iii) arylsulfonyl, iv) Het-ALK-C(O)— with Het representing a heterocycloalkyl group which is optionally substituted with one or more ($C_1$-$C_4$)alkyl groups and ALK represents a ($C_1$-$C_6$)alkylene group optionally substituted with one or more hydroxyl or (di)(hydroxy)($C_1$-$C_4$)(alkyl)amino groups; v) optionally substituted aryl, optionally substituted with at least one radical chosen from a) $C_1$-$C_6$ alkyl, b) hydroxyl, c) hydroxysulfonyl, d) $C_1$-$C_4$ alkoxy, e) carboxyl (—COOH), f) ($C_1$-$C_4$)alkoxycarbonyl, g) amino, h) (di)($C_1$-$C_4$) alkylamino, one of the alkyl radicals optionally substituted with a hydroxyl or hydroxysulfonyl radical —$SO_3H$, or —$OSO_3H$, vi) optionally substituted aryl($C_1$-$C_4$)alkyl, viii) optionally substituted $C_1$-$C_{20}$ alkyl, optionally interrupted with one or more heteroatoms and/or with one or more groups comprising at least one heteroatom, when said alkyl radical is substituted, it is substituted with one or more atoms or groups chosen from: a) halogens, b) hydroxyl, c) ($C_1$-$C_6$)alkylcarbonylamino, d) 5- or 6-membered heterocycloalkyl e) (di)($C_1$-$C_4$)(alkyl)amino, f) hydroxysulfonyl($C_1$-$C_4$)alkylamino, or hydroxysulfonyloxy($C_1$-$C_4$)alkylamino, g) (di)(hydroxy) ($C_1$-$C_4$)(alkyl)amino, h) 5- or 6-membered heteroaryl, and i) formylamino (~NHCOH);

group (a): —$N(R_7)$—$X_1$—$W_1$ (a)

wherein in group (a):

$R_7$ represents a hydrogen or a $C_1$-$C_4$ alkyl radical, $X_1$ represents a divalent radical chosen from $C_1$-$C_{20}$ alkylene optionally interrupted with one or more heteroatoms or groups chosen from oxygen, nitrogen and sulfur, CO, SO, $SO_2$, arylene, or combinations thereof;

$W_1$ represents a cationic radical chosen from:

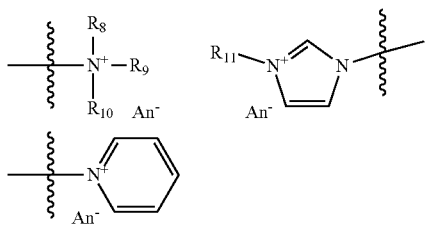

with $R_8$, $R_9$, $R_{10}$ and $R_{11}$, which may be identical or different, representing a $C_1$-$C_6$ alkyl group, a benzyl radical, a $C_1$-$C_6$ alkyl sulfonate radical; the radicals $R_8$ and $R_9$ optionally form, with the nitrogen atom to which they are attached, a saturated or unsaturated, optionally substituted 5- to 7-membered heterocycle, optionally comprising another non-nitrogen heteroatom, An⁻ represents an anionic counterion;

$T_1$ represents a linear or branched divalent hydrocarbon-based chain comprising from 1 to 20 carbon atoms, optionally interrupted with one or more heteroatoms or groups, or combinations thereof, chosen from oxygen, sulfur, $N(R_b)$, C(O), —$N^+(R_8)(R_9)$-An, optionally cationic and optionally substituted heteroaryl, An with $R_8$ and $R_9$, which may be identical or different, representing a $C_1$-$C_6$ alkyl radical; $R_b$ representing a hydrogen atom or a (hydroxy)($C_1$-$C_4$)alkyl group;

n is an integer ranging from 1 to 3;

being the part of the bond that is connected to the rest of the molecule;

wherein:

the naphthoquinone and anthraquinone dye(s) of formula (Va), (VIa) or (VI'a) include at least one radical $R_1$, $R_3$, $R_4$, $R_1'$, $R_3'$, or $R_4'$, other than a hydrogen atom; and when the compounds of formula (Va), (VIa) or (VI'a) are cationic, they comprise an anionic counterion An or An⁻ to ensure the electrical neutrality, or they comprise a sulfonate group, and M⁺ and An or An⁻ may be absent to ensure the electrical neutrality of the molecule; and/or a5) hydrazone dyes, chosen from the compounds of formula (VIIa) below, the geometrical isomers thereof, the tautomers thereof, the organic or mineral, acid or base salts thereof, the solvates thereof, and mixtures thereof:

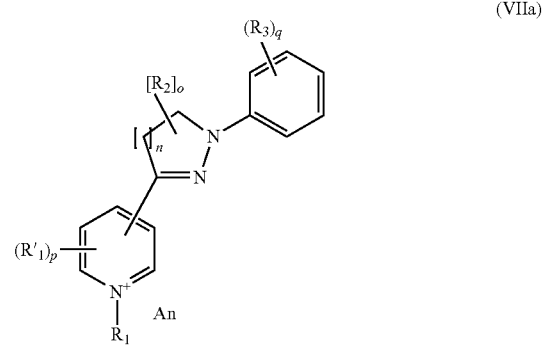

(VIIa)

in which formula (VIIa):

$R_1$, which may be identical or different, represent:
an optionally substituted $C_1$-$C_{20}$ alkyl radical, optionally interrupted with one or more heteroatoms and/or with one or more groups comprising at least one heteroatom;
a $C_1$-$C_4$ trialkylsilyl radical;
an optionally substituted phenyl radical;
an optionally substituted benzyl radical;

$R'_1$, which may be identical or different, represents:
a halogen atom;
an optionally substituted $C_1$-$C_{16}$ alkyl radical;
a hydroxyl radical;
a $C_1$-$C_4$ alkoxy radical;
an amino radical optionally substituted with one or two identical or different $C_1$-$C_4$ alkyl radicals, optionally bearing at least one hydroxyl group;
an alkylcarbonylamino radical (RCO—NR'—) in which the radical R represents a $C_1$-$C_4$ alkyl radical and R' represents a hydrogen or a $C_1$-$C_4$ alkyl radical;
an alkylcarbonylamino group ($RSO_2$—NR'—) in which the radical R represents a $C_1$-$C_4$ alkyl radical and the radical R' represents a hydrogen atom or a $C_1$-$C_4$ alkyl radical;

two adjacent radicals R'1 may form, together with the carbon atoms to which they are attached, a saturated or unsaturated, substituted or unsubstituted 5- or 6-membered aromatic or non-aromatic (hetero)cyclic radical;

p is an integer between 0 and 4;

$R_2$, which may be identical or different, represents:
a hydrogen atom,
an optionally substituted (hetero)aryl radical;
an optionally substituted $C_1$-$C_{16}$ alkyl radical;
two adjacent radicals $R_2$ may form an optionally substituted, saturated or unsaturated, 5- to 7-membered (hetero)cycle, optionally fused to another aromatic nucleus, optionally comprising another nitrogen or non-nitrogen heteroatom;

is an integer equal to 0, 1, 2, 3, or 4;

n is an integer equal to 1 or 2;

$R_3$ represents:
a hydrogen;
an optionally substituted $C_1$-$C_{20}$ alkyl radical;
a halogen atom;
a hydroxyl group;
a $C_1$-$C_4$ alkoxy group;
an alkoxycarbonyl group (RO—CO—) in which R represents a $C_1$-$C_4$ alkyl radical;
an alkylcarbonyl radical (RCO—O—) in which R represents a $C_1$-$C_4$ alkyl radical;
an optionally substituted aryloxy group;
a group $NR'_3R''_3$ in which $R'_3$ and $R''_3$ represent, independently of each other: i) a hydrogen atom, ii) a $C_1$-$C_4$ alkyl radical, optionally bearing at least one hydroxyl or $C_1$-$C_2$ group, said alkyl radicals optionally forming, with the nitrogen atom to which they are attached, and optionally aromatic, optionally substituted, saturated or unsaturated, 5- or 7-membered heterocycle, optionally comprising another nitrogen or non-nitrogen heteroatom;
a phenylamino radical;
an aminophenylamino radical;
a 4-N,N-diethylaminophenylamino radical;
a methoxyphenylamino radical;
an alkylcarbonylamino group (RCO—NR'—) in which the radical R represents a $C_1$-$C_4$ alkyl radical and the radical R' represents a hydrogen atom or a $C_1$-$C_4$ alkyl radical;
a ureido group $(N(R)_2—CO—NR'—)$ in which the radicals R and R', independently of each other, represent a hydrogen atom or a $C_1$-$C_4$ alkyl radical;
an alkylthio radical (R—S—) in which the group R represents a $C_1$-$C_4$ alkyl radical;
two adjacent radicals $R_3$ may form, together with the carbon atoms to which they are attached, a substituted or unsubstituted 5- or 6-membered aromatic or non-aromatic (hetero)cyclic radical;

q is an integer between 0 and 5; and one of the radicals $R'_3$ or $R''_3$ optionally forms, with the nitrogen atom to which it is attached and with a carbon atom of the aromatic nucleus located ortho to the $NR'_3R''_3$ group, a substituted or unsubstituted, 5- or 6-membered saturated or unsaturated heterocycle;

An represents an anionic counterion or a mixture of organic or inorganic anions which ensure the electrical neutrality of the compounds of formula (VIIa);

a6) tetraazapentamethine dyes, chosen from the compounds of formula (VIIIa) and/or (IXa) below, geometrical isomers thereof, tautomers thereof, organic or mineral, acid or base salts thereof, solvates thereof, or mixtures thereof:

in which formulae (VIIIa) and (IXa):
$R_4$ and $R'_4$, which may be identical or different, represent:
a linear or branched $C_1$-$C_8$ alkyl radical optionally substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, or carboxyl radicals;
$R_5$, $R'_5$, $R_6$ and $R'_6$, which may be identical or different, represent:
a hydrogen atom,
a linear or branched $C_1$-$C_{16}$ hydrocarbon-based chain, this chain optionally being saturated or unsaturated with 1 to 3 unsaturations, this chain being unsubstituted or substituted with one to 3 radicals chosen from hydroxyl, $C_1$-$C_2$ alkoxy, (poly)hydroxy($C_2$-$C_4$) alkoxy, amino, $C_1$-$C_2$ (di)alkylamino, carboxyl, sulfonylamino, (poly)hydroxy($C_2$-$C_4$)alkylamino or a halogen atom;
a phenyl radical optionally substituted with one to three radicals chosen from hydroxyl, $C_1$-$C_2$ alkoxy, (poly)hydroxy($C_2$-$C_4$)alkoxy, amino and $C_1$-$C_2$ (di)alkylamino, carboxyl, sulfonylamino and (poly)hydroxy ($C_2$-$C_4$)alkylamino radicals, or a halogen atom;
a heteroaryl radical chosen from pyrazolyl, pyrrolyl, imidazolyl, thiazolyl, oxazolyl, triazolyl, pyridyl, pyrimidinyl, triazinyl, pyrazinyl, or pyridazinyl radicals, wherein the hydrocarbon-based chain is optionally interrupted with one or two oxygen, nitrogen or sulfur atoms or with an SO2 radical, it being understood that $R_5$, $R'_5$, $R_6$ and $R'_6$ do not include any peroxide bonds, or any diazo or nitroso radicals,
An represents an anionic counterion or a mixture of organic or inorganic anions which ensure the electrical neutrality of the compounds of formula (VIIIa) or (IXa);

a7) nitro dyes, chosen from the compounds of formula (Xa) below, geometrical isomers thereof, tautomers thereof, organic or mineral, acid or base salts thereof, solvates thereof, or mixtures thereof:

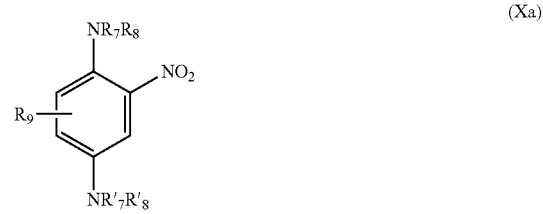

in which formula (Xa):
$R_7$, $R'_7$, $R_8$ and $R'_8$, which may be identical or different, represent:
a hydrogen atom,
a linear or branched $C_1$-$C_{18}$ hydrocarbon-based chain, this chain optionally being saturated or unsaturated with one to four unsaturations, this chain being unsubstituted or substituted with one to three radicals chosen from hydroxyl, $C_1$-$C_2$ alkoxy, (poly)hydroxy($C_2$-$C_4$)alkoxy, amino, $C_1$-$C_2$ (di)alkylamino, carboxyl, sulfonylamino, (poly)hydroxy($C_2$-$C_4$)alkylamino or a halogen atom, hydroxycarbonyl, hydroxysulfonyl, aminocarbonylmethyl, piperidyl, carbonylamino, aminocarbonylamino, chloromethylcarbonylamino, ($C_1$-$C_2$)alkoxycarbonyl, imidazolyl;
a phenyl radical optionally substituted with one to three radicals chosen from hydroxyl, $C_1$-$C_2$ alkoxy, (poly)hydroxy($C_2$-$C_4$)alkoxy, amino, $C_1$-$C_2$ (di)alkylamino, carboxyl, sulfonylamino and (poly)hydroxy($C_2$-$C_4$)alkylamino radicals, or a halogen atom;
$R_9$ represents:
a hydrogen;
an optionally substituted $C_1$-$C_{20}$ alkyl radical;
a halogen atom;
a $C_1$-$C_4$ alkoxy group;
an alkylcarbonyl radical (RCO—O—) in which R represents a $C_1$-$C_4$ alkyl radical;
a phenyl radical;
a8) azomethine dyes and the leuco forms thereof, chosen from the compounds of formula (XIa) and/or (XIIa) below, geometrical isomers thereof, tautomers thereof, organic or mineral, acid or base salts thereof, solvates thereof, and mixtures thereof:

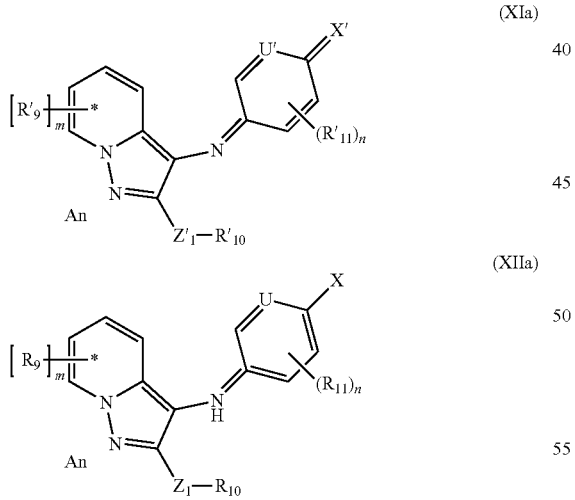

(XIa)

(XIIa)

in which formulae (XIa) and (XIIa):
$Z_1$ and $Z'_1$, which may be identical or different, represent:
a covalent single bond,
an oxygen atom,
a radical —$NR_{12}(R_{13})$p-, with p being equal to 0 or 1, and
when p is equal to 0 then $R_{12}$ represents a hydrogen atom or a $C_1$-$C_6$ alkyl radical, or $R_{12}$, with Rio, form, together with the nitrogen atom to which they are attached, a substituted or unsubstituted, saturated or unsaturated, aromatic or nonaromatic, 5- to 8-membered heterocycle, optionally containing one or more heteroatoms or groups chosen from N, O, S, $SO_2$ and —CO—, and
when p is equal to 1, —$NR_{12}R_{13}$— is a cationic radical in which $R_{12}$ and $R_{13}$ independently represent an alkyl radical,
$Z_1$ and/or $Z'_1$ may also represent a divalent radical —S—, —SO— or —$SO_2$— when $R_1$ is a methyl radical;
$R_{10}$ and $R'_{10}$ represent, independently of each other:
a hydrogen;
an optionally substituted $C_1$-$C_1$ alkyl radical optionally interrupted with a heteroatom or a group chosen from O, N, Si, S, SO and $SO_2$,
a $C_1$-$C_1$ alkyl radical substituted and/or interrupted with a cationic radical,
a halogen;
an $SO_3H$ radical,
a substituted or unsubstituted, saturated, unsaturated or aromatic, 5- to 8-membered ring, optionally containing one or more heteroatoms or groups chosen from N, O, S, $S(O)_2$ and —CO—, the ring optionally being cationic and/or substituted with a cationic radical,
when $Z_1$ and/or $Z'_1$ represent a covalent bond, then $R_1$ may also represent a radical: 1) optionally substituted $C_1$-$C_6$ alkylcarbonyl —O—C(O)—R, —C(O)—O—R, —N(R)—C(O)—R' or —C(O)—NRR' in which R and R' independently represent a hydrogen atom or ii) an optionally substituted $C_1$-$C_6$ alkyl radical;
$R_9$ and $R'_9$, which may be identical or different, represent:
a hydrogen atom,
a hydroxyl radical;
a $C_1$-$C_6$ alkoxy radical,
a $C_1$-$C_6$ alkylthio radical;
an amino radical;
a monoalkylamino radical;
a $C_1$-$C_6$ dialkylamino radical in which the alkyl radicals optionally form, with the nitrogen atom to which they are attached, a saturated or unsaturated, aromatic or nonaromatic, 5- to 8-membered heterocycle, which optionally contains one or more heteroatoms or groups chosen from N, O, S, $SO_2$ and CO;
an optionally substituted $C_1$-$C_6$ alkylcarbonyl radical;
a radical —O—C(O)—R, —C(O)—O—R, N(R)—C(O)—R' or —C(O)—NRR' with R and R' as defined previously;
a halogen;
an —$NHSO_3H$ radical;
an optionally substituted $C_1$-$C_4$ alkyl radical;
a saturated, unsaturated or aromatic, optionally substituted carbon-based ring;
or two radicals $R_9$, and/or two radicals R'9 may form in pairs a saturated or unsaturated ring,
m and m' are integers ranging from 0 to 4,
n and n' are integers ranging from 0 to 4 when U and/or U' represent a carbon atom and from 0 to 3 when U and/or U' represent(s) a nitrogen atom
U and/or U' represent a carbon atom substituted with a radical $R_{11}$ and/or $R'_{11}$,
X and/or X' represent:
an oxygen atom;
an NH radical;

the radicals $R_{11}$ and/or $R'_{11}$, which may be identical or different, represent, independently of each other:
a hydrogen;
an amino radical;
a linear or branched $C_1$-$C_4$ alkyl radical;
an alkoxy radical —OR in which R represents a $C_1$-$C_4$ alkyl radical optionally substituted with a hydroxyl;

a halogen chosen from chlorine, fluorine and bromine;
a radical —$NR_{13}$ in which $R_{13}$ represents a linear $C_1$-$C_4$ alkyl optionally substituted with a hydroxyl, with a di($C_1$-$C_3$)alkylamino or with a tri($C_1$-$C_3$)alkylammonium.

5. The process of claim 4, wherein a) the at least one blue, violet, or green dye is chosen from the following dyes:

Dye 7

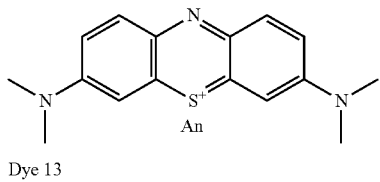

Dye 8     Family (Ia)

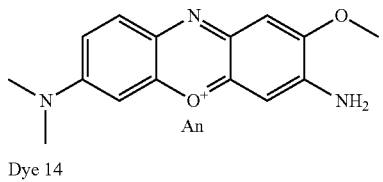

Family (Ia)

Dye 13

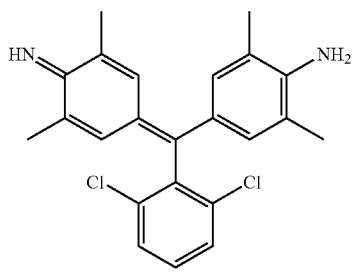

Dye 14     Family (IVa)

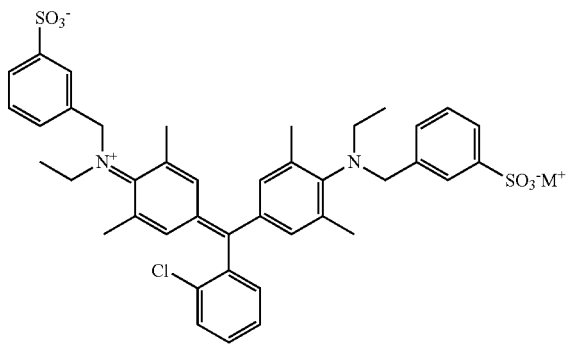

Family (IVa)

Dye 4

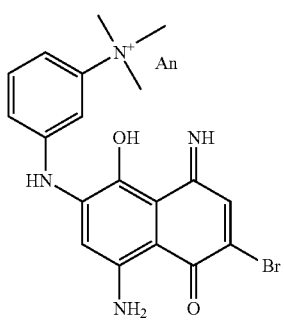

Dye 4'     Family (Va)

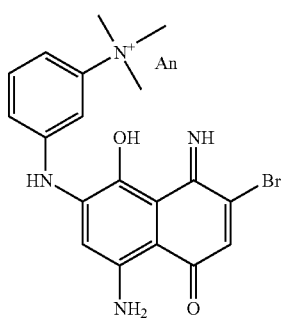

Family (Va)

Dye 3

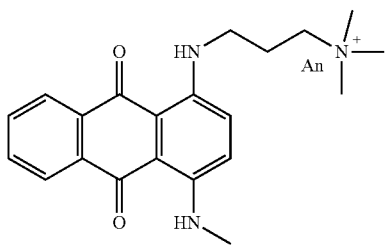

Family (VIa)

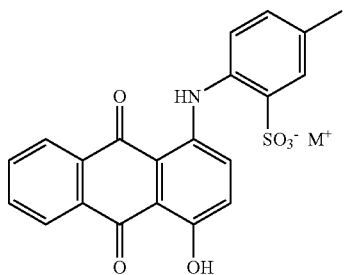

Family (VIa)

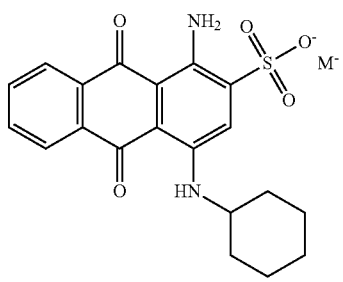
Dye 1
Family (VIa)
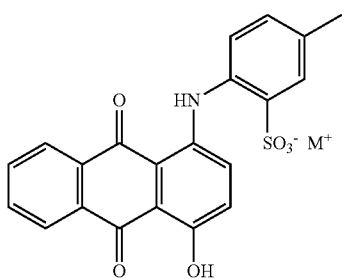
Dye 2
Family (VIa)
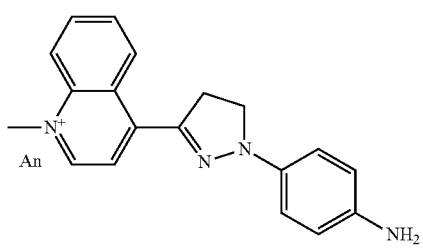
Dye 9
Family (VIIa)
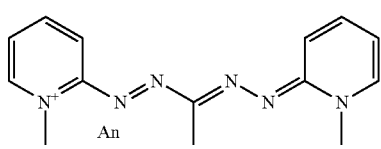
Dye 10
Family (VIIIa)
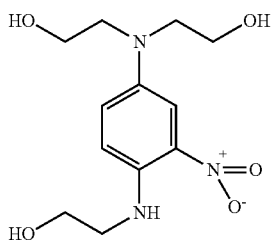
Dye 15
Family (Xa)
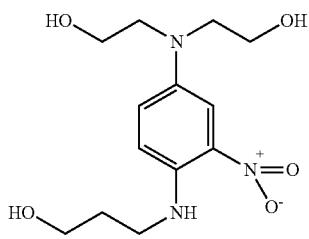
Dye 16
Family (Xa)
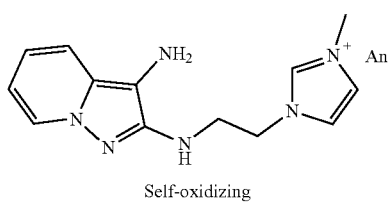
Dye 17
Self-oxidizing
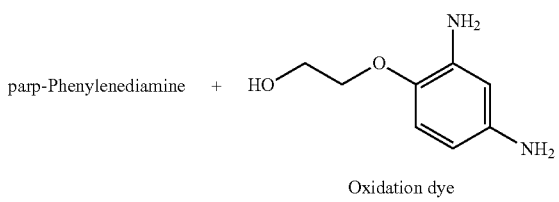
Oxidation dye
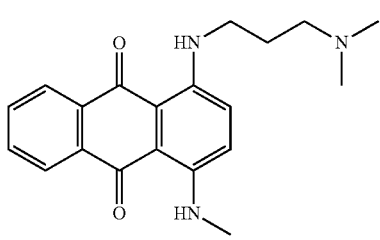 [SMILES: CNc1ccc(NCCCN(C)C)c2c1C(=O)c1ccccc1C2=O]
Family (VIa)

Dye 18

Family (VI'a)

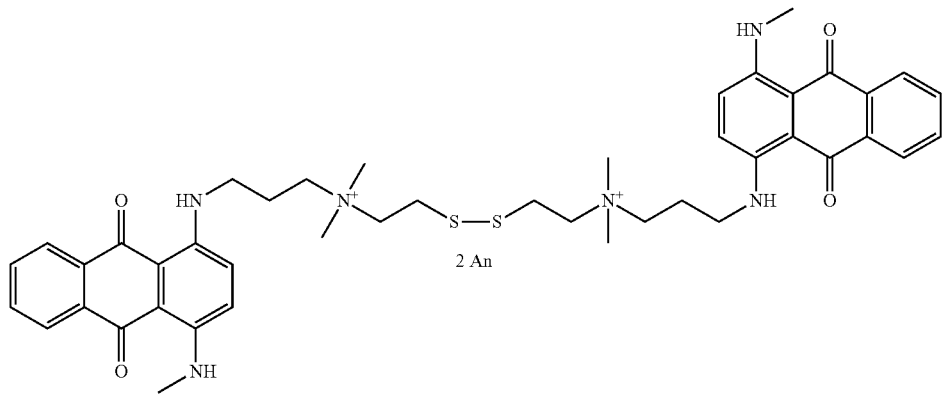

wherein An represents a halide, and M⁺ represents a cationic counterion.

6. The process of claim 1, wherein a) the at least one blue, violet or green dye is chosen from a9) self-oxidizing dyes of formulae (I'a) to (IV'a) below:

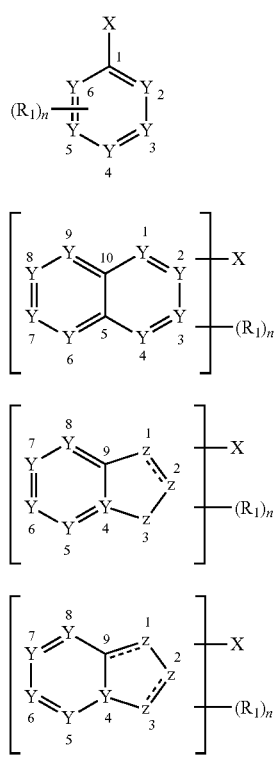

and organic or mineral acid or base salts thereof, optical isomers, geometrical isomers and tautomers thereof, or solvates thereof;

wherein in formulae (I'a) to (IV'a):

---- represents a single bond or a double bond;

X represents i) an amino radical, ii) a $C_1$-$C_6$ (di)alkylamino radical which may optionally be substituted with one or more hydroxyl, $C_1$-$C_6$ alkoxy, amino, $C_1$-$C_6$ alkylamino, carboxylic (—$CO_2H$) or sulfonic (—$SO_3H$) radicals; iii) a hydroxyl radical;

$R_1$ represents a radical covalently bonded to a carbon atom, chosen from:
  i) hydroxyl,
  ii) thiol —SH,
  iii) (di)($C_1$-$C_{12}$ alkyl)amino the alkyl groups of which may optionally be substituted with one or more radicals from among: a) hydroxyl, b) $C_1$-$C_6$ alkoxy, c) amino, d) amide (—$CONH_2$), e) $C_1$-$C_6$ (di)alkylamino, f) carboxylic (—$CO_2H$), g) sulfonic (—$SO_3H$), h) piperidine, i) pyridine, j) pyrrolidine, k) morpholine, l) $C_1$-$C_6$ N-alkyl piperazino, m) benzene, n) halogen, o) nitrile, p) tetrahydrofuran, q) $C_1$-$C_6$ N-alkyl pyrrolidine, r) imidazole, s) $C_1$-$C_6$ trialkylammonium, t) $C_1$-$C_6$ N-alkylimidazolium, u) $C_1$-$C_6$ N,N dialkylpiperazinium, v) $C_1$-$C_6$ N,N dialkylpiperazinium, w) $C_1$-$C_6$ N-alkyl,N'-alkyl piperazinium, x) $C_1$-$C_6$ N-alkylpiperidinium, y) $C_1$-$C_6$ N-alkylmorpholinium, z) $C_1$-$C_6$ N-alkylpyrrolidinium, aa) $C_1$-$C_6$ N-alkylpyridinium, ab) $C_1$-$C_6$ (di)alkylacetamido, ac) $NHSO_2R_2$, ad) $C_1$-$C_6$ alkylcarbonyl, ae) urea (—$NHCONH_2$), af) acetamido $CH_3CONH$—, ag) -aminocarbonyl —$CONH_2$,
  iv) $C_1$-$C_6$ alkyl which may be optionally substituted with one or more radicals a) to ag) as defined for iii) above;
  v) $C_1$-$C_6$ alkyloxy are optionally substituted with one or more radicals a) to ag) as defined for iii) above, the alkyl chain of the alkoxy optionally being interrupted with one or more oxygen atoms;
  vi) $C_1$-$C_6$ alkylthio are optionally substituted with one or more radicals a) to ag) as defined for iii) above;
  vii) halogen;
  viii) —NHPh;
  ix) arylthio —S-Ph;
  x) aryloxy;
  xi) —$NHCOR_2$;
  xii) —$OCOR_2$;
  xiii) —$SCOR_2$;
  xiv) —$NHCONHR_2$;
  xv) —$NHCSNHR_2$;
  xvi) —$NHSO_2R_2$;
  xvii) —$OSO_2R_2$;
  xviii) —$SOR_2$;
  xix) —$SO_2R_2$;

xx) —SO$_2$NHR$_2$;

xxi) piperidino which may be functionalized with one or more —CONH$_2$, C$_1$-C$_6$ alkyl which is optionally functionalized with a hydroxyl or C$_1$-C$_6$ N-alkylimidazolium radical;

a pyrrolidino radical which is optionally functionalized with one or more hydroxyl, C$_1$-C$_6$ alkyl, —NHR$_2$, amino, C$_1$-C$_6$ trialkylammonium, C$_1$-C$_6$ N-alkylimidazolium or (di)(C$_1$-C$_6$)alkylamino radicals;

xxii) piperazino which may be functionalized with one or more C$_1$-C$_6$ alkyl radicals;

xxiii) C$_1$-C$_6$ N,N-dialkylpiperazinium;

xxiv) diazepane;

xxv) morpholino;

xxvi) azepane;

xxvii) —CO$_2$R$_2$;

xxviii) —SO$_3$R$_2$;

xxix) —CONHR$_2$;

xxx) nitrile (—CN);

xxxi) —NHCO$_2$R$_2$;

xxxii) —COR$_2$;

xxxiii) —NHCNHNH$_2$;

a phenyl radical;

R$_2$ represents i) a hydrogen atom, ii) a C$_1$-C$_{12}$ alkyl radical, iii) a phenyl radical, or iv) a 4-methylphenyl radical;

n represents an integer between 1 and 6;

Y represents a carbon or a nitrogen atom;

Z represents i) a carbon atom, ii) an oxygen atom, iii) a nitrogen atom, iv) a radical —NR$_3$ in which R$_3$ represents:

a hydrogen atom;

a C$_1$-C$_6$ alkyl radical which is optionally substituted with one or more hydroxyl, C$_1$-C$_6$ alkoxy, amino, C$_1$-C$_6$ alkylamino, carboxylic (—CO$_2$H) or sulfonic (—SO$_3$H) radicals;

wherein:

when n is greater than or equal to two, the radicals R$_1$ are identical or different;

when the compounds of formulae (I'a) to (IV'a) comprise a cationic group, it is combined with an anionic counterion to achieve the electrical neutrality of the molecule, the compounds of formula (I'a) contain at least three substituents chosen from X and R$_1$ which are electron-donating via the mesomeric effect (+M);

the compounds of formula (II'a) or (III'a) contain at least two substituents chosen from X and R$_1$ which are electron-donating via the mesomeric effect (+M);

for formula (II'a), X or R$_1$ are bonded to the carbon atoms 1 to 4 or 6 to 9;

for formula (III'a) or (IV'a), X or R$_1$ are bonded to the carbon atoms 1, 2 and 5 to 8 or to a carbon or nitrogen atom 3.

7. The process of claim 1, wherein the at least one blue, violet, or green dye a) is chosen from a10) oxidation dyes chosen from one or more oxidation bases chosen from para-phenylenediamines, bis(phenyl)alkylenediamines, ortho-aminophenols, heterocyclic bases, or the corresponding addition salts, and optionally combined with one or more coupling agents.

8. The process of claim 1, wherein b) the at least one disulfide, thiol, or protected-thiol fluorescent dye is chosen from those of formula (Ib):

A-(X)$_p$—C$_{sat}$—S—U, organic or mineral acid or base salts thereof, optical and geometric isomers thereof, tautomers thereof, or solvates thereof, wherein in formula (Ib):

U represents a radical chosen from:

a) —S—C'$_{sat}$—(X')$_{p'}$-A'; and b) —Y;

A and A', which may be identical or different, represent a radical containing at least one quaternized cationic fluorescent chromophore or at least one fluorescent chromophore bearing a quaternized or quaternizable cationic group;

Y represents i) a hydrogen atom; or ii) a thiol-function-protecting group;

X and X', which may be identical or different, represent a linear or branched, saturated or unsaturated divalent C$_1$-C$_{30}$ hydrocarbon-based chain, optionally interrupted and/or optionally terminated at one or both of its ends with one or more divalent groups or combinations thereof chosen from:

—N(R)—, —N$^+$(R)(R)—, —O—, —S—, —C(O)—, —S(O)— and —SO$_2$—, with R, which may be identical or different, chosen from a hydrogen and a C$_1$-C$_4$ alkyl, hydroxyalkyl, or aminoalkyl radical;

an aromatic or non-aromatic, saturated or unsaturated, fused or non-fused (hetero)cyclic radical optionally comprising one or more identical or different, optionally substituted heteroatoms;

p and p', which may be identical or different, are equal to 0 or 1;

C$_{sat}$ and C'$_{sat}$, which may be identical or different, represent an optionally substituted linear or branched, or cyclic, C$_1$-C$_{18}$ alkylene chain.

9. The process of claim 8, wherein the at least one fluorescent dye of formula (Ib) is such that, when p and/or p' is equal to 1, X and/or X', which may be identical or different, represent the following sequence: -(T)$_t$-(Z)$_z$-(T')$_{t'}$-, the sequence being bonded in formula (Ib) symmetrically as follows:—C$_{sat}$ (or C'$_{sat}$)-(T)$_t$-(Z)$_z$-(A or A'); wherein:

T and T', which may be identical or different, represent one or more radicals or combinations thereof chosen from: —O—; —S—; —N(R)—; —N$^+$(R)(R°)—; —S(O)—; —S(O)$_2$—; —C(O)—; with R, R°, which may be identical or different, representing a hydrogen atom, a C$_1$-C$_4$ alkyl radical, C$_1$-C$_4$ hydroxyalkyl radical or an aryl(C$_1$-C$_4$)alkyl radical; and a cationic or non-cationic heterocycloalkyl or heteroaryl radical; the indices t and t', which may be identical or different, are equal to 0 or 1;

Z represents:

—(CH$_2$)$_m$— with m an integer between 1 and 8;

—(CH$_2$CH$_2$O)$_q$— or —(OCH$_2$CH$_2$)$_q$— in which q is an integer between 1 and 5 inclusive;

an aryl, alkylaryl or arylalkyl radical in which the alkyl radical is C$_1$-C$_4$, being optionally substituted with at least one group SO$_3$M with M representing a hydrogen atom, an alkali metal or an ammonium group substituted with one or more identical or different, linear or branched C$_1$-C$_{18}$ alkyl radicals optionally bearing at least one hydroxyl;

z is equal to 0 or 1.

10. The process of claim 8, wherein the at least one disulfide, thiol, or protected-thiol fluorescent dye of formula (Ib) is such that A and/or A' are chosen from chromophores derived from acridine, acridone, benzanthrone, benzimidazole, benzimidazolone, benzindole, benzoxazole, benzopyran, benzothiazole, coumarin, difluoro{2-[(2H-pyrrol-2-ylidene-kN)methyl]-1H-pyrrolato-kN}boron (BODIPY®), diketopyrrolopyrrole, fluorindine, (poly)methine, naphthalimide, naphthanilide, naphthylamine, oxadiazole, oxazine, perilone, perinone, perylene, polyene/carotenoid, squarane, stilbene and xanthene fluorescent dyes; wherein (poly)methine or naphthalimides are chosen from:

formulae (IIb) and (IIIb) below:

   (IIb)

   (IIIb)

with, in formula (IIb) or (IIIb):

W⁺ representing a cationic heterocyclic or heteroaryl group;

W'⁺ representing a divalent heterocyclic or heteroaryl radical as defined for W⁺;

Ar representing an aryl group, optionally substituted with i) one or more halogen atoms; ii) one or more groups $(C_1-C_8)$alkyl; iii) one or more hydroxyl groups; iv) one or more $(C_1-C_8)$alkoxy groups; v) one or more hydroxy$(C_1-C_8)$alkyl groups, vi) one or more amino or $(di)(C_1-C_8)$alkylamino groups, vii) one or more acylamino groups; viii) one or more heterocycloalkyl groups;

Ar' is a divalent aryl radical as defined for Ar;

m' represents an integer between 1 and 4 inclusive;

$R^c$, $R^d$, which may be identical or different, represent a hydrogen atom or an optionally substituted $(C_1-C_8)$ alkyl group, por alternatively $R^c$ contiguous with W⁺or W'+ and/or $R^d$ contiguous with Ar or Ar" form, with the atoms that bear them, a (hetero)cycloalkyl;

Q⁻ is an organic or mineral anionic counterion;

(*) represents the part of the chromophore bonded to the rest of formula (Ib);

or formula (IVb) or (Vb):

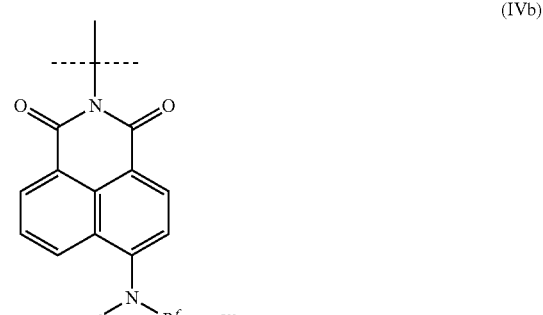   (IVb)

ou

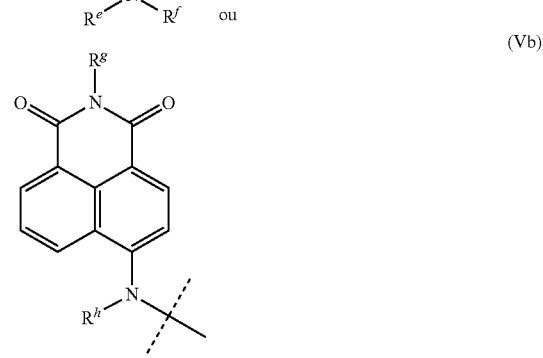   (Vb)

wherein formulae (IVb) and (Vb):
$R^e$, $R^f$, $R^g$ and $R^h$, which may be identical or different, represent a hydrogen atom or a $C_1$-$C_6$ alkyl group which is optionally substituted;

representing the bond which bonds the naphthalimidyl radical to the rest of the molecule via X or X', if p=1, or p'=1; or via $C_{sat}$ or $C_{sat'}$, if p=0 or p'=0.

11. The process of claim 1, wherein b) the at least one disulfide, thiol, or protected-thiol fluorescent dye a) is chosen from the dyes of formulae (VIb) to (Xb') below:

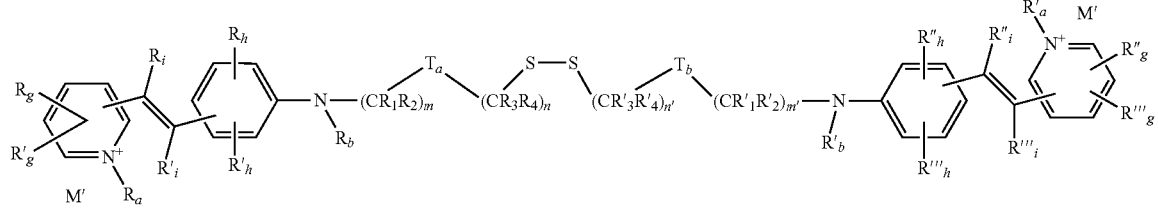

(VIb)

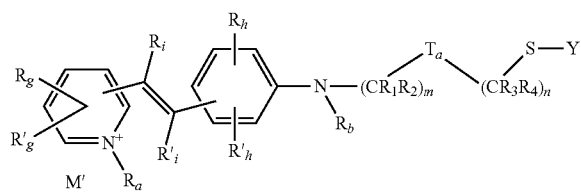

(VI'b)

(VIIb)
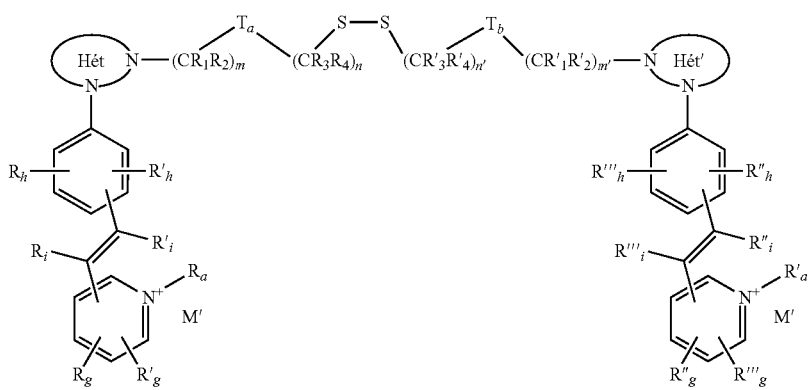
(VII'b)
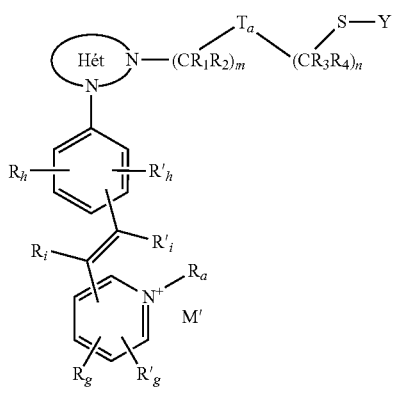
(VIIIb)
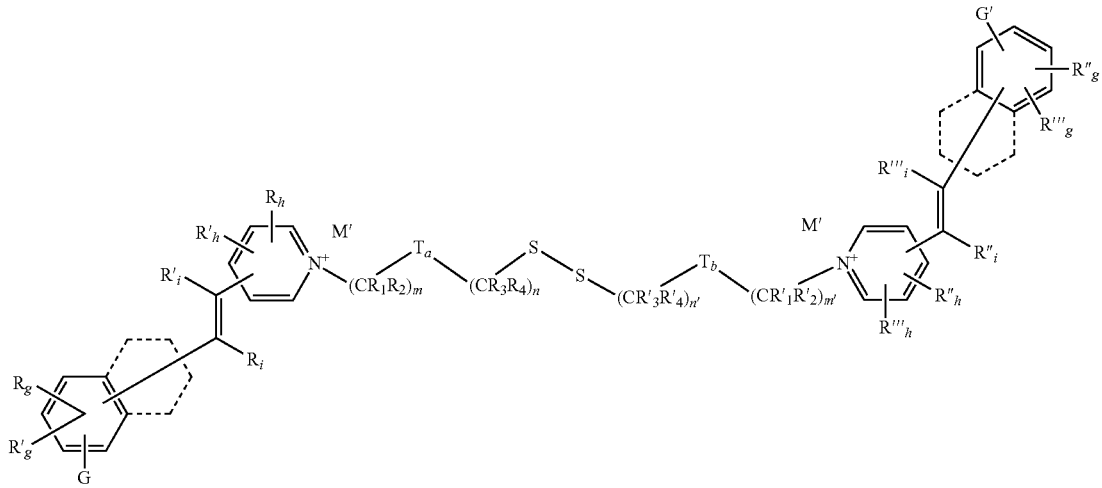
(VIIIb')
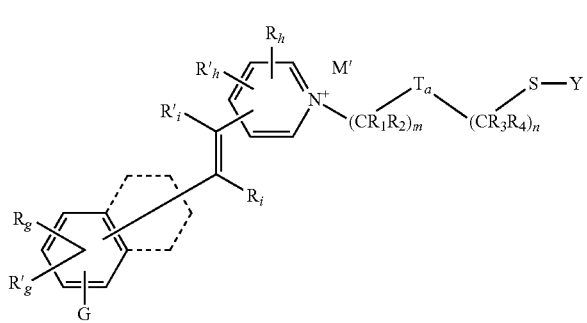

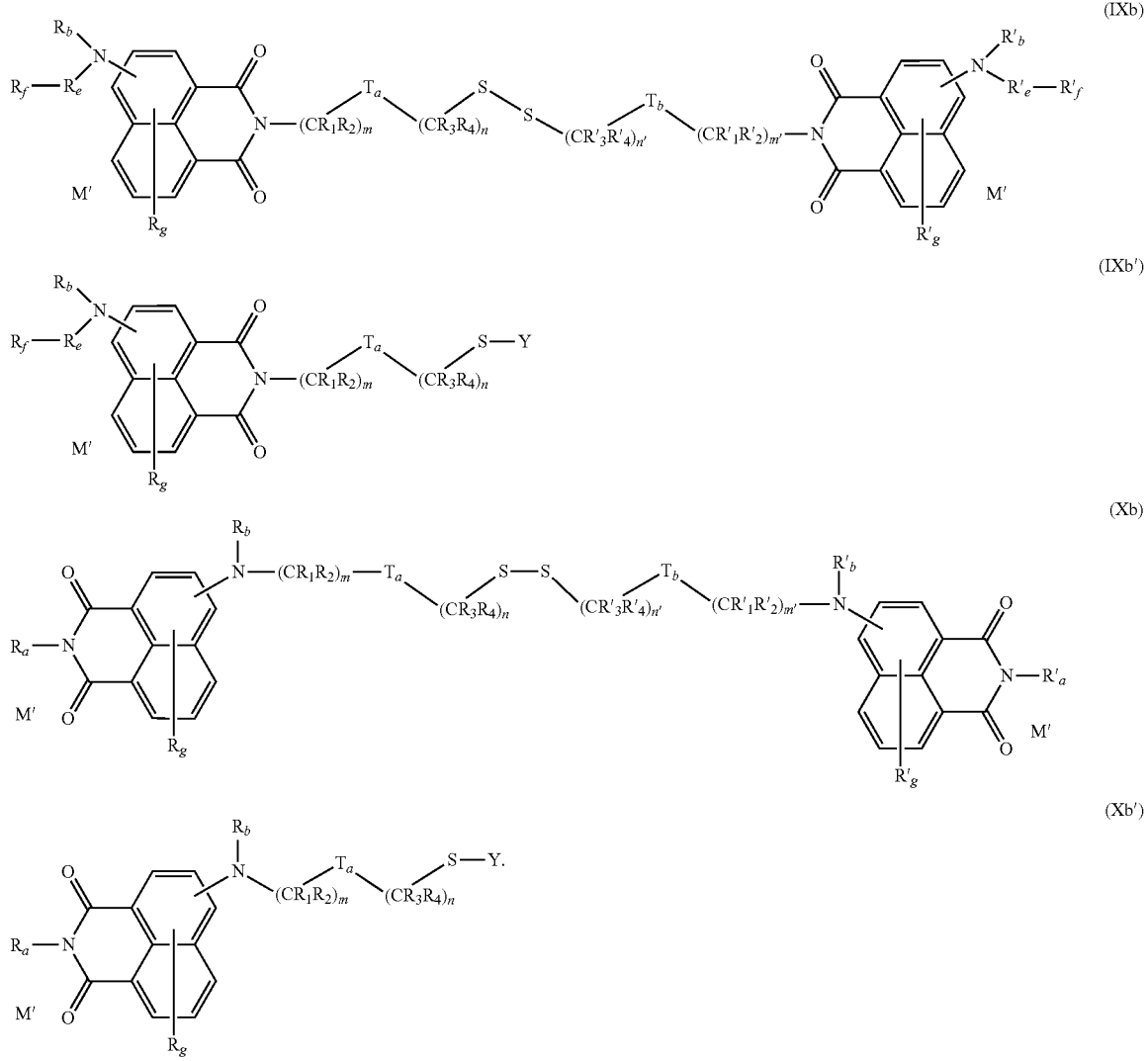

organic or mineral acid or base salts thereof, optical and geometric isomers thereof, tautomers thereof, or solvates thereof;

wherein in formulae (VIb) to (Xb'):

G and G', which may be identical or different, represent a group —$NR_cR_d$, —$NR'_cR'_d$ or $C_1$-$C_6$ alkoxy which is optionally substituted;

$R_a$ and $R'_a$, which may be identical or different, represent an aryl($C_1$-$C_4$)alkyl group or a $C_1$-$C_6$ alkyl group optionally substituted with a hydroxyl or amino, $C_1$-$C_4$ alkylamino or $C_1$-$C_4$ dialkylamino group, said alkyl radicals optionally forming, with the nitrogen atom that bears them, a 5- to 7-membered heterocycle, optionally comprising another nitrogen or non-nitrogen heteroatom;

$R_b$ and $R'_b$, which may be identical or different, represent a hydrogen atom, an aryl($C_1$-$C_4$)alkyl group, or a $C_1$-$C_6$ alkyl group that is optionally substituted;

$R_c$, $R'_c$, $R_d$ and $R'_d$, which may be identical or different, represent a hydrogen atom, an aryl($C_1$-$C_4$)alkyl or $C_1$-$C_6$ alkoxy group or a $C_1$-$C_6$ alkyl group that is optionally substituted; or alternatively two adjacent radicals $R_c$ and $R_d$, $R'_c$ and $R'_d$ borne by the same nitrogen atom together form a heterocyclic or heteroaryl group;

$R_e$ and $R'_e$, which may be identical or different, represent a linear or branched $C_1$-$C_6$ alkylene or $C_2$-$C_6$ alkenylene hydrocarbon-based chain;

$R_f$ and $R'_f$, which may be identical or different, represent a group di($C_1$-$C_4$)alkylamino, (R''')(R''')N— or a quaternary ammonium group (R'')(R''')(R'''')N$^+$— in which R'', R''' and R'''', which may be identical or different, represent a hydrogen atom or a $C_1$-$C_4$ alkyl group or alternatively (R'')(R''')(R'''')N$^+$— represents an optionally substituted cationic heteroaryl group;

$R_g$, $R'_g$, $R''_g$, $R'''_g$, $R_h$, $R'_h$, $R''_h$ and $R'''_h$, which may be identical or different, represent a hydrogen atom, a halogen atom, an amino, $C_1$-$C_4$ alkylamino, $C_1$-$C_4$ dialkylamino, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with a group chosen from $C_1$-$C_{12}$ alkoxy, hydroxyl, cyano, carboxyl, amino, $C_1$-$C_4$ alkylamino and $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom; or alternatively two groups $R_g$ and $R'_g$; $R''_g$ and $R'''_g$; $R_h$ and $R'_h$; $R''_h$ and $R'''_h$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, $C_1$-$C_4$ alkylamino, $C_1$-$C_4$ dialkylamino, nitro, cyano, carboxyl, hydroxyl or trifluoromethyl group, an acylamino, $C_1$-$C_4$ alkoxy, (poly)hydroxy($C_2$-$C_4$)alkoxy, alkylcarbonyloxy, alkoxycarbonyl or alkylcarbonylamino radical, an acylamino, carbamoyl or alkylsulfonylamino radical, an aminosulfonyl radical, or a $C_1$-$C_{16}$ alkyl radical optionally substituted with: a group chosen from $C_1$-$C_{12}$ alkoxy, hydroxyl, cyano, carboxyl, amino, $C_1$-$C_4$ alkylamino, $C_1$-$C_4$ dialkylamino, or alternatively the two alkyl radicals borne by the nitrogen atom of the amino group form a 5- to 7-membered heterocycle optionally comprising another nitrogen or non-nitrogen heteroatom;

or alternatively when G represents —$NR_cR_d$ and G' represents —$NR'_cR'_d$, two groups $R_c$ and $R'_g$; $R'_c$ and $R''_g$; $R_d$ and $R_g$; $R'_d$ and $R'''_g$ together form a saturated heteroaryl or heterocycle, optionally substituted with one or more $C_1$-$C_6$ alkyl, groups;

$R_i$, $R'_i$, $R''_i$, and $R'''_i$, which may be identical or different, represent a hydrogen atom or a $C_1$-$C_4$ alkyl group;

$R_1$, $R_2$, $R_3$, $R_4$, $R'_1$, $R'_2$, $R'_3$ and $R'_4$, which may be identical or different, represent a hydrogen atom or a $C_1$-$C_4$ alkyl, $C_1$-$C_{12}$ alkoxy, hydroxyl, cyano, carboxyl, amino, $C_1$-$C_4$ alkylamino or $C_1$-$C_4$ dialkylamino group, said alkyl radicals optionally forming, with the nitrogen atom which bears them, a 5- to 7-membered heterocycle optionally comprising another nitrogen or non-nitrogen heteroatom;

$T_a$ and $T_b$, which may be identical or different, represent i) either a covalent bond s, ii) or one or more radicals or combinations thereof chosen from —$SO_2$—, —O—, —S—, —N(R)—, —$N^+(R)(R^o)$—and —CO—, with R and $R^o$, which may be identical or different, representing a hydrogen atom, a $C_1$-$C_4$ alkyl or a $C_1$-$C_4$ hydroxyalkyl radical; or an aryl($C_1$-$C_4$)alkyl radical;

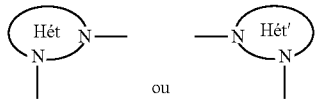

ou which may be identical or different, represent an optionally substituted heterocyclic group;

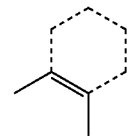

represents an aryl or heteroaryl group fused to the imidazolium or phenyl ring; or alternatively is absent from the imidazolium or phenyl ring;

m, m', n and n', which may be identical or different, represent an integer between 0 and 6 inclusive, with m+n and m'+n', which may be identical or different, representing an integer between 1 and 10 inclusive;

Y represents a hydrogen atom, or a group chosen from:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
cationic 5- or 6-membered monocyclic heteroaryl; these groups being optionally substituted with one or more identical or different ($C_1$-$C_4$)alkyl groups;
cationic 8- to 11-membered bicyclic heteroaryl; these groups being optionally substituted with one or more identical or different ($C_1$-$C_4$)alkyl groups;
cationic heterocycle having the following formula:

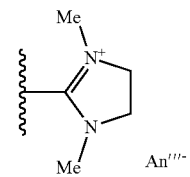 [SMILES: *C1=[N+](C)CCN1C]

—$C(NH_2)=N^+H_2$; $An''''^-$; with $An''''^-$ being an anionic counterion;
—$C(NH_2)=NH$;
$SO_3^-$, $M^+$ with $M^+$ representing an alkali metal; and
M' representing an anionic counterion, derived from a salt of an organic or mineral acid, or from an organic or mineral base that ensures the electrical neutrality of the molecule.

12. The process of claim 1, wherein b) the at least one disulfide, thiol, or protected-thiol fluorescent dye is chosen from the dyes of formulae (XVIb) to (XVI'''b) below:

(XVIb)

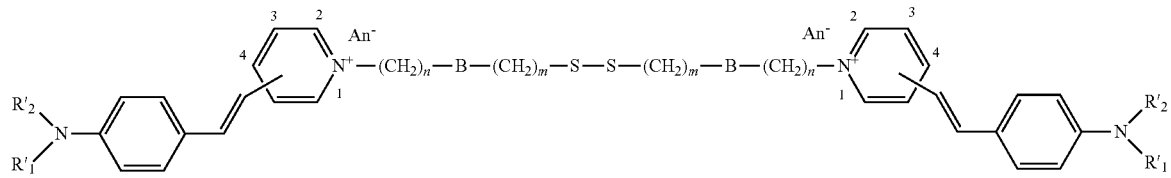

-continued

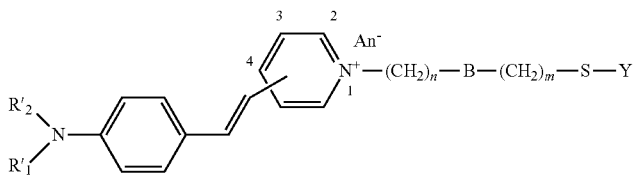
(XVI'b)

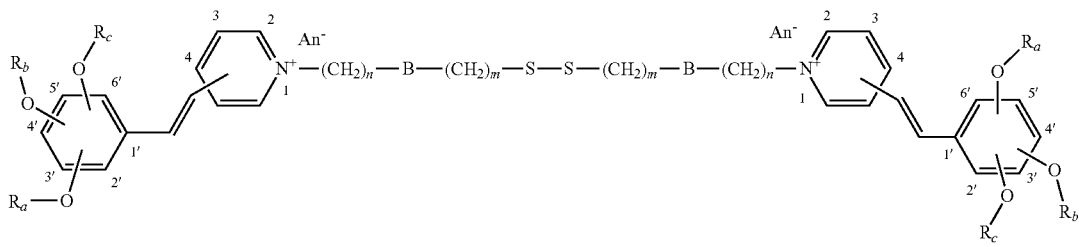
(XVI"b)

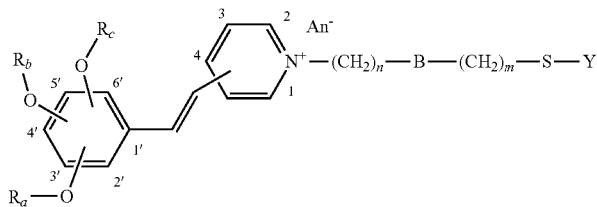
(XVI'''b)

and organic or mineral acid or base salts thereof, optical and geometric isomers and tautomers thereof, or solvates thereof;

wherein formula (XVIb) or (XVI'''b):

$R'_1$ represents a $C_1$-$C_4$ alkyl group substituted with one or more hydroxyl groups, or —C(O)OR' with R' representing a hydrogen atom, a $C_1$-$C_4$ alkyl group, or a group —C(O)—O⁻ and, in the latter case, an anionic counterion An⁻ is absent;

$R'_2$ represents a $C_1$-$C_4$ alkyl group optionally substituted with one or more hydroxyl groups;

$R_a$, $R_b$ and $R_c$ represent a ($C_1$-$C_6$)alkyl group, they are in positions 3', 4' and 5', or 2', 4' and 5' or 2', 4' and 6', An⁻ represents an anionic counterion;

B represents a bond or a divalent amido group —C(O)—N(R)- or —N(R)—C(O)—, with R representing a hydrogen atom or a ($C_1$-$C_6$)alkyl group;

n and m, which may be identical or different, represent an integer between 1 and 4 inclusive;

Y represents a hydrogen atom, or a group chosen from:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
cationic 5- or 6-membered monocyclic heteroaryl; these groups being optionally substituted with one or more identical or different ($C_1$-$C_4$)alkyl groups;
cationic 8- to 11-membered bicyclic heteroaryl; these groups being optionally substituted with one or more identical or different ($C_1$-$C_4$)alkyl groups;
cationic heterocycle having the following formula:

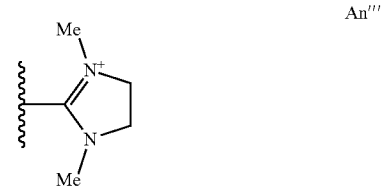 [SMILES: *C1=[N+](C)CCN1C]

—C(NH$_2$)=N⁺H$_2$; An''''⁻; with An''''⁻ being an anionic counterion;
—C(NH$_2$)=NH;
SO$_3$⁻, M⁺ with M⁺ representing an alkali metal;
wherein the bond between the pyridinium ring and the double bond of the ethylene or styryl group is located in position 2 or 4 of the pyridinium.

13. The process of claim 1, wherein b) the at least one disulfide, thiol, or protected-thiol fluorescent dye is chosen from the dyes having the following chemical structures:

8
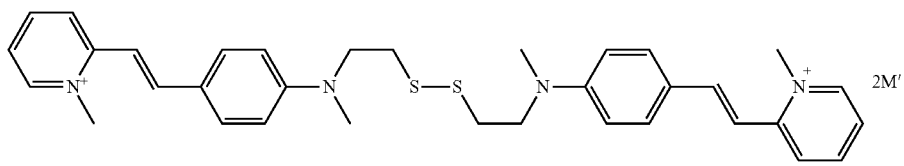
9
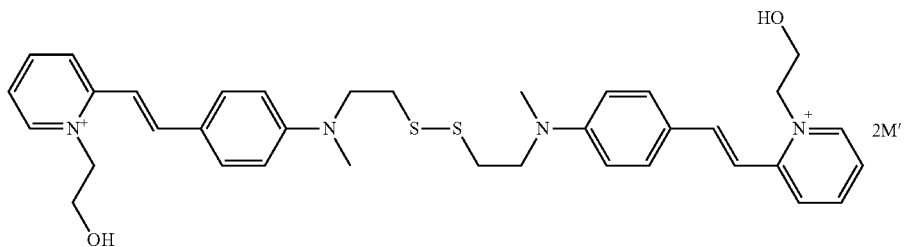
10
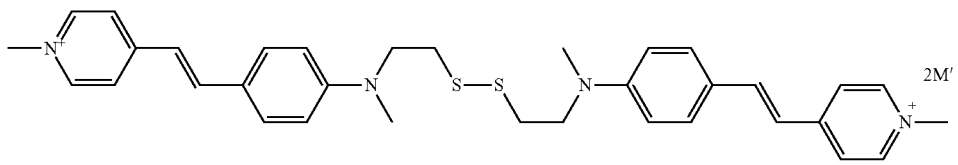
11
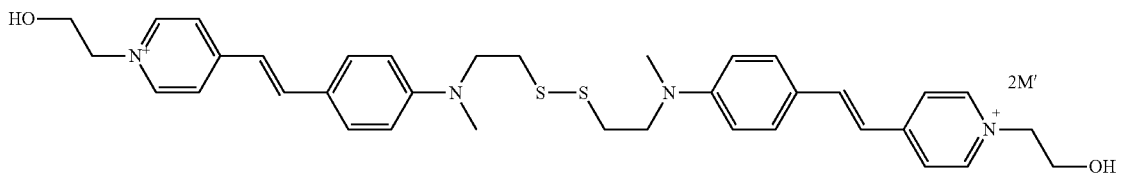
16
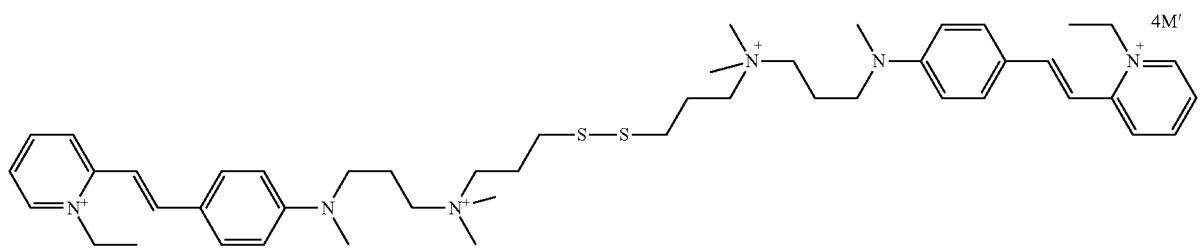
17
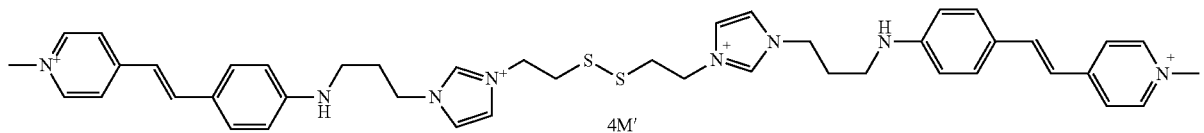
18
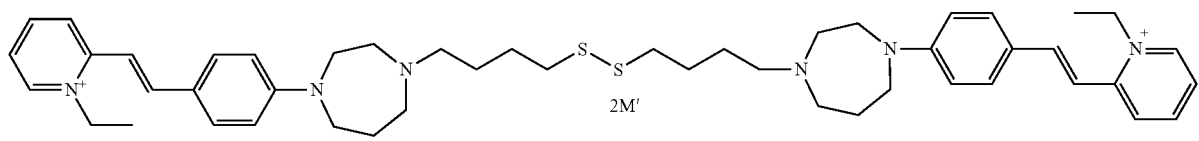
20
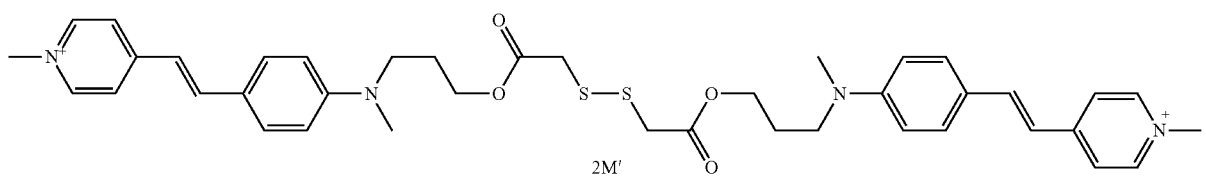

21
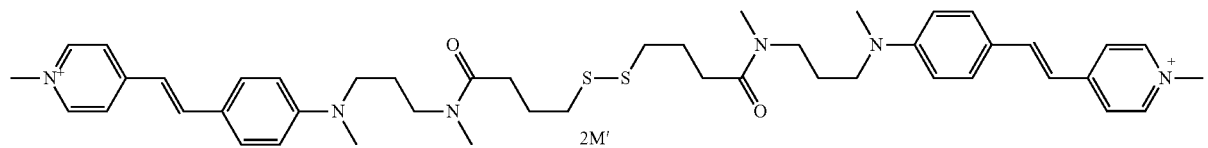
2M'
22
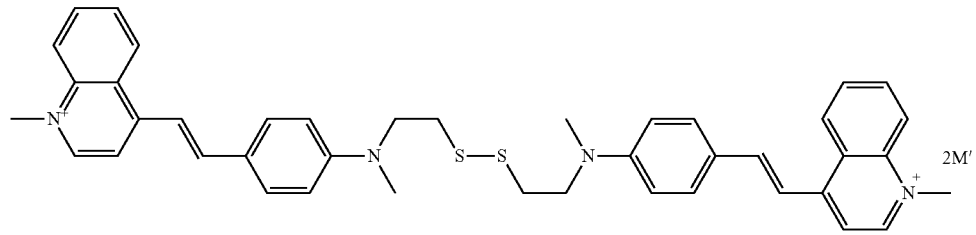
2M'
23
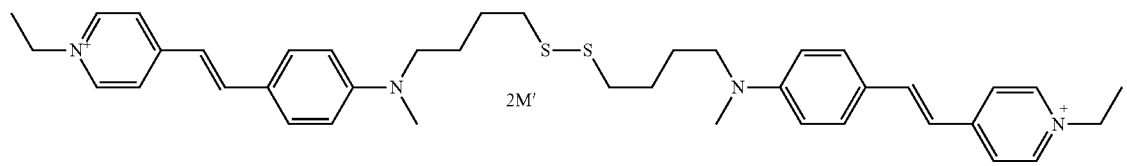
2M'
24
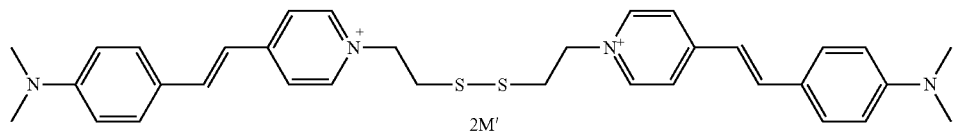
2M'
25
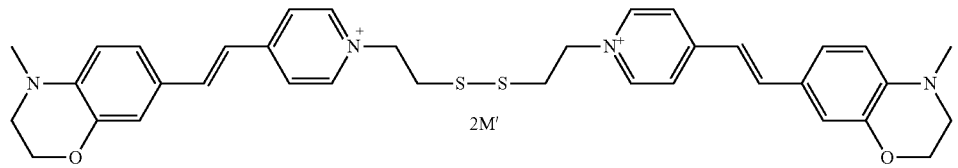
2M'
26
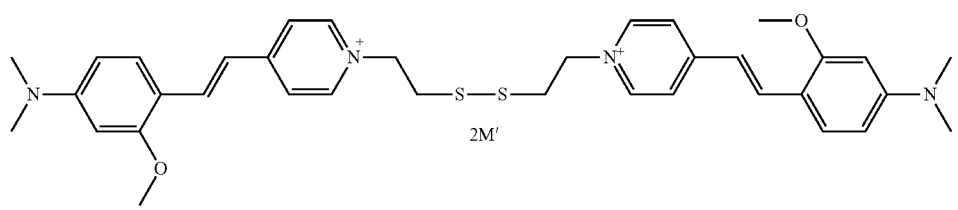
2M'
27
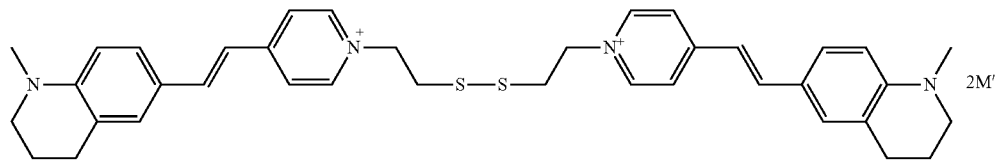
2M'
28
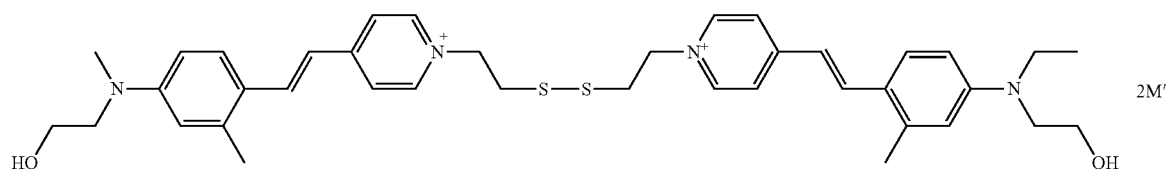
2M'
29
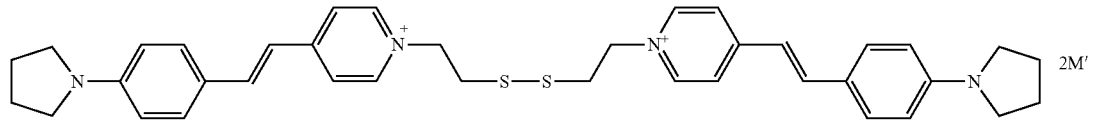
2M'

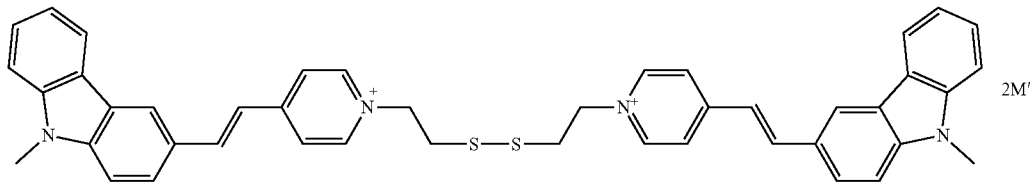
30
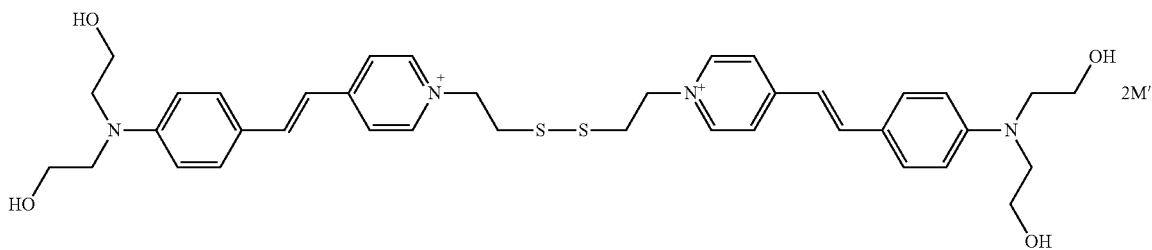
31
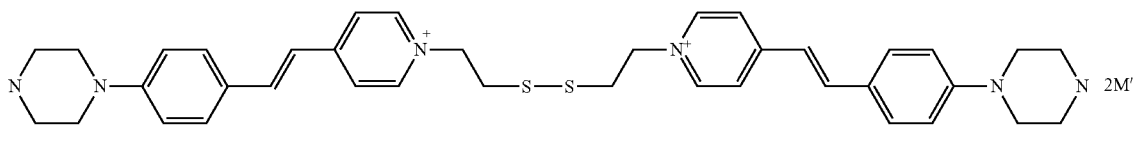
32
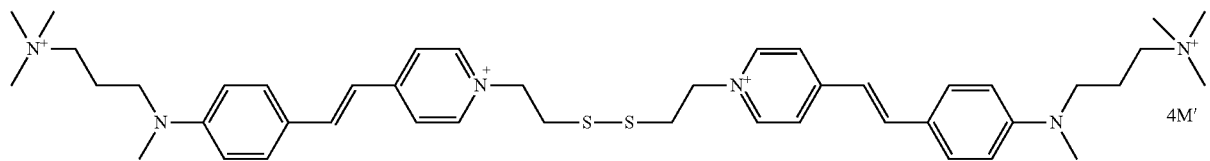
33
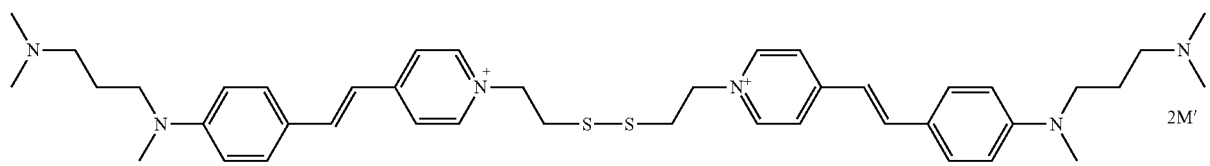
34
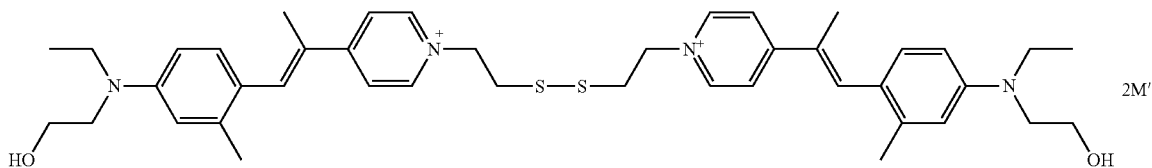
35
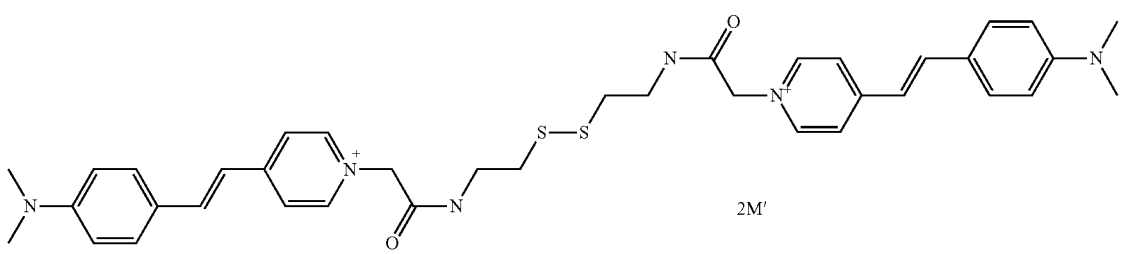
36
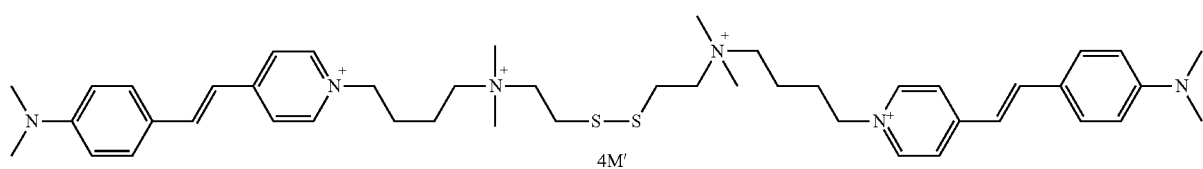
37

151 152
-continued
38
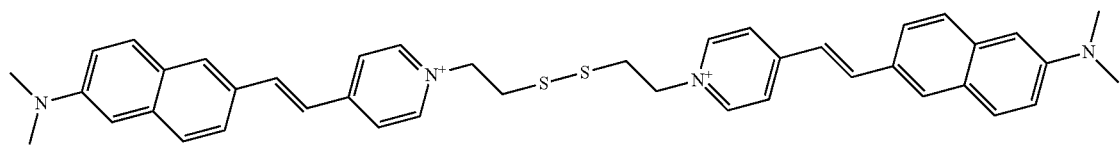
2M'
39
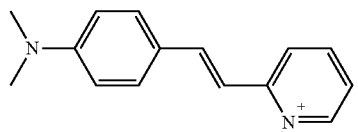
2M'
40
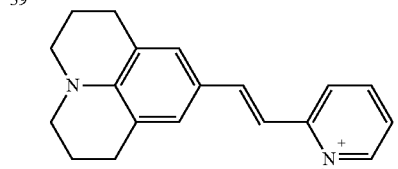
2M'
41
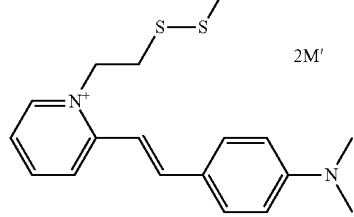
2M'
42
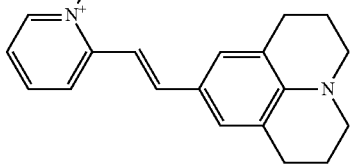
2M'
43
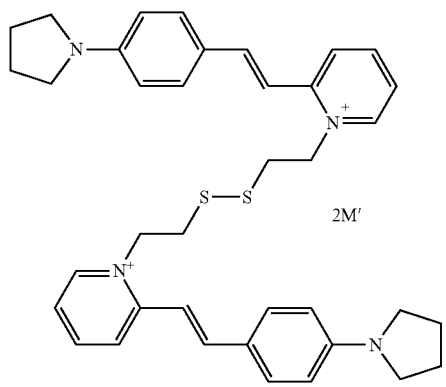
2M'
44
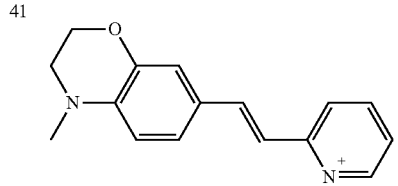
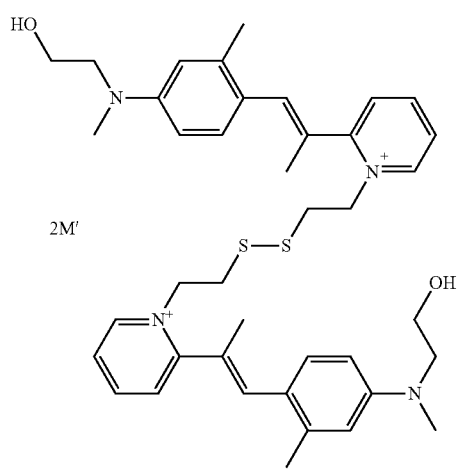
2M'
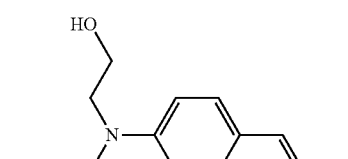

-continued
| | |
|---|---|
| 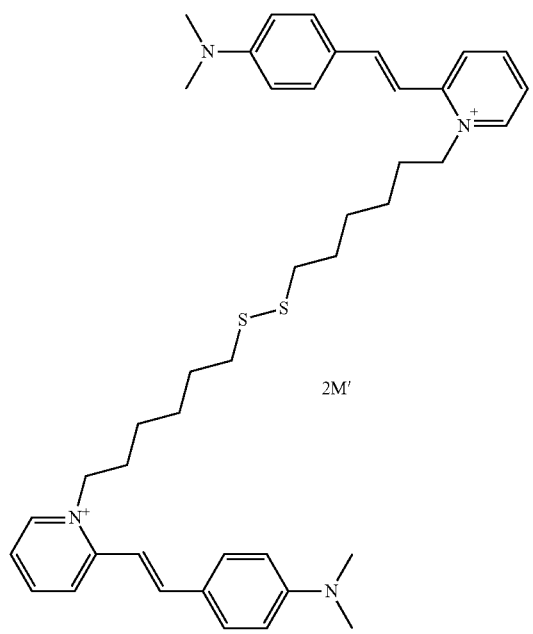 | 45 |
| 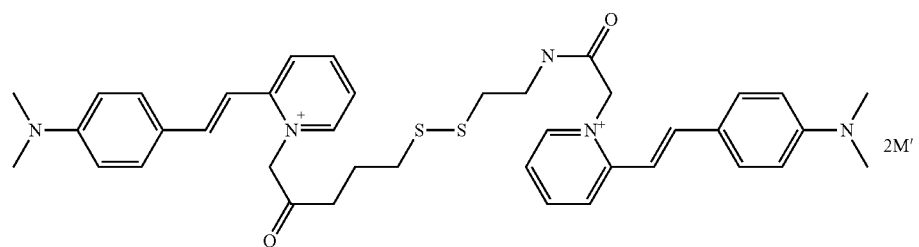 | 46 |
| 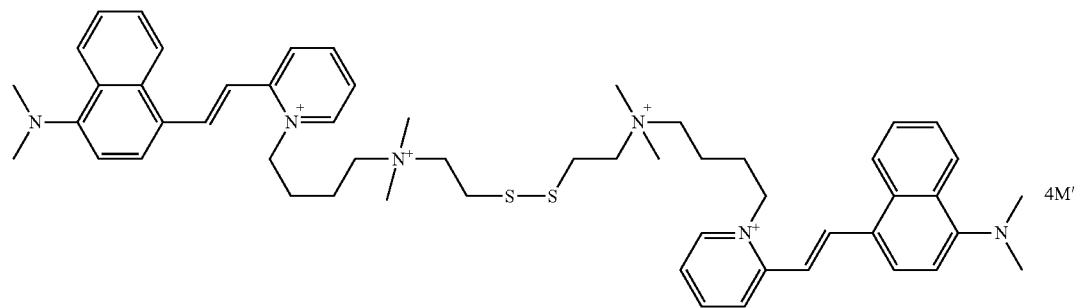 | 47 |
| 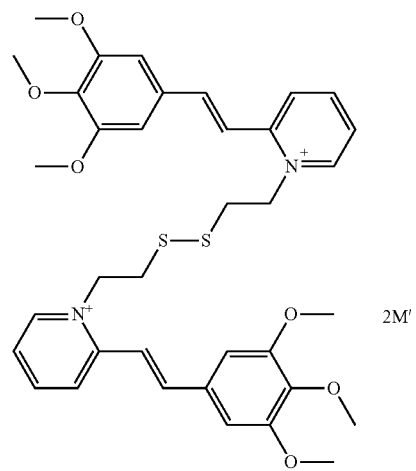 | 48 |

-continued
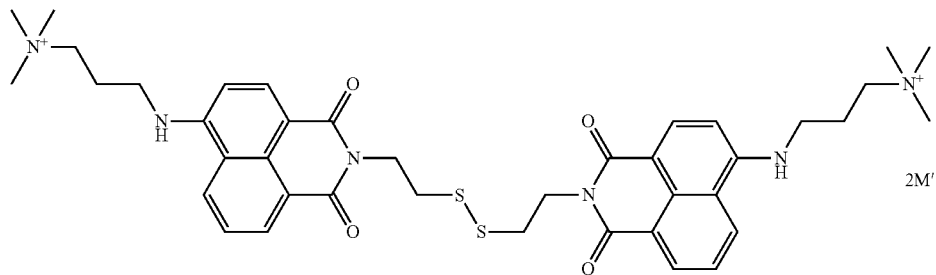
49
2M'
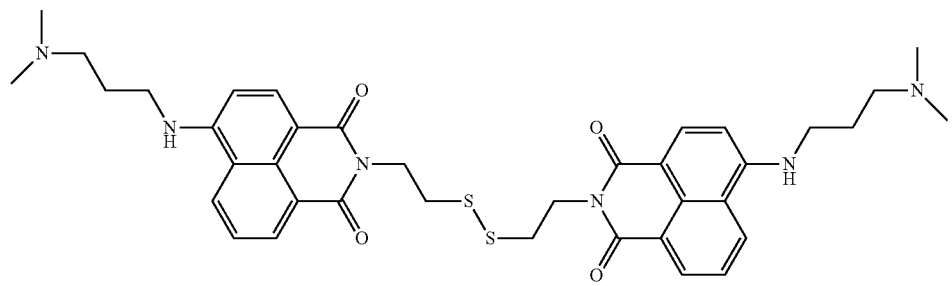
49bis
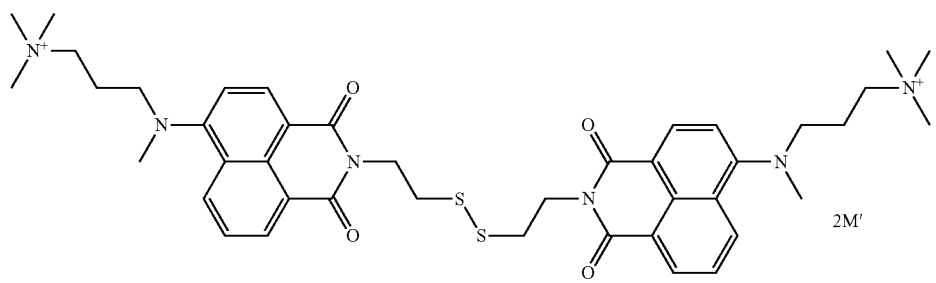
50
2M'
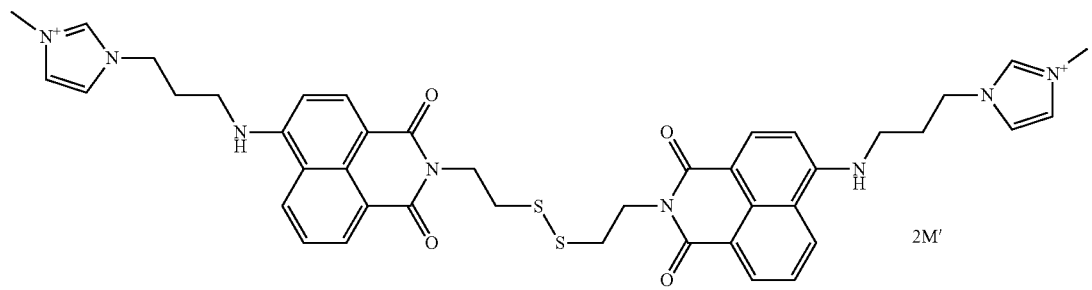
51
2M'
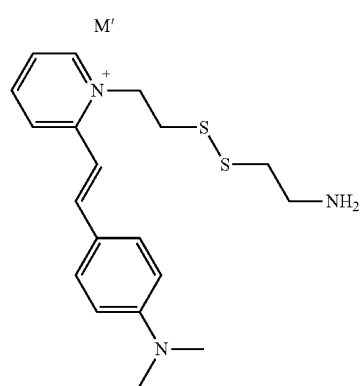
52
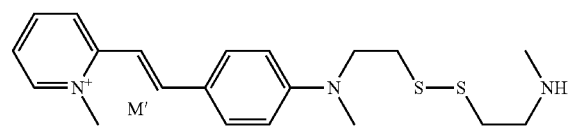
53

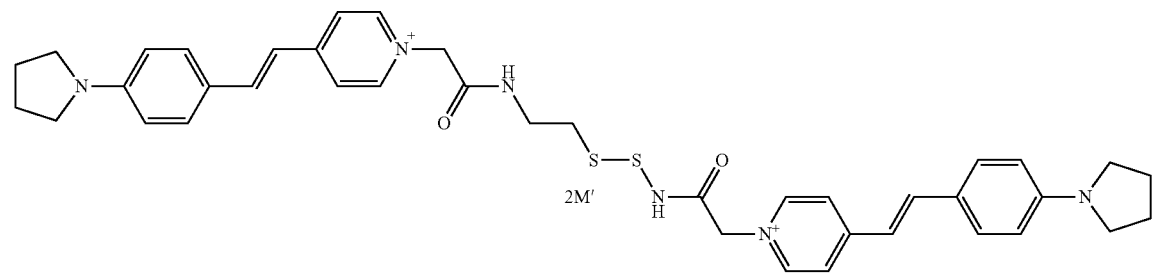
54
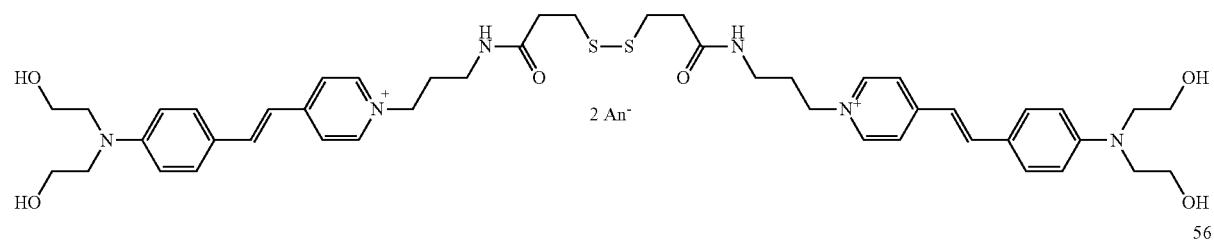
55
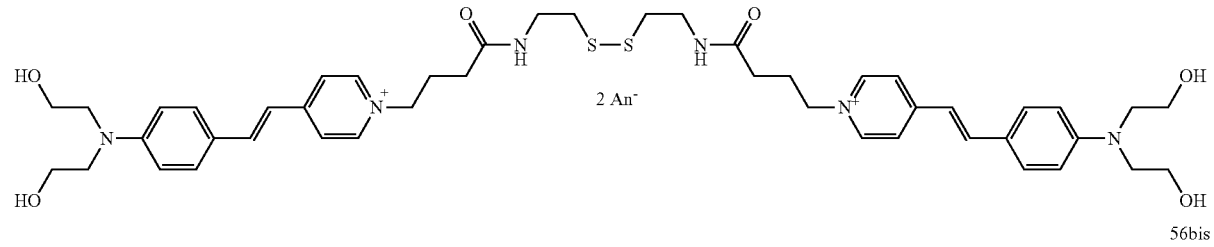
56
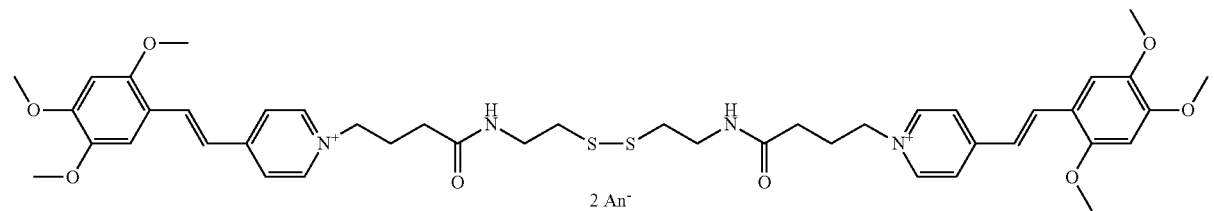
56bis
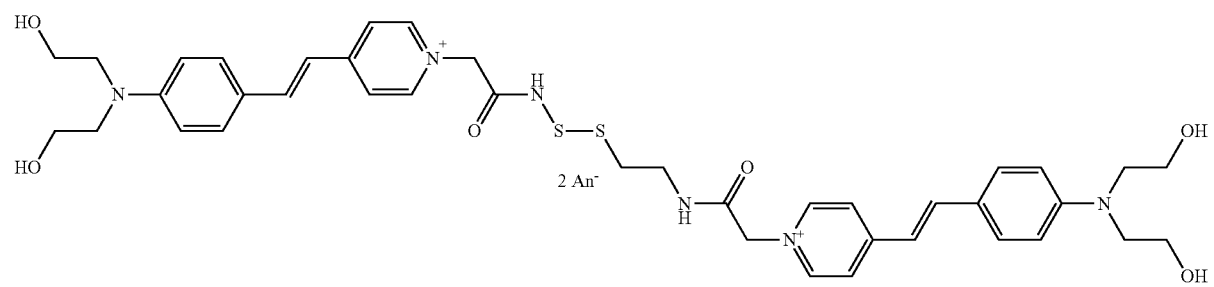
57
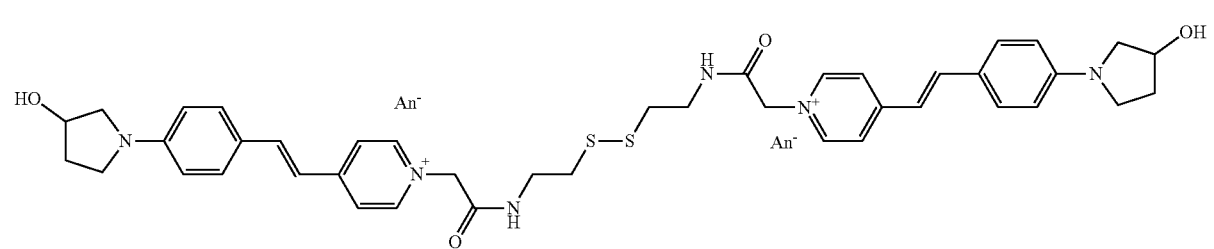
58

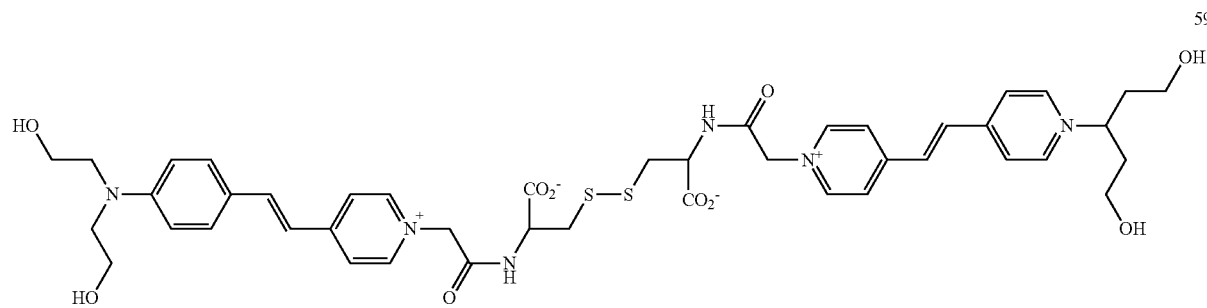
59
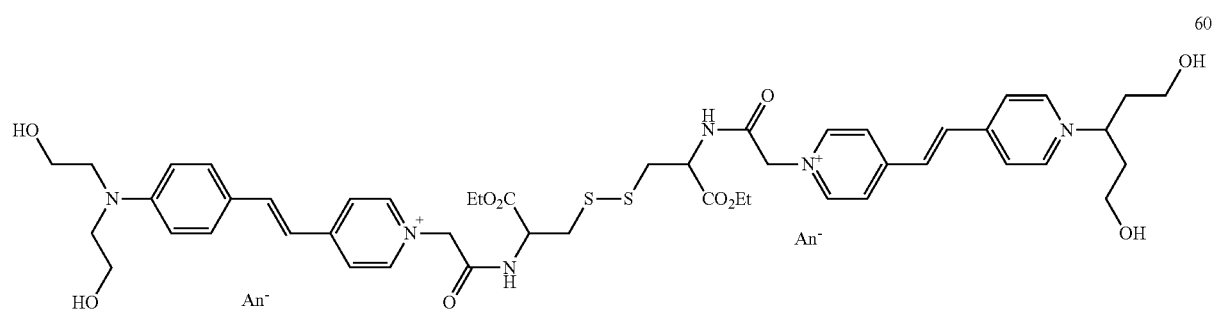
60
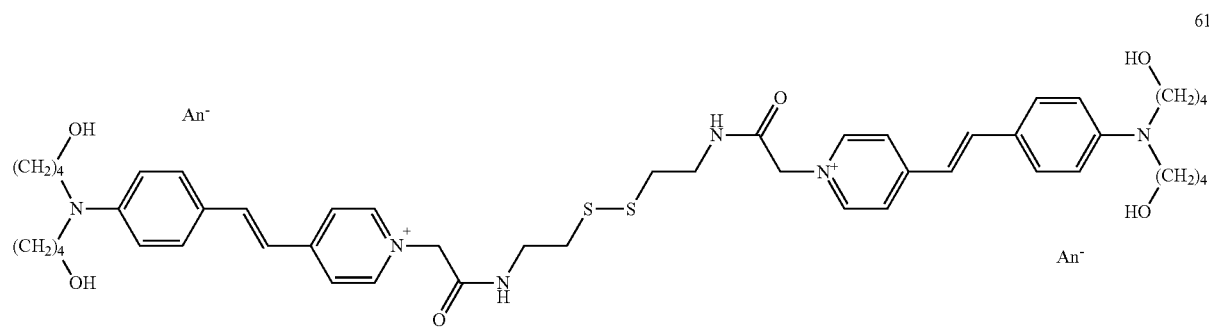
61
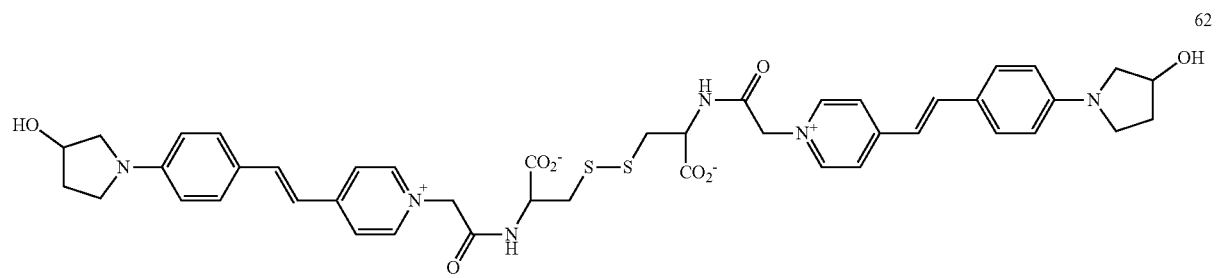
62
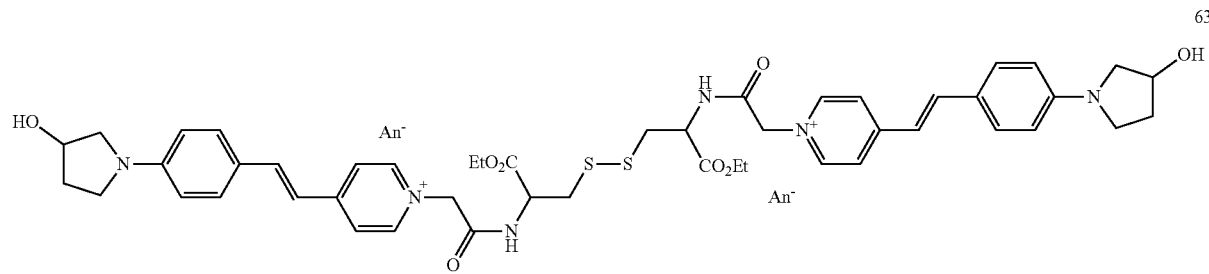
63

-continued
64
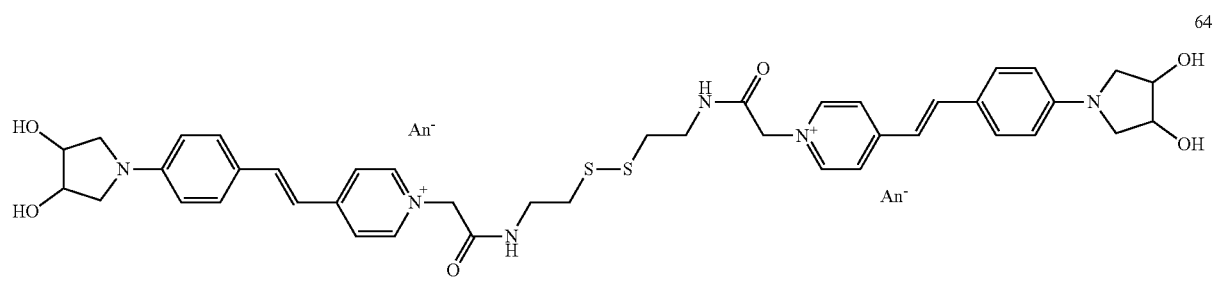
65
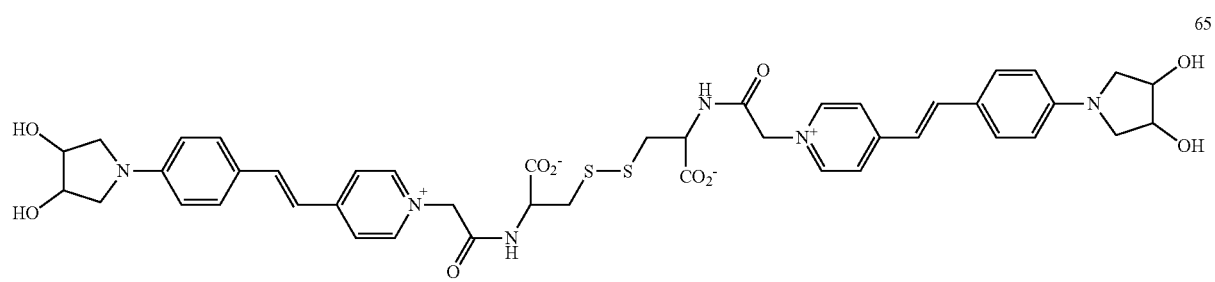
67
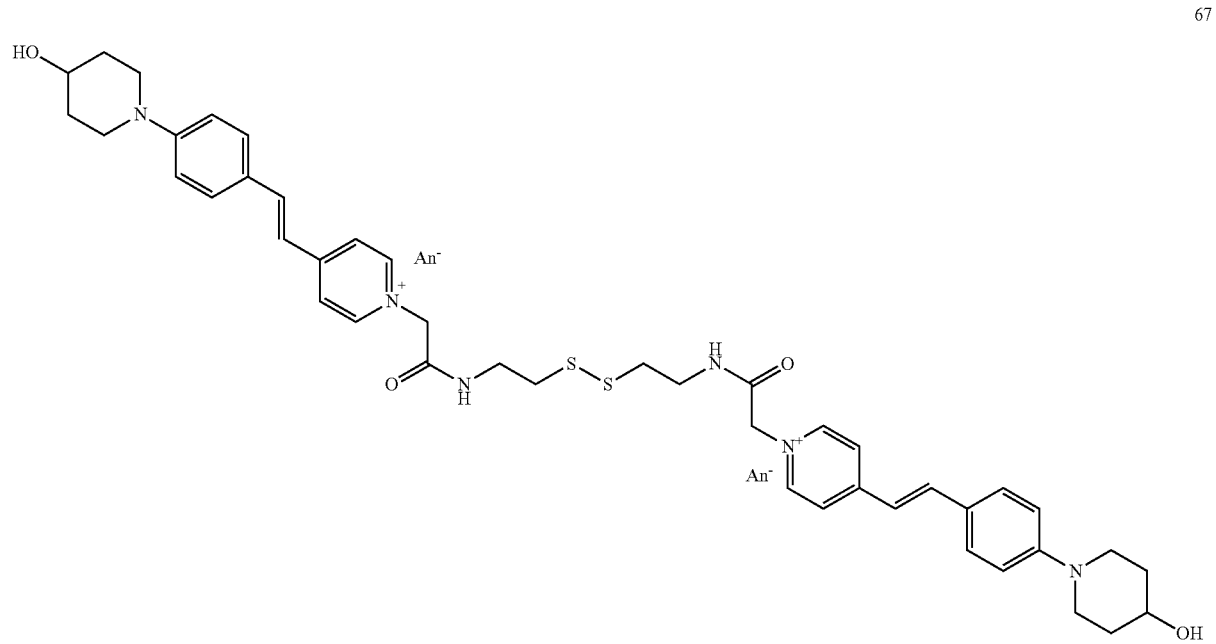
68
69
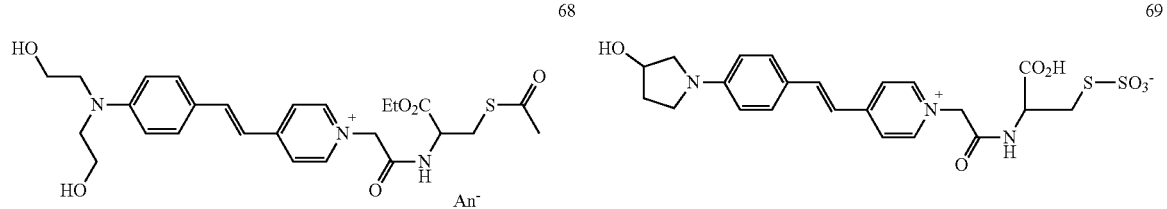

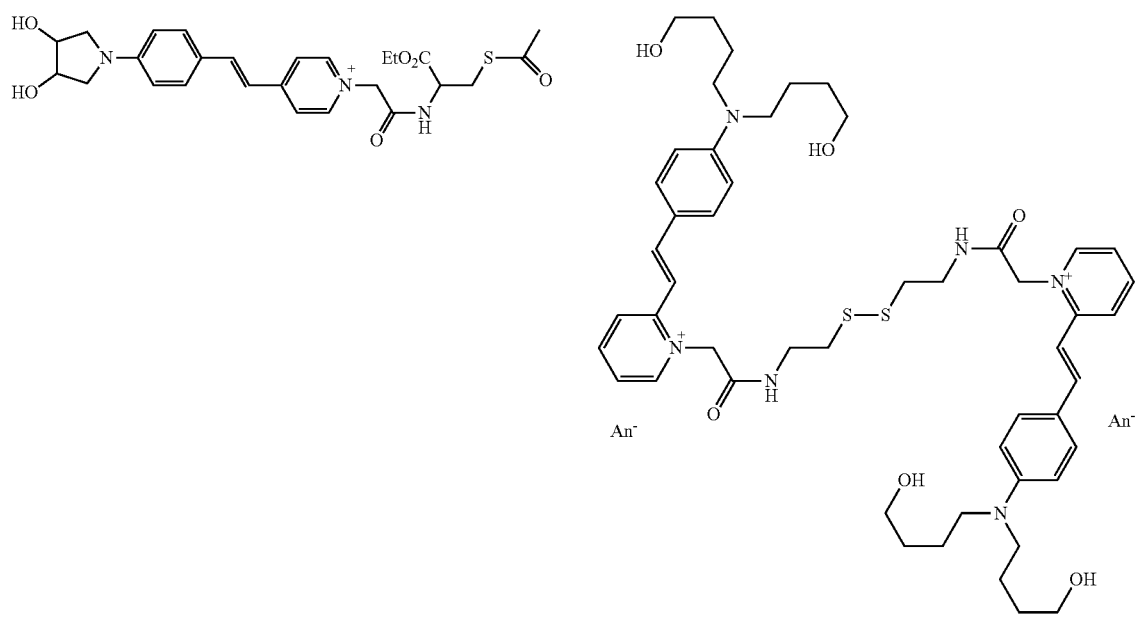
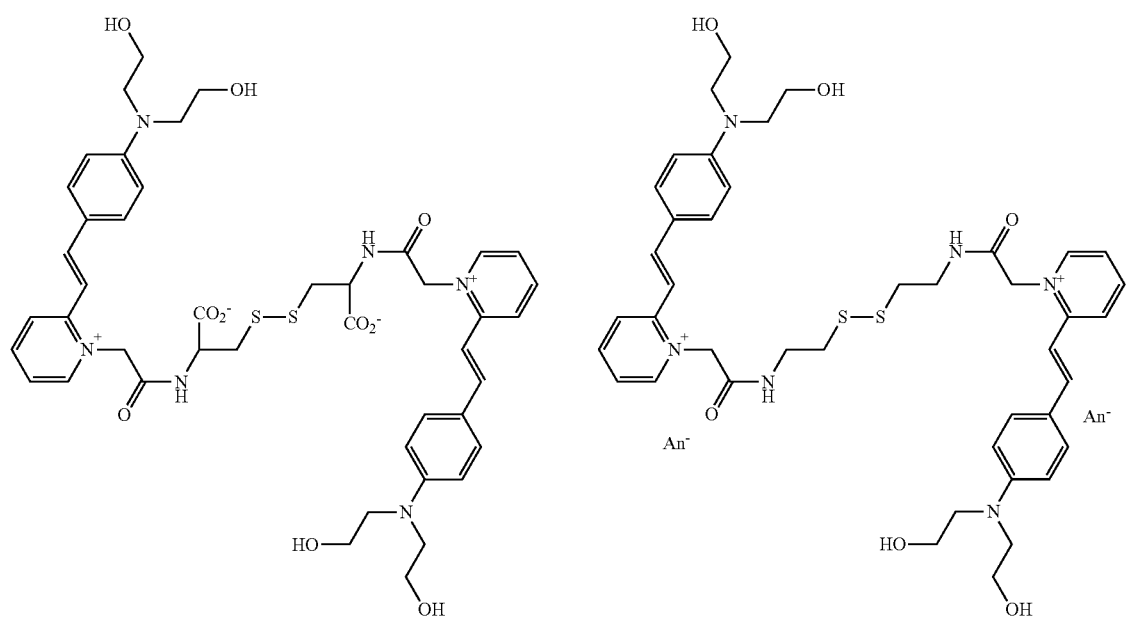

-continued
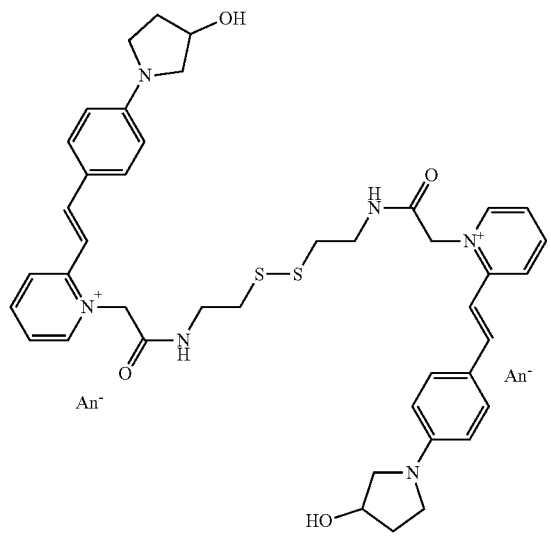
74
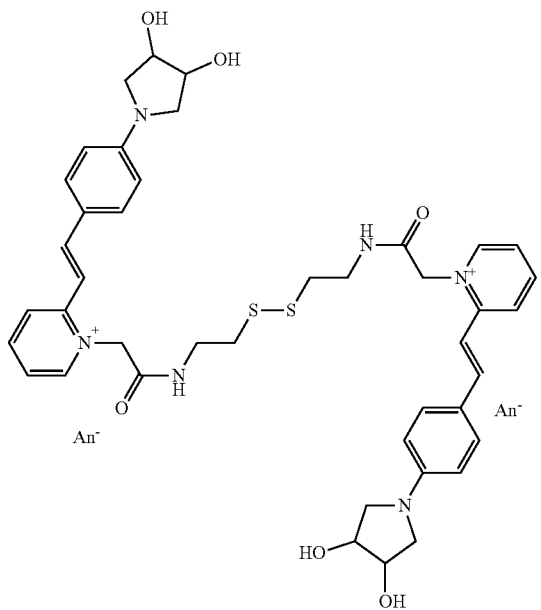
75
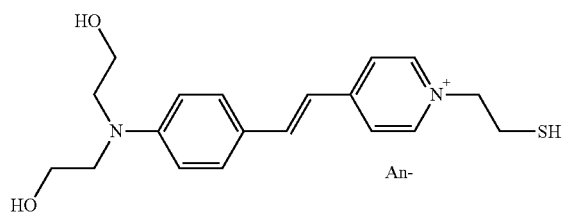
76
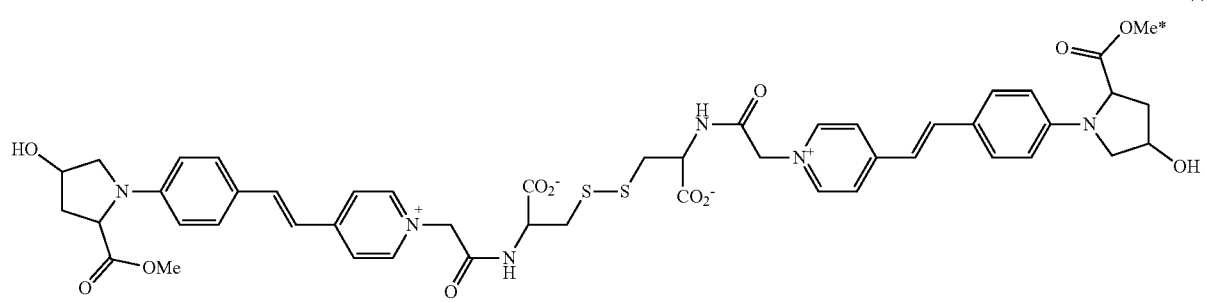
77
Me* represents an alkali metal or 1/2 an alkaline-earth metal; or a methyl
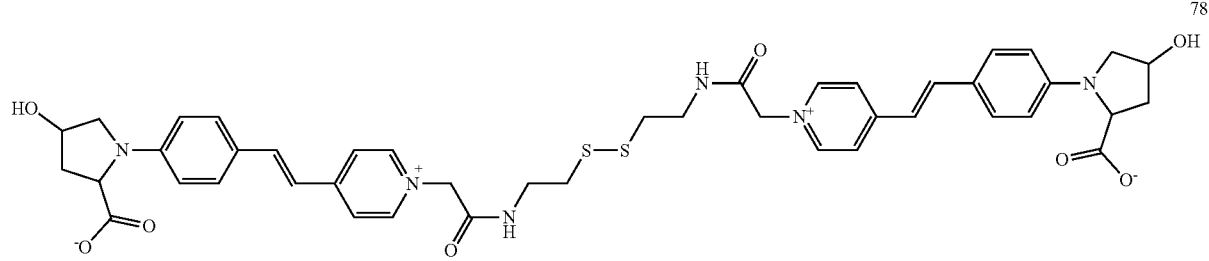
78

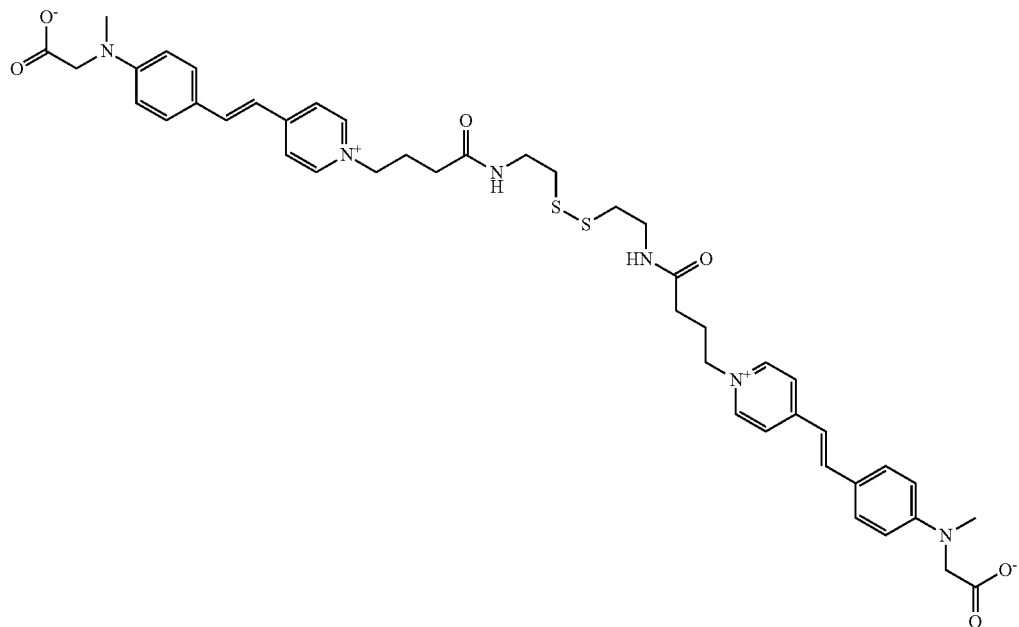
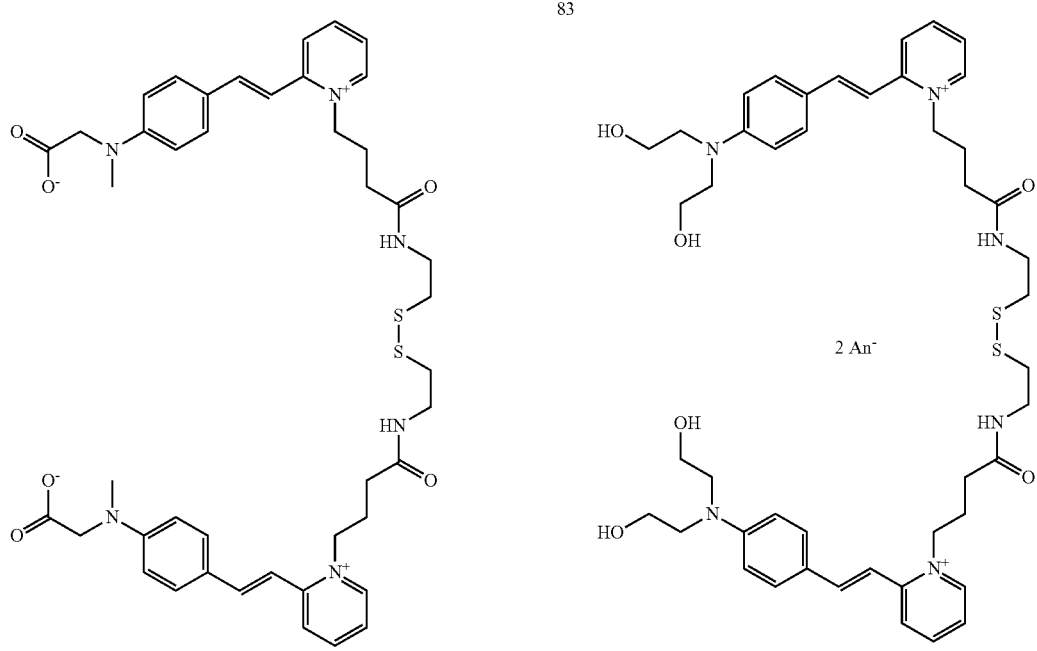
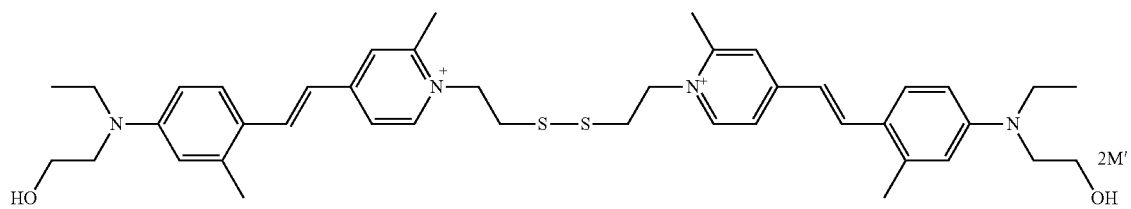

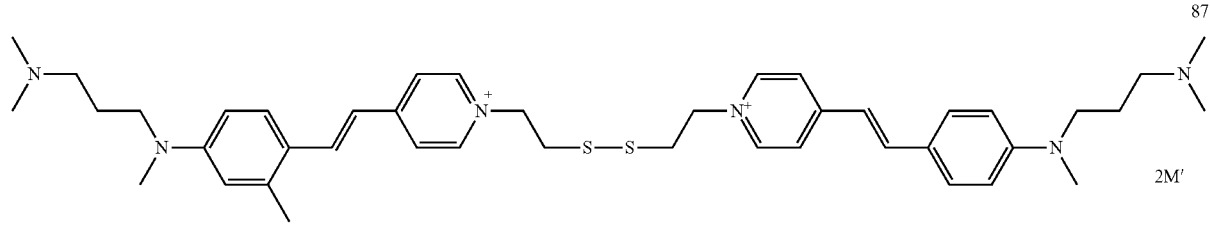
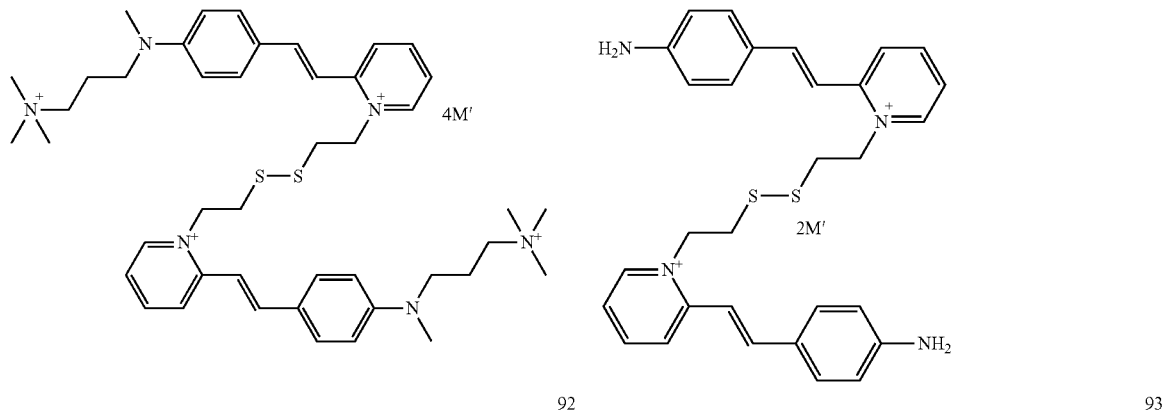
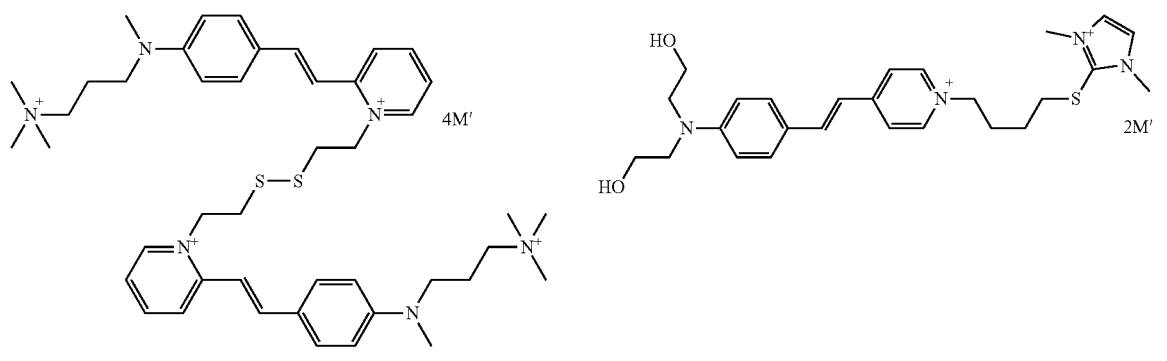
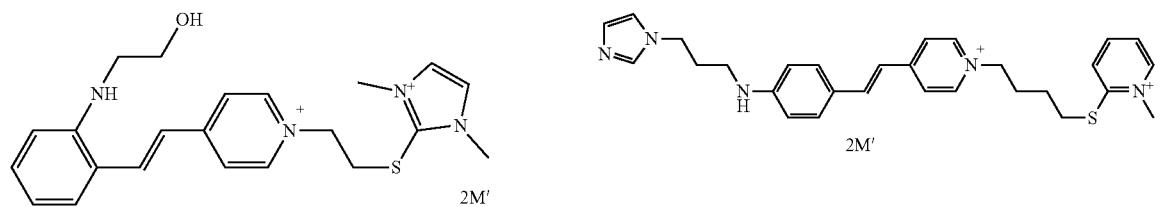
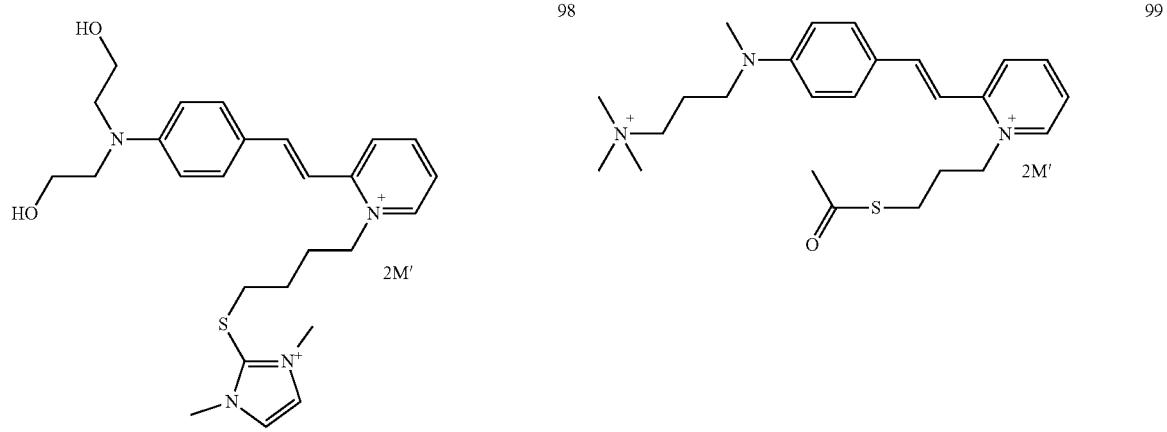

-continued
100
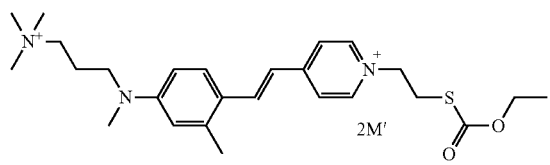
101
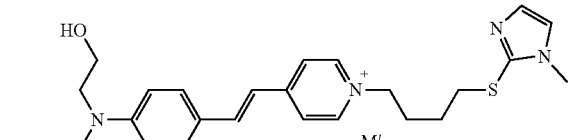
102
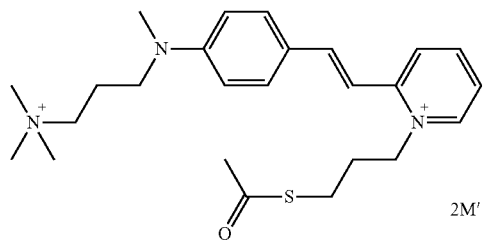
102
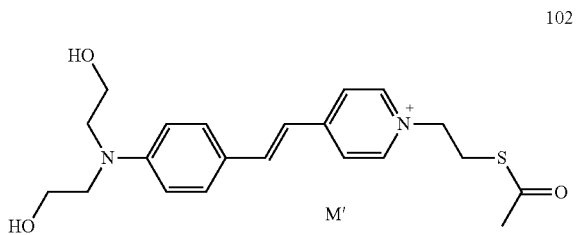
104
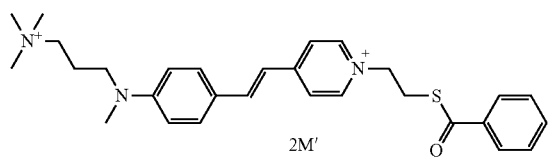
105
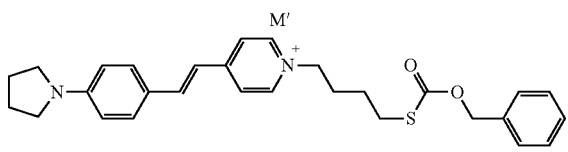
106
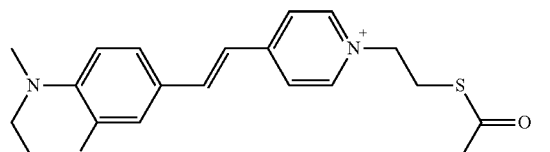
107
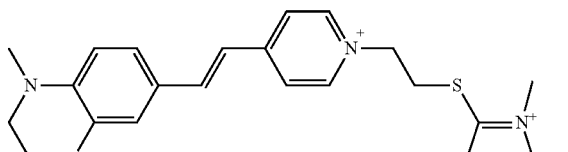
108
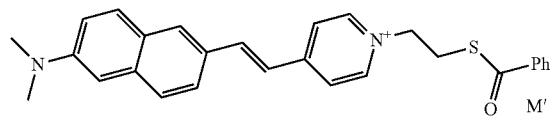
109
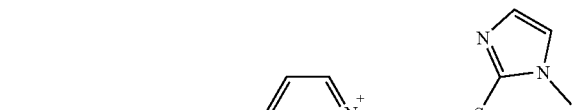
110
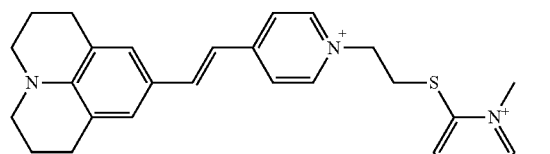
111
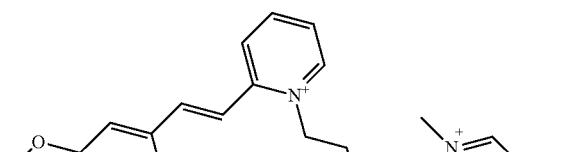

-continued

112 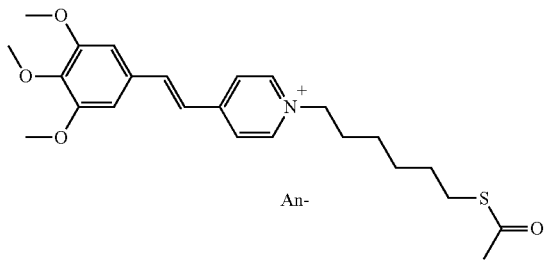

113 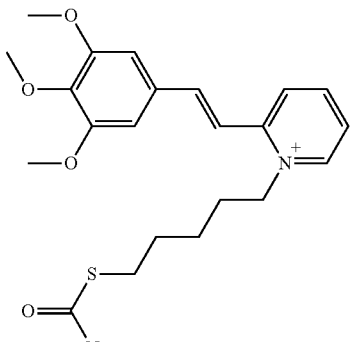

114 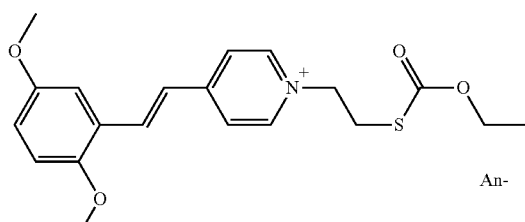

115 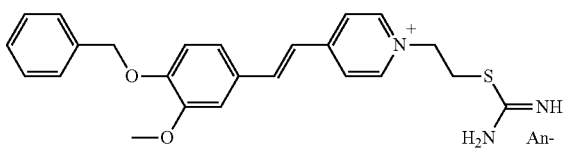

116 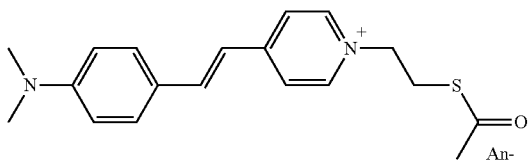

117 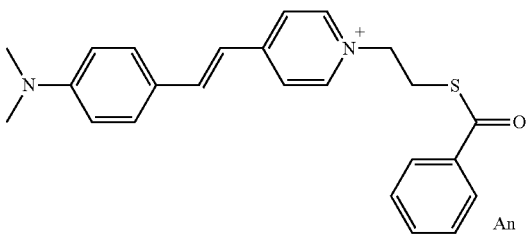

118 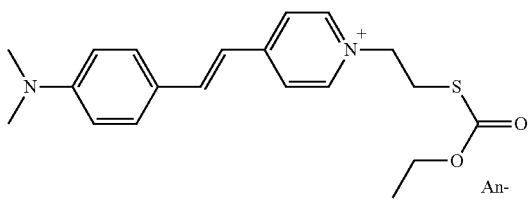

119 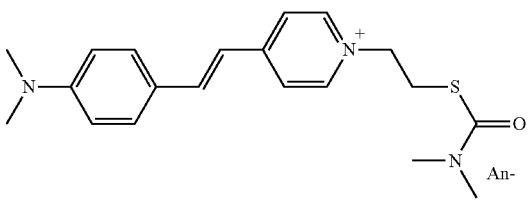

120 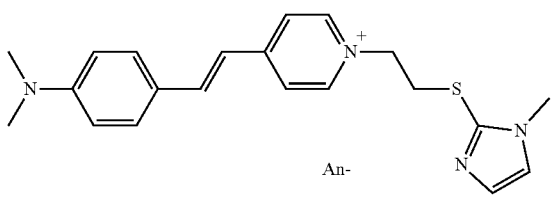

with An⁻ and M', which may be identical or different, representing anionic counterions.

14. The process of claim 1, further comprising applying to said keratin materials one or more reducing agents c), said reducing agent(s) c) optionally being applied before, at the same time as, or after the application of b) the at least one blue, violet, or green dye, or alternatively the one or more reducing agents c) are present with the at least one blue, violet, or green dye a); wherein the one or more reducing agents are chosen from i) the reducing agents of formula (Ic) below, addition salts thereof, or mixtures thereof:

$$H(X)_q(R_{10})_t \quad (Ic)$$

wherein in formula (Ic),

X represents P, S or $SO_2$, q represents an integer equal to 0 or 1, t represents an integer equal to 1 or 2, and $R_{10}$ represents a linear or branched, saturated or unsaturated $C_1$ to $C_{20}$ alkyl radical, optionally interrupted with a heteroatom, and/or optionally substituted with one or more radicals chosen from hydroxyl, halo, amine, carboxyl, (($C_1$-$C_{30}$)alkoxy)carbonyl, amido, ((C$_1$-C$_{30}$)alkyl)aminocarbonyl, ((C$_1$-C$_{30}$)acyl)amino, mono- or dialkylamino, and mono- or dihydroxylamino radicals;

ii) thioglycolic acid, iii) thiolactic acid, iv) glyceryl monothioglycolate, v) cysteamine, vi)N-acetylcysteamine, vii)N-propionylcysteamine, viii) cysteine, ix)N-acetylcysteine, x) thiomalic acid, xi) pantetheine, xii) 2,3-dimercaptosuccinic acid, xiii)N-(mercaptoalkyl)-w-hydroxyalkylamides, xiv)N-mono or N,N-dialkylmercapto-4-butyramides, xv) aminomercaptoalkylamides, xvi)N-(mercaptoalkyl)succinamic acid derivatives, xvii)N-(mercaptoalkyl)succinimide acid derivatives, xviii) alkylaminomercaptoalkylamides, ix) an azeotropic mixture of 2-hydroxypropyl thioglyconate and of (2-hydroxy-1-methyl)ethyl thioglycolate, x) mercaptoalkylaminoamides, xi)N-mercaptoalkylalkanediamides, xii) formamidine sulfinic acid derivatives, the addition salts thereof or mixtures thereof.

15. The process of claim 1, wherein the at least one blue, violet or green dyes a), and the at least one disulfide, thiol or protected-thiol fluorescent dyes b), are applied jointly to the keratin materials.

16. The process of claim 1, comprising at least the two successive steps below:
    a first step of applying to the light keratin materials a cosmetic composition comprising the one or more disulfide, thiol or protected-thiol fluorescent dyes b), followed by
    a second step of applying to the light keratin materials a cosmetic composition comprising the one or more blue, violet or green dyes a).

17. The process of claim 1, wherein the process comprises at least the two successive steps below:
    a first step of applying to the light keratin materials a cosmetic composition comprising one or more blue, violet or green dyes a), followed by
    a second step of applying to the light keratin materials a cosmetic composition comprising one or more disulfide, thiol or protected-thiol fluorescent dyes b).

18. The process of claim 1, wherein the process further comprises applying to the light keratin materials one or more oxidizing agents, which may be applied separately or jointly with one of the ingredients a) or b).

19. The process of claim 17, wherein the pH of the cosmetic composition(s) is between 6 and 11 inclusive.

20. A multi-compartment device comprising a first compartment comprising at least one blue, violet, or green dye a) chosen from:
    a1) phenoxazinium, phenothiazinium, or phenazinium dyes;
    a3) triarylmethane dyes;
    a4) naphthoquinone or anthraquinone dyes;
    a5) hydrazone dyes;
    a6) tetraazapentamethine dyes;
    a7) nitro dyes;
    a8) azomethine dyes;
    a9) self-oxidizing dyes; and/or
    a10) oxidation dyes;
    a second compartment comprising at least one disulfide, thiol, or protected-thiol fluorescent dye b);
    optionally a third compartment comprising at least one reducing agent c); and
    optionally a fourth compartment comprising at least one oxidizing agent d);
    wherein the multi-compartment device does not contain an additional dye other than the dyes a) and b).

* * * * *